US012590871B2

(12) United States Patent
Bhaumik et al.

(10) Patent No.: US 12,590,871 B2
(45) Date of Patent: Mar. 31, 2026

(54) METHODS AND SYSTEMS FOR PREPARING AND ANALYZING CELLULAR SAMPLES FOR MORPHOLOGICAL CHARACTERISTICS AND BIOMARKER EXPRESSION

(71) Applicants:Ventana Medical Systems, Inc., Tucson, AZ (US); Roche Diagnostics Operations, Inc., Indianapolis, IN (US); Roche Diagnostics Hematology, Inc., Brighton, MA (US)

(72) Inventors: Srabani Bhaumik, Oro Valley, AZ (US); Simon J. Davidson, Steinhausen (CH); Jerome W. Kosmeder, II, Tucson, AZ (US); Katherine K. Mui, Chelmsford, MA (US); Esteban Roberts, Tucson, AZ (US); Noemi Sebastiao, Tucson, AZ (US); David J. Zahniser, Wellesley, MA (US)

(73) Assignees: Ventana Medical Systems, Inc., Tucson, AZ (US); Roche Diagnostics Operations, Inc., Indianapolis, IN (US); Roche Diagnostics Hematology, Inc., Brighton, MA (US)

( * ) Notice: Subject to any disclaimer, the term of this patent is extended or adjusted under 35 U.S.C. 154(b) by 797 days.

(21) Appl. No.: 17/303,092

(22) Filed: May 19, 2021

(65) Prior Publication Data

US 2021/0270704 A1 Sep. 2, 2021

Related U.S. Application Data

(63) Continuation of application No. PCT/EP2019/081959, filed on Nov. 20, 2019.

(Continued)

(51) Int. Cl.
*G01N 1/30* (2006.01)
*G01N 33/50* (2006.01)

(52) U.S. Cl.
CPC ........... *G01N 1/30* (2013.01); *G01N 33/5094* (2013.01); *G01N 2001/302* (2013.01); *G01N 2001/305* (2013.01)

(58) Field of Classification Search
CPC ................. G01N 1/30; G01N 33/5094; G01N 2001/302; G01N 2001/305
See application file for complete search history.

(56) References Cited

U.S. PATENT DOCUMENTS

| | | | | |
|---|---|---|---|---|
| 10,379,014 B2 * | 8/2019 | Calatzis | ........... | G01N 35/00029 |
| 2004/0197839 A1 | 10/2004 | Daniely et al. | | |

(Continued)

FOREIGN PATENT DOCUMENTS

| | | |
|---|---|---|
| CN | 103797368 A | 5/2014 |
| CN | 106468714 A | 3/2017 |

(Continued)

OTHER PUBLICATIONS

Shi et al., Antigen Retrieval Technique Utilizing Citrate Buffer or Urea Solution for Immunohistochemical Demonstration of Androgen Receptor in Formalin-fixed Paraffin Sections, 1993, Jour of Histochem and Cytochem, vol. 41, No. 11, p. 1600 (Year: 1993).*

(Continued)

*Primary Examiner* — Robert B Mondesi
*Assistant Examiner* — Naghmeh Nina Moazzami
(74) *Attorney, Agent, or Firm* — Charney IP Law LLC; Thomas M. Finetti

(57) ABSTRACT

This disclosure relates generally to the use of automated platforms in the preparation of biomarker-stained cellular samples for microscopic analysis and use of such stained cells in the diagnosis of certain conditions. Disclosed herein (Continued)

is a method of affinity staining a Romanowsky-type stained sample on automated advanced staining systems, wherein the automated advanced stainer destains the sample prior to contact with a biomarker-specific reagent. Also disclosed herein are methods of processing body fluid samples for morphological and biomarker analysis by depositing cells of the sample onto one or more solid supports, staining at least one such solid support with a Romanowsky-type stain and staining at least one such solid support for one or more biomarkers useful for categorizing one or more cells of the sample.

21 Claims, 29 Drawing Sheets
(26 of 29 Drawing Sheet(s) Filed in Color)

Specification includes a Sequence Listing.

Related U.S. Application Data

(60) Provisional application No. 62/770,072, filed on Nov. 20, 2018.

(56) References Cited

U.S. PATENT DOCUMENTS

| | | | |
|---|---|---|---|
| 2010/0317002 A1 | 12/2010 | Daniely | |
| 2014/0141997 A1 | 5/2014 | Mahyuddin | |

FOREIGN PATENT DOCUMENTS

| | | | | |
|---|---|---|---|---|
| CN | 108026584 A | 5/2018 | | |
| EP | 3978926 B1 | 8/2024 | | |
| WO | WO-2013101989 A1 * | 7/2013 | .......... | C12Q 1/6886 |

OTHER PUBLICATIONS

McClellan et al., A Method for the Immunohistochemical Identification and Localization of Osterix in Periosteum-Wrapped Constructs for Tissue Engineering of Bone, 2017, Journal of Histochemistry & Cytochemistry, vol. 65(7), p. 410 (Year: 2017).*

D'Amico et al., State of the art in antigen retrieval for immunohistochemistry, 2007, Journal of Immunological Methods 341: 1-18, p. 7 (Year: 2007).*

Zhang et al., Fully automated 5-plex fluorescent immunohistochemistry with tyramide signal amplification and same species antibodies, Laboratory Investigation, vol. 97, Issue 7, 2017, pp. 873-885 (Year: 2017).*

Al Mussaed et al., Simultaneous existence of acute myeloid leukemia and chronic lymphocytic leukemia: a case report, BMC Cancer, 2016, pp. 1-7, 16: 739.

Andree et al., "Challenges in circulating tumor cell detection by the CellSearch system", Molecular Oncology, 2016, vol. 10, Issue 3, pp. 395-407.

Bain, 4—Preparation and staining methods for blood and bone marrow films, in Dacie and Lewis Practical Haematology (Twelfth Edition), 2017, pp. 50-60.

Barcia, The Giemsa Stain: Its History and Applications, History of Surgical Pathology, 2007, vol. 15, Issue 3, pp. 292-296.

Beraki E et al., Establishing a protocol for immunocytochemical staining and chromogenic in situ hybridization of Giemsa and Diff-Quick prestained cytological smears., Cytojournal., (2012), pp. 118, Abstract.

Blom et al., Systems pathology by multiplexed immunohistochemistry and whole-slide digital image analysis, Scientific Reports, 2017, vol. 7, Article No. 15580.

Bruegel et al., Multicenter evaluation of the COBAS m 511 integrated hematology analyzer, Int. J. Laboratory Hematology, Jul. 20, 2018, https://doi.org/10.1111/ijlh.12903 (e-publication ahead of print).

Buck et al., Measurement of pH. Definition, Standards, And Procedures, 2002, Pure Appl. Chem., vol. 74, Issue 11, pp. 2169-2200.

Castella G T et al., Improved immunocytochemical identification of neural, endothelial, and inflammatory cell types in paraffin-embedded injured adult rat spinal cord., J Neuroscience Meth, (2004), pp. 1-11, vol. 139 Issue 1.

Chiaretti, S., et al., Diagnosis and subclassification of acute lymphoblastic leukemia, 2014, Mediterr J Hematol Infect Dis, 2014, vol. 6, Issue 1, e2014073.

Choi U.S et al., Immunocytochemical detection of Ki-67 in Diff-Quik-stained cytological smears of canine mammary gland tumours, Cytopathology, (2011), pp. 115-120, vol. 22 Issue 2.

Dong et al. B-Cell Lymphomas with Coexpression of CD5 and CD10, Am J 5 Clin Pathol, 2003, vol. 119, Issue 2, pp. 218-230.

Horobin How Romanowsky stains work and why they remain valuable—including a proposed universal Romanowsky staining mechanism and a rational troubleshooting scheme, Biotechnic & Histochemistry, 2011, vol. 86, Issue 1, pp. 36-51.

Inoue T et al., Chromosomal numerical aberrations of exfoliated cells in the urine detected by fluorescence in situ hybridization: clinical implication for the detection of bladder cancer., Urol Res, (2000), pp. 57-61, vol. 28 Issue 1.

International Search Report and Written Opinion mailed Mar. 16, 2020 in connection with PCT/EP2019/081959 filed Nov. 20, 2019, 21 pages.

Koh, Chapter Sixteen—Preparation of Cells for Microscopy using Cytospin, Methods in Enzymology, 2013, vol. 533, pp. 235-240.

Krafts et al., Romanowsky staining in cytopathology: history, advantages and limitations, 15 Biotechnic & Histochemistry, 2011, vol. 86, Issue 2, pp. 82-93 ("Krafts II").

Krafts et al., The color purple: from royalty to laboratory, with apologies to Malachowski, Biotechnic & Histochemistry, 2011, vol. 86, Issue 1, pp. 7-35 ("Krafts I").

Krebs et al., Circulating tumour cells: their utility in cancer management and predicting outcomes, Ther Adv Med Oncol., 2010, vol. 2, Issue 6, pp. 351-365.

Kumar et al., "Automated analysis of immunohistochemistry images identifies candidate location biomarkers for cancers, Proceedings of the National Academy of Sciences", Dec. 23, 2014, 20 vol. 111, Issue 51, pp. 18249-18254.

Ligthart et al., "Unbiased and Automated Identification of a Circulating Tumour Cell Definition That Associates with Overall Survival", 2011, vol. 6, Issue 11, e27419.

Malcikova, J., et al. "ERIC recommendations for TP53 mutation analysis in chronic lymphocytic leukemia-update on methodological approaches and results interpretation", Feb. 2, 2018, Leukemia, vol. 32, Issue 5, pp. 1070-1080.

Meyerson et al., "D Cyclins in CD5+ B-Cell Lymphoproliferative Disorders: Cyclin D1 and Cyclin D2 Identify Diagnostic Groups and Cyclin D1 Correlates With ZAP-70 Expression in Chronic Lymphocytic Leukemia", Am J Clin Pathol, 2006, vol. 125, Issue 5, pp. 241-250.

Neklason, D. W. et al., Activating mutation in MET oncogene in familial colorectal cancer, BMC Cancer, 2011, vol. 11, No. 424.

Nickoloff et al., Mechanisms of leukemia translocations, Curr Opin Hematol, 2008, vol. 15, Issue 4, pp. 338-345.

Pajor et al., State-of-the-art FISHing: Automated analysis of cytogenetic aberrations in interphase nuclei, Cytometry A, 2012, vol. 81 A, Issue 8, pp. 649-663.

Park et al., Morphological Differences between Circulating Tumor Cells from 5 Prostate Cancer Patients and Cultured Prostate Cancer Cells, PLoS ONE, 2014, vol. 9, Issue 1: e85264, https://doi.org/10.1371/journal.pone.0085264.

Parker & Zhang, Fusion genes in solid tumors: an emerging target for cancer diagnosis and treatment, China J. Cancer, 2013, vol. 32, Issue 11, pp. 594-603.

Prichard, J. W., Overview of Automated Immunohistochemistry, Arch Pathol Lab Med, (2014), pp. 1578-1582, vol. 138.

Schlotens et al., Automated identification of circulating tumor cells by image cytometry, Cytometry A, 2012, vol. 81, Issue 2: pp. 138-148.

Shah, J., et al. A dual colour fluorescence in situ hybridization (FISH) assay for identifying the zoonotic malaria parasite *Plasmo-*

(56)  References Cited

OTHER PUBLICATIONS

*dium knowlesi* with a potential application for the specific diagnosis of knowlesi malaria in peripheral-level laboratories of Southeast Asia, Parasit Vectors, 2017, vol. 10, Issue 1, pp. 342.

Stack et al, Multiplexed immunohistochemistry, imaging, and quantitation: A review, with an assessment of Tyramide signal amplification, multispectral imaging and multiplex analysis, Methods, 2014, pp. 46-58, vol. 70.

Stokes, "Principles of Cytocentrifugation", Laboratory Medicine, 2004, vol. 35, Issue 7, pp. 434-437.

Van De Donk et al., Monoclonal antibodies targeting CD38 in hematological malignancies and beyond, Immunol Rev, 2016, pp. 95-112, vol. 270, Issue 1.

Van der Logt et al., Fully Automated Fluorescent in situ Hybridization (FISH) Staining and Digital Analysis of HER2 in Breast Cancer: A Validation Study, PLoS ONE, 2015; vol. 10, Issue 4, e0123201.

Winkelman et al., A Novel Automated Slide-Based Technology for Visualization, Counting, and Characterization of the Formed Elements of Blood, Arch Pathol Lab Med, 2017, vol. 141, pp. 30 1107-1112.

Zahniser & Hurley, "Automated Slide Preparation System for the Clinical Laboratory", Comm. In Clinical Cytometry, 1996, vol. 26, pp. 60-64.

* cited by examiner

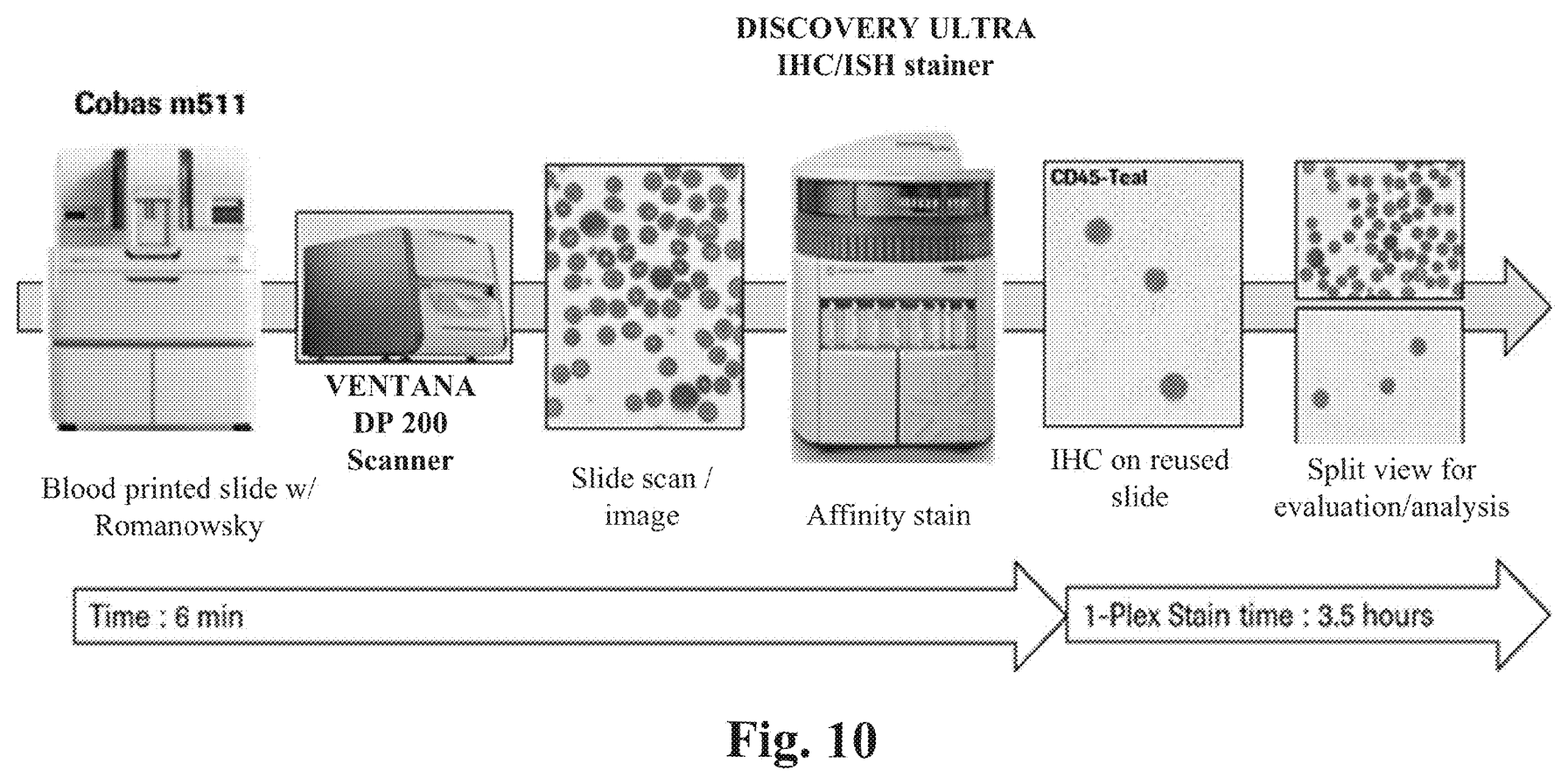

Cobas m511

Blood printed slide w/ Romanowsky

VENTANA DP 200 Scanner

Slide scan / image

DISCOVERY ULTRA IHC/ISH stainer

Affinity stain

CD45-Teal

IHC on reused slide

Split view for evaluation/analysis

Time : 6 min

1-Plex Stain time : 3.5 hours

Fig. 10

MeOH

NBF

Romanowsky

DISCOVERY
Purple

MeOH

NBF

Romanowsky          DISCOVERY
                    Teal

DAPI + CD5 (R6G) + CD2 (Red610) + CD45 (FAM) + CD4 (Cy5)

Merged

Romanowsky

SEQUENCE LISTING

```
<160> NUMBER OF SEQ ID NOS: 24

<210> SEQ ID NO 1
<211> LENGTH: 351
<212> TYPE: PRT
<213> ORGANISM: Homo sapiens

<400> SEQUENCE: 1

Met Ser Phe Pro Cys Lys Phe Val Ala Ser Phe Leu Leu Ile Phe Asn
1               5                   10                  15

Val Ser Ser Lys Gly Ala Val Ser Lys Glu Ile Thr Asn Ala Leu Glu
            20                  25                  30

Thr Trp Gly Ala Leu Gly Gln Asp Ile Asn Leu Asp Ile Pro Ser Phe
        35                  40                  45

Gln Met Ser Asp Asp Ile Asp Asp Ile Lys Trp Glu Lys Thr Ser Asp
    50                  55                  60

Lys Lys Lys Ile Ala Gln Phe Arg Lys Glu Lys Glu Thr Phe Lys Glu
65                  70                  75                  80
```

-continued

```
Lys Asp Thr Tyr Lys Leu Phe Lys Asn Gly Thr Leu Lys Ile Lys His
                85                  90                  95

Leu Lys Thr Asp Asp Gln Asp Ile Tyr Lys Val Ser Ile Tyr Asp Thr
               100                 105                 110

Lys Gly Lys Asn Val Leu Glu Lys Ile Phe Asp Leu Lys Ile Gln Glu
               115                 120                 125

Arg Val Ser Lys Pro Lys Ile Ser Trp Thr Cys Ile Asn Thr Thr Leu
           130                 135                 140

Thr Cys Glu Val Met Asn Gly Thr Asp Pro Glu Leu Asn Leu Tyr Gln
145                 150                 155                 160

Asp Gly Lys His Leu Lys Leu Ser Gln Arg Val Ile Thr His Lys Trp
               165                 170                 175

Thr Thr Ser Leu Ser Ala Lys Phe Lys Cys Thr Ala Gly Asn Lys Val
               180                 185                 190

Ser Lys Glu Ser Ser Val Glu Pro Val Ser Cys Pro Glu Lys Gly Leu
               195                 200                 205

Asp Ile Tyr Leu Ile Ile Gly Ile Cys Gly Gly Gly Ser Leu Leu Met
           210                 215                 220

Val Phe Val Ala Leu Leu Val Phe Tyr Ile Thr Lys Arg Lys Lys Gln
225                 230                 235                 240

Arg Ser Arg Arg Asn Asp Glu Glu Leu Glu Thr Arg Ala His Arg Val
               245                 250                 255

Ala Thr Glu Glu Arg Gly Arg Lys Pro His Gln Ile Pro Ala Ser Thr
               260                 265                 270

Pro Gln Asn Pro Ala Thr Ser Gln His Pro Pro Pro Pro Gly His
               275                 280                 285

Arg Ser Gln Ala Pro Ser His Arg Pro Pro Pro Gly His Arg Val
           290                 295                 300

Gln His Gln Pro Gln Lys Arg Pro Pro Ala Pro Ser Gly Thr Gln Val
305                 310                 315                 320

His Gln Gln Lys Gly Pro Pro Leu Pro Arg Pro Arg Val Gln Pro Lys
               325                 330                 335

Pro Pro His Gly Ala Ala Glu Asn Ser Leu Ser Pro Ser Ser Asn
               340                 345                 350
```

```
<210> SEQ ID NO 2
<211> LENGTH: 182
<212> TYPE: PRT
<213> ORGANISM: Homo sapiens

<400> SEQUENCE: 2
```

```
Met Glu Gln Gly Lys Gly Leu Ala Val Leu Ile Leu Ala Ile Ile Leu
1               5                   10                  15

Leu Gln Gly Thr Leu Ala Gln Ser Ile Lys Gly Asn His Leu Val Lys
               20                  25                  30

Val Tyr Asp Tyr Gln Glu Asp Gly Ser Val Leu Leu Thr Cys Asp Ala
           35                  40                  45

Glu Ala Lys Asn Ile Thr Trp Phe Lys Asp Gly Lys Met Ile Gly Phe
       50                  55                  60

Leu Thr Glu Asp Lys Lys Lys Trp Asn Leu Gly Ser Asn Ala Lys Asp
65                  70                  75                  80

Pro Arg Gly Met Tyr Gln Cys Lys Gly Ser Gln Asn Lys Ser Lys Pro
               85                  90                  95

Leu Gln Val Tyr Tyr Arg Met Cys Gln Asn Cys Ile Glu Leu Asn Ala
```

-continued

```
                    100             105             110

Ala Thr Ile Ser Gly Phe Leu Phe Ala Glu Ile Val Ser Ile Phe Val
        115             120             125

Leu Ala Val Gly Val Tyr Phe Ile Ala Gly Gln Asp Gly Val Arg Gln
    130             135             140

Ser Arg Ala Ser Asp Lys Gln Thr Leu Leu Pro Asn Asp Gln Leu Tyr
145             150             155             160

Gln Pro Leu Lys Asp Arg Glu Asp Asp Gln Tyr Ser His Leu Gln Gly
            165             170             175

Asn Gln Leu Arg Arg Asn
            180

<210> SEQ ID NO 3
<211> LENGTH: 458
<212> TYPE: PRT
<213> ORGANISM: Homo sapiens

<400> SEQUENCE: 3

Met Asn Arg Gly Val Pro Phe Arg His Leu Leu Leu Val Leu Gln Leu
1               5               10              15

Ala Leu Leu Pro Ala Ala Thr Gln Gly Lys Lys Val Val Leu Gly Lys
            20              25              30

Lys Gly Asp Thr Val Glu Leu Thr Cys Thr Ala Ser Gln Lys Lys Ser
            35              40              45

Ile Gln Phe His Trp Lys Asn Ser Asn Gln Ile Lys Ile Leu Gly Asn
    50              55              60

Gln Gly Ser Phe Leu Thr Lys Gly Pro Ser Lys Leu Asn Asp Arg Ala
65              70              75              80

Asp Ser Arg Arg Ser Leu Trp Asp Gln Gly Asn Phe Pro Leu Ile Ile
            85              90              95

Lys Asn Leu Lys Ile Glu Asp Ser Asp Thr Tyr Ile Cys Glu Val Glu
            100             105             110

Asp Gln Lys Glu Glu Val Gln Leu Leu Val Phe Gly Leu Thr Ala Asn
            115             120             125

Ser Asp Thr His Leu Leu Gln Gly Gln Ser Leu Thr Leu Thr Leu Glu
    130             135             140

Ser Pro Pro Gly Ser Ser Pro Ser Val Gln Cys Arg Ser Pro Arg Gly
145             150             155             160

Lys Asn Ile Gln Gly Gly Lys Thr Leu Ser Val Ser Gln Leu Glu Leu
            165             170             175

Gln Asp Ser Gly Thr Trp Thr Cys Thr Val Leu Gln Asn Gln Lys Lys
            180             185             190

Val Glu Phe Lys Ile Asp Ile Val Val Leu Ala Phe Gln Lys Ala Ser
            195             200             205

Ser Ile Val Tyr Lys Lys Glu Gly Glu Gln Val Glu Phe Ser Phe Pro
    210             215             220

Leu Ala Phe Thr Val Glu Lys Leu Thr Gly Ser Gly Glu Leu Trp Trp
225             230             235             240

Gln Ala Glu Arg Ala Ser Ser Ser Lys Ser Trp Ile Thr Phe Asp Leu
            245             250             255

Lys Asn Lys Glu Val Ser Val Lys Arg Val Thr Gln Asp Pro Lys Leu
            260             265             270

Gln Met Gly Lys Lys Leu Pro Leu His Leu Thr Leu Pro Gln Ala Leu
            275             280             285
```

```
Pro Gln Tyr Ala Gly Ser Gly Asn Leu Thr Leu Ala Leu Glu Ala Lys
    290             295                 300

Thr Gly Lys Leu His Gln Glu Val Asn Leu Val Val Met Arg Ala Thr
305                 310                 315                 320

Gln Leu Gln Lys Asn Leu Thr Cys Glu Val Trp Gly Pro Thr Ser Pro
            325                 330                 335

Lys Leu Met Leu Ser Leu Lys Leu Glu Asn Lys Glu Ala Lys Val Ser
            340                 345                 350

Lys Arg Glu Lys Ala Val Trp Val Leu Asn Pro Glu Ala Gly Met Trp
        355                 360                 365

Gln Cys Leu Leu Ser Asp Ser Gly Gln Val Leu Leu Glu Ser Asn Ile
        370                 375                 380

Lys Val Leu Pro Thr Trp Ser Thr Pro Val Gln Pro Met Ala Leu Ile
385                 390                 395                 400

Val Leu Gly Gly Val Ala Gly Leu Leu Leu Phe Ile Gly Leu Gly Ile
                405                 410                 415

Phe Phe Cys Val Arg Cys Arg His Arg Arg Arg Gln Ala Glu Arg Met
            420                 425                 430

Ser Gln Ile Lys Arg Leu Leu Ser Glu Lys Lys Thr Cys Gln Cys Pro
        435                 440                 445

His Arg Phe Gln Lys Thr Cys Ser Pro Ile
        450                 455
```

```
<210> SEQ ID NO 4
<211> LENGTH: 495
<212> TYPE: PRT
<213> ORGANISM: Homo sapiens

<400> SEQUENCE: 4

Met Pro Met Gly Ser Leu Gln Pro Leu Ala Thr Leu Tyr Leu Leu Gly
1               5                   10                  15

Met Leu Val Ala Ser Cys Leu Gly Arg Leu Ser Trp Tyr Asp Pro Asp
            20                  25                  30

Phe Gln Ala Arg Leu Thr Arg Ser Asn Ser Lys Cys Gln Gly Gln Leu
        35                  40                  45

Glu Val Tyr Leu Lys Asp Gly Trp His Met Val Cys Ser Gln Ser Trp
    50                  55                  60

Gly Arg Ser Ser Lys Gln Trp Glu Asp Pro Ser Gln Ala Ser Lys Val
65                  70                  75                  80

Cys Gln Arg Leu Asn Cys Gly Val Pro Leu Ser Leu Gly Pro Phe Leu
            85                  90                  95

Val Thr Tyr Thr Pro Gln Ser Ser Ile Ile Cys Tyr Gly Gln Leu Gly
            100                 105                 110

Ser Phe Ser Asn Cys Ser His Ser Arg Asn Asp Met Cys His Ser Leu
            115                 120                 125

Gly Leu Thr Cys Leu Glu Pro Gln Lys Thr Thr Pro Pro Thr Thr Arg
        130                 135                 140

Pro Pro Pro Thr Thr Thr Pro Glu Pro Thr Ala Pro Pro Arg Leu Gln
145                 150                 155                 160

Leu Val Ala Gln Ser Gly Gly Gln His Cys Ala Gly Val Val Glu Phe
                165                 170                 175

Tyr Ser Gly Ser Leu Gly Gly Thr Ile Ser Tyr Glu Ala Gln Asp Lys
            180                 185                 190

Thr Gln Asp Leu Glu Asn Phe Leu Cys Asn Asn Leu Gln Cys Gly Ser
        195                 200                 205
```

-continued

```
Phe Leu Lys His Leu Pro Glu Thr Glu Ala Gly Arg Ala Gln Asp Pro
    210                 215             220

Gly Glu Pro Arg Glu His Gln Pro Leu Pro Ile Gln Trp Lys Ile Gln
225                 230             235                 240

Asn Ser Ser Cys Thr Ser Leu Glu His Cys Phe Arg Lys Ile Lys Pro
            245             250                 255

Gln Lys Ser Gly Arg Val Leu Ala Leu Leu Cys Ser Gly Phe Gln Pro
            260             265             270

Lys Val Gln Ser Arg Leu Val Gly Gly Ser Ser Ile Cys Glu Gly Thr
        275             280             285

Val Glu Val Arg Gln Gly Ala Gln Trp Ala Ala Leu Cys Asp Ser Ser
    290             295             300

Ser Ala Arg Ser Ser Leu Arg Trp Glu Glu Val Cys Arg Glu Gln Gln
305             310             315                 320

Cys Gly Ser Val Asn Ser Tyr Arg Val Leu Asp Ala Gly Asp Pro Thr
            325             330             335

Ser Arg Gly Leu Phe Cys Pro His Gln Lys Leu Ser Gln Cys His Glu
            340             345             350

Leu Trp Glu Arg Asn Ser Tyr Cys Lys Lys Val Phe Val Thr Cys Gln
    355             360             365

Asp Pro Asn Pro Ala Gly Leu Ala Ala Gly Thr Val Ala Ser Ile Ile
    370             375             380

Leu Ala Leu Val Leu Leu Val Val Leu Leu Val Val Cys Gly Pro Leu
385             390             395                 400

Ala Tyr Lys Lys Leu Val Lys Lys Phe Arg Gln Lys Lys Gln Arg Gln
            405             410             415

Trp Ile Gly Pro Thr Gly Met Asn Gln Asn Met Ser Phe His Arg Asn
            420             425             430

His Thr Ala Thr Val Arg Ser His Ala Glu Asn Pro Thr Ala Ser His
        435             440             445

Val Asp Asn Glu Tyr Ser Gln Pro Pro Arg Asn Ser His Leu Ser Ala
    450             455             460

Tyr Pro Ala Leu Glu Gly Ala Leu His Arg Ser Ser Met Gln Pro Asp
465             470             475                 480

Asn Ser Ser Asp Ser Asp Tyr Asp Leu His Gly Ala Gln Arg Leu
            485             490             495

<210> SEQ ID NO 5
<211> LENGTH: 240
<212> TYPE: PRT
<213> ORGANISM: Homo sapiens

<400> SEQUENCE: 5

Met Ala Gly Pro Pro Arg Leu Leu Leu Leu Pro Leu Leu Leu Ala Leu
1               5               10              15

Ala Arg Gly Leu Pro Gly Ala Leu Ala Ala Gln Glu Val Gln Gln Ser
            20              25              30

Pro His Cys Thr Thr Val Pro Val Gly Ala Ser Val Asn Ile Thr Cys
        35              40              45

Ser Thr Ser Gly Gly Leu Arg Gly Ile Tyr Leu Arg Gln Leu Gly Pro
    50              55              60

Gln Pro Gln Asp Ile Ile Tyr Tyr Glu Asp Gly Val Val Pro Thr Thr
65              70              75              80

Asp Arg Arg Phe Arg Gly Arg Ile Asp Phe Ser Gly Ser Gln Asp Asn
```

```
                      85                 90                 95
Leu Thr Ile Thr Met His Arg Leu Gln Leu Ser Asp Thr Gly Thr Tyr
            100                 105                 110

Thr Cys Gln Ala Ile Thr Glu Val Asn Val Tyr Gly Ser Gly Thr Leu
            115                 120                 125

Val Leu Val Thr Glu Glu Gln Ser Gln Gly Trp His Arg Cys Ser Asp
        130                 135                 140

Ala Pro Pro Arg Ala Ser Ala Leu Pro Ala Pro Thr Gly Ser Ala
145                 150                 155                 160

Leu Pro Asp Pro Gln Thr Ala Ser Ala Leu Pro Asp Pro Pro Ala Ala
                165                 170                 175

Ser Ala Leu Pro Ala Ala Leu Ala Val Ile Ser Phe Leu Leu Gly Leu
            180                 185                 190

Gly Leu Gly Val Ala Cys Val Leu Ala Arg Thr Gln Ile Lys Lys Leu
        195                 200                 205

Cys Ser Trp Arg Asp Lys Asn Ser Ala Ala Cys Val Val Tyr Glu Asp
        210                 215                 220

Met Ser His Ser Arg Cys Asn Thr Leu Ser Ser Pro Asn Gln Tyr Gln
225                 230                 235                 240

<210> SEQ ID NO 6
<211> LENGTH: 235
<212> TYPE: PRT
<213> ORGANISM: Homo sapiens

<400> SEQUENCE: 6

Met Ala Leu Pro Val Thr Ala Leu Leu Leu Pro Leu Ala Leu Leu Leu
1               5                   10                  15

His Ala Ala Arg Pro Ser Gln Phe Arg Val Ser Pro Leu Asp Arg Thr
                20                  25                  30

Trp Asn Leu Gly Glu Thr Val Glu Leu Lys Cys Gln Val Leu Leu Ser
            35                  40                  45

Asn Pro Thr Ser Gly Cys Ser Trp Leu Phe Gln Pro Arg Gly Ala Ala
        50                  55                  60

Ala Ser Pro Thr Phe Leu Leu Tyr Leu Ser Gln Asn Lys Pro Lys Ala
65                  70                  75                  80

Ala Glu Gly Leu Asp Thr Gln Arg Phe Ser Gly Lys Arg Leu Gly Asp
                85                  90                  95

Thr Phe Val Leu Thr Leu Ser Asp Phe Arg Arg Glu Asn Glu Gly Tyr
            100                 105                 110

Tyr Phe Cys Ser Ala Leu Ser Asn Ser Ile Met Tyr Phe Ser His Phe
            115                 120                 125

Val Pro Val Phe Leu Pro Ala Lys Pro Thr Thr Thr Pro Ala Pro Arg
        130                 135                 140

Pro Pro Thr Pro Ala Pro Thr Ile Ala Ser Gln Pro Leu Ser Leu Arg
145                 150                 155                 160

Pro Glu Ala Cys Arg Pro Ala Ala Gly Gly Ala Val His Thr Arg Gly
                165                 170                 175

Leu Asp Phe Ala Cys Asp Ile Tyr Ile Trp Ala Pro Leu Ala Gly Thr
                180                 185                 190

Cys Gly Val Leu Leu Leu Ser Leu Val Ile Thr Leu Tyr Cys Asn His
        195                 200                 205

Arg Asn Arg Arg Arg Val Cys Lys Cys Pro Arg Pro Val Val Lys Ser
        210                 215                 220
```

```
Gly Asp Lys Pro Ser Leu Ser Ala Arg Tyr Val
225                 230                 235
```

```
<210> SEQ ID NO 7
<211> LENGTH: 750
<212> TYPE: PRT
<213> ORGANISM: Homo sapiens

<400> SEQUENCE: 7
```

```
Met Gly Lys Ser Glu Ser Gln Met Asp Ile Thr Asp Ile Asn Thr Pro
1               5                   10                  15

Lys Pro Lys Lys Lys Gln Arg Trp Thr Pro Leu Glu Ile Ser Leu Ser
                20                  25                  30

Val Leu Val Leu Leu Leu Thr Ile Ile Ala Val Thr Met Ile Ala Leu
            35                  40                  45

Tyr Ala Thr Tyr Asp Asp Gly Ile Cys Lys Ser Ser Asp Cys Ile Lys
    50                  55                  60

Ser Ala Ala Arg Leu Ile Gln Asn Met Asp Ala Thr Thr Glu Pro Cys
65                  70                  75                  80

Thr Asp Phe Phe Lys Tyr Ala Cys Gly Gly Trp Leu Lys Arg Asn Val
                85                  90                  95

Ile Pro Glu Thr Ser Ser Arg Tyr Gly Asn Phe Asp Ile Leu Arg Asp
                100                 105                 110

Glu Leu Glu Val Val Leu Lys Asp Val Leu Gln Glu Pro Lys Thr Glu
            115                 120                 125

Asp Ile Val Ala Val Gln Lys Ala Lys Ala Leu Tyr Arg Ser Cys Ile
    130                 135                 140

Asn Glu Ser Ala Ile Asp Ser Arg Gly Gly Glu Pro Leu Leu Lys Leu
145                 150                 155                 160

Leu Pro Asp Ile Tyr Gly Trp Pro Val Ala Thr Glu Asn Trp Glu Gln
                165                 170                 175

Lys Tyr Gly Ala Ser Trp Thr Ala Glu Lys Ala Ile Ala Gln Leu Asn
                180                 185                 190

Ser Lys Tyr Gly Lys Lys Val Leu Ile Asn Leu Phe Val Gly Thr Asp
                195                 200                 205

Asp Lys Asn Ser Val Asn His Val Ile His Ile Asp Gln Pro Arg Leu
    210                 215                 220

Gly Leu Pro Ser Arg Asp Tyr Tyr Glu Cys Thr Gly Ile Tyr Lys Glu
225                 230                 235                 240

Ala Cys Thr Ala Tyr Val Asp Phe Met Ile Ser Val Ala Arg Leu Ile
                245                 250                 255

Arg Gln Glu Glu Arg Leu Pro Ile Asp Glu Asn Gln Leu Ala Leu Glu
                260                 265                 270

Met Asn Lys Val Met Glu Leu Glu Lys Glu Ile Ala Asn Ala Thr Ala
                275                 280                 285

Lys Pro Glu Asp Arg Asn Asp Pro Met Leu Leu Tyr Asn Lys Met Thr
    290                 295                 300

Leu Ala Gln Ile Gln Asn Asn Phe Ser Leu Glu Ile Asn Gly Lys Pro
305                 310                 315                 320

Phe Ser Trp Leu Asn Phe Thr Asn Glu Ile Met Ser Thr Val Asn Ile
                325                 330                 335

Ser Ile Thr Asn Glu Glu Asp Val Val Val Tyr Ala Pro Glu Tyr Leu
                340                 345                 350

Thr Lys Leu Lys Pro Ile Leu Thr Lys Tyr Ser Ala Arg Asp Leu Gln
    355                 360                 365
```

```
Asn Leu Met Ser Trp Arg Phe Ile Met Asp Leu Val Ser Ser Leu Ser
    370             375             380

Arg Thr Tyr Lys Glu Ser Arg Asn Ala Phe Arg Lys Ala Leu Tyr Gly
385             390             395             400

Thr Thr Ser Glu Thr Ala Thr Trp Arg Arg Cys Ala Asn Tyr Val Asn
                405             410             415

Gly Asn Met Glu Asn Ala Val Gly Arg Leu Tyr Val Glu Ala Ala Phe
            420             425             430

Ala Gly Glu Ser Lys His Val Val Glu Asp Leu Ile Ala Gln Ile Arg
            435             440             445

Glu Val Phe Ile Gln Thr Leu Asp Asp Leu Thr Trp Met Asp Ala Glu
        450             455             460

Thr Lys Lys Arg Ala Glu Glu Lys Ala Leu Ala Ile Lys Glu Arg Ile
465             470             475             480

Gly Tyr Pro Asp Asp Ile Val Ser Asn Asp Asn Lys Leu Asn Asn Glu
                485             490             495

Tyr Leu Glu Leu Asn Tyr Lys Glu Asp Glu Tyr Phe Glu Asn Ile Ile
            500             505             510

Gln Asn Leu Lys Phe Ser Gln Ser Lys Gln Leu Lys Lys Leu Arg Glu
            515             520             525

Lys Val Asp Lys Asp Glu Trp Ile Ser Gly Ala Ala Val Val Asn Ala
        530             535             540

Phe Tyr Ser Ser Gly Arg Asn Gln Ile Val Phe Pro Ala Gly Ile Leu
545             550             555             560

Gln Pro Pro Phe Phe Ser Ala Gln Gln Ser Asn Ser Leu Asn Tyr Gly
                565             570             575

Gly Ile Gly Met Val Ile Gly His Glu Ile Thr His Gly Phe Asp Asp
            580             585             590

Asn Gly Arg Asn Phe Asn Lys Asp Gly Asp Leu Val Asp Trp Trp Thr
            595             600             605

Gln Gln Ser Ala Ser Asn Phe Lys Glu Gln Ser Gln Cys Met Val Tyr
        610             615             620

Gln Tyr Gly Asn Phe Ser Trp Asp Leu Ala Gly Gly Gln His Leu Asn
625             630             635             640

Gly Ile Asn Thr Leu Gly Glu Asn Ile Ala Asp Asn Gly Gly Leu Gly
            645             650             655

Gln Ala Tyr Arg Ala Tyr Gln Asn Tyr Ile Lys Lys Asn Gly Glu Glu
            660             665             670

Lys Leu Leu Pro Gly Leu Asp Leu Asn His Lys Gln Leu Phe Phe Leu
            675             680             685

Asn Phe Ala Gln Val Trp Cys Gly Thr Tyr Arg Pro Glu Tyr Ala Val
        690             695             700

Asn Ser Ile Lys Thr Asp Val His Ser Pro Gly Asn Phe Arg Ile Ile
705             710             715             720

Gly Thr Leu Gln Asn Ser Ala Glu Phe Ser Glu Ala Phe His Cys Arg
            725             730             735

Lys Asn Ser Tyr Met Asn Pro Glu Lys Lys Cys Arg Val Trp
            740             745             750
```

<210> SEQ ID NO 8
<211> LENGTH: 297
<212> TYPE: PRT
<213> ORGANISM: Homo sapiens

```
<400> SEQUENCE: 8

Met Thr Thr Pro Arg Asn Ser Val Asn Gly Thr Phe Pro Ala Glu Pro
1               5                   10                  15

Met Lys Gly Pro Ile Ala Met Gln Ser Gly Pro Lys Pro Leu Phe Arg
            20                  25                  30

Arg Met Ser Ser Leu Val Gly Pro Thr Gln Ser Phe Phe Met Arg Glu
            35                  40                  45

Ser Lys Thr Leu Gly Ala Val Gln Ile Met Asn Gly Leu Phe His Ile
    50                  55                  60

Ala Leu Gly Gly Leu Leu Met Ile Pro Ala Gly Ile Tyr Ala Pro Ile
65                  70                  75                  80

Cys Val Thr Val Trp Tyr Pro Leu Trp Gly Gly Ile Met Tyr Ile Ile
                85                  90                  95

Ser Gly Ser Leu Leu Ala Ala Thr Glu Lys Asn Ser Arg Lys Cys Leu
            100                 105                 110

Val Lys Gly Lys Met Ile Met Asn Ser Leu Ser Leu Phe Ala Ala Ile
            115                 120                 125

Ser Gly Met Ile Leu Ser Ile Met Asp Ile Leu Asn Ile Lys Ile Ser
    130                 135                 140

His Phe Leu Lys Met Glu Ser Leu Asn Phe Ile Arg Ala His Thr Pro
145                 150                 155                 160

Tyr Ile Asn Ile Tyr Asn Cys Glu Pro Ala Asn Pro Ser Glu Lys Asn
                165                 170                 175

Ser Pro Ser Thr Gln Tyr Cys Tyr Ser Ile Gln Ser Leu Phe Leu Gly
            180                 185                 190

Ile Leu Ser Val Met Leu Ile Phe Ala Phe Phe Gln Glu Leu Val Ile
            195                 200                 205

Ala Gly Ile Val Glu Asn Glu Trp Lys Arg Thr Cys Ser Arg Pro Lys
    210                 215                 220

Ser Asn Ile Val Leu Leu Ser Ala Glu Glu Lys Lys Glu Gln Thr Ile
225                 230                 235                 240

Glu Ile Lys Glu Glu Val Val Gly Leu Thr Glu Thr Ser Ser Gln Pro
                245                 250                 255

Lys Asn Glu Glu Asp Ile Glu Ile Ile Pro Ile Gln Glu Glu Glu Glu
            260                 265                 270

Glu Glu Thr Glu Thr Asn Phe Pro Glu Pro Pro Gln Asp Gln Glu Ser
            275                 280                 285

Ser Pro Ile Glu Asn Asp Ser Ser Pro
    290                 295

<210> SEQ ID NO 9
<211> LENGTH: 321
<212> TYPE: PRT
<213> ORGANISM: Homo sapiens

<400> SEQUENCE: 9

Met Glu Glu Gly Gln Tyr Ser Glu Ile Glu Glu Leu Pro Arg Arg Arg
1               5                   10                  15

Cys Cys Arg Arg Gly Thr Gln Ile Val Leu Leu Gly Leu Val Thr Ala
            20                  25                  30

Ala Leu Trp Ala Gly Leu Leu Thr Leu Leu Leu Trp His Trp Asp
            35                  40                  45

Thr Thr Gln Ser Leu Lys Gln Leu Glu Glu Arg Ala Ala Arg Asn Val
    50                  55                  60
```

```
Ser Gln Val Ser Lys Asn Leu Glu Ser His His Gly Asp Gln Met Ala
65                  70                  75                  80

Gln Lys Ser Gln Ser Thr Gln Ile Ser Gln Glu Leu Glu Glu Leu Arg
                85                  90                  95

Ala Glu Gln Gln Arg Leu Lys Ser Gln Asp Leu Glu Leu Ser Trp Asn
                100                 105                 110

Leu Asn Gly Leu Gln Ala Asp Leu Ser Ser Phe Lys Ser Gln Glu Leu
                115                 120                 125

Asn Glu Arg Asn Glu Ala Ser Asp Leu Leu Glu Arg Leu Arg Glu Glu
                130                 135                 140

Val Thr Lys Leu Arg Met Glu Leu Gln Val Ser Ser Gly Phe Val Cys
145                 150                 155                 160

Asn Thr Cys Pro Glu Lys Trp Ile Asn Phe Gln Arg Lys Cys Tyr Tyr
                165                 170                 175

Phe Gly Lys Gly Thr Lys Gln Trp Val His Ala Arg Tyr Ala Cys Asp
                180                 185                 190

Asp Met Glu Gly Gln Leu Val Ser Ile His Ser Pro Glu Glu Gln Asp
                195                 200                 205

Phe Leu Thr Lys His Ala Ser His Thr Gly Ser Trp Ile Gly Leu Arg
                210                 215                 220

Asn Leu Asp Leu Lys Gly Glu Phe Ile Trp Val Asp Gly Ser His Val
225                 230                 235                 240

Asp Tyr Ser Asn Trp Ala Pro Gly Glu Pro Thr Ser Arg Ser Gln Gly
                245                 250                 255

Glu Asp Cys Val Met Met Arg Gly Ser Gly Arg Trp Asn Asp Ala Phe
                260                 265                 270

Cys Asp Arg Lys Leu Gly Ala Trp Val Cys Asp Arg Leu Ala Thr Cys
                275                 280                 285

Thr Pro Pro Ala Ser Glu Gly Ser Ala Glu Ser Met Gly Pro Asp Ser
                290                 295                 300

Arg Pro Asp Pro Asp Gly Arg Leu Pro Thr Pro Ser Ala Pro Leu His
305                 310                 315                 320

Ser
```

```
<210> SEQ ID NO 10
<211> LENGTH: 385
<212> TYPE: PRT
<213> ORGANISM: Homo sapiens

<400> SEQUENCE: 10
```

```
Met Leu Val Arg Arg Gly Ala Arg Ala Gly Pro Arg Met Pro Arg Gly
1                   5                   10                  15

Trp Thr Ala Leu Cys Leu Leu Ser Leu Leu Pro Ser Gly Phe Met Ser
                20                  25                  30

Leu Asp Asn Asn Gly Thr Ala Thr Pro Glu Leu Pro Thr Gln Gly Thr
                35                  40                  45

Phe Ser Asn Val Ser Thr Asn Val Ser Tyr Gln Glu Thr Thr Thr Pro
                50                  55                  60

Ser Thr Leu Gly Ser Thr Ser Leu His Pro Val Ser Gln His Gly Asn
65                  70                  75                  80

Glu Ala Thr Thr Asn Ile Thr Glu Thr Thr Val Lys Phe Thr Ser Thr
                85                  90                  95

Ser Val Ile Thr Ser Val Tyr Gly Asn Thr Asn Ser Ser Val Gln Ser
                100                 105                 110
```

```
Gln Thr Ser Val Ile Ser Thr Val Phe Thr Thr Pro Ala Asn Val Ser
        115                 120                 125

Thr Pro Glu Thr Thr Leu Lys Pro Ser Leu Ser Pro Gly Asn Val Ser
    130                 135                 140

Asp Leu Ser Thr Thr Ser Thr Ser Leu Ala Thr Ser Pro Thr Lys Pro
145                 150                 155                 160

Tyr Thr Ser Ser Ser Pro Ile Leu Ser Asp Ile Lys Ala Glu Ile Lys
                165                 170                 175

Cys Ser Gly Ile Arg Glu Val Lys Leu Thr Gln Gly Ile Cys Leu Glu
            180                 185                 190

Gln Asn Lys Thr Ser Ser Cys Ala Glu Phe Lys Lys Asp Arg Gly Glu
            195                 200                 205

Gly Leu Ala Arg Val Leu Cys Gly Glu Glu Gln Ala Asp Ala Asp Ala
    210                 215                 220

Gly Ala Gln Val Cys Ser Leu Leu Leu Ala Gln Ser Glu Val Arg Pro
225                 230                 235                 240

Gln Cys Leu Leu Leu Val Leu Ala Asn Arg Thr Glu Ile Ser Ser Lys
                245                 250                 255

Leu Gln Leu Met Lys Lys His Gln Ser Asp Leu Lys Lys Leu Gly Ile
            260                 265                 270

Leu Asp Phe Thr Glu Gln Asp Val Ala Ser His Gln Ser Tyr Ser Gln
            275                 280                 285

Lys Thr Leu Ile Ala Leu Val Thr Ser Gly Ala Leu Leu Ala Val Leu
            290                 295                 300

Gly Ile Thr Gly Tyr Phe Leu Met Asn Arg Arg Ser Trp Ser Pro Thr
305                 310                 315                 320

Gly Glu Arg Leu Gly Glu Asp Pro Tyr Tyr Thr Glu Asn Gly Gly Gly
                325                 330                 335

Gln Gly Tyr Ser Ser Gly Pro Gly Thr Ser Pro Glu Ala Gln Gly Lys
                340                 345                 350

Ala Ser Val Asn Arg Gly Ala Gln Glu Asn Gly Thr Gly Gln Ala Thr
            355                 360                 365

Ser Arg Asn Gly His Ser Ala Arg Gln His Val Val Ala Asp Thr Glu
    370                 375                 380

Leu
385

<210> SEQ ID NO 11
<211> LENGTH: 300
<212> TYPE: PRT
<213> ORGANISM: Homo sapiens

<400> SEQUENCE: 11

Met Ala Asn Cys Glu Phe Ser Pro Val Ser Gly Asp Lys Pro Cys Cys
1               5                   10                  15

Arg Leu Ser Arg Arg Ala Gln Leu Cys Leu Gly Val Ser Ile Leu Val
            20                  25                  30

Leu Ile Leu Val Val Val Leu Ala Val Val Val Pro Arg Trp Arg Gln
        35                  40                  45

Gln Trp Ser Gly Pro Gly Thr Thr Lys Arg Phe Pro Glu Thr Val Leu
    50                  55                  60

Ala Arg Cys Val Lys Tyr Thr Glu Ile His Pro Glu Met Arg His Val
65                  70                  75                  80

Asp Cys Gln Ser Val Trp Asp Ala Phe Lys Gly Ala Phe Ile Ser Lys
                85                  90                  95
```

-continued

```
His Pro Cys Asn Ile Thr Glu Glu Asp Tyr Gln Pro Leu Met Lys Leu
            100                 105                 110

Gly Thr Gln Thr Val Pro Cys Asn Lys Ile Leu Leu Trp Ser Arg Ile
            115                 120                 125

Lys Asp Leu Ala His Gln Phe Thr Gln Val Gln Arg Asp Met Phe Thr
            130                 135                 140

Leu Glu Asp Thr Leu Leu Gly Tyr Leu Ala Asp Asp Leu Thr Trp Cys
145                 150                 155                 160

Gly Glu Phe Asn Thr Ser Lys Ile Asn Tyr Gln Ser Cys Pro Asp Trp
                165                 170                 175

Arg Lys Asp Cys Ser Asn Asn Pro Val Ser Val Phe Trp Lys Thr Val
            180                 185                 190

Ser Arg Arg Phe Ala Glu Ala Ala Cys Asp Val Val His Val Met Leu
            195                 200                 205

Asn Gly Ser Arg Ser Lys Ile Phe Asp Lys Asn Ser Thr Phe Gly Ser
            210                 215                 220

Val Glu Val His Asn Leu Gln Pro Glu Lys Val Gln Thr Leu Glu Ala
225                 230                 235                 240

Trp Val Ile His Gly Gly Arg Glu Asp Ser Arg Asp Leu Cys Gln Asp
                245                 250                 255

Pro Thr Ile Lys Glu Leu Glu Ser Ile Ile Ser Lys Arg Asn Ile Gln
            260                 265                 270

Phe Ser Cys Lys Asn Ile Tyr Arg Pro Asp Lys Phe Leu Gln Cys Val
            275                 280                 285

Lys Asn Pro Glu Asp Ser Ser Cys Thr Ser Glu Ile
            290                 295                 300
```

```
<210> SEQ ID NO 12
<211> LENGTH: 1306
<212> TYPE: PRT
<213> ORGANISM: Homo sapiens

<400> SEQUENCE: 12
```

```
Met Thr Met Tyr Leu Trp Leu Lys Leu Leu Ala Phe Gly Phe Ala Phe
1               5                   10                  15

Leu Asp Thr Glu Val Phe Val Thr Gly Gln Ser Pro Thr Pro Ser Pro
            20                  25                  30

Thr Gly Leu Thr Thr Ala Lys Met Pro Ser Val Pro Leu Ser Ser Asp
            35                  40                  45

Pro Leu Pro Thr His Thr Thr Ala Phe Ser Pro Ala Ser Thr Phe Glu
    50                  55                  60

Arg Glu Asn Asp Phe Ser Glu Thr Thr Thr Ser Leu Ser Pro Asp Asn
65                  70                  75                  80

Thr Ser Thr Gln Val Ser Pro Asp Ser Leu Asp Asn Ala Ser Ala Phe
                85                  90                  95

Asn Thr Thr Gly Val Ser Ser Val Gln Thr Pro His Leu Pro Thr His
            100                 105                 110

Ala Asp Ser Gln Thr Pro Ser Ala Gly Thr Asp Thr Gln Thr Phe Ser
            115                 120                 125

Gly Ser Ala Ala Asn Ala Lys Leu Asn Pro Thr Pro Gly Ser Asn Ala
            130                 135                 140

Ile Ser Asp Val Pro Gly Glu Arg Ser Thr Ala Ser Thr Phe Pro Thr
145                 150                 155                 160

Asp Pro Val Ser Pro Leu Thr Thr Thr Leu Ser Leu Ala His His Ser
```

```
                    165                 170                 175
Ser Ala Ala Leu Pro Ala Arg Thr Ser Asn Thr Thr Ile Thr Ala Asn
                180                 185                 190

Thr Ser Asp Ala Tyr Leu Asn Ala Ser Glu Thr Thr Thr Leu Ser Pro
            195                 200                 205

Ser Gly Ser Ala Val Ile Ser Thr Thr Thr Ile Ala Thr Thr Pro Ser
        210                 215                 220

Lys Pro Thr Cys Asp Glu Lys Tyr Ala Asn Ile Thr Val Asp Tyr Leu
225                 230                 235                 240

Tyr Asn Lys Glu Thr Lys Leu Phe Thr Ala Lys Leu Asn Val Asn Glu
                245                 250                 255

Asn Val Glu Cys Gly Asn Asn Thr Cys Thr Asn Asn Glu Val His Asn
                260                 265                 270

Leu Thr Glu Cys Lys Asn Ala Ser Val Ser Ile Ser His Asn Ser Cys
            275                 280                 285

Thr Ala Pro Asp Lys Thr Leu Ile Leu Asp Val Pro Pro Gly Val Glu
        290                 295                 300

Lys Phe Gln Leu His Asp Cys Thr Gln Val Glu Lys Ala Asp Thr Thr
305                 310                 315                 320

Ile Cys Leu Lys Trp Lys Asn Ile Glu Thr Phe Thr Cys Asp Thr Gln
                325                 330                 335

Asn Ile Thr Tyr Arg Phe Gln Cys Gly Asn Met Ile Phe Asp Asn Lys
            340                 345                 350

Glu Ile Lys Leu Glu Asn Leu Glu Pro Glu His Glu Tyr Lys Cys Asp
            355                 360                 365

Ser Glu Ile Leu Tyr Asn Asn His Lys Phe Thr Asn Ala Ser Lys Ile
        370                 375                 380

Ile Lys Thr Asp Phe Gly Ser Pro Gly Glu Pro Gln Ile Ile Phe Cys
385                 390                 395                 400

Arg Ser Glu Ala Ala His Gln Gly Val Ile Thr Trp Asn Pro Pro Gln
            405                 410                 415

Arg Ser Phe His Asn Phe Thr Leu Cys Tyr Ile Lys Glu Thr Glu Lys
            420                 425                 430

Asp Cys Leu Asn Leu Asp Lys Asn Leu Ile Lys Tyr Asp Leu Gln Asn
            435                 440                 445

Leu Lys Pro Tyr Thr Lys Tyr Val Leu Ser Leu His Ala Tyr Ile Ile
        450                 455                 460

Ala Lys Val Gln Arg Asn Gly Ser Ala Ala Met Cys His Phe Thr Thr
465                 470                 475                 480

Lys Ser Ala Pro Pro Ser Gln Val Trp Asn Met Thr Val Ser Met Thr
            485                 490                 495

Ser Asp Asn Ser Met His Val Lys Cys Arg Pro Pro Arg Asp Arg Asn
            500                 505                 510

Gly Pro His Glu Arg Tyr His Leu Glu Val Glu Ala Gly Asn Thr Leu
            515                 520                 525

Val Arg Asn Glu Ser His Lys Asn Cys Asp Phe Arg Val Lys Asp Leu
        530                 535                 540

Gln Tyr Ser Thr Asp Tyr Thr Phe Lys Ala Tyr Phe His Asn Gly Asp
545                 550                 555                 560

Tyr Pro Gly Glu Pro Phe Ile Leu His His Ser Thr Ser Tyr Asn Ser
            565                 570                 575

Lys Ala Leu Ile Ala Phe Leu Ala Phe Leu Ile Ile Val Thr Ser Ile
            580                 585                 590
```

Ala Leu Leu Val Val Leu Tyr Lys Ile Tyr Asp Leu His Lys Lys Arg
        595                 600                 605

Ser Cys Asn Leu Asp Glu Gln Gln Glu Leu Val Glu Arg Asp Asp Glu
        610                 615                 620

Lys Gln Leu Met Asn Val Glu Pro Ile His Ala Asp Ile Leu Leu Glu
625                 630                 635                 640

Thr Tyr Lys Arg Lys Ile Ala Asp Glu Gly Arg Leu Phe Leu Ala Glu
                645                 650                 655

Phe Gln Ser Ile Pro Arg Val Phe Ser Lys Phe Pro Ile Lys Glu Ala
                660                 665                 670

Arg Lys Pro Phe Asn Gln Asn Lys Asn Arg Tyr Val Asp Ile Leu Pro
        675                 680                 685

Tyr Asp Tyr Asn Arg Val Glu Leu Ser Glu Ile Asn Gly Asp Ala Gly
        690                 695                 700

Ser Asn Tyr Ile Asn Ala Ser Tyr Ile Asp Gly Phe Lys Glu Pro Arg
705                 710                 715                 720

Lys Tyr Ile Ala Ala Gln Gly Pro Arg Asp Glu Thr Val Asp Asp Phe
                725                 730                 735

Trp Arg Met Ile Trp Glu Gln Lys Ala Thr Val Ile Val Met Val Thr
                740                 745                 750

Arg Cys Glu Glu Gly Asn Arg Asn Lys Cys Ala Glu Tyr Trp Pro Ser
        755                 760                 765

Met Glu Glu Gly Thr Arg Ala Phe Gly Asp Val Val Val Lys Ile Asn
        770                 775                 780

Gln His Lys Arg Cys Pro Asp Tyr Ile Ile Gln Lys Leu Asn Ile Val
785                 790                 795                 800

Asn Lys Lys Glu Lys Ala Thr Gly Arg Glu Val Thr His Ile Gln Phe
                805                 810                 815

Thr Ser Trp Pro Asp His Gly Val Pro Glu Asp Pro His Leu Leu Leu
                820                 825                 830

Lys Leu Arg Arg Arg Val Asn Ala Phe Ser Asn Phe Phe Ser Gly Pro
        835                 840                 845

Ile Val Val His Cys Ser Ala Gly Val Gly Arg Thr Gly Thr Tyr Ile
        850                 855                 860

Gly Ile Asp Ala Met Leu Glu Gly Leu Glu Ala Glu Asn Lys Val Asp
865                 870                 875                 880

Val Tyr Gly Tyr Val Val Lys Leu Arg Arg Gln Arg Cys Leu Met Val
                885                 890                 895

Gln Val Glu Ala Gln Tyr Ile Leu Ile His Gln Ala Leu Val Glu Tyr
                900                 905                 910

Asn Gln Phe Gly Glu Thr Glu Val Asn Leu Ser Glu Leu His Pro Tyr
        915                 920                 925

Leu His Asn Met Lys Lys Arg Asp Pro Pro Ser Glu Pro Ser Pro Leu
        930                 935                 940

Glu Ala Glu Phe Gln Arg Leu Pro Ser Tyr Arg Ser Trp Arg Thr Gln
945                 950                 955                 960

His Ile Gly Asn Gln Glu Glu Asn Lys Ser Lys Asn Arg Asn Ser Asn
                965                 970                 975

Val Ile Pro Tyr Asp Tyr Asn Arg Val Pro Leu Lys His Glu Leu Glu
                980                 985                 990

Met Ser Lys Glu Ser Glu His Asp  Ser Asp Glu Ser Ser  Asp Asp Asp
        995                 1000                1005

```
Ser Asp  Ser Glu Glu Pro Ser  Lys Tyr Ile Asn Ala  Ser Phe Ile
    1010             1015             1020

Met Ser  Tyr Trp Lys Pro Glu  Val Met Ile Ala Ala  Gln Gly Pro
    1025             1030             1035

Leu Lys  Glu Thr Ile Gly Asp  Phe Trp Gln Met Ile  Phe Gln Arg
    1040             1045             1050

Lys Val  Lys Val Ile Val Met  Leu Thr Glu Leu Lys  His Gly Asp
    1055             1060             1065

Gln Glu  Ile Cys Ala Gln Tyr  Trp Gly Glu Gly Lys  Gln Thr Tyr
    1070             1075             1080

Gly Asp  Ile Glu Val Asp Leu  Lys Asp Thr Asp Lys  Ser Ser Thr
    1085             1090             1095

Tyr Thr  Leu Arg Val Phe Glu  Leu Arg His Ser Lys  Arg Lys Asp
    1100             1105             1110

Ser Arg  Thr Val Tyr Gln Tyr  Gln Tyr Thr Asn Trp  Ser Val Glu
    1115             1120             1125

Gln Leu  Pro Ala Glu Pro Lys  Glu Leu Ile Ser Met  Ile Gln Val
    1130             1135             1140

Val Lys  Gln Lys Leu Pro Gln  Lys Asn Ser Ser Glu  Gly Asn Lys
    1145             1150             1155

His His  Lys Ser Thr Pro Leu  Leu Ile His Cys Arg  Asp Gly Ser
    1160             1165             1170

Gln Gln  Thr Gly Ile Phe Cys  Ala Leu Leu Asn Leu  Leu Glu Ser
    1175             1180             1185

Ala Glu  Thr Glu Glu Val Val  Asp Ile Phe Gln Val  Val Lys Ala
    1190             1195             1200

Leu Arg  Lys Ala Arg Pro Gly  Met Val Ser Thr Phe  Glu Gln Tyr
    1205             1210             1215

Gln Phe  Leu Tyr Asp Val Ile  Ala Ser Thr Tyr Pro  Ala Gln Asn
    1220             1225             1230

Gly Gln  Val Lys Lys Asn Asn  His Gln Glu Asp Lys  Ile Glu Phe
    1235             1240             1245

Asp Asn  Glu Val Asp Lys Val  Lys Gln Asp Ala Asn  Cys Val Asn
    1250             1255             1260

Pro Leu  Gly Ala Pro Glu Lys  Leu Pro Glu Ala Lys  Glu Gln Ala
    1265             1270             1275

Glu Gly  Ser Glu Pro Thr Ser  Gly Thr Glu Gly Pro  Glu His Ser
    1280             1285             1290

Val Asn  Gly Pro Ala Ser Pro  Ala Leu Asn Gln Gly  Ser
    1295             1300             1305
```

<210> SEQ ID NO 13
<211> LENGTH: 354
<212> TYPE: PRT
<213> ORGANISM: Homo sapiens

<400> SEQUENCE: 13

```
Met Arg Leu Ala Val Leu Phe Ser Gly Ala Leu Leu Gly Leu Leu Ala
1               5                  10                  15

Ala Gln Gly Thr Gly Asn Asp Cys Pro His Lys Lys Ser Ala Thr Leu
            20                  25                  30

Leu Pro Ser Phe Thr Val Thr Pro Thr Val Thr Glu Ser Thr Gly Thr
        35                  40                  45

Thr Ser His Arg Thr Thr Lys Ser His Lys Thr Thr Thr His Arg Thr
    50                  55                  60
```

-continued

```
Thr Thr Thr Gly Thr Thr Ser His Gly Pro Thr Thr Ala Thr His Asn
65                  70                  75                  80

Pro Thr Thr Thr Ser His Gly Asn Val Thr Val His Pro Thr Ser Asn
                85                  90                  95

Ser Thr Ala Thr Ser Gln Gly Pro Ser Thr Ala Thr His Ser Pro Ala
            100                 105                 110

Thr Thr Ser His Gly Asn Ala Thr Val His Pro Thr Ser Asn Ser Thr
            115                 120                 125

Ala Thr Ser Pro Gly Phe Thr Ser Ser Ala His Pro Glu Pro Pro
        130                 135                 140

Pro Ser Pro Ser Pro Ser Pro Thr Ser Lys Glu Thr Ile Gly Asp Tyr
145                 150                 155                 160

Thr Trp Thr Asn Gly Ser Gln Pro Cys Val His Leu Gln Ala Gln Ile
                165                 170                 175

Gln Ile Arg Val Met Tyr Thr Thr Gln Gly Gly Gly Glu Ala Trp Gly
            180                 185                 190

Ile Ser Val Leu Asn Pro Asn Lys Thr Lys Val Gln Gly Ser Cys Glu
            195                 200                 205

Gly Ala His Pro His Leu Leu Leu Ser Phe Pro Tyr Gly His Leu Ser
        210                 215                 220

Phe Gly Phe Met Gln Asp Leu Gln Gln Lys Val Val Tyr Leu Ser Tyr
225                 230                 235                 240

Met Ala Val Glu Tyr Asn Val Ser Phe Pro His Ala Ala Gln Trp Thr
                245                 250                 255

Phe Ser Ala Gln Asn Ala Ser Leu Arg Asp Leu Gln Ala Pro Leu Gly
            260                 265                 270

Gln Ser Phe Ser Cys Ser Asn Ser Ser Ile Ile Leu Ser Pro Ala Val
        275                 280                 285

His Leu Asp Leu Leu Ser Leu Arg Leu Gln Ala Ala Gln Leu Pro His
        290                 295                 300

Thr Gly Val Phe Gly Gln Ser Phe Ser Cys Pro Ser Asp Arg Ser Ile
305                 310                 315                 320

Leu Leu Pro Leu Ile Ile Gly Leu Ile Leu Leu Gly Leu Leu Ala Leu
                325                 330                 335

Val Leu Ile Ala Phe Cys Ile Ile Arg Arg Arg Pro Ser Ala Tyr Gln
            340                 345                 350

Ala Leu
```

```
<210> SEQ ID NO 14
<211> LENGTH: 295
<212> TYPE: PRT
<213> ORGANISM: Homo sapiens

<400> SEQUENCE: 14
```

```
Met Glu His Gln Leu Leu Cys Cys Glu Val Glu Thr Ile Arg Arg Ala
1               5                   10                  15

Tyr Pro Asp Ala Asn Leu Leu Asn Asp Arg Val Leu Arg Ala Met Leu
            20                  25                  30

Lys Ala Glu Glu Thr Cys Ala Pro Ser Val Ser Tyr Phe Lys Cys Val
        35                  40                  45

Gln Lys Glu Val Leu Pro Ser Met Arg Lys Ile Val Ala Thr Trp Met
        50                  55                  60

Leu Glu Val Cys Glu Glu Gln Lys Cys Glu Glu Glu Val Phe Pro Leu
65                  70                  75                  80
```

-continued

```
Ala Met Asn Tyr Leu Asp Arg Phe Leu Ser Leu Glu Pro Val Lys Lys
                85                  90                  95

Ser Arg Leu Gln Leu Leu Gly Ala Thr Cys Met Phe Val Ala Ser Lys
            100                 105                 110

Met Lys Glu Thr Ile Pro Leu Thr Ala Glu Lys Leu Cys Ile Tyr Thr
            115                 120                 125

Asp Asn Ser Ile Arg Pro Glu Glu Leu Leu Gln Met Glu Leu Leu Leu
        130                 135                 140

Val Asn Lys Leu Lys Trp Asn Leu Ala Ala Met Thr Pro His Asp Phe
145                 150                 155                 160

Ile Glu His Phe Leu Ser Lys Met Pro Glu Ala Glu Glu Asn Lys Gln
                165                 170                 175

Ile Ile Arg Lys His Ala Gln Thr Phe Val Ala Leu Cys Ala Thr Asp
            180                 185                 190

Val Lys Phe Ile Ser Asn Pro Pro Ser Met Val Ala Ala Gly Ser Val
            195                 200                 205

Val Ala Ala Val Gln Gly Leu Asn Leu Arg Ser Pro Asn Asn Phe Leu
        210                 215                 220

Ser Tyr Tyr Arg Leu Thr Arg Phe Leu Ser Arg Val Ile Lys Cys Asp
225                 230                 235                 240

Pro Asp Cys Leu Arg Ala Cys Gln Glu Gln Ile Glu Ala Leu Leu Glu
                245                 250                 255

Ser Ser Leu Arg Gln Ala Gln Gln Asn Met Asp Pro Lys Ala Ala Glu
            260                 265                 270

Glu Glu Glu Glu Glu Glu Glu Glu Val Asp Leu Ala Cys Thr Pro Thr
            275                 280                 285

Asp Val Arg Asp Val Asp Ile
    290                 295
```

<210> SEQ ID NO 15
<211> LENGTH: 745
<212> TYPE: PRT
<213> ORGANISM: Homo sapiens

<400> SEQUENCE: 15

```
Met Gly Val Pro Phe Phe Ser Ser Leu Arg Cys Met Val Asp Leu Gly
1               5                   10                  15

Pro Cys Trp Ala Gly Gly Leu Thr Ala Glu Met Lys Leu Leu Leu Ala
            20                  25                  30

Leu Ala Gly Leu Leu Ala Ile Leu Ala Thr Pro Gln Pro Ser Glu Gly
        35                  40                  45

Ala Ala Pro Ala Val Leu Gly Glu Val Asp Thr Ser Leu Val Leu Ser
    50                  55                  60

Ser Met Glu Glu Ala Lys Gln Leu Val Asp Lys Ala Tyr Lys Glu Arg
65                  70                  75                  80

Arg Glu Ser Ile Lys Gln Arg Leu Arg Ser Gly Ser Ala Ser Pro Met
                85                  90                  95

Glu Leu Leu Ser Tyr Phe Lys Gln Pro Val Ala Ala Thr Arg Thr Ala
            100                 105                 110

Val Arg Ala Ala Asp Tyr Leu His Val Ala Leu Asp Leu Leu Glu Arg
            115                 120                 125

Lys Leu Arg Ser Leu Trp Arg Arg Pro Phe Asn Val Thr Asp Val Leu
        130                 135                 140

Thr Pro Ala Gln Leu Asn Val Leu Ser Lys Ser Ser Gly Cys Ala Tyr
```

```
145              150              155              160

Gln Asp Val Gly Val Thr Cys Pro Glu Gln Asp Lys Tyr Arg Thr Ile
            165              170              175

Thr Gly Met Cys Asn Asn Arg Arg Ser Pro Thr Leu Gly Ala Ser Asn
            180              185              190

Arg Ala Phe Val Arg Trp Leu Pro Ala Glu Tyr Glu Asp Gly Phe Ser
        195              200              205

Leu Pro Tyr Gly Trp Thr Pro Gly Val Lys Arg Asn Gly Phe Pro Val
    210              215              220

Ala Leu Ala Arg Ala Val Ser Asn Glu Ile Val Arg Phe Pro Thr Asp
225              230              235              240

Gln Leu Thr Pro Asp Gln Glu Arg Ser Leu Met Phe Met Gln Trp Gly
            245              250              255

Gln Leu Leu Asp His Asp Leu Asp Phe Thr Pro Glu Pro Ala Ala Arg
        260              265              270

Ala Ser Phe Val Thr Gly Val Asn Cys Glu Thr Ser Cys Val Gln Gln
        275              280              285

Pro Pro Cys Phe Pro Leu Lys Ile Pro Pro Asn Asp Pro Arg Ile Lys
    290              295              300

Asn Gln Ala Asp Cys Ile Pro Phe Phe Arg Ser Cys Pro Ala Cys Pro
305              310              315              320

Gly Ser Asn Ile Thr Ile Arg Asn Gln Ile Asn Ala Leu Thr Ser Phe
            325              330              335

Val Asp Ala Ser Met Val Tyr Gly Ser Glu Glu Pro Leu Ala Arg Asn
            340              345              350

Leu Arg Asn Met Ser Asn Gln Leu Gly Leu Leu Ala Val Asn Gln Arg
        355              360              365

Phe Gln Asp Asn Gly Arg Ala Leu Leu Pro Phe Asp Asn Leu His Asp
    370              375              380

Asp Pro Cys Leu Leu Thr Asn Arg Ser Ala Arg Ile Pro Cys Phe Leu
385              390              395              400

Ala Gly Asp Thr Arg Ser Ser Glu Met Pro Glu Leu Thr Ser Met His
            405              410              415

Thr Leu Leu Leu Arg Glu His Asn Arg Leu Ala Thr Glu Leu Lys Ser
            420              425              430

Leu Asn Pro Arg Trp Asp Gly Glu Arg Leu Tyr Gln Glu Ala Arg Lys
        435              440              445

Ile Val Gly Ala Met Val Gln Ile Ile Thr Tyr Arg Asp Tyr Leu Pro
    450              455              460

Leu Val Leu Gly Pro Thr Ala Met Arg Lys Tyr Leu Pro Thr Tyr Arg
465              470              475              480

Ser Tyr Asn Asp Ser Val Asp Pro Arg Ile Ala Asn Val Phe Thr Asn
            485              490              495

Ala Phe Arg Tyr Gly His Thr Leu Ile Gln Pro Phe Met Phe Arg Leu
        500              505              510

Asp Asn Arg Tyr Gln Pro Met Glu Pro Asn Pro Arg Val Pro Leu Ser
        515              520              525

Arg Val Phe Phe Ala Ser Trp Arg Val Val Leu Glu Gly Gly Ile Asp
    530              535              540

Pro Ile Leu Arg Gly Leu Met Ala Thr Pro Ala Lys Leu Asn Arg Gln
545              550              555              560

Asn Gln Ile Ala Val Asp Glu Ile Arg Glu Arg Leu Phe Glu Gln Val
            565              570              575
```

```
Met Arg Ile Gly Leu Asp Leu Pro Ala Leu Asn Met Gln Arg Ser Arg
            580                 585                 590

Asp His Gly Leu Pro Gly Tyr Asn Ala Trp Arg Arg Phe Cys Gly Leu
            595                 600                 605

Pro Gln Pro Glu Thr Val Gly Gln Leu Gly Thr Val Leu Arg Asn Leu
            610                 615                 620

Lys Leu Ala Arg Lys Leu Met Glu Gln Tyr Gly Thr Pro Asn Asn Ile
625                 630                 635                 640

Asp Ile Trp Met Gly Gly Val Ser Glu Pro Leu Lys Arg Lys Gly Arg
                645                 650                 655

Val Gly Pro Leu Leu Ala Cys Ile Ile Gly Thr Gln Phe Arg Lys Leu
            660                 665                 670

Arg Asp Gly Asp Arg Phe Trp Trp Glu Asn Glu Gly Val Phe Ser Met
            675                 680                 685

Gln Gln Arg Gln Ala Leu Ala Gln Ile Ser Leu Pro Arg Ile Ile Cys
            690                 695                 700

Asp Asn Thr Gly Ile Thr Thr Val Ser Lys Asn Asn Ile Phe Met Ser
705                 710                 715                 720

Asn Ser Tyr Pro Arg Asp Phe Val Asn Cys Ser Thr Leu Pro Ala Leu
                725                 730                 735

Asn Leu Ala Ser Trp Arg Glu Ala Ser
            740                 745

<210> SEQ ID NO 16
<211> LENGTH: 391
<212> TYPE: PRT
<213> ORGANISM: Homo sapiens

<400> SEQUENCE: 16

Met Asp Leu Glu Lys Asn Tyr Pro Thr Pro Arg Thr Ser Arg Thr Gly
1                   5                   10                  15

His Gly Gly Val Asn Gln Leu Gly Gly Val Phe Val Asn Gly Arg Pro
                20                  25                  30

Leu Pro Asp Val Val Arg Gln Arg Ile Val Glu Leu Ala His Gln Gly
            35                  40                  45

Val Arg Pro Cys Asp Ile Ser Arg Gln Leu Arg Val Ser His Gly Cys
        50                  55                  60

Val Ser Lys Ile Leu Gly Arg Tyr Tyr Glu Thr Gly Ser Ile Lys Pro
65                  70                  75                  80

Gly Val Ile Gly Gly Ser Lys Pro Lys Val Ala Thr Pro Lys Val Val
                85                  90                  95

Glu Lys Ile Ala Glu Tyr Lys Arg Gln Asn Pro Thr Met Phe Ala Trp
            100                 105                 110

Glu Ile Arg Asp Arg Leu Leu Ala Glu Arg Val Cys Asp Asn Asp Thr
            115                 120                 125

Val Pro Ser Val Ser Ser Ile Asn Arg Ile Ile Arg Thr Lys Val Gln
        130                 135                 140

Gln Pro Pro Asn Gln Pro Val Pro Ala Ser Ser His Ser Ile Val Ser
145                 150                 155                 160

Thr Gly Ser Val Thr Gln Val Ser Ser Val Ser Thr Asp Ser Ala Gly
                165                 170                 175

Ser Ser Tyr Ser Ile Ser Gly Ile Leu Gly Ile Thr Ser Pro Ser Ala
            180                 185                 190

Asp Thr Asn Lys Arg Lys Arg Asp Glu Gly Ile Gln Glu Ser Pro Val
```

```
            195                 200                 205

Pro Asn Gly His Ser Leu Pro Gly Arg Asp Phe Leu Arg Lys Gln Met
    210                 215                 220

Arg Gly Asp Leu Phe Thr Gln Gln Gln Leu Glu Val Leu Asp Arg Val
225                 230                 235                 240

Phe Glu Arg Gln His Tyr Ser Asp Ile Phe Thr Thr Thr Glu Pro Ile
                245                 250                 255

Lys Pro Glu Gln Thr Thr Glu Tyr Ser Ala Met Ala Ser Leu Ala Gly
                260                 265                 270

Gly Leu Asp Asp Met Lys Ala Asn Leu Ala Ser Pro Thr Pro Ala Asp
                275                 280                 285

Ile Gly Ser Ser Val Pro Gly Pro Gln Ser Tyr Pro Ile Val Thr Gly
    290                 295                 300

Arg Asp Leu Ala Ser Thr Thr Leu Pro Gly Tyr Pro Pro His Val Pro
305                 310                 315                 320

Pro Ala Gly Gln Gly Ser Tyr Ser Ala Pro Thr Leu Thr Gly Met Val
                325                 330                 335

Pro Gly Ser Glu Phe Ser Gly Ser Pro Tyr Ser His Pro Gln Tyr Ser
                340                 345                 350

Ser Tyr Asn Asp Ser Trp Arg Phe Pro Asn Pro Gly Leu Leu Gly Ser
                355                 360                 365

Pro Tyr Tyr Tyr Ser Ala Ala Ala Arg Gly Ala Ala Pro Pro Ala Ala
    370                 375                 380

Ala Thr Ala Tyr Asp Arg His
385                 390
```

```
<210> SEQ ID NO 17
<211> LENGTH: 509
<212> TYPE: PRT
<213> ORGANISM: Homo sapiens

<400> SEQUENCE: 17

Met Asp Pro Pro Arg Ala Ser His Leu Ser Pro Arg Lys Lys Arg Pro
1               5                   10                  15

Arg Gln Thr Gly Ala Leu Met Ala Ser Ser Pro Gln Asp Ile Lys Phe
            20                  25                  30

Gln Asp Leu Val Val Phe Ile Leu Glu Lys Lys Met Gly Thr Thr Arg
        35                  40                  45

Arg Ala Phe Leu Met Glu Leu Ala Arg Arg Lys Gly Phe Arg Val Glu
    50                  55                  60

Asn Glu Leu Ser Asp Ser Val Thr His Ile Val Ala Glu Asn Asn Ser
65                  70                  75                  80

Gly Ser Asp Val Leu Glu Trp Leu Gln Ala Gln Lys Val Gln Val Ser
                85                  90                  95

Ser Gln Pro Glu Leu Leu Asp Val Ser Trp Leu Ile Glu Cys Ile Arg
                100                 105                 110

Ala Gly Lys Pro Val Glu Met Thr Gly Lys His Gln Leu Val Val Arg
            115                 120                 125

Arg Asp Tyr Ser Asp Ser Thr Asn Pro Gly Pro Pro Lys Thr Pro Pro
    130                 135                 140

Ile Ala Val Gln Lys Ile Ser Gln Tyr Ala Cys Gln Arg Arg Thr Thr
145                 150                 155                 160

Leu Asn Asn Cys Asn Gln Ile Phe Thr Asp Ala Phe Asp Ile Leu Ala
                165                 170                 175
```

Glu Asn Cys Glu Phe Arg Glu Asn Glu Asp Ser Cys Val Thr Phe Met
                180                     185                     190

Arg Ala Ala Ser Val Leu Lys Ser Leu Pro Phe Thr Ile Ile Ser Met
                195                     200                     205

Lys Asp Thr Glu Gly Ile Pro Cys Leu Gly Ser Lys Val Lys Gly Ile
                210                     215                     220

Ile Glu Glu Ile Ile Glu Asp Gly Glu Ser Ser Glu Val Lys Ala Val
225                     230                     235                     240

Leu Asn Asp Glu Arg Tyr Gln Ser Phe Lys Leu Phe Thr Ser Val Phe
                        245                     250                     255

Gly Val Gly Leu Lys Thr Ser Glu Lys Trp Phe Arg Met Gly Phe Arg
                260                     265                     270

Thr Leu Ser Lys Val Arg Ser Asp Lys Ser Leu Lys Phe Thr Arg Met
                275                     280                     285

Gln Lys Ala Gly Phe Leu Tyr Tyr Glu Asp Leu Val Ser Cys Val Thr
                290                     295                     300

Arg Ala Glu Ala Glu Ala Val Ser Val Leu Val Lys Glu Ala Val Trp
305                     310                     315                     320

Ala Phe Leu Pro Asp Ala Phe Val Thr Met Thr Gly Gly Phe Arg Arg
                        325                     330                     335

Gly Lys Lys Met Gly His Asp Val Asp Phe Leu Ile Thr Ser Pro Gly
                340                     345                     350

Ser Thr Glu Asp Glu Glu Gln Leu Leu Gln Lys Val Met Asn Leu Trp
                355                     360                     365

Glu Lys Lys Gly Leu Leu Leu Tyr Tyr Asp Leu Val Glu Ser Thr Phe
                370                     375                     380

Glu Lys Leu Arg Leu Pro Ser Arg Lys Val Asp Ala Leu Asp His Phe
385                     390                     395                     400

Gln Lys Cys Phe Leu Ile Phe Lys Leu Pro Arg Gln Arg Val Asp Ser
                        405                     410                     415

Asp Gln Ser Ser Trp Gln Glu Gly Lys Thr Trp Lys Ala Ile Arg Val
                420                     425                     430

Asp Leu Val Leu Cys Pro Tyr Glu Arg Arg Ala Phe Ala Leu Leu Gly
                435                     440                     445

Trp Thr Gly Ser Arg Gln Phe Glu Arg Asp Leu Arg Arg Tyr Ala Thr
                450                     455                     460

His Glu Arg Lys Met Ile Leu Asp Asn His Ala Leu Tyr Asp Lys Thr
465                     470                     475                     480

Lys Arg Ile Phe Leu Lys Ala Glu Ser Glu Glu Glu Ile Phe Ala His
                        485                     490                     495

Leu Gly Leu Asp Tyr Ile Glu Pro Trp Glu Arg Asn Ala
                500                     505

<210> SEQ ID NO 18
<211> LENGTH: 619
<212> TYPE: PRT
<213> ORGANISM: Homo sapiens

<400> SEQUENCE: 18

Met Pro Asp Pro Ala Ala His Leu Pro Phe Phe Tyr Gly Ser Ile Ser
1                       5                       10                      15

Arg Ala Glu Ala Glu Glu His Leu Lys Leu Ala Gly Met Ala Asp Gly
                20                      25                      30

Leu Phe Leu Leu Arg Gln Cys Leu Arg Ser Leu Gly Gly Tyr Val Leu
                35                      40                      45

-continued

```
Ser Leu Val His Asp Val Arg Phe His His Phe Pro Ile Glu Arg Gln
    50                  55                  60

Leu Asn Gly Thr Tyr Ala Ile Ala Gly Gly Lys Ala His Cys Gly Pro
65                  70                  75                  80

Ala Glu Leu Cys Glu Phe Tyr Ser Arg Asp Pro Asp Gly Leu Pro Cys
                85                  90                  95

Asn Leu Arg Lys Pro Cys Asn Arg Pro Ser Gly Leu Glu Pro Gln Pro
                100                 105                 110

Gly Val Phe Asp Cys Leu Arg Asp Ala Met Val Arg Asp Tyr Val Arg
            115                 120                 125

Gln Thr Trp Lys Leu Glu Gly Glu Ala Leu Glu Gln Ala Ile Ile Ser
    130                 135                 140

Gln Ala Pro Gln Val Glu Lys Leu Ile Ala Thr Thr Ala His Glu Arg
145                 150                 155                 160

Met Pro Trp Tyr His Ser Ser Leu Thr Arg Glu Glu Ala Glu Arg Lys
                165                 170                 175

Leu Tyr Ser Gly Ala Gln Thr Asp Gly Lys Phe Leu Leu Arg Pro Arg
            180                 185                 190

Lys Glu Gln Gly Thr Tyr Ala Leu Ser Leu Ile Tyr Gly Lys Thr Val
            195                 200                 205

Tyr His Tyr Leu Ile Ser Gln Asp Lys Ala Gly Lys Tyr Cys Ile Pro
    210                 215                 220

Glu Gly Thr Lys Phe Asp Thr Leu Trp Gln Leu Val Glu Tyr Leu Lys
225                 230                 235                 240

Leu Lys Ala Asp Gly Leu Ile Tyr Cys Leu Lys Glu Ala Cys Pro Asn
                245                 250                 255

Ser Ser Ala Ser Asn Ala Ser Gly Ala Ala Ala Pro Thr Leu Pro Ala
                260                 265                 270

His Pro Ser Thr Leu Thr His Pro Gln Arg Arg Ile Asp Thr Leu Asn
            275                 280                 285

Ser Asp Gly Tyr Thr Pro Glu Pro Ala Arg Ile Thr Ser Pro Asp Lys
    290                 295                 300

Pro Arg Pro Met Pro Met Asp Thr Ser Val Tyr Glu Ser Pro Tyr Ser
305                 310                 315                 320

Asp Pro Glu Glu Leu Lys Asp Lys Lys Leu Phe Leu Lys Arg Asp Asn
                325                 330                 335

Leu Leu Ile Ala Asp Ile Glu Leu Gly Cys Gly Asn Phe Gly Ser Val
                340                 345                 350

Arg Gln Gly Val Tyr Arg Met Arg Lys Lys Gln Ile Asp Val Ala Ile
            355                 360                 365

Lys Val Leu Lys Gln Gly Thr Glu Lys Ala Asp Thr Glu Glu Met Met
    370                 375                 380

Arg Glu Ala Gln Ile Met His Gln Leu Asp Asn Pro Tyr Ile Val Arg
385                 390                 395                 400

Leu Ile Gly Val Cys Gln Ala Glu Ala Leu Met Leu Val Met Glu Met
                405                 410                 415

Ala Gly Gly Gly Pro Leu His Lys Phe Leu Val Gly Lys Arg Glu Glu
            420                 425                 430

Ile Pro Val Ser Asn Val Ala Glu Leu Leu His Gln Val Ser Met Gly
            435                 440                 445

Met Lys Tyr Leu Glu Glu Lys Asn Phe Val His Arg Asp Leu Ala Ala
    450                 455                 460
```

```
Arg Asn Val Leu Leu Val Asn Arg His Tyr Ala Lys Ile Ser Asp Phe
465             470             475             480

Gly Leu Ser Lys Ala Leu Gly Ala Asp Asp Ser Tyr Tyr Thr Ala Arg
                485             490             495

Ser Ala Gly Lys Trp Pro Leu Lys Trp Tyr Ala Pro Glu Cys Ile Asn
            500             505             510

Phe Arg Lys Phe Ser Ser Arg Ser Asp Val Trp Ser Tyr Gly Val Thr
            515             520             525

Met Trp Glu Ala Leu Ser Tyr Gly Gln Lys Pro Tyr Lys Lys Met Lys
        530             535             540

Gly Pro Glu Val Met Ala Phe Ile Glu Gln Gly Lys Arg Met Glu Cys
545             550             555             560

Pro Pro Glu Cys Pro Pro Glu Leu Tyr Ala Leu Met Ser Asp Cys Trp
                565             570             575

Ile Tyr Lys Trp Glu Asp Arg Pro Asp Phe Leu Thr Val Glu Gln Arg
            580             585             590

Met Arg Ala Cys Tyr Tyr Ser Leu Ala Ser Lys Val Glu Gly Pro Pro
            595             600             605

Gly Ser Thr Gln Lys Ala Glu Ala Ala Cys Ala
        610             615

<210> SEQ ID NO 19
<211> LENGTH: 556
<212> TYPE: PRT
<213> ORGANISM: Homo sapiens

<400> SEQUENCE: 19

Met Pro Pro Pro Arg Leu Leu Phe Phe Leu Leu Phe Leu Thr Pro Met
1               5               10              15

Glu Val Arg Pro Glu Glu Pro Leu Val Val Lys Val Glu Glu Gly Asp
            20              25              30

Asn Ala Val Leu Gln Cys Leu Lys Gly Thr Ser Asp Gly Pro Thr Gln
        35              40              45

Gln Leu Thr Trp Ser Arg Glu Ser Pro Leu Lys Pro Phe Leu Lys Leu
    50              55              60

Ser Leu Gly Leu Pro Gly Leu Gly Ile His Met Arg Pro Leu Ala Ile
65              70              75              80

Trp Leu Phe Ile Phe Asn Val Ser Gln Gln Met Gly Gly Phe Tyr Leu
                85              90              95

Cys Gln Pro Gly Pro Pro Ser Glu Lys Ala Trp Gln Pro Gly Trp Thr
            100             105             110

Val Asn Val Glu Gly Ser Gly Glu Leu Phe Arg Trp Asn Val Ser Asp
            115             120             125

Leu Gly Gly Leu Gly Cys Gly Leu Lys Asn Arg Ser Ser Glu Gly Pro
        130             135             140

Ser Ser Pro Ser Gly Lys Leu Met Ser Pro Lys Leu Tyr Val Trp Ala
145             150             155             160

Lys Asp Arg Pro Glu Ile Trp Glu Gly Glu Pro Pro Cys Leu Pro Pro
            165             170             175

Arg Asp Ser Leu Asn Gln Ser Leu Ser Gln Asp Leu Thr Met Ala Pro
            180             185             190

Gly Ser Thr Leu Trp Leu Ser Cys Gly Val Pro Pro Asp Ser Val Ser
        195             200             205

Arg Gly Pro Leu Ser Trp Thr His Val His Pro Lys Gly Pro Lys Ser
        210             215             220
```

```
Leu Leu Ser Leu Glu Leu Lys Asp Asp Arg Pro Ala Arg Asp Met Trp
225             230             235             240

Val Met Glu Thr Gly Leu Leu Leu Pro Arg Ala Thr Ala Gln Asp Ala
                245             250             255

Gly Lys Tyr Tyr Cys His Arg Gly Asn Leu Thr Met Ser Phe His Leu
                260             265             270

Glu Ile Thr Ala Arg Pro Val Leu Trp His Trp Leu Leu Arg Thr Gly
                275             280             285

Gly Trp Lys Val Ser Ala Val Thr Leu Ala Tyr Leu Ile Phe Cys Leu
            290             295             300

Cys Ser Leu Val Gly Ile Leu His Leu Gln Arg Ala Leu Val Leu Arg
305             310             315             320

Arg Lys Arg Lys Arg Met Thr Asp Pro Thr Arg Arg Phe Phe Lys Val
                325             330             335

Thr Pro Pro Pro Gly Ser Gly Pro Gln Asn Gln Tyr Gly Asn Val Leu
                340             345             350

Ser Leu Pro Thr Pro Thr Ser Gly Leu Gly Arg Ala Gln Arg Trp Ala
            355             360             365

Ala Gly Leu Gly Gly Thr Ala Pro Ser Tyr Gly Asn Pro Ser Ser Asp
            370             375             380

Val Gln Ala Asp Gly Ala Leu Gly Ser Arg Ser Pro Pro Gly Val Gly
385             390             395             400

Pro Glu Glu Glu Glu Gly Glu Gly Tyr Glu Glu Pro Asp Ser Glu Glu
                405             410             415

Asp Ser Glu Phe Tyr Glu Asn Asp Ser Asn Leu Gly Gln Asp Gln Leu
                420             425             430

Ser Gln Asp Gly Ser Gly Tyr Glu Asn Pro Glu Asp Glu Pro Leu Gly
            435             440             445

Pro Glu Asp Glu Asp Ser Phe Ser Asn Ala Glu Ser Tyr Glu Asn Glu
            450             455             460

Asp Glu Glu Leu Thr Gln Pro Val Ala Arg Thr Met Asp Phe Leu Ser
465             470             475             480

Pro His Gly Ser Ala Trp Asp Pro Ser Arg Glu Ala Thr Ser Leu Gly
                485             490             495

Ser Gln Ser Tyr Glu Asp Met Arg Gly Ile Leu Tyr Ala Ala Pro Gln
                500             505             510

Leu Arg Ser Ile Arg Gly Gln Pro Gly Pro Asn His Glu Glu Asp Ala
            515             520             525

Asp Ser Tyr Glu Asn Met Asp Asn Pro Asp Gly Pro Asp Pro Ala Trp
            530             535             540

Gly Gly Gly Gly Arg Met Gly Thr Trp Ser Thr Arg
545             550             555
```

<210> SEQ ID NO 20
<211> LENGTH: 260
<212> TYPE: PRT
<213> ORGANISM: Homo sapiens

<400> SEQUENCE: 20

```
Met Ala Arg Pro His Pro Trp Trp Leu Cys Val Leu Gly Thr Leu Val
1               5               10              15

Gly Leu Ser Ala Thr Pro Ala Pro Lys Ser Cys Pro Glu Arg His Tyr
                20              25              30

Trp Ala Gln Gly Lys Leu Cys Cys Gln Met Cys Glu Pro Gly Thr Phe
```

```
                35                    40                    45
Leu Val Lys Asp Cys Asp Gln His Arg Lys Ala Ala Gln Cys Asp Pro
    50                    55                    60

Cys Ile Pro Gly Val Ser Phe Ser Pro Asp His His Thr Arg Pro His
65                    70                    75                    80

Cys Glu Ser Cys Arg His Cys Asn Ser Gly Leu Leu Val Arg Asn Cys
                85                    90                    95

Thr Ile Thr Ala Asn Ala Glu Cys Ala Cys Arg Asn Gly Trp Gln Cys
                100                   105                   110

Arg Asp Lys Glu Cys Thr Glu Cys Asp Pro Leu Pro Asn Pro Ser Leu
                115                   120                   125

Thr Ala Arg Ser Ser Gln Ala Leu Ser Pro His Pro Gln Pro Thr His
    130                   135                   140

Leu Pro Tyr Val Ser Glu Met Leu Glu Ala Arg Thr Ala Gly His Met
145                   150                   155                   160

Gln Thr Leu Ala Asp Phe Arg Gln Leu Pro Ala Arg Thr Leu Ser Thr
                165                   170                   175

His Trp Pro Pro Gln Arg Ser Leu Cys Ser Ser Asp Phe Ile Arg Ile
                180                   185                   190

Leu Val Ile Phe Ser Gly Met Phe Leu Val Phe Thr Leu Ala Gly Ala
                195                   200                   205

Leu Phe Leu His Gln Arg Arg Lys Tyr Arg Ser Asn Lys Gly Glu Ser
    210                   215                   220

Pro Val Glu Pro Ala Glu Pro Cys His Tyr Ser Cys Pro Arg Glu Glu
225                   230                   235                   240

Glu Gly Ser Thr Ile Pro Ile Gln Glu Asp Tyr Arg Lys Pro Glu Pro
                245                   250                   255

Ala Cys Ser Pro
                260

<210> SEQ ID NO 21
<211> LENGTH: 171
<212> TYPE: PRT
<213> ORGANISM: Homo sapiens

<400> SEQUENCE: 21

Met Glu His Ser Thr Phe Leu Ser Gly Leu Val Leu Ala Thr Leu Leu
1                   5                     10                    15

Ser Gln Val Ser Pro Phe Lys Ile Pro Ile Glu Glu Leu Glu Asp Arg
                20                    25                    30

Val Phe Val Asn Cys Asn Thr Ser Ile Thr Trp Val Glu Gly Thr Val
                35                    40                    45

Gly Thr Leu Leu Ser Asp Ile Thr Arg Leu Asp Leu Gly Lys Arg Ile
    50                    55                    60

Leu Asp Pro Arg Gly Ile Tyr Arg Cys Asn Gly Thr Asp Ile Tyr Lys
65                    70                    75                    80

Asp Lys Glu Ser Thr Val Gln Val His Tyr Arg Met Cys Gln Ser Cys
                85                    90                    95

Val Glu Leu Asp Pro Ala Thr Val Ala Gly Ile Ile Val Thr Asp Val
                100                   105                   110

Ile Ala Thr Leu Leu Leu Ala Leu Gly Val Phe Cys Phe Ala Gly His
                115                   120                   125

Glu Thr Gly Arg Leu Ser Gly Ala Ala Asp Thr Gln Ala Leu Leu Arg
    130                   135                   140
```

```
Asn Asp Gln Val Tyr Gln Pro Leu Arg Asp Arg Asp Asp Ala Gln Tyr
145                 150                 155                 160

Ser His Leu Gly Gly Asn Trp Ala Arg Asn Lys
                165                 170

<210> SEQ ID NO 22
<211> LENGTH: 207
<212> TYPE: PRT
<213> ORGANISM: Homo sapiens

<400> SEQUENCE: 22

Met Gln Ser Gly Thr His Trp Arg Val Leu Gly Leu Cys Leu Leu Ser
1                 5                  10                  15

Val Gly Val Trp Gly Gln Asp Gly Asn Glu Glu Met Gly Gly Ile Thr
                20                  25                  30

Gln Thr Pro Tyr Lys Val Ser Ile Ser Gly Thr Thr Val Ile Leu Thr
                35                  40                  45

Cys Pro Gln Tyr Pro Gly Ser Glu Ile Leu Trp Gln His Asn Asp Lys
        50                  55                  60

Asn Ile Gly Gly Asp Glu Asp Lys Asn Ile Gly Ser Asp Glu Asp
65                  70                  75                  80

His Leu Ser Leu Lys Glu Phe Ser Glu Leu Glu Gln Ser Gly Tyr Tyr
                85                  90                  95

Val Cys Tyr Pro Arg Gly Ser Lys Pro Glu Asp Ala Asn Phe Tyr Leu
                100                 105                 110

Tyr Leu Arg Ala Arg Val Cys Glu Asn Cys Met Glu Met Asp Val Met
        115                 120                 125

Ser Val Ala Thr Ile Val Ile Val Asp Ile Cys Ile Thr Gly Gly Leu
        130                 135                 140

Leu Leu Leu Val Tyr Tyr Trp Ser Lys Asn Arg Lys Ala Lys Ala Lys
145                 150                 155                 160

Pro Val Thr Arg Gly Ala Gly Ala Gly Gly Arg Gln Arg Gly Gln Asn
                165                 170                 175

Lys Glu Arg Pro Pro Pro Val Pro Asn Pro Asp Tyr Glu Pro Ile Arg
                180                 185                 190

Lys Gly Gln Arg Asp Leu Tyr Ser Gly Leu Asn Gln Arg Arg Ile
                195                 200                 205

<210> SEQ ID NO 23
<211> LENGTH: 164
<212> TYPE: PRT
<213> ORGANISM: Homo sapiens

<400> SEQUENCE: 23

Met Lys Trp Lys Ala Leu Phe Thr Ala Ala Ile Leu Gln Ala Gln Leu
1                 5                  10                  15

Pro Ile Thr Glu Ala Gln Ser Phe Gly Leu Leu Asp Pro Lys Leu Cys
                20                  25                  30

Tyr Leu Leu Asp Gly Ile Leu Phe Ile Tyr Gly Val Ile Leu Thr Ala
                35                  40                  45

Leu Phe Leu Arg Val Lys Phe Ser Arg Ser Ala Asp Ala Pro Ala Tyr
        50                  55                  60

Gln Gln Gly Gln Asn Gln Leu Tyr Asn Glu Leu Asn Leu Gly Arg Arg
65                  70                  75                  80

Glu Glu Tyr Asp Val Leu Asp Lys Arg Arg Gly Arg Asp Pro Glu Met
                85                  90                  95
```

-continued

```
Gly Gly Lys Pro Gln Arg Arg Lys Asn Pro Gln Glu Gly Leu Tyr Asn
            100             105             110

Glu Leu Gln Lys Asp Lys Met Ala Glu Ala Tyr Ser Glu Ile Gly Met
        115             120             125

Lys Gly Glu Arg Arg Arg Gly Lys Gly His Asp Gly Leu Tyr Gln Gly
    130             135             140

Leu Ser Thr Ala Thr Lys Asp Thr Tyr Asp Ala Leu His Met Gln Ala
145             150             155             160

Leu Pro Pro Arg

<210> SEQ ID NO 24
<211> LENGTH: 210
<212> TYPE: PRT
<213> ORGANISM: Homo sapiens

<400> SEQUENCE: 24

Met Arg Pro Arg Leu Trp Leu Leu Leu Ala Ala Gln Leu Thr Val Leu
1               5               10              15

His Gly Asn Ser Val Leu Gln Gln Thr Pro Ala Tyr Ile Lys Val Gln
            20              25              30

Thr Asn Lys Met Val Met Leu Ser Cys Glu Ala Lys Ile Ser Leu Ser
        35              40              45

Asn Met Arg Ile Tyr Trp Leu Arg Gln Arg Gln Ala Pro Ser Ser Asp
    50              55              60

Ser His His Glu Phe Leu Ala Leu Trp Asp Ser Ala Lys Gly Thr Ile
65              70              75              80

His Gly Glu Glu Val Glu Gln Glu Lys Ile Ala Val Phe Arg Asp Ala
            85              90              95

Ser Arg Phe Ile Leu Asn Leu Thr Ser Val Lys Pro Glu Asp Ser Gly
        100             105             110

Ile Tyr Phe Cys Met Ile Val Gly Ser Pro Glu Leu Thr Phe Gly Lys
        115             120             125

Gly Thr Gln Leu Ser Val Val Asp Phe Leu Pro Thr Thr Ala Gln Pro
    130             135             140

Thr Lys Lys Ser Thr Leu Lys Lys Arg Val Cys Arg Leu Pro Arg Pro
145             150             155             160

Glu Thr Gln Lys Gly Pro Leu Cys Ser Pro Ile Thr Leu Gly Leu Leu
            165             170             175

Val Ala Gly Val Leu Val Leu Leu Val Ser Leu Gly Val Ala Ile His
            180             185             190

Leu Cys Cys Arg Arg Arg Arg Ala Arg Leu Arg Phe Met Lys Gln Phe
        195             200             205

Tyr Lys
    210
```

METHODS AND SYSTEMS FOR PREPARING AND ANALYZING CELLULAR SAMPLES FOR MORPHOLOGICAL CHARACTERISTICS AND BIOMARKER EXPRESSION

CROSS-REFERENCE TO RELATED APPLICATIONS

This is a continuation of International Application Serial No. PCT/EP2019/081959, filed Nov. 20, 2019, which claims the benefit of U.S. Provisional Patent Application No. 62/770,072, filed Nov. 20, 2018, the content of each of which is incorporated herein by reference in its entirety.

SEQUENCE LISTING INCORPORATION BY REFERENCE

This application hereby incorporates-by-reference a sequence listing submitted herewith in a computer-readable format, having a file name of "P35157US1_SEQLIST_ST25," created on May 18, 2021, which is 85,747 bytes in size.

BACKGROUND OF THE INVENTION

Field of the Invention

The invention relates to methods and systems for the detection, characterization, and enumeration of discrete populations of cells in cellular samples.

Description of Related Art

Cellular samples are frequently used for diagnostics, including screening for and diagnosing cancers of the blood, lymphatic system, cervix, lung, and breast. In the typical workflow, one portion of the sample is used for morphological analysis. These morphologically stained samples typically are not reused. In many cases (such as for diagnosis of blood cancers), a separate portion of the sample is evaluated for molecular diagnosis by flow cytometry. This is a time consuming and expensive workflow. Moreover, it does not allow for a one to one comparison between cells that may have been identified as abnormal morphologically and the molecular stains.

In other cases, a separate portion of the sample is evaluated for biomarkers, for example, by immunocytochemistry, thus requiring additional sample (which may not always be available) and does not allow for one to one comparison between cells that may have been identified as abnormal morphologically and the molecular stains.

BRIEF SUMMARY OF THE INVENTION

This disclosure relates generally to the use of automated platforms in the preparation of biomarker-stained cellular samples for microscopic analysis and use of such stained cells in the diagnosis of certain conditions.

Disclosed herein is a method of affinity staining a Romanowsky-type stained sample on automated advanced staining systems. Typically, the sample is destained during a process step preceding contacting the sample with a biomarker-specific reagent (such as an antibody or an in situ hybridization probe). In some embodiments, the sample is destained using a reagent that has additional uses on the automated advanced staining platform, such as cell conditioning solutions (which may be used, for example, for antigen retrieval), wash solutions, blocking solutions (which may be used, for example, to block endogenous sites at which biomarker-specific reagents may bind non-specifically), endogenous inhibitor solutions (which may be used to block activity of endogenous enzymes), diluents, and the like. As a specific example, the sample is at least partially destained during a cell conditioning step. These methods may be used in diagnostic workflows on a variety of sample types, including tissue sections, body fluid samples, body fluid fractions, fine needle aspirates, washings, and scrape or brush samples.

Also disclosed herein are methods of processing body fluid samples for morphological and biomarker analysis. The body fluid sample is deposited in a thin layer onto one or more solid supports. At least one of the samples is stained with a Romanowsky-type stain and evaluated for morphology, and at least one of the samples is stained for one or more biomarkers useful for categorizing one or more cells of the sample. In an embodiment, the sample stained with the Romanowsky-type stain is also the sample stained for the one or more biomarkers, which may be a simplex stain or a multiplex stain. In some embodiments, the biomarker stain is performed on the Romanowsky-type stained sample without performing a separate destain step. In another embodiment, an unstained sample is stained for the one or more biomarkers. Where more than one biomarker is evaluated separately, a separate sample may be provided for each biomarker, or a single printed sample may be stained for all biomarkers in a multiplex format, or a combination of simplex and multiplex stained printed samples may be used. In a specific embodiment, the method is used for identifying cell populations in a blood sample.

Other features and embodiments will be apparent through review of this disclosure.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

FIG. 10 is a workflow to reuse Romanowsky-type stained slides for immunoenzymatic evaluation.

DETAILED DESCRIPTION OF THE INVENTION

I. Definitions

Figure 1:
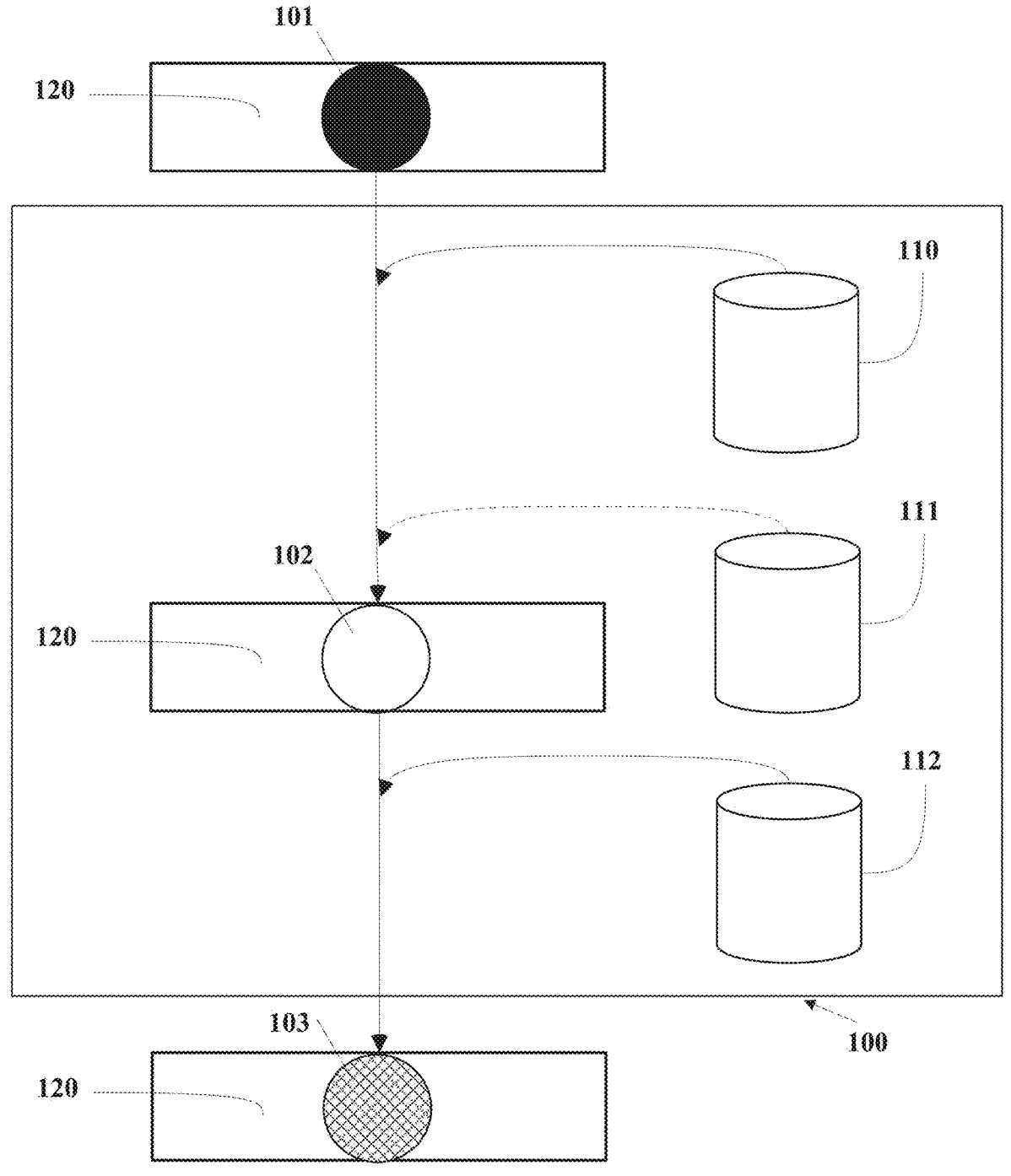
FIG. 1 illustrates an exemplary workflow for destaining and affinity staining one or more biomarkers in a Romanowsky-type stained sample.

Unless defined otherwise, technical and scientific terms used herein have the same meaning as commonly understood by a person of ordinary skill in the art. See, e.g., Lackie, DICTIONARY OF CELL AND MOLECULAR BIOLOGY, Elsevier (4th ed. 2007); Sambrook et al., MOLECULAR CLONING, A LABORATORY MANUAL, Cold Springs Harbor Press (Cold Springs Harbor, N.Y. 1989). The term "a" or "an" is intended to mean "one or more." The terms "comprise," "comprises," and "comprising," when preceding the recitation of a step or an element, are intended to mean that the addition of further steps or elements is optional and not excluded. Unless otherwise stated, all pH values recited herein are pH values as measured at 25° C. as described by Buck et al.

Affinity assay: A process involving staining a biomarker in a cellular sample by binding a biomarker-specific reagent to biomarkers within the sample in a manner that deposits a detectable moiety on the sample in proximity to the biomarker-specific reagent bound thereto, such that regions of the sample containing biomarker may be detected microscopically. Examples include immunohistochemistry (IHC), immunocytochemistry (ICC), chromogenic in situ hybridization (CISH), fluorescent in situ hybridization (FISH), and silver in situ hybridization (SISH).

Affinity enzymatic reaction: An affinity assay in which the biomarker-specific reagent localizes an enzyme (such as a peroxidase enzyme or a phosphatase enzyme) to regions of the sample that contain the biomarker, and a set of detection reagents is reacted with the enzyme to deposit a dye on the sample.

Antibody: The term "antibody" herein is used in the broadest sense and encompasses various antibody structures, including but not limited to monoclonal antibodies, polyclonal antibodies, multispecific antibodies (e.g., bispecific antibodies), and antibody fragments so long as they exhibit the desired antigen-binding activity.

Antibody fragment: An "antibody fragment" refers to a molecule other than an intact antibody that comprises a portion of an intact antibody that binds the antigen to which the intact antibody binds. Examples of antibody fragments include but are not limited to Fv, Fab, Fab', Fab'-SH, F(ab')2; diabodies; linear antibodies; single-chain antibody molecules (e.g. scFv); and multispecific antibodies formed from antibody fragments.

Biomarker: As used herein, the term "biomarker" shall refer to any molecule or group of molecules found in a biological sample that can be used to characterize the biological sample or a subject from which the biological sample is obtained. For example, a biomarker may be a molecule or group of molecules whose presence, absence, or relative abundance is: characteristic of a particular cell or tissue type or state; and/or characteristic of a particular pathological condition or state; and/or indicative of the severity of a pathological condition, the likelihood of progression or regression of the pathological condition, and/or the likelihood that the pathological condition will respond to a particular treatment. As another example, the biomarker may be a cell type or a microorganism (such as a bacterium, *mycobacterium*, fungus, virus, and the like), or a substituent molecule or group of molecules thereof.

Biomarker-specific reagent: A specific detection reagent that is capable of specifically binding directly to a biomarker in the cellular sample. Examples include a primary antibodies immunoreactive with biomarkers of the sample and nucleic acid hybridization probes complementary to nucleic acid biomarkers of the sample.

Brightfield label: A detectable moiety that is suitable for staining cellular samples for brightfield microscopy. Examples include chromogenic dyes, metallographic dyes, and chromophore-containing dyes capable of being converted from a species that does not adhere to a cellular sample to a species that is capable of adhering to the cellular sample (such as DAB).

Cellular sample: As used herein, the term "cellular sample" refers to any sample containing intact cells, such as cell cultures, bodily fluid samples or surgical specimens taken for pathological, histological, or cytological interpretation.

Detectable moiety: A molecule or material that can produce a detectable signal (such as visually, electronically or otherwise) that indicates the presence (i.e. qualitative analysis) and/or concentration (i.e. quantitative analysis) of the detectable moiety deposited on a sample. A detectable signal can be generated by any known or yet to be discovered mechanism including absorption, emission and/or scattering of a photon (including radio frequency, microwave frequency, infrared frequency, visible frequency and ultraviolet frequency photons). The term "detectable moiety" includes chromogenic, fluorescent, phosphorescent, and luminescent molecules and materials, catalysts (such as enzymes) that convert one substance into another substance to provide a detectable difference (such as by converting a colorless substance into a colored substance or vice versa, or by producing a precipitate or increasing sample turbidity). In some examples, the detectable moiety is a fluorophore, which belongs to several common chemical classes including coumarins, fluoresceins (or fluorescein derivatives and analogs), rhodamines, resorufins, luminophores and cyanines. Additional examples of fluorescent molecules can be found in Molecular Probes Handbook—A Guide to Fluorescent Probes and Labeling Technologies, Molecular Probes, Eugene, OR, ThermoFisher Scientific, 11th Edition. In other embodiments, the detectable moiety is a molecule detectable via brightfield microscopy, such as dyes including diaminobenzidine (DAB), 4-(dimethylamino) azobenzene-4'-sulfonamide (DABSYL), tetramethylrhodamine (DISCOVERY Purple), N,N'-biscarboxypentyl-5,5'-disulfonatoindo-dicarbocyanine (Cy5), and Rhodamine 110 (Rhodamine). In other examples, the detectable moiety is a nanoparticle, such as a gold or silver nanoparticle. Other detectable moieties exist or may be developed in the future and should be considered within the scope of "detectable moiety."

Detection reagent: A "detection reagent" is any reagent that is used to deposit a stain in proximity to a biomarker-specific reagent bound to a cellular sample. Non-limiting examples include secondary detection reagents (such as secondary antibodies capable of binding to a primary antibody), tertiary detection reagents (such as tertiary antibodies capable of binding to secondary antibodies), enzymes directly or indirectly associated with the biomarker-specific reagent, chemicals reactive with such enzymes to effect deposition of a fluorescent or chromogenic stain, wash reagents used between staining steps, and the like.

Fluorescence label: A detectable moiety that is suitable for staining biomarkers for fluorescence microscopy. Examples include fluorescent and phosphorescent dyes and nanomaterials (such as quantum dots).

Immunoenzymatic assay: An affinity enzymatic assay in which the biomarker-specific reagent is an antibody.

Monoclonal antibody: An antibody obtained from a population of substantially homogeneous antibodies, i.e., the individual antibodies comprising the population are identical and/or bind the same epitope, except for possible variant antibodies, e.g., containing naturally occurring mutations or arising during production of a monoclonal antibody preparation, such variants generally being present in minor amounts. In contrast to polyclonal antibody preparations, which typically include different antibodies directed against different determinants (epitopes), each monoclonal antibody of a monoclonal antibody preparation is directed against a single determinant on an antigen. Thus, the modifier "monoclonal" indicates the character of the antibody as being obtained from a substantially homogeneous population of antibodies, and is not to be construed as requiring production of the antibody by any particular method. For example, the monoclonal antibodies to be used in accordance with the present invention may be made by a variety of techniques, including but not limited to the hybridoma method, recombinant DNA methods, phage-display methods, and methods utilizing transgenic animals containing all or part of the human immunoglobulin loci, or a combination thereof.

Multiplex stain: An affinity assay in which multiple biomarker-specific reagents that bind to different biomarkers are applied to a single section and stained with different color stains.

Romanowsky-type stain: A metachromatic stain useful for staining cytology samples, wherein the stain comprises a cationic thiazine dye (such as polychrome methylene blue, azure A, azure B, azure C, azure IV, sym-dimethylthionine, thionine, methylene violet Bernsthen, methylthionoline, toluidine blue, and combinations thereof) and an anionic halogenated fluorescein dye (such as eosin A, eosin Y, eosin G, and combinations thereof).

Sample: As used herein, the term "sample" shall refer to any material obtained from a subject capable of being tested for the presence or absence of a biomarker.

Secondary detection reagent: A specific detection reagent capable of specifically binding to a biomarker-specific reagent.

Simplex stain: An affinity assay in which each biomarker-specific reagent applied to a sample is stained with the same stain.

Specific detection reagent: Any composition of matter that is capable of specifically binding to a target chemical structure in the context of a cellular sample. As used herein, the phrase "specific binding," "specifically binds to," or "specific for" or other similar iterations refers to measurable and reproducible interactions between a target and a specific detection reagent, which is determinative of the presence of the target in the presence of a heterogeneous population of molecules including biological molecules. For example, an antibody that specifically binds to a target is an antibody that binds this target with greater affinity, avidity, more readily, and/or with greater duration than it binds to other targets. In one embodiment, the extent of binding of a specific detection reagent to an unrelated target is less than about 10% of the binding of the antibody to the target as measured, e.g., by a radioimmunoassay (RIA). In certain embodiments, a biomarker-specific reagent that specifically binds to a target has a dissociation constant (Kd) of $\leq 1$ μM, $\leq 100$ nM, $\leq 10$ nM, $\leq 1$ nM, or $\leq 0.1$ nM. In another embodiment, specific binding can include, but does not require exclusive binding. Exemplary specific detection reagents include nucleic acid probes specific for particular nucleotide sequences; antibodies and antigen binding fragments thereof; and engineered specific binding compositions, including ADNECTINs (scaffold based on 10th FN3 fibronectin; Bristol-Myers-Squibb Co.), AFFIBODYs (scaffold based on Z domain of protein A from *S. aureus*; Affibody AB, Solna, Sweden), AVIMERs (scaffold based on domain A/LDL receptor; Amgen, Thousand Oaks, CA), dAbs (scaffold based on VH or VL antibody domain; GlaxoSmithKline PLC, Cambridge, UK), DARPins (scaffold based on Ankyrin repeat proteins; Molecular Partners AG, Zürich, CH), ANTICALINs (scaffold based on lipocalins; Pieris AG, Freising, DE), NANO-BODYs (scaffold based on VHH (camelid Ig); Ablynx N/V, Ghent, BE), TRANS-BODYs (scaffold based on Transferrin; Pfizer Inc., New York, NY), SMIPs (Emergent Biosolutions, Inc., Rockville, MD), and TETRANECTINs (scaffold based on C-type lectin domain (CTLD), tetranectin; Borean Pharma A/S, Aarhus, DK). Descriptions of such engineered specific binding structures are reviewed by Wurch et al., Development of Novel Protein Scaffolds as Alternatives to Whole Antibodies for Imaging and Therapy: Status on Discovery Research and Clinical Validation, Current Pharmaceutical Biotechnology, Vol. 9, pp. 502-509 (2008), the content of which is incorporated by reference.

Stain: When used as a noun, the term "stain" shall refer to any substance that can be used to visualize specific molecules or structures in a cellular sample for microscopic analysis, including brightfield microscopy, fluorescent microscopy, electron microscopy, and the like. When used as a verb, the term "stain" shall refer to any process that results in deposition of a stain on a cellular sample.

Subject: As used herein, the term "subject" or "individual" is a mammal. Mammals include, but are not limited to, domesticated animals (e.g., cows, sheep, cats, dogs, and horses), primates (e.g., humans and non-human primates such as monkeys), rabbits, and rodents (e.g., mice and rats).

II. Affinity Staining Methods on Romanowsky-Type Stained Samples

It has surprisingly been found that biomarker affinity staining can be performed directly on a Romanowsky-type stained sample on an automated advanced staining system. An exemplary workflow for affinity staining Romanowsky-type stained samples is illustrated at FIG. 1. The Romanowsky-type stained sample 101 is contacted with a first solution 110 on an automated advanced staining system 100 at a temperature and for a period of time that results in at least partially destaining of the sample. In some embodiments, the first solution 110 is a cell conditioning solution. In some embodiments, the first solution 110 is the cell conditioning solution, and the sample is contacted with the cell conditioning solution under conditions that effect both an epitope retrieval and at least partial destaining of the sample. If needed, the sample is further contacted with one or more additional solutions 111 to obtain a fully destained sample 102. The destained sample 102 is then affinity stained with one or more sets of biomarker-specific reagents and detection reagents 120 to obtain a biomarker-stained sample 103. The affinity staining may be in a simplex format or a multiplex format.

II.A. Romanowsky-Type Stained Samples

In an embodiment, the Romanowsky-type stained sample 101 is a cellular sample, such as a tissue sample or a cytology sample. In an exemplary embodiment, the sample is a formalin fixed, paraffin embedded tissue sample (FF-PET). In an exemplary embodiment, the Romanowsky-type stained sample 101 is a cytology sample. In an embodiment, the cytology sample is from a sample type selected from the group consisting of a body fluid sample (such as whole blood, bone marrow, urine, semen, saliva, sputum, nipple discharge, breast milk, synovial fluid, cerebrospinal fluid (CSF), ascites fluid, peritoneal fluid, pericardial fluid, bile, gastric fluid, mucus, lymphatic fluid, perspiration, lacrimal fluid, vomit, pleural fluid, cerumen, nasal discharge/secretions, or skene's gland fluid), body fluid fractions (such as blood fractions, including plasma, buffy coat, and erythrocyte fractions), fine needle aspirates (such as bone marrow aspirate), washings (such as bronchial lavage, bronchoalveolar lavage, nasal lavage, douche, or enema), and scrape or brush samples (such as scrapings or brushes from the cervix, anus, mouth, esophagus, stomach, or bronchi).

The Romanowsky-type stained sample 101 may be stained with any Romanowsky-type stain. An overview of the history of Romanowsky-type stains and various specific methodologies for making and using Romanowsky-type stains can be found at, for example, Bain, Horobin, Krafts I, and Krafts II, each incorporated by reference in its entirety. In an embodiment, the Romanowsky-type stain comprises azure B and eosin A or eosin Y (or a combination thereof). In an embodiment, the Romanowsky-type stain is selected from the group consisting of Romanowsky stain, Malachowski stain, Giemsa stain, May-Gruenwald stain, May-Gruenwald-Giemsa (MGG) stain, Jenner stain, Wright stain, Leishman stain, and DIFF-QUICK (proprietary modified Wright stain).

II.B. Solid Supports

In an embodiment, the Romanowsky-type stained sample 101 is deposited on a solid support 120. Generally, solid support 120 can be implemented as any of a wide variety of different sample carriers. Sample carriers can be planar (e.g., microscope slides, coverslips, plates, trays, and other members that extend in two dimensions and have a relatively narrow thickness). Alternatively, sample carriers can be non-planar, and can be implemented as cups, tubes, vials, and other similar containers, with cross-sectional shapes that include, but are not limited to, circular, elliptical, square, rectangular, triangular, and other polygonal shapes. The type of sample carrier used can depend on the type of sample and process requirements in a preparative workflow. For example, to support tissue samples, planar microscope slides and coverslips can be used. Where the sample includes a relatively high proportion of liquid, sample carriers with one or more wells or cups (e.g., a single-well or multi-well sample plate) may be more convenient.

In general, sample carriers are used to carry (e.g., contain or support) samples at various processing stations. Sample carriers can be constructed from a variety of materials, including but not limited to glasses, plastics, metals, and natural materials such as mica, quartz, and sapphire.

In certain embodiments, sample carriers include one or more fiducial marks, indicators, or reference marks. These marks can be used to register the position of the sample carriers within a coordinate system of an automated sample handling and preparation system and/or establish an instrument-independent coordinate system. In systems with multiple processing stations, the marks can be located and used to determine coordinate transformations that can be applied to convert coordinates of one processing station into coordinates of another processing station.

In an embodiment, the solid support 120 is compatible with microscopic evaluation. In an embodiment, the solid support is compatible with brightfield or fluorescence microscopy and allows a substantial portion of cells of interest to remain adhered to the solid support throughout the staining processes described herein. In an embodiment, the solid support is a microscope slide.

II.C Automated Advanced Staining Platform

Destaining of the Romanowsky stained slide and affinity staining of the destained sample are performed on an automated advanced staining platform 100. Automated advanced staining platforms typically include at least: reservoirs of the various reagents used in the staining protocols, a reagent dispense unit in fluid communication with the reservoirs for dispensing reagent to onto a slide, a waste removal system for removing used reagents and other waste from the solid support, and a control system that coordinates the actions of the reagent dispense unit and waste removal system. In addition to performing staining steps, many automated advanced staining platforms can also perform steps ancillary to staining (or are compatible with separate systems that perform such ancillary steps), including: slide baking (for adhering the sample to the slide), dewaxing (also referred to as deparaffinization), antigen retrieval, counterstaining, dehydration and clearing, and coverslipping. Prichard, incorporated herein by reference in its entirety, describes several specific examples of automated advanced staining platforms and their various features, including the intelliPATH (Biocare Medical), WAVE (Celerus Diagnostics), DAKO OMNIS and DAKO AUTOSTAINER LINK 48 (Agilent Technologies), BENCHMARK (Ventana Medical Systems, Inc.), Leica BOND, and Lab Vision Autostainer (Thermo Scientific) automated slide stainers. Additionally, Ventana Medical Systems, Inc. is the assignee of a number of United States patents disclosing systems and methods for performing automated analyses, including U.S. Pat. Nos. 5,650,327, 5,654,200, 6,296,809, 6,352,861, 6,827,901 and 6,943,029, and U.S. Published Patent Application Nos. 20030211630 and 20040052685, each of which is incorporated herein by reference in its entirety. Commercially-available staining units typically operate on one of the following principles: (1) open individual slide staining, in which slides are positioned horizontally and reagents are dispensed as a puddle on the surface of the slide containing a tissue sample (such as implemented on the DAKO AUTOSTAINER Link 48 (Agilent Technologies) and intelliPATH (Biocare Medical) stainers); (2) liquid overlay technology, in which reagents are either covered with or dispensed through an inert fluid layer deposited over the sample (such as implemented on VENTANA BenchMark and DIS- COVERY stainers); (3) capillary gap staining, in which the slide surface is placed in proximity to another surface (which may be another slide or a coverplate) to create a narrow gap, through which capillary forces draw up and keep liquid reagents in contact with the samples (such as the staining principles used by DAKO TECHMATE, Leica BOND, and DAKO OMNIS stainers). Some iterations of capillary gap staining do not mix the fluids in the gap (such as on the DAKO TECHMATE and the Leica BOND). In variations of capillary gap staining termed dynamic gap staining, capillary forces are used to apply sample to the slide, and then the parallel surfaces are translated relative to one another to agitate the reagents during incubation to effect reagent mixing (such as the staining principles implemented on DAKO OMNIS slide stainers (Agilent)). In translating gap staining, a translatable head is positioned over the slide. A lower surface of the head is spaced apart from the slide by a first gap sufficiently small to allow a meniscus of liquid to form from liquid on the slide during translation of the slide. A mixing extension having a lateral dimension less than the width of a slide extends from the lower surface of the translatable head to define a second gap smaller than the first gap between the mixing extension and the slide. During translation of the head, the lateral dimension of the mixing extension is sufficient to generate lateral movement in the liquid on the slide in a direction generally extending from the second gap to the first gap. See WO 2011-139978 A1. It has recently been proposed to use inkjet technology to deposit reagents on slides. See WO 2016-170008 A1. This list of staining technologies is not intended to be comprehensive, and any fully or semi-automated system for performing biomarker staining via affinity staining.

II.D. De-Staining & Cell Conditioning

The solid support 120 having Romanowsky-type stained sample 101 is loaded onto an automated slide staining platform 100 and destained using the first solution 110 and the optional additional reagents 111 to obtain a fully destained sample 102. As used herein, a "fully destained sample" is a sample in which the Romanowsky-type stain is retained on the sample at a level that does not substantially interfere with binding between a biomarker-specific reagent and biomarkers contained in the sample. Unless otherwise stated or claimed, the steps of contacting the sample with the first solution 110 and the optional additional solution(s) 111 do not need to be performed in any particular order, so long as the end result is a fully destained sample that is ready for affinity staining. In an embodiment, the fully destained sample 102 is obtained before the sample is contacted with a biomarker-specific reagent.

In an embodiment, the first solution 110 and the optional additional solutions 111 are reagents that serve a purpose on the automated advanced staining platform 100 other than destaining. Exemplary reagents having additional utilities on the automated advanced staining platform include cell conditioning solutions (which may be used, for example, for antigen retrieval), wash solutions, blocking solutions (which may be used, for example, to block endogenous sites at which biomarker-specific reagents may bind non-specifically), endogenous inhibitor solutions (which may be used to block activity of endogenous enzymes), diluents, and the like. In an embodiment, the first solution 110 and the optional additional solutions 111 are selected from the group consisting of a cell conditioning solution, a wash solution, a blocking solution, and an endogenous inhibitor solution. In an embodiment, the first solution 110 comprises a cell conditioning solution and the additional solution(s) 111 comprise a wash solution.

In an embodiment, the destain is performed as a part of a cell conditioning step on a formalin fixed cellular sample, wherein the cell conditioning step comprises performing an antigen retrieval in the presence of the first solution 110, wherein the first solution is a cell conditioning solution, and performing one or more additional steps in the presence of the one or more additional solutions 111. The cell conditioning step generally prepares the sample to accept a biomarker-specific reagent by performing an epitope retrieval process (also referred to as antigen retrieval). Exemplary epitope retrieval processes include: heat-induced epitope retrieval (HIER), which involves heating the sample (generally in the range of 80° C.-125° C.) in various solutions at different pH levels; protease-based epitope retrieval (PBER), in which samples are digested by proteolytic enzymes prior to staining; and combinations of HIER and PBER. Various specific epitope retrieval processes are reviewed by Shi et al., D'Amico et al., Yamashita et al., Vinod et al., and Warford et al., although this is not exhaustive. Whether to perform epitope retrieval and the particular form of epitope retrieval to use depends on the specific biomarker-specific reagent selected, and may need to be empirically determined for each biomarker-specific reagent used.

In an embodiment, the cell conditioning solution is a basic cell conditioning solution compatible with HIER, for example, having a pH in a range of about pH 8 to about pH 10. Exemplary types of basic cell conditioning solutions include ethylenediaminetetraacetic acid ("EDTA")-based solutions, tris (hydroxymethyl)aminomethane ("Tris")-based solutions, EDTA/Tris-based solutions, and Tris-buffered saline based solutions Exemplary commercially available basic cell conditioning solutions include VENTANA cell conditioning solution 1 (CC1), which is a Tris-based solution at pH 8.5 (Roche); EnVision FLEX Target Retrieval, High pH (Agilent), which is a Tris/EDTA-based solution at pH 9; eBioscience™ IHC Antigen Retrieval Solution—High pH (ThermoFisher), which is a Tris/EDTA-based solution at pH 9; BOND Epitope Retrieval Solution 2 (Leica Biosystems), which is an EDTA-based solution at pH 8.9-9.1; BOND Novocastra™ Epitope Retrieval Solution pH 8, which is an EDTA-based solution at pH 8; and BOND Novocastra™ Epitope Retrieval Solution pH 9, which is a Tris/EDTA-based solution at pH 9.

In another embodiment, the cell conditioning solution is an acidic cell conditioning solution compatible with HIER, for example, having a pH in a range of about pH 1 to about pH 6.5. In some embodiments, the acidic cell conditioning solution is slightly acidic, in the range of about pH 5 to about pH 6.5. Exemplary types of slightly acidic HIER cell conditioning solutions include citrate-based cell conditioning solutions and citrate-EDTA cell conditioning solutions. Exemplary commercially available acidic cell conditioning solutions include VENTANA ULTRA cell conditioning solution 2 (CC2), which is a citrate-based solution at pH 6 (Roche, see also U.S. Pat. No. 6,855,552); EnVision FLEX Target Retrieval, High pH (Agilent), which is a citrate-based solution at pH 6.1; eBioscience™ IHC Antigen Retrieval Solution-Low pH (ThermoFisher), which is a citrate-based solution at pH 6; BOND Epitope Retrieval Solution 2 (Leica Biosystems), which is an citrate-based solution at pH 6.0; BOND Novocastra™ Epitope Retrieval Solution pH 6, which is a citrate-based solution at pH 6.

In an embodiment, the cell conditioning step 111 comprises one or more wash steps, wherein at least one of the one or more additional solutions 111 comprises a wash solution. Washing steps may be performed before and/or after any of the aforementioned processes of the cell conditioning step by applying and then removing one or more passes of a wash solution. Wash solutions typically are buffered saline solutions, which may also contain small amounts of detergent. Exemplary wash solutions include, for example, Phosphate Buffered Saline (PBS), PBS-Tween20 (polysorbate 20), Tris Buffered Saline (TBS), TBS-Tween20, Tris-HCl, Tris-HC-Tween20, Phosphate Solution (PB), AP Solution, and the like. In a specific embodiment, the cell conditioning step comprises a HIER followed by one or more wash steps. In a specific embodiment, the cell conditioning step comprises HIER using a basic cell conditioning solution followed by one or more wash steps. In another specific embodiment, the cell conditioning step comprises HIER using an acidic cell conditioning solution followed by one or more wash steps. In a specific embodiment, the cell conditioning step comprises a PBER followed by one or more wash steps. In a specific embodiment, the cell conditioning step comprises PBER using a basic cell conditioning solution followed by one or more wash steps. In another specific embodiment, the cell conditioning step comprises PBER using an acidic cell conditioning solution followed by one or more wash steps.

In an embodiment, the cell conditioning step 111 further comprises a step that blocks activity of endogenous proteins (referred to herein as an "endogenous inhibition step"), wherein at least one of the one or more additional solutions 111 further comprises an inhibiting agent. For example, where the detection reagents depend on biotin and biotin-binding proteins, it may be necessary to block endogenous biotin using, for example, free, unlabeled biotin-binding proteins. Likewise, many detection schemes rely on activity of enzymes, including phosphatases and peroxidases, which necessitates neutralization of endogenous enzymes having similar activities. Kits are commercially available for such performing such an inhibition processes, e.g., Endogenous Biotin Blocking Kit (Cat. No. E21390, ThermoFisher Scientific), Endogenous Avidin/Biotin Blocking Kit (Cat. No. ab64212, Abcam, plc.), Endogenous Biotin Blocking Kit Cat. No. 760-050, Ventana Medical Systems, Inc.), Hydrogen Peroxide Blocking Reagent (Cat. No. ab64218, Abcam plc.), Peroxidase and Alkaline Phosphatase Blocking Reagent, (Code S2003, Agilent Technologies), among others.

In an embodiment, the cell conditioning step further comprises a step that blocks sites on the sample to which the biomarker-specific reagent may bind non-specifically (referred to herein as a "blocking step"), wherein the one or more additional solutions 111 comprises a blocking agent. Common blocking agents include buffered solutions of normal serum, non-fat dry milk, BSA (bovine serum albumin), and gelatin, as well as commercially available blocking agents such as eBioscience™ immunoenzymatic/ICC Blocking Solution—High Protein (Cat. No. 00-4952-54, ThermoFisher Scientific), eBioscience™ immunoenzymatic/ICC Blocking Solution-Low Protein (Cat. No. 00-4953-54, ThermoFisher Scientific), DISCOVERY antibody Block (Cat. No. 760-4204, Ventana Medical Systems, Inc.), among others.

II.E. Simplex and Multiplex Affinity Staining

In an embodiment, the destained sample 102 is affinity stained by a simplex method to obtain a simplex-stained biomarker-stained sample 103. In an embodiment, the simplex method comprises reacting the destained sample 102 with a set of biomarker-specific reagents and detection reagents 112 that results in a biomarker-stained sample 103 having a fluorescent label or brightfield label in proximity to the biomarker of interest. In an embodiment, the simplex method is for a biomarker in a sample type according to Table 1:

TABLE 1

| Biomarker | Biomarker Type | Sample source |
|---|---|---|
| CD2 | Protein or mRNA | Blood |
| CD3 | Protein or mRNA | Blood |
| CD4 | Protein or mRNA | Blood |
| CD5 | Protein or mRNA | Blood |
| CD7 | Protein or mRNA | Blood |
| CD8 | Protein or mRNA | Blood |
| CD10 | Protein or mRNA | Blood |
| CD20 | Protein or mRNA | Blood |
| CD23 | Protein or mRNA | Blood |
| CD34 | Protein or mRNA | Blood |
| CD38 | Protein or mRNA | Blood |
| CD45, LCA | Protein or mRNA | Blood |
| CD68 | Protein or mRNA | Blood |
| CyclinD1 | Protein or mRNA | Blood |
| MPO | Protein or mRNA | Blood |
| PAX-5 | Protein or mRNA | Blood |
| TdT | Protein or mRNA | Blood |
| ZAP-70 | Protein or mRNA | Blood |
| Kappa or Lambda light chains | Protein or mRNA | Blood, FFPET |
| Cytokeratin (OSCAR) | Protein | Blood, FFPET |
| Met gene probe | protein, mRNA, DNA | Blood |
| Chromosome 12 probe | DNA | Blood |
| mir205 | miRNA | Blood, other body fluids |

In some embodiments, the biomarker-specific reagents and detection reagents 112 are applied in a multiplex staining method.

In multiplex methods, the biomarker-specific reagents and detection reagents 112 are applied in a manner that allows the different biomarkers to be differentially labeled. One way to accomplish differential labelling of different biomarkers is to select combinations of biomarker-specific reagents and detection reagents 112 that will not result in off-target cross-reactivity between different biomarker-specific reagents or detection reagents (termed "combination staining"). For example, where secondary detection reagents are used, each secondary detection reagent is capable of binding to only one of the biomarker-specific reagents used on the section. For example, primary antibodies could be selected that are derived from different animal species (such as mouse, rabbit, rat, and got antibodies), in which case species-specific secondary antibodies may be used. As another example, each primary antibody or nucleic acid in situ hybridization probe may include a different hapten or epitope tag, and the secondary specific detection reagents (such as secondary antibodies) are selected to specifically bind to the hapten or epitope tag. Additionally, each set of detection reagents should be adapted to deposit a different detectable entity on the section, such as by depositing a different enzyme or a different fluorescent entity in proximity to each biomarker-specific reagent. An example of such an arrangement is shown at U.S. Pat. No. 8,603,765. Such arrangements have the potential advantage of being able to have each set of biomarker-specific reagents and associated specific binding reagents present on the sample at the same time and/or to perform staining with cocktails of biomarker-specific reagents and detection reagents, thereby reducing the number of staining steps. However, such arrangements may not always be feasible, as reagents may cross-react with different enzymes, and the various antibodies may cross-react with one another, leading to aberrant staining.

Another way to accomplish differential labelling of different biomarkers is to sequentially stain the sample for each biomarker. In such an embodiment, a first biomarker-specific reagent is reacted with the section, followed by a secondary detection reagent to the first biomarker-specific reagent and other detection reagents resulting in deposition of a first detectable entity. The section is then treated to remove the biomarker-specific reagents and associated detection reagents from the section while leaving the deposited stain in place. The process is repeated for subsequent biomarker-specific reagent. Examples of methods for removing the biomarker-specific reagents and associated detection reagents while leaving the dye that was deposited by heating the sample in the presence of a solution that elutes the biomarker-specific reagents and associated detection reagents from the sample (termed a "heat-kill method"), such as those disclosed by Stack and PCT/EP2016/057955, the contents of which are incorporated by reference.

As will be appreciated by the skilled artisan, combination staining and sequential staining methods may be combined. For example, where only a subset of the biomarker-specific reagents are compatible with combination staining, the sequential staining method can be modified, wherein biomarker-specific reagents compatible with combination staining are applied to the sample using a combination staining method, and the remaining biomarker-specific reagents are applied using a sequential staining method.

In some embodiments, the multiplex method is a fluorescent multiplex method. In some embodiments, the multiplex method is a brightfield multiplex method. Exemplary biomarker combinations that may be useful in multiplex staining are set forth in Table 2.

TABLE 2

| Combination | Sample | Biomarker | Biomarker Type |
|---|---|---|---|
| 1 | Blood | CD2 | Protein or mRNA |
| | | CD4 | Protein or mRNA |
| | | CD5 | Protein or mRNA |
| | | CD8 | Protein or mRNA |
| | | CD45 | Protein or mRNA |
| 2 | Blood | CD3 | Protein or mRNA |
| | | CD5 | Protein or mRNA |
| | | CD10 | Protein or mRNA |
| | | CD23 | Protein or mRNA |
| | | CyclinD1 | Protein or mRNA |
| 3 | Blood | CD3 | Protein or mRNA |
| | | CD5 | Protein or mRNA |
| | | CD23 | Protein or mRNA |
| | | CyclinD1 | Protein or mRNA |
| | | Pax5 | Protein or mRNA |
| 4 | Blood | CD3 | Protein or mRNA |
| | | CD5 | Protein or mRNA |
| | | CD23 | Protein or mRNA |
| | | CD38 | Protein or mRNA |
| | | ZAP-70 | Protein or mRNA |
| 5 | Blood | CD7 | Protein or mRNA |
| | | CD34 | Protein or mRNA |
| | | MPO | Protein or mRNA |
| | | Pax5 | Protein or mRNA |
| | | TdT | Protein or mRNA |

In an embodiment, the set of biomarker-specific reagents and detection reagents 112 comprise reagents to perform a fluorescent multiplex according to a combination of Table 2.

II.F. Biomarker-Specific Reagents and Detection Reagents

Staining of samples in both simplex and multiplex is effected by reacting the destained sample 102 with biomarker-specific reagents and a set of detection reagents 112, resulting in deposition of a detectable moiety on the sample in proximity to biomarkers contained within the sample.

In some embodiments, the detectable moiety is directly conjugated to the biomarker-specific reagent, and thus is deposited on the sample upon binding of the biomarker-specific reagent to its target (generally referred to as a direct labeling method). Direct labeling methods are often more directly quantifiable, but may not have sufficient sensitivity for the application.

In other embodiments, deposition of the detectable moiety is effected by the use of a secondary detection reagent that associates with the biomarker-specific reagent (generally referred to as an indirect labeling method). Indirect labeling methods increase the number of detectable moieties that can be deposited in proximity to the biomarker-specific reagent, and thus are often more sensitive than direct labeling methods, particularly when used in combination with dyes.

One example of an indirect method uses an enzymatic reaction localized to the biomarker-specific reagent to deposit the detectable moiety. Suitable enzymes for such reactions are well-known and include, but are not limited to, oxidoreductases, hydrolases, and peroxidases. Specific enzymes explicitly included are horseradish peroxidase (HRP), alkaline phosphatase (AP), acid phosphatase, glucose oxidase, β-galactosidase, β-glucuronidase, and β-lactamase. The enzyme may be directly conjugated to the biomarker-specific reagent, or may be indirectly associated with the biomarker-specific reagent via a labeling conjugate. As used herein, a "labeling conjugate" comprises:

(a) a specific detection reagent; and (b) an enzyme conjugated to the specific detection reagent, wherein the enzyme is reactive with a chromogen or fluorophore, signaling conjugate, or enzyme-reactive dye under appropriate reaction conditions to effect in situ generation of the dye and/or deposition of the dye on the tissue sample.

In non-limiting examples, the specific detection reagent of the labeling conjugate may be a secondary detection reagent (such as a species-specific secondary antibody bound to a primary antibody, an anti-hapten antibody bound to a hapten-conjugated primary antibody, or a biotin-binding protein bound to a biotinylated primary antibody), a tertiary detection reagent (such as a species-specific tertiary antibody bound to a secondary antibody, an anti-hapten antibody bound to a hapten-conjugated secondary antibody, or a biotin-binding protein bound to a biotinylated secondary antibody), or other such arrangements. An enzyme thus localized to the sample-bound biomarker-specific reagent can then be used in a number of schemes to deposit a detectable moiety. In some cases, the enzyme reacts with a chromogenic compound/substrate. Particular non-limiting examples of chromogenic compounds/substrates include 4-nitrophenylphospate (pNPP), fast red, bromochloroindolyl phosphate (BCIP), nitro blue tetrazolium (NBT), BCIP/NBT, fast red, AP Orange, AP blue, tetramethylbenzidine (TMB), 2,2'-azino-di-[3-ethylbenzothiazoline sulphonate] (ABTS), o-dianisidine, 4-chloronaphthol (4-CN), nitrophenyl-β-D-galactopyranoside (ONPG), o-phenylenediamine (OPD), 5-bromo-4-chloro-3-indolyl-β-galactopyranoside (X-Gal), methylumbelliferyl-β-D-galactopyranoside (MU-Gal), p-nitrophenyl-α-D-galactopyranoside (PNP), 5-bromo-4-chloro-3-indolyl-β-D-glucuronide (X-Gluc), 3-amino-9-ethyl carbazol (AEC), fuchsin, iodonitrotetrazolium (INT), tetrazolium blue, or tetrazolium violet.

In some embodiments, the enzyme can be used in a metallographic detection scheme. Metallographic detection methods include using an enzyme such as alkaline phosphatase in combination with a water-soluble metal ion and a redox-inactive substrate of the enzyme. In some embodiments, the substrate is converted to a redox-active agent by the enzyme, and the redox-active agent reduces the metal ion, causing it to form a detectable precipitate. (see, for example, U.S. patent application Ser. No. 11/015,646, filed Dec. 20, 2004, PCT Publication No. 2005/003777 and U.S. Patent Application Publication No. 2004/0265922; each of which is incorporated by reference herein in its entirety). Metallographic detection methods include using an oxidoreductase enzyme (such as horseradish peroxidase) along with a water soluble metal ion, an oxidizing agent and a reducing agent, again to for a detectable precipitate. (See, for example, U.S. Pat. No. 6,670,113, which is incorporated by reference herein in its entirety). In some embodiments, the enzymatic action occurs between the enzyme and the dye itself, wherein the reaction converts the dye from a non-binding species to a species deposited on the sample. For example, reaction of DAB with a peroxidase (such as horseradish peroxidase) oxidizes the DAB, causing it to precipitate. In yet other embodiments, the detectable moiety is deposited via a signaling conjugate comprising a latent reactive moiety configured to react with the enzyme to form a reactive species that can bind to the sample or to other detection components. These reactive species are capable of reacting with the sample proximal to their generation, i.e. near the enzyme, but rapidly convert to a non-reactive species so that the signaling conjugate is not deposited at sites distal from the site at which the enzyme is deposited. Examples of latent reactive moieties include: quinone methide (QM) analogs, such as those described at WO2015124703A1, and tyramide conjugates, such as those described at, WO2012003476A2, each of which is hereby incorporated by reference herein in its entirety. In some examples, the latent reactive moiety is directly conjugated to a dye, such as N,N'-biscarboxypentyl-5,5'-disulfonato-indo-dicarbocyanine (Cy5), 4-(dimethylamino) azobenzene-4'-sulfonamide (DABSYL), tetramethylrhodamine (DISCO Purple), and Rhodamine 110 (Rhodamine). In other examples, the latent reactive moiety is conjugated to one member of a specific binding pair, and the dye is linked to the other member of the specific binding pair. In other examples, the latent reactive moiety is linked to one member of a specific binding pair, and an enzyme is linked to the other member of the specific binding pair, wherein the enzyme is (a) reactive with a chromogenic substrate to effect generation of the dye, or (b) reactive with a dye to effect deposition of the dye (such as DAB). Examples of specific binding pairs include:

(1) a biotin or a biotin derivative (such as desthiobiotin) linked to the latent reactive moiety, and a biotin-binding entity (such as avidin, streptavidin, deglycosylated avidin (such as NEUTRAVIDIN), or a biotin binding protein having a nitrated tyrosine at its biotin binding site (such as CAPTAVIDIN)) linked to a dye or to an enzyme reactive with a chromogenic substrate or reactive with a dye (for example, a peroxidase linked to the biotin-binding protein when the dye is DAB); and (2) a hapten linked to the latent reactive moiety, and an anti-hapten antibody linked to a dye or to an enzyme reactive with a chromogenic substrate or reactive with a dye (for example, a peroxidase linked to the biotin-binding protein when the dye is DAB).

Non-limiting examples of commercially available detection reagents or kits comprising detection reagents suitable for use with present methods include: VENTANA ultra View detection systems (secondary antibodies conjugated to enzymes, including HRP and AP); VENTANA iVIEW detection systems (biotinylated anti-species secondary antibodies and streptavidin-conjugated enzymes); VENTANA OptiView detection systems (OptiView) (anti-species secondary antibody conjugated to a hapten and an anti-hapten tertiary antibody conjugated to an enzyme multimer); VENTANA Amplification kit (unconjugated secondary antibodies, which can be used with any of the foregoing VENTANA detection systems to amplify the number of enzymes deposited at the site of primary antibody binding); VENTANA OptiView Amplification system (Anti-species secondary antibody conjugated to a hapten, an anti-hapten tertiary antibody conjugated to an enzyme multimer, and a tyramide conjugated to the same hapten. In use, the secondary antibody is contacted with the sample to effect binding to the primary antibody. Then the sample is incubated with the anti-hapten antibody to effect association of the enzyme to the secondary antibody. The sample is then incubated with the tyramide to effect deposition of additional hapten molecules. The sample is then incubated again with the anti-hapten antibody to effect deposition of additional enzyme molecules. The sample is then incubated with the detectable moiety to effect dye deposition); VENTANA DISCOVERY, DISCOVERY OmniMap, DISCOVERY UltraMap anti-hapten antibody, secondary antibody, chromogen, fluorophore, and dye kits, each of which are available from Ventana Medical Systems, Inc. (Tucson, Arizona); PowerVision and PowerVision+ immunoenzymatic Detection Systems (secondary antibodies directly polymerized with HRP or AP into compact polymers bearing a high ratio of enzymes to antibodies); and DAKO EnVision™+ System (enzyme labeled polymer that is conjugated to secondary antibodies).

Non-limiting examples of biomarker-specific reagent and detection reagent combinations 112 are set forth in Table 3 are specifically included.

TABLE 3

| | |
|---|---|
| A. Biomarker-specific reagent linked directly to detectable moiety | |
| | Biomarker-specific reagent-Dye conjugate |
| B. Biomarker-specific reagent linked to enzyme reacting with detectable moiety | |
| | Biomarker-specific reagent—Enzyme conjugate + DAB |
| | Biomarker-specific reagent—Enzyme conjugate + Chromogen |
| | Biomarker-specific reagent—Enzyme conjugate + Fluorophore |
| C. Biomarker-specific reagent linked to Enzyme reacting with signaling conjugate | |
| C1. Signaling conjugate comprises detectable moiety | Biomarker-specific reagent—Enzyme conjugate + QM-Dye conjugate |
| | Biomarker-specific reagent—Enzyme conjugate + Tyramide-Dye conjugate |
| C2. Signaling conjugate comprises enzyme that reacts directly with detectable moiety | Biomarker-specific reagent—Enzyme conjugate + QM-Enzyme conjugate + DAB |
| | Biomarker-specific reagent—Enzyme conjugate + QM-Enzyme conjugate + Chromogen |
| | Biomarker-specific reagent—Enzyme conjugate + Tyramide-Enzyme conjugate + DAB |
| | Biomarker-specific reagent—Enzyme conjugate + Tyramide-Enzyme conjugate + Chromogen |
| | Biomarker-specific reagent—Enzyme conjugate + Tyramide-Enzyme conjugate + Fluorophore |
| C3. Signaling conjugate comprises enzyme that reacts with second signaling conjugate comprising detectable moiety | Biomarker-specific reagent—Enzyme conjugate + QM-Enzyme conjugate + QM-Dye conjugate |
| | Biomarker-specific reagent—Enzyme conjugate + QM-Enzyme conjugate + Tyramide-Dye conjugate |
| | Biomarker-specific reagent—Enzyme conjugate + Tyramide-Enzyme conjugate + QM-Dye conjugate |
| | Biomarker-specific reagent—Enzyme conjugate + Tyramide-Enzyme conjugate + Tyramide-Dye conjugate |
| C4. Signaling conjugate comprises member of a specific binding pair and other member of binding pair is linked to detectable moiety | Biomarker-specific reagent—Enzyme conjugate + Tyramide-(biotin/hapten) conjugate + Dye-(avidin/anti-hapten biomarker-specific reagent) conjugate |
| | Biomarker-specific reagent—Enzyme conjugate + QM-(biotin/hapten) conjugate + Dye-(avidin/anti-hapten biomarker-specific reagent) conjugate |
| C5. Signaling conjugate comprises member of a specific binding pair and other member of binding pair is linked to enzyme reactive with detectable moiety | Biomarker-specific reagent—Enzyme conjugate + QM-(biotin/hapten) conjugate + Enzyme-(avidin/anti-hapten biomarker-specific reagent) conjugate + DAB |
| | Biomarker-specific reagent—Enzyme conjugate + QM-(biotin/hapten) conjugate + Enzyme-(avidin/anti-hapten biomarker-specific reagent) conjugate + Chromogen |
| | Biomarker-specific reagent—Enzyme conjugate + QM-(biotin/hapten) conjugate + Enzyme-(avidin/anti-hapten biomarker-specific reagent) conjugate + Fluorophore |
| | Biomarker-specific reagent—Enzyme conjugate + Tyramide-(biotin/hapten) conjugate + Enzyme-(avidin/anti-hapten biomarker-specific reagent) conjugate + DAB |
| | Biomarker-specific reagent—Enzyme conjugate + Tyramide-(biotin/hapten) conjugate + Enzyme-(avidin/anti-hapten biomarker-specific reagent) conjugate + Chromogen |

TABLE 3-continued

|  | Biomarker-specific reagent—Enzyme conjugate + Tyramide-(biotin/hapten) conjugate + Enzyme-(avidin/anti-hapten biomarker-specific reagent) conjugate + Fluorophore |
| C6. Signaling conjugate comprises member of a specific binding pair and other member of binding pair is linked to enzyme reactive with second detectable moiety linked to a detectable moiety | Biomarker-specific reagent—Enzyme conjugate + QM-(biotin/hapten) conjugate + Enzyme-(avidin/anti-hapten biomarker-specific reagent) conjugate + Tyramide-Dye conjugate |
|  | Biomarker-specific reagent—Enzyme conjugate + QM-(biotin/hapten) conjugate + Enzyme-(avidin/anti-hapten biomarker-specific reagent) conjugate + QM-Dye conjugate |
|  | Biomarker-specific reagent—Enzyme conjugate + Tyramide-(biotin/hapten) conjugate + Enzyme-(avidin/anti-hapten biomarker-specific reagent) conjugate + Tyramide-Dye conjugate |
|  | Biomarker-specific reagent—Enzyme conjugate + Tyramide-(biotin/hapten) conjugate + Enzyme-(avidin/anti-hapten biomarker-specific reagent) conjugate + QM-Dye conjugate |
| D. Biomarker-specific reagent linked to member of specific binding pair | |
| D1. Dye linked to other member of specific binding pair | Biomarker-specific reagent-(biotin/hapten) conjugate + Dye-(avidin/anti-hapten biomarker-specific reagent) conjugate |
| D2. Enzyme linked to other member of specific binding pair, wherein the enzyme is reactive with detectable moiety | Biomarker-specific reagent-(biotin/hapten) conjugate + Enzyme-(avidin/anti-hapten biomarker-specific reagent) conjugate + DAB |
|  | Biomarker-specific reagent-(biotin/hapten) conjugate + Enzyme-(avidin/anti-hapten biomarker-specific reagent) conjugate + Chromogen |
|  | Biomarker-specific reagent-(biotin/hapten) conjugate + Enzyme-(avidin/anti-hapten biomarker-specific reagent) conjugate + QM-Dye conjugate |
|  | Biomarker-specific reagent-(biotin/hapten) conjugate + Enzyme-(avidin/anti-hapten biomarker-specific reagent) conjugate + Tyramide-Dye conjugate |
| E. Secondary detection reagent linked directly to detectable moiety | |
| Biomarker-specific reagent + 2° specific detection reagent-Dye conjugate | |
| F. Secondary detection reagent linked to Enzyme reacting with detectable moiety | |
| Biomarker-specific reagent + 2° specific detection reagent—Enzyme conjugate + DAB | |
| Biomarker-specific reagent + 2° specific detection reagent—Enzyme conjugate + Chromogen | |
| Biomarker-specific reagent + 2° specific detection reagent—Enzyme conjugate + Fluorophore | |
| G. Secondary detection reagent linked to Enzyme reacting with signaling conjugate | |
| G1. Signaling conjugate comprises detectable moiety | Biomarker-specific reagent + 2° specific detection reagent-Enzyme conjugate + QM-Dye conjugate |
|  | Biomarker-specific reagent + 2° specific detection reagent-Enzyme conjugate + Tyramide-Dye conjugate |
| G2. Signaling conjugate comprises enzyme that reacts directly with detectable moiety | Biomarker-specific reagent + 2° specific detection reagent-Enzyme conjugate + QM-Enzyme conjugate + DAB |
|  | Biomarker-specific reagent + 2° specific detection reagent-Enzyme conjugate + QM-Enzyme conjugate + Chromogen |
|  | Biomarker-specific reagent + 2° specific detection reagent-Enzyme conjugate + Tyramide-Enzyme conjugate + DAB |
|  | Biomarker-specific reagent + 2° specific detection reagent-Enzyme conjugate + Tyramide-Enzyme conjugate + Chromogen |
|  | Biomarker-specific reagent + 2° specific detection reagent-Enzyme conjugate + Tyramide-Enzyme conjugate + Fluorophore |
| G3. Signaling conjugate comprises enzyme that reacts with second signaling conjugate comprising detectable moiety | Biomarker-specific reagent + 2° specific detection reagent-Enzyme conjugate + QM-Enzyme conjugate + QM-Dye conjugate |
|  | Biomarker-specific reagent + 2° specific detection reagent-Enzyme conjugate + QM-Enzyme conjugate + Tyramide-Dye conjugate |
|  | Biomarker-specific reagent + 2° specific detection reagent-Enzyme conjugate + Tyramide-Enzyme conjugate + QM-Dye conjugate |
|  | Biomarker-specific reagent + 2° specific detection reagent—Enzyme conjugate + Tyramide-Enzyme conjugate + Tyramide-Dye conjugate |
| G4. Signaling conjugate comprises member of a specific binding pair and other member of binding pair | Biomarker-specific reagent + 2° specific detection reagent-Enzyme conjugate + Tyramide-(biotin/hapten) conjugate + Dye-(avidin/anti-hapten biomarker-specific reagent) conjugate |

TABLE 3-continued

| | |
|---|---|
| is linked to detectable moiety | Biomarker-specific reagent + 2° specific detection reagent-Enzyme conjugate + QM-(biotin/hapten) conjugate + Dye-(avidin/anti-hapten biomarker-specific reagent) conjugate |
| G5. Signaling conjugate comprises member of a specific binding pair and other member of binding pair is linked to enzyme reactive with detectable moiety | Biomarker-specific reagent + 2° specific detection reagent-Enzyme conjugate + QM-(biotin/hapten) conjugate + Enzyme-(avidin/anti-hapten biomarker-specific reagent) conjugate + DAB |
| | Biomarker-specific reagent + 2° specific detection reagent-Enzyme conjugate + QM-(biotin/hapten) conjugate + Enzyme-(avidin/anti-hapten biomarker-specific reagent) conjugate + Chromogen |
| | Biomarker-specific reagent + 2° specific detection reagent-Enzyme conjugate + QM-(biotin/hapten) conjugate + Enzyme-(avidin/anti-hapten biomarker-specific reagent) conjugate + Fluorophore |
| | Biomarker-specific reagent + 2° specific detection reagent-Enzyme conjugate + Tyramide-(biotin/hapten) conjugate + Enzyme-(avidin/anti-hapten biomarker-specific reagent) conjugate + DAB |
| | Biomarker-specific reagent + 2° specific detection reagent-Enzyme conjugate + Tyramide-(biotin/hapten) conjugate + Enzyme-(avidin/anti-hapten biomarker-specific reagent) conjugate + Chromogen |
| | Biomarker-specific reagent + 2° specific detection reagent-Enzyme conjugate + Tyramide-(biotin/hapten) conjugate + Enzyme-(avidin/anti-hapten biomarker-specific reagent) conjugate + Fluorophore |
| G6. Signaling conjugate comprises member of a specific binding pair and other member of binding pair is linked to enzyme reactive with second detectable moiety linked to a detectable moiety | Biomarker-specific reagent + 2° specific detection reagent-Enzyme conjugate + QM-(biotin/hapten) conjugate + Enzyme-(avidin/anti-hapten biomarker-specific reagent) conjugate + Tyramide-Dye conjugate |
| | Biomarker-specific reagent + 2° specific detection reagent-Enzyme conjugate + QM-(biotin/hapten) conjugate + Enzyme-(avidin/anti-hapten biomarker-specific reagent) conjugate + QM-Dye conjugate |
| | Biomarker-specific reagent + 2° specific detection reagent-Enzyme conjugate + Tyramide-(biotin/hapten) conjugate + Enzyme-(avidin/anti-hapten biomarker-specific reagent) conjugate + Tyramide-Dye conjugate |
| | Biomarker-specific reagent + 2° specific detection reagent-Enzyme conjugate + Tyramide-(biotin/hapten) conjugate + Enzyme-(avidin/anti-hapten biomarker-specific reagent) conjugate + QM-Dye conjugate |
| H. Secondary detection reagent linked to member of specific binding pair | |
| H1. Dye linked to other member of specific binding pair | Biomarker-specific reagent + 2° specific detection reagent-(biotin/hapten) conjugate + Dye-(avidin/anti-hapten biomarker-specific reagent) conjugate |
| | Biomarker-specific reagent + 2° specific detection reagent-(biotin/hapten) conjugate + Enzyme-(avidin/anti-hapten biomarker-specific reagent) conjugate + DAB |
| | Biomarker-specific reagent + 2° specific detection reagent-(biotin/hapten) conjugate + Enzyme-(avidin/anti-hapten biomarker-specific reagent) conjugate + Chromogen |
| H2. Enzyme linked to other member of specific binding pair, wherein the enzyme is reactive with detectable moiety | Biomarker-specific reagent + 2° specific detection reagent-(biotin/hapten) conjugate + Enzyme-(avidin/anti-hapten biomarker-specific reagent) conjugate + Fluorophore |
| | Biomarker-specific reagent + 2° specific detection reagent-(biotin/hapten) conjugate + Enzyme-(avidin/anti-hapten biomarker-specific reagent) conjugate + QM-Dye conjugate |
| | Biomarker-specific reagent + 2° specific detection reagent-(biotin/hapten) conjugate + Enzyme-(avidin/anti-hapten biomarker-specific reagent) conjugate + Tyramide-Dye conjugate |
| I. Tertiary specific detection reagent linked directly to detectable moiety | |
| Biomarker-specific reagent + 2° specific detection reagent + 3° specific detection reagent-Dye conjugate | |
| J. Tertiary specific detection reagent linked to Enzyme reacting with detectable moiety | |
| Biomarker-specific reagent + 2° specific detection reagent + 3° specific detection reagent-Enzyme conjugate + DAB | |
| Biomarker-specific reagent + 2° specific detection reagent + 3° specific detection reagent-Enzyme conjugate + Chromogen | |
| Biomarker-specific reagent + 2° specific detection reagent + 3° specific detection reagent-Enzyme conjugate + Fluorophore | |

TABLE 3-continued

| K. Tertiary specific detection reagent linked to Enzyme reacting with signaling conjugate | |
|---|---|
| K1. Signaling conjugate comprises detectable moiety | Biomarker-specific reagent + 2° specific detection reagent + 3° specific detection reagent—Enzyme conjugate + QM-Dye conjugate |
| | Biomarker-specific reagent + 2° specific detection reagent + 3° specific detection reagent—Enzyme conjugate + Tyramide-Dye conjugate |
| K2. Signaling conjugate comprises enzyme that reacts directly with detectable moiety | Biomarker-specific reagent + 2° specific detection reagent + 3° specific detection reagent—Enzyme conjugate + QM-Enzyme conjugate + DAB |
| | Biomarker-specific reagent + 2° specific detection reagent + 3° specific detection reagent—Enzyme conjugate + QM-Enzyme conjugate + Chromogen |
| | Biomarker-specific reagent + 2° specific detection reagent + 3° specific detection reagent—Enzyme conjugate + QM-Enzyme conjugate + Fluorophore |
| | Biomarker-specific reagent + 2° specific detection reagent + 3° specific detection reagent—Enzyme conjugate + Tyramide-Enzyme conjugate + DAB |
| | Biomarker-specific reagent + 2° specific detection reagent + 3° specific detection reagent—Enzyme conjugate + Tyramide-Enzyme conjugate + Chromogen |
| | Biomarker-specific reagent + 2° specific detection reagent + 3° specific detection reagent—Enzyme conjugate + Tyramide-Enzyme conjugate + Fluorophore |
| K3. Signaling conjugate comprises enzyme that reacts with second signaling conjugate comprising detectable moiety | Biomarker-specific reagent + 2° specific detection reagent + 3° specific detection reagent—Enzyme conjugate + QM-Enzyme conjugate + QM-Dye conjugate |
| | Biomarker-specific reagent + 2° specific detection reagent + 3° specific detection reagent—Enzyme conjugate + QM-Enzyme conjugate + Tyramide-Dye conjugate |
| | Biomarker-specific reagent + 2° specific detection reagent + 3° specific detection reagent—Enzyme conjugate + Tyramide-Enzyme conjugate + QM-Dye conjugate |
| | Biomarker-specific reagent + 2° specific detection reagent + 3° specific detection reagent—Enzyme conjugate + Tyramide-Enzyme conjugate + Tyramide-Dye conjugate |
| K4. Signaling conjugate comprises member of a specific binding pair and other member of binding pair is linked to detectable moiety | Biomarker-specific reagent + 2° specific detection reagent + 3° specific detection reagent—Enzyme conjugate + Tyramide-(biotin/hapten) conjugate + Dye-(avidin/anti-hapten biomarker-specific reagent) conjugate |
| | Biomarker-specific reagent + 2° specific detection reagent + 3° specific detection reagent—Enzyme conjugate + QM-(biotin/hapten) conjugate + Dye-(avidin/anti-hapten biomarker-specific reagent) conjugate |
| K5. Signaling conjugate comprises member of a specific binding pair and other member of binding pair is linked to enzyme reactive with detectable moiety | Biomarker-specific reagent + 2° specific detection reagent + 3° specific detection reagent—Enzyme conjugate + QM-(biotin/hapten) conjugate + Enzyme-(avidin/anti-hapten biomarker-specific reagent) conjugate + DAB |
| | Biomarker-specific reagent + 2° specific detection reagent + 3° specific detection reagent—Enzyme conjugate + QM-(biotin/hapten) conjugate + Enzyme-(avidin/anti-hapten biomarker-specific reagent) conjugate + Chromogen |
| | Biomarker-specific reagent + 2° specific detection reagent + 3° specific detection reagent—Enzyme conjugate + QM-(biotin/hapten) conjugate + Enzyme-(avidin/anti-hapten biomarker-specific reagent) conjugate + Fluorophore |
| | Biomarker-specific reagent + 2° specific detection reagent + 3° specific detection reagent—Enzyme conjugate + Tyramide-(biotin/hapten) conjugate + Enzyme-(avidin/anti-hapten biomarker-specific reagent) conjugate + DAB |
| | Biomarker-specific reagent + 2° specific detection reagent + 3° specific detection reagent—Enzyme conjugate + Tyramide-(biotin/hapten) conjugate + Enzyme-(avidin/anti-hapten biomarker-specific reagent) conjugate + Chromogen |
| | Biomarker-specific reagent + 2° specific detection reagent + 3° specific detection reagent—Enzyme conjugate + Tyramide-(biotin/hapten) conjugate + Enzyme-(avidin/anti-hapten biomarker-specific reagent) conjugate + Fluorophore |

TABLE 3-continued

| | Biomarker-specific reagent + 2° specific detection reagent + 3° specific detection reagent—Enzyme conjugate + QM-(biotin/hapten) conjugate + Enzyme-(avidin/anti-hapten biomarker-specific reagent) conjugate + Tyramide-Dye conjugate |
|---|---|
| K6. Signaling conjugate comprises member of a specific binding pair and other member of binding pair is linked to enzyme reactive with second detectable moiety linked to a detectable moiety | Biomarker-specific reagent + 2° specific detection reagent + 3° specific detection reagent—Enzyme conjugate + QM-(biotin/hapten) conjugate + Enzyme-(avidin/anti-hapten biomarker-specific reagent) conjugate + QM-Dye conjugate |
| | Biomarker-specific reagent + 2° specific detection reagent + 3° specific detection reagent—Enzyme conjugate + Tyramide-(biotin/hapten) conjugate + Enzyme-(avidin/anti-hapten biomarker-specific reagent) conjugate + Tyramide-Dye conjugate |
| | Biomarker-specific reagent + 2° specific detection reagent + 3° specific detection reagent—Enzyme conjugate + Tyramide-(biotin/hapten) conjugate + Enzyme-(avidin/anti-hapten biomarker-specific reagent) conjugate + QM-Dye conjugate |
| L. Tertiary specific detection reagent linked to member of specific binding pair | |
| L1. Dye linked to other member of specific binding pair | Biomarker-specific reagent + 2° specific detection reagent + 3° specific detection reagent-(biotin/hapten) conjugate + Dye-(avidin/anti-hapten biomarker-specific reagent) conjugate |
| | Biomarker-specific reagent + 2° specific detection reagent + 3° specific detection reagent-(biotin/hapten) conjugate + Enzyme-(avidin/anti-hapten biomarker-specific reagent) conjugate + DAB |
| | Biomarker-specific reagent + 2° specific detection reagent + 3° specific detection reagent-(biotin/hapten) conjugate + Enzyme-(avidin/anti-hapten biomarker-specific reagent) conjugate + Chromogen |
| L2. Enzyme linked to other member of specific binding pair, wherein the enzyme is reactive with detectable moiety | Biomarker-specific reagent + 2° specific detection reagent + 3° specific detection reagent-(biotin/hapten) conjugate + Enzyme-(avidin/anti-hapten biomarker-specific reagent) conjugate + Fluorophore |
| | Biomarker-specific reagent + 2° specific detection reagent + 3° specific detection reagent-(biotin/hapten) conjugate + Enzyme-(avidin/anti-hapten biomarker-specific reagent) conjugate + QM-Dye conjugate |
| | Biomarker-specific reagent + 2° specific detection reagent + 3° specific detection reagent-(biotin/hapten) conjugate + Enzyme-(avidin/anti-hapten biomarker-specific reagent) conjugate + Tyramide-Dye conjugate |

In a specific embodiment, the biomarker-specific reagents and the specific detection reagents 112 set forth in Table 3 are antibodies, probes for genomic in situ hybridization, or probes for mRNA in situ hybridization. As would be appreciated by a person having ordinary skill in the art, the detection scheme for each of the biomarker-specific reagent may be the same, or it may be different. In an embodiment, the affinity stain is a simplex stain according to Table 1, using a detection scheme according to Table 3. In an embodiment, the affinity stain is a multiplex stain according to Table 2, using combination staining and a detection scheme according to Table 3. In an embodiment, the affinity stain is a multiplex stain according to Table 2, using heat-kill method and a staining and a detection scheme according to Table 3.

Table 4 provides some biomarkers that may be detected in the present methods.

TABLE 4

| Biomarker | | Consensus protein sequence |
|---|---|---|
| | CD2 | SEQ ID NO: 1 |
| CD3 | γ-chain | SEQ ID NO: 2 |
| | δ-chain | SEQ ID NO: 21 |
| | ε-chain | SEQ ID NO: 22 |

TABLE 4-continued

| Biomarker | | Consensus protein sequence |
|---|---|---|
| | ζ-chain | SEQ ID NO: 23 |
| CD4 | | SEQ ID NO: 3 |
| CD5 | | SEQ ID NO: 4 |
| CD7 | | SEQ ID NO: 5 |
| CD8 | α-chain | SEQ ID NO: 6 |
| | β-chain | SEQ ID NO: 24 |
| CD10 | | SEQ ID NO: 7 |
| CD19 | | SEQ ID NO: 19 |
| CD20 | | SEQ ID NO: 8 |
| CD23 | | SEQ ID NO: 9 |
| CD27 | | SEQ ID NO: 20 |
| CD34 | | SEQ ID NO: 10 |
| CD38 | | SEQ ID NO: 11 |
| CD45, LCA | | SEQ ID NO: 12 |
| CD68 | | SEQ ID NO: 13 |
| Cyclin D1 | | SEQ ID NO: 14 |
| Myeloperoxidase (MPO) | | SEQ ID NO: 15 |
| Paired box protein Pax-5 (PAX5) | | SEQ ID NO: 16 |
| DNA nucleotidylexotransferase (TdT) | | SEQ ID NO: 17 |
| Tyrosine-protein kinase ZAP-70 (ZAP-70) | | SEQ ID NO: 18 |

As used herein, a protein-specific biomarker-specific reagent that binds to a polypeptide referred to in Table 4 shall mean a biomarker-specific reagent that binds to a polypeptide comprising the recited SEQ ID NO reflected for biomarker, or a protein comprising the same. As used herein, a nucleic acid-specific biomarker-specific reagent that binds to a gene or mRNA encoding a biomarker referred to in Table 4 shall mean a biomarker-specific reagent capable of hybridizing to a nucleic acid encoding the recited SEQ ID NO reflected for biomarker. Some of the recited biomarkers are complexes of 2 or more polypeptide chains. For example, CD3 is a cell surface receptor complex that is frequently used as a defining biomarker for cells having a T-cell lineage. The CD3 complex is composed of 4 distinct polypeptide chains: CD3-gamma chain, CD3-delta chain, CD3epsilon chain, and CD3-zeta chain. CD3-gamma and CD3-delta each form heterodimers with CD3-epsilon (εγ-homodimer and εδ-heterodimer) while CD3-zeta forms a homodimer (ζζ-homodimer). Functionally, the εγ-homodimer, εδ-heterodimer, and ζζ-homodimer form a signaling complex with T-cell receptor complexes. As used herein, the term "human CD3 protein biomarker" or "CD3" encompasses any CD3-gamma chain, CD3-delta chain, CD3epsilon chain, and CD3-zeta chain polypeptide having a canonical human sequence and natural variants thereof that maintain the function of the canonical sequence; εγ-homodimers, εδ-heterodimers, and ζζ-homodimers including one or more of CD3-gamma chain, CD3-delta chain, CD3epsilon chain, and CD3-zeta chain polypeptide having a canonical human sequence and natural variants thereof that maintain the function of the canonical sequence; and any signaling complex including one or more of the foregoing CD3 homodimers or heterodimers. As used herein, a human CD3 protein biomarker-specific agent encompasses any biomarker-specific agent that specifically binds a structure (such as an epitope) within a canonical CD3-gamma chain polypeptide, CD3-delta chain polypeptide, CD3-epsilon chain polypeptide, or CD3-zeta chain polypeptide, or that binds to a structure (such as an epitope) located within εγ-homodimer, εδ-heterodimer, or ζζ-homodimer. As another example, CD8 is a heterodimeric, disulphide linked, transmembrane glycoprotein found on the cytotoxic-suppressor T cell subset, on thymocytes, on certain natural killer cells, and in a subpopulation of bone marrow cells. Exemplary sequences for (and isoforms and variants of) the human alpha- and beta-chain of the CD8 receptor can be found at Uniprot Accession Nos. P01732 (the canonical amino acid sequence for which is disclosed herein at SEQ ID NO: 6) and P10966 (the canonical amino acid sequence for which is disclosed herein at SEQ ID NO: 24), respectively. As used herein, the term "human CD8 protein biomarker" or "CD8" encompasses any CD8-alpha chain polypeptide having a canonical human sequence and natural variants thereof that maintain the function of the canonical sequence; any CD8-beta chain polypeptide having a canonical human sequence and natural variants thereof that maintain the function of the canonical sequence; any dimers including a CD8-alpha chain polypeptide having a canonical human sequence and natural variants thereof that maintain the function of the canonical sequence and/or a CD8-beta chain polypeptide having a canonical human sequence and natural variants thereof that maintain the function of the canonical sequence. In some embodiments, a human CD8 protein biomarker-specific agent encompasses any biomarker-specific agent that specifically binds a structure (such as an epitope) within CD8-alpha chain polypeptide, CD8-beta chain polypeptide, or that binds to a structure (such as an epitope) located within a CD8 dimer.

In an embodiment, the sample is a blood sample, and the affinity stain is a simplex stain according to Table 1, using a detection scheme according to Table 3, wherein the biomarker-specific reagent is specific for a protein according to Table 4 or an mRNA encoding a protein according to Table 4. In an embodiment, the sample is a blood sample, the affinity stain is a multiplex stain according to Table 2 using combination staining and a detection scheme according to Table 3, and wherein the biomarker-specific reagents are specific for a protein according to Table 4 or an mRNA encoding a protein according to Table 4. In an embodiment, the sample is a blood sample, the affinity stain is a multiplex stain according to Table 2, using heat-kill method and a staining and a detection scheme according to Table 3, and wherein the biomarker-specific reagents are specific for a protein according to Table 4 or an mRNA encoding a protein according to Table 4.

II.G Counterstaining

If desired, the biomarker-stained slides 103 may be counterstained to assist in identifying morphologically relevant areas for identifying ROIs, either manually or automatically. Examples of counterstains include chromogenic nuclear counterstains, such as a Romanowsky-type stain (stains purple), hematoxylin (stains from blue to violet), Methylene blue (stains blue), toluidine blue (stains nuclei deep blue and polysaccharides pink to red), nuclear fast red (also called Kernechtrot dye, stains red), and methyl green (stains green); non-nuclear chromogenic stains, such as eosin (stains pink); fluorescent nuclear stains, including 4', 6-di-amino-2-pheylindole (DAPI, stains blue), propidium iodide (stains red), Hoechst stain (stains blue), nuclear green DCS1 (stains green), nuclear yellow (Hoechst S769121, stains yellow under neutral pH and stains blue under acidic pH), DRAQ5 (stains red), DRAQ7 (stains red); fluorescent non-nuclear stains, such as fluorophore-labelled phalloidin, (stains filamentous actin, color depends on conjugated fluorophore).

III. Methods and Systems for Staining and Analysis of Cytology Samples

In an embodiment, the systems and methods for affinity staining Romanowsky-stained cytology samples are integrated into a workflow for cytological and biomarker analysis of cytology samples.

Figure 2:
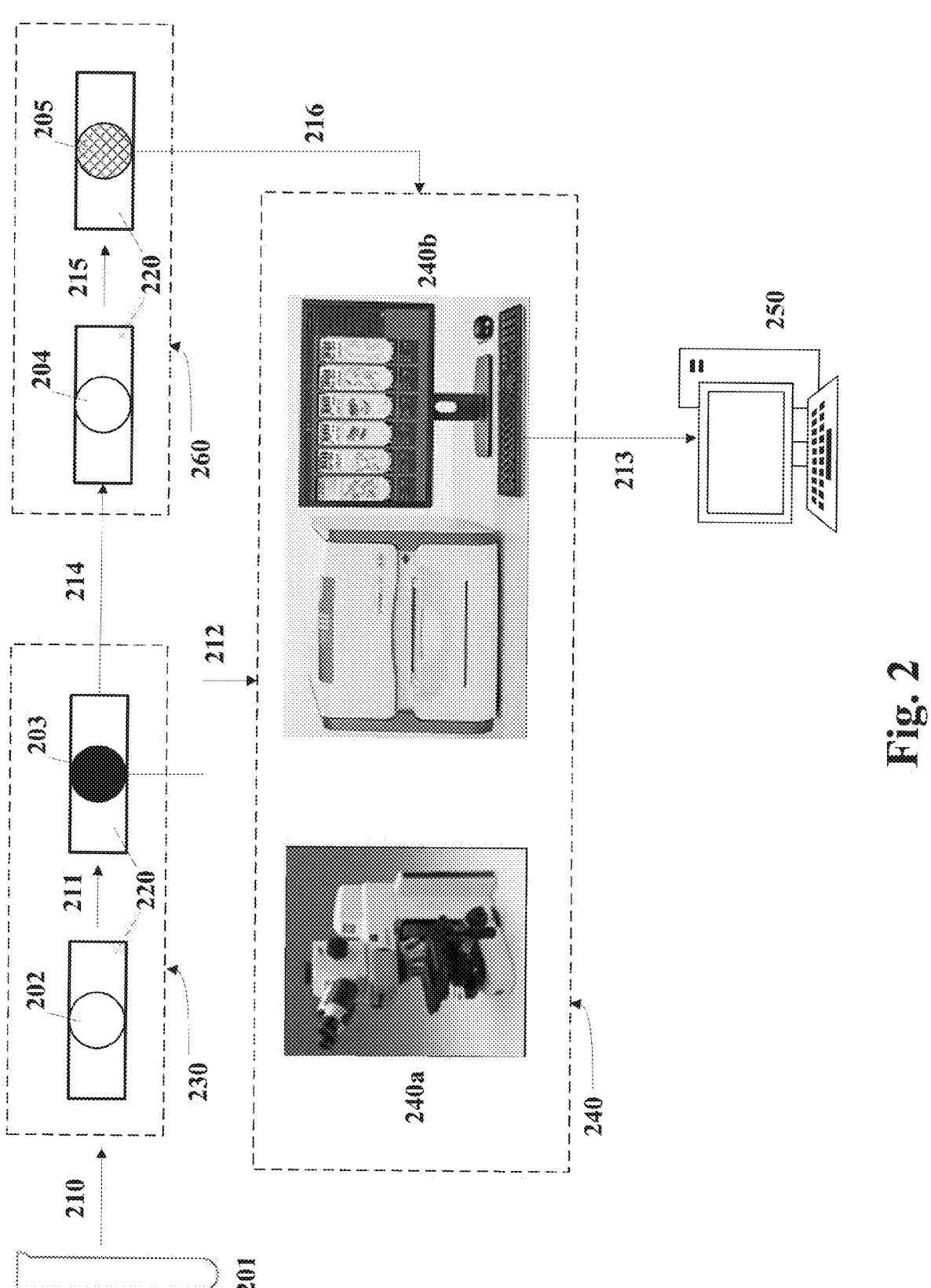
FIG. 2 illustrates an exemplary workflow for staining and evaluating cytology samples.

An exemplary workflow is illustrated at FIG. 2. Cellular samples 201 are obtained and applied 210 to a solid support 220 to obtain a cytology preparation 202. The cytology preparation 202 is stained with a Romanowsky-type stain 211 to obtain a Romanowsky-type stained cytology sample 203. The Romanowsky-type stained cytology sample 203 is then imaged on an imaging platform 240 for morphological analysis 212, which may comprise manual microscopic evaluation 240a and/or generating a digital image 240b of the Romanowsky-type stained cytology sample 203). Where a digital image is obtained, morphological analysis 212 may further comprise digital image analysis 213 on an image analysis platform 250. The solid support 220 is placed on an automated advanced staining platform 260, and the Romanowsky-type stained cytology sample 203 is subjected to a destaining step 214 to obtain a fully destained cytology sample 204. The fully destained cytology sample 204 is then affinity stained with or more sets biomarker-specific reagents and detection reagents 215 to obtain a biomarker-stained cytology sample 205. The biomarker-stained cytology sample 205 is then evaluated for biomarker-expression 216 (which may include manual microscopic evaluation 240a and/or generating a digital image of the biomarker-stained cytology sample 205 on a scanning platform 240b).

Where a digital image is obtained, biomarker analysis 216 may further comprise digital image analysis 213 on an image analysis platform 250.

III.A Samples

In an exemplary embodiment, the cellular sample 201 is from a sample type selected from the group consisting of a body fluid sample (such as whole blood, bone marrow, urine, semen, saliva, sputum, nipple discharge, breast milk, synovial fluid, cerebrospinal fluid (CSF), ascites fluid, peritoneal fluid, pericardial fluid, bile, gastric fluid, mucus, lymphatic fluid, perspiration, lacrimal fluid, vomit, pleural fluid, cerumen, nasal discharge/secretions, or skene's gland fluid), body fluid fractions (such as blood fractions, including plasma, buffy coat, and erythrocyte fractions), fine needle aspirates (such as bone marrow aspirate), washings (such as bronchial lavage, bronchoalveolar lavage, nasal lavage, douche, or enema), and scrape or brush samples (such as scrapings or brushes from the cervix, anus, mouth, esophagus, stomach, or bronchi).

III.B Solid Supports

Solid supports 220 useful in the present methods and systems generally are those that are compatible with brightfield or fluorescence microscopy. In some embodiments, a solid support 220 is selected that retains a substantial portion of cells of interest from the cellular sample 201 to remain adhered to the solid support 220 throughout the staining processes described herein. In an embodiment, the solid support 220 is a microscope slide. Microscope slides are typically thin (0.085-2.0 mm) glass or plastic substrates with flat parallel surfaces used to attach cells for analytical purposes. Microscope slides may be coated or uncoated depending upon the end use. More generally, solid support 220 can be implemented as any of a wide variety of different sample carriers. Sample carriers can be planar (e.g., microscope slides, coverslips, plates, trays, and other members that extend in two dimensions and have a relatively narrow thickness). Alternatively, sample carriers can be non-planar, and can be implemented as cups, tubes, vials, and other similar containers, with cross-sectional shapes that include, but are not limited to, circular, elliptical, square, rectangular, triangular, and other polygonal shapes. The type of sample carrier used can depend on the type of sample and process requirements in a preparative workflow. For example, to support tissue samples, planar microscope slides and coverslips can be used. Where the sample includes a relatively high proportion of liquid, sample carriers with one or more wells or cups (e.g., a single-well or multi-well sample plate) may be more convenient.

In general, sample carriers are used to carry (e.g., contain or support) samples at various processing stations. Sample carriers can be constructed from a variety of materials, including but not limited to glasses, plastics, metals, and natural materials such as mica, quartz, and sapphire.

In certain embodiments, sample carriers include one or more fiducial marks, indicators, or reference marks. These marks can be used to register the position of the sample carriers within a coordinate system of an automated sample handling and preparation system and/or establish an instrument-independent coordinate system. In systems with multiple processing stations, the marks can be located and used to determine coordinate transformations that can be applied to convert coordinates of one processing station into coordinates of another processing station

III.C Obtaining Thin Layers

The cellular sample 201 is applied to the solid support 220 in a manner that obtains cytology preparation. In an embodiment, the cytology preparation 202 is a thin layer cytology preparation. Exemplary methods of obtaining thin layer cytology preparations from cellular samples include cytocentrifugation, filter-transfer, gravity sedimentation, and cell printing.

In cytocentrifugation, a cell sample 201 is provided as a liquid sample (such as a suspension in a carrier solution or as a body fluid sample), placed in contact with the solid support 220, and centrifuged. Force generated by the centrifugation causes the cells to sediment on the surface of the solid support 220, thereby forming the cytology preparation 202. The quality and content of the thin layer obtained by cytocentrifugation may be optimized by, for example, manipulating the sample prior to centrifugation, for example, by adjusting cell concentration, liquifying or diluting viscous samples, removing precipitates or debris, lysing erythrocytes in blood samples, fixing the sample, etc. See generally Stokes. Typical cytocentrifugation systems include a centrifugation chamber assembly and a rotor. The centrifugation chamber assembly typically includes a solid support and a vessel for carrying the suspension of the cell sample 201. When assembled, the vessel places a surface of the suspension in contact with a surface of the solid support 220. Centrifugation chambers can generally be divided into two classes: chambers that facilitate removal of fluid during sedimentation (for example, by placing an absorbent material adjacent to an interface between the vessel and the solid support) and chambers that facilitate retention of the liquid throughout centrifugation (for example, by placing a seal around the periphery of an interface between the vessel and the surface of the solid support). Illustrations of such arrangements can be seen at Stokes at F1, incorporated herein by reference. In operation, an assembled centrifugation chamber is attached to the rotor in an orientation such that rotation of the rotor causes the cells of the cell sample 201 to be sediment on the surface of the solid support 220. Exemplary commercially available cytocentrifugation systems include CYTOSPIN systems from Thermo Scientific. Exemplary protocols for performing cytocentrifugation can be found at, for example, Koh. In some specific embodiments, the sample is a prepared by a cytocentrifugation onto a microscope slide.

In filter-transfer cytology preparation techniques, the cell sample 201 is passed through a filter. Pores in the filter are sized such that cell fragments and other detritus in the sample pass through the filter, while cells are retained on a surface of the filter. The surface of the filter is then pressed against the surface of a solid support, thereby depositing a thin layer of cells on the solid support 220 to obtain the cytology preparation 202. Typical systems for filter-transfer cytology preparation include a filter (in some cases, a disposable filter), and a receptacle for placing the liquid sample in contact with a surface of the filter. In some cases, liquid flows through the filter by gravity. In other cases, the system includes a means for applying an external force (such as a centrifuge or vacuum) to the filter to draw the fluid through the filter. Exemplary commercially available filter-transfer cytology preparation systems include THINPREP system from Hologic (formerly Cytyc Corporation). Exemplary considerations for performing filter-transfer cytology preparation can be found at Zahniser and Hurley. In some specific embodiments, the sample is a prepared by a filter-transfer onto a microscope slide. In some specific embodiments, the sample is a cervical cytology sample prepared by a filter-transfer method.

In gravity sedimentation cytology preparation, a liquid cell sample 201 is placed over a surface of the solid support, and cells in the sample are allowed to sediment under gravity onto the surface of the solid support 220 to obtain the cytology preparation 202. Systems for performing gravity sedimentation cytology preparation typically include at least a chamber that can be mounted on top of the solid support to hold the liquid sample 201 in proximity to the surface of the solid support 220. In some cases, a solid support 220 made of a material or coated with a material that improves adherence of cells to the surface of the solid support is also provided. Exemplary commercially available gravity sedimentation cytology preparation systems include SURE-PATH system and the PREPSTAIN system, both from BD Biosystems, Inc. In some embodiments, the sample is a prepared by a gravity sedimentation onto a microscope slide.

In cell printing methods, small volumes (for example, from 0.1 to 10 µl) of a liquid cell sample 201 are deposited at discrete locations on a surface of the solid support 220, and the deposited sample is allowed to dry on the surface to obtain the cytology preparation 202. For example, liquid sample 201 may be flowed through an applicator tip that is moved relative to the surface of the solid support (e.g. in parallel rows or in concentric circles on the surface of the solid support), thereby forming a monolayer having a substantially uniform distribution of cells on the surface of the solid support 220. Exemplary systems for performing cell printing typically include at least an applicator tip for dispensing a known volume of the liquid cellular sample 201 and means for changing the position of the applicator tip relative to the surface of the solid support 220 (e.g. means for moving the tip, means for moving the solid support, or both). Exemplary commercially available cell printing systems include COBAS m 511 integrated hematology analyzer from Roche, various aspects of which are describe at U.S. Pat. Nos. 8,815,537, 9,116,087, 9,217,695, and 9,602,777, each of which is incorporated by reference in its entirety. Exemplary methodologies for using cell printing systems for generating cytology slides can be found at Bruegel. In some specific embodiments, the sample is a body fluid sample printed on a slide. In some specific embodiments, the sample is a whole blood sample printed on a slide.

In a cell printing system such as the COBAS m 511 system, a sample featuring a suspension of cells in a fluid medium is prepared on a sample carrier such as a microscope slide for analysis. Where the sample corresponds to a whole blood sample or a suspension of blood components in a fluid, the cell printing system prepares a layer of cells on the sample carrier. In certain embodiments, the layer of cells that is deposited effectively corresponds to a monolayer in which the cells are approximately homogeneously distributed. The cell layer can include any one or more of red blood cells, white blood cells, and platelets.

To deposit the sample on the sample carrier, the system may optionally dilute the sample (e.g., with a buffer solution, a stain solution, or more generally, any diluent material) and an aliquot of the diluted sample is applied to the sample carrier. Following application of the sample, cells within the sample begin to settle to the surface of the sample carrier. If applied under certain conditions, the settled cells do not overlap, and instead form the desired monolayer.

In general, cell printing systems such as the COBAS m 511 integrated hematology analyzer include an applicator and a stage that supports the sample carrier. The sample is discharged from the applicator as relative motion occurs between the applicator and stage. By carefully controlling the relative positions of the applicator and stage (as well as various other system parameters), the sample can be applied to the sample carrier in a reproducible manner.

In some embodiments, the sample is applied to the surface of the sample carrier in a series of rows. For example, the applicator may be positioned at a top left corner of a sample region on the sample carrier, and relative motion in one direction (say, the x-direction) of the applicator and the stage occurs as the sample is discharged from the applicator, depositing a row of sample onto the sample carrier. At the end of the row, relative motion of the applicator and the stage occurs in an orthogonal direction (say, the y-direction) to begin a new sample row. The width of a single sample row when initially applied to the sample carrier can be between 300 microns and 1000 microns. In general, the row thickness (i.e., measured in a direction orthogonal to the relative motion of the applicator and stage during discharge of the sample) increases as the flow rate of fluid out of the applicator increases and/or the translation speed of the applicator relative to the stage decreases.

As noted above, when the applied sample features suspended cells in a fluid medium, the cells settle onto the surface of the sample carrier within a few seconds after they are applied to the surface. The number of cells applied to the sample carrier according to the foregoing methods can vary significantly based on the number of cells per unit volume in the sample, and any dilution steps prior to discharging the sample onto the sample carrier. For example, assuming whole blood is analyzed at a 1:3 blood: diluent ratio, about 900,000 red blood cells, 45,000 platelets, and 1,000 white blood cells would be placed on the slide.

For blood samples, the microscopic appearance of the sample deposited on a sample carrier is similar to the appearance of a well-prepared blood "smear". However, while many manually-prepared smears typically have a wedge shape—with differing distributions of cells at the margins-samples applied to sample carriers using automated cell printing systems typically have a more homogeneous distribution of cells, even at the margins. Moreover, the morphology of white and red blood cells typically is not altered, as it can be in manually-prepared blood smears.

In some embodiments, a sample is diluted before it is applied to the surface of a sample carrier. Various diluents can be used, depending upon the nature the sample, including (but not limited to) salt solutions and protein solutions. Salt solutions range from "physiological saline" (0.9 N), to complex mixtures of salts, to the commercial preparation Plasmalyte that simulates virtually all the salts found in human blood serum. Protein solutions can range from simple solutions of bovine albumin to Plasmanate®, a commercial preparation with selected human plasma proteins. Such preparations can vary in protein concentrations, buffers, pH, osmolarity, osmolality, buffering capacity, and additives of various types. Synthetic or "substitute" versions of these solutions may also be usable, including Ficoll® or Dextran or other polysaccharides. Other substitutes may be used. An example of a diluent is Plasmalyte plus Plasmanate® in the proportion of 4:1 (Plasmalyte: Plasmanate®). Another example of a diluent is 5% albumin. When preparing samples from whole blood, a dilution of 2 parts blood to 1 part diluent can be used, where the diluent is a physiologically compatible solution, but a range of dilution from 0:1 (no dilution) to 10:1 (diluent: blood) can be used.

To apply the sample (diluted or undiluted) to the sample carrier, fluid flow through the applicator is controlled. The flow rate through the applicator, the height of the applicator above the sample carrier, and the relative translation speed between the applicator and the sample carrier are all controlled to adjust the distribution of sample on the sample carrier surface.

As discussed above, the sample can be applied to the sample carrier in a pattern of rows by discharging the sample from the applicator during relative motion between the applicator and the stage. More generally, the sample can be applied to the sample carrier in a wide variety of different patterns. Examples of such patterns include, but are not limited to, boustrophedon patterns, raster patterns, continuous spiral patterns, patterns of multiple concentric circles, patterns of multiple parallel lines, and serpentine patterns.

In some embodiments, where the sample includes cells, the sample can be applied to the sample carrier to form a monolayer of cells (e.g., a layer of cells approximately one cell thick). The height of the sample layer applied can range from less than 1 micron to 10 microns or more. The sample can be applied in one continuous flow or in multiple flows that are spaced apart or are applied side-by-side or even contacting each other.

In certain embodiments, the flow rate of the sample dispensed from the applicator can be 0.1 microliters per second while the applicator is translated at a speed of 30 millimeters per second relative to the surface of the sample carrier, at a height of about 5 to 100 microns, e.g., 15 to 50 microns, 10 to 15 microns, 20 to 40 microns, 5 to 15 microns, about 12 microns. As another example, when applying an undiluted blood sample to the surface of a sample carrier, the sample flow rate through the applicator can be approximately 0.04 microliters per second, e.g., 0.02 to 0.10, 0.02 to 0.05, or 0.03 to 0.04 microliters per second, while the applicator is translated at a speed of about 50 millimeters per second, e.g., 10 to 100, 20 to 80, 30 to 70 millimeters per second relative to the sample carrier surface, and while the applicator is at a height of 10, 12, 14, 15, 20, or 25 microns above the sample carrier surface.

Certain types of cells such as red blood cells tend to aggregate when present in large numbers, leading to stacking which can be more prevalent in the first few rows of dispensed sample on a sample carrier than in later-dispensed rows, leading to an inhomogeneous distribution of cells on the surface of the sample carrier. To mitigate cell stacking, the rate at which the sample applicator is translated relative to the sample carrier (i.e., relative to the stage that supports the sample carrier) can be increased. In general, the sample applicator can be translated relative to the sample carrier using a variety of techniques. For example, in some embodiments, the stage which supports the sample carrier is translated, while the sample applicator remains essentially fixed in position. In certain embodiments, the applicator is translated while the sample carrier mounted on the stage remains essentially fixed in position. In some embodiments, both the applicator and the stage are translated. Each of the foregoing techniques results in translation of the sample applicator relative to the sample carrier. Further it should be understood that unless specifically disclosed otherwise herein, references to "translating" the applicator imply a relative translation of the applicator with respect to the stage and sample carrier, and can be implemented by translating the applicator while the sample carrier remains essentially fixed in position, by translating the stage while the applicator remains essentially fixed in position, and by translating both the applicator and the stage.

In some embodiments, the relative translation speed between the applicator the sample carrier on the stage can be between 40 mm/s and 90 mm/s (e.g., between 50 mm/s and 80 mm/s, between 60 mm/s and 70 mm/s) to significantly reduce or eliminate cell stacking on the sample carrier.

In certain embodiments, "target" cells (i.e., cells with a depressed central pallor) can form on the sample carrier from red blood cells that dry too slowly after being dispensed onto the surface of the sample carrier. To reduce or eliminate target cell formation and loss of the shape of the central pallor of red blood cells, the rate of cell drying can be controlled by adjusting the sample dispensing rate through the applicator. Adjusting the dispensing rate to a suitably high value also helps to prevent cell stacking. In some embodiments, for example, the fluid dispensing rate through the applicator is 0.020 µL/s or more (e.g., 0.030 µL/s or more, 0.035 µL/s or more, 0.040 µL/s or more, 0.050 µL/s or more, 0.060 µL/s or more, 0.070 µL/s or more, 0.075 µL/s or more, 0.080 µL/s or more, 0.090 µL/s or more, 0.100 µL/s or more) to reduce target cell formation and cell stacking on the sample carrier. In certain embodiments, ranges of sample dispensing rates that fall within the ranges disclosed above can be used. For example, the sample dispensing rate through the applicator can be between 0.035 µL/s and 0.075 µL/s.

More generally, the sample dispensing rate and relative translation speed of the applicator are matched to one another to yield samples of sufficient quality. If the applicator is translated relative to the sample carrier surface at a rate that is too high relative to the sample dispensing rate, then the sample is "pulled" from the applicator, resulting in a non-uniform distribution of sample (i.e., cells) on the sample carrier surface, and loss of the cells' natural shape (e.g., loss of pallor). Conversely, if the applicator is translated at a rate that is too low relative to the sample dispensing rate, then sample fluid pools near the applicator tip, which also results in a non-uniform cell distribution. Accordingly, the applicator translation speed and sample dispensing rate are selected in combination to ensure that cells are uniformly deposited, that they retain their natural shape, and that the overall deposition process occurs within a suitably short processing time.

For samples that are applied to the sample carrier surface in a pattern of rows, adjusting the row separation (e.g., by controlling the displacement of the applicator between dispensing of the sample in adjacent rows) can be used to compensate for several phenomena that affect the quality of prepared samples. In general, as the amount by which adjacent rows overlap increases, the uniformity of the sample layer on the sample carrier increases. However, when the amount of overlap increases, deposited cells take longer to dry on the sample carrier, which can lead to shape distortion (e.g., loss of central pallor and/or target cell formation). In general, row separations of between 0.20 mm and 0.60 mm (e.g., between 0.25 mm and 0.55 mm, 0.30 mm and 0.40 mm) can be used to compensate for such factors.

Sample fluids differ in their viscosities, and even different samples of a particular type of fluid such as blood can have different viscosities. Adjusting the row separation can compensate for such variations between samples. In general, as the viscosity of a sample increases, the adjacent row separation is increased (e.g., the extent of overlap between adjacent rows is reduced) to avoid forming overlapped regions with cell concentrations that are significantly larger than in non-overlapped regions; as more viscous fluids do not flow as freely as less viscous solutions, inhomogeneous distributions of cells on the sample carrier do not disperse as readily as in less viscous solutions). It has been observed that for blood samples in general, a row separation of about 0.4 mm yields rows that flow toward each other and just touch, yielding a highly uniform sample.

The viscosity of the sample that is dispensed onto the sample carrier can change during deposition, so that the viscosity of the first few rows differs from the viscosity of the final few rows that are dispensed. For example, if the final rows dispensed have a lower viscosity, they will flow together and overlap to a greater extent than the first few rows. To compensate for this variation, the separation between adjacent rows can be adjusted during the dispensing of the sample onto the sample carrier. For example, the separation between adjacent rows can be increased during dispensing of the sample so that despite the differences in viscosity, the amount of overlap between adjacent rows remains approximately the same. The separation can be adjusted in linear fashion between successive rows. Alternatively, the separation can be adjusted in non-linear fashion (e.g., according to an exponential function).

Maintaining a "wet edge" during dispensing of rows of a sample onto the sample carrier can be an important aspect of the sample deposition process to ensure that deposited samples are uniform. The "wet edge" refers to the edge of the previously dispensed row that is nearest to the row of sample currently being dispensed onto the sample carrier surface. Maintaining a "wet" edge refers to ensuring that the edge of the previously dispensed sample row that is nearest to the current row does not completely dry before the current row is deposited, and therefore flows together with the row that is being currently dispensed so that the rows contact one another. By ensuring that the previous row is not completely dry, sample from the previous row and from the current row can flow together when the current row is deposited, leading to a more uniform distribution of cells on the sample carrier surface when the sample is subsequently dried.

More generally, maintaining a "wet edge" refers to adjusting properties of the fluid deposition system to ensure that each row of sample dries for only a certain length of time before a subsequent sample row is dispensed, to ensure that successively dispensed rows flow together to contact one another and leave a distribution of cells on the sample carrier surface that is relatively uniform on the surface once sample dispensing is complete and the sample dries. Because maintaining a "wet edge" is an important aspect to ensure that the deposited cells retain their shape and are distributed homogeneously, adjustment of the row length can be used to directly influence the quality of the samples that are applied to the substrate carrier.

Typically, row lengths are adjusted so that rows of dispensed sample occupy a percentage of the available area on the sample carrier surface. In some embodiments, for example, the sample carrier surface is rectangular in shape, and dispensed rows of fluid extend along 60% or more (e.g., 70% or more, 80% or more, 90% or more, 95% or more, 99% or more) of the longer dimension of the rectangular surface. The row length can be adjusted during dispensing, so that not all rows of sample have the same length. For example, the row length can be changed to account for changes in the composition of the sample, the temperature, and/or the humidity during sample deposition.

In certain embodiments, rows of sample can be dispensed along different directions on the surface of the sample carrier. For example, to shorten the row length on a sample carrier with a rectangular surface, rows of sample can be deposited by translating the applicator in a direction parallel to the shorter dimension of the rectangular surface. More generally, rows of sample can be deposited by translating the applicator in any direction relative to the plane of the sample carrier surface. Thus, for example, to dispense rows of sample that are intermediate in length between the short and long dimensions of a rectangular sample carrier surface, the rows of sample can be dispensed at an angle to both surface edges; the angle can be selected to adjust the time delay between successive rows.

When translating the applicator in a direction parallel to the shorter dimension of the rectangular surface, certain row lengths provide particularly advantageous conditions for maintaining a "wet edge" during sample deposition, and for drying the deposited sample. In particular, high quality preparations (e.g., sample carriers on which cells are deposited uniformly and cell morphology is preserved) are obtained when the dispensed rows of sample extend along 80% or more (e.g., 85% or more, 90% or more, 95% or more) of the shorter dimension of the rectangular surface of the sample carrier.

III.D Fixation

In an embodiment, the cytology preparations 202 may be fixed or unfixed.

In an embodiment, the fixation is a chemical fixation process, comprising a precipitating fixative and/or a cross-linking fixative. Exemplary precipitating fixatives include alcohols (such as methanol and ethanol), acetone, and picric acid. Exemplary cross-linking fixatives include aldehydes, such as glutaraldehyde- and/or formalin-based solutions. Examples of aldehydes and common working concentrations used for fixation include: formaldehyde (standard working concentration of 5-10% formalin for most cellular samples, although concentrations as high as 20% formalin have been used for certain tissues); glyoxal (standard working concentration 17 to 86 mM); and glutaraldehyde (standard working concentration of 200 mM). Specific examples of common fixative solutions are set forth in Table 5:

TABLE 5

| Solution | Standard Composition |
| --- | --- |
| Neutral Buffered Formalin | 5-20% formalin + phosphate solution |
| Formal Calcium | 10% formalin + 10 g/L calcium chloride |
| Formal Saline | 10% formalin + 9 g/L sodium chloride |
| Zinc Formalin | 10% formalin + 1 g/L zinc sulphate |
| Helly's Fixative | 50 mL 100% formalin + 1 L aqueous solution containing 25 g/L potassium dichromate + 10 g/L sodium sulfate + 50 g/L mercuric chloride |
| B-5 Fixative | 2 mL 100% formalin + 20 mL aqueous solution containing 6 g/L mercuric chloride + 12.5 g/L sodium acetate (anhydrous) |
| Hollande's Solution | 100 mL 100% formalin + 15 mL Acetic acid + 1 L aqueous solution comprising 25 g copper acetate and 40 g picric acid |
| Bouin's Solution | 250 mL 100% formalin + 750 mL saturated aqueous picric acid + 50 mL glacial acetic acid |
| Carnoy's solution | 6:3:1 (v/v) absolute ethanol:chloroform:glacial acetic acid |
| Methacarn | 6:3:1 (v/v) absolute methanol:chloroform:glacial acetic acid |
| Gendre's solution | 16:3:1 (v/v) of 95% ethanol saturated with picric acid:40% formaldehyde:glacial acetic acid |

TABLE 5-continued

| Solution | Standard Composition |
|---|---|
| Clarke's solution | 3:1 (v/v) absolute ethanol:glacial acetic acid |
| Alcoholic formalin | 9:1 (v/v) 95% ethanol:40% formaldehyde, optionally including calcium acetate |
| Formol acetic alcohol | 17:2:1 (v/v) absolute ethanol:40% formaldehyde:glacial acetic acid |
| Methanol | From 60-100% Methanol, including 95%, 96%, 97%, 98%, 99% or absolute Methanol |
| Ethanol | From 60-100% Ethanol, including 95%, 96%, 97%, 98%, 99% or absolute Ethanol |
| Acetone | Acetone |
| Methanol-Acetone | 1:1 (v/v) absolute methanol + acetone |
| Methanol-Ethanol | 1:1 (v/v) methanol + ethanol |

In an embodiment, the fixative is selected from one of the fixatives of Table 5. In an embodiment, the sample is fixed with a fixative comprising formalin. In another specific embodiment, the fixative is a neutral buffered formalin (NBF). In another embodiment, the fixative is 10% NBF. In another specific embodiment, the fixative comprises methanol. In another embodiment, the fixative is from 90% to 100% methanol, such as 90%, 91%, 92%, 93%, 94%, 95%, 96%, 97%, 98%, 99%, or absolute methanol. In another embodiment, the fixative is from 90% to 100% ethanol, such as 90%, 91%, 92%, 93%, 94%, 95%, 96%, 97%, 98%, 99%, or absolute ethanol. Fixation may occur before the sample is deposited on the solid surface or after. In an embodiment, the cell sample 201 is first fixed, and then deposited on a solid support via an automated cytology preparation system 230 to obtain the cytology preparation 202. For example, on the PREPSTAIN system, cell samples 201 are collected and then placed in a fixative solution for transport. Once in the laboratory, the fixed cell sample 201 is enriched via density gradient centrifugation, and the enriched cell sample is deposited on a solid support 220 via gravity sedimentation to obtain the cytology preparation 202. In some embodiments, the sample is first deposited on a solid support via an automated cytology preparation system 230 and then fixed. For example, whole blood samples processed on a COBAS m 511 platform (Roche) are first printed, air dried, and then fixed on the solid support.

III.E Romanowsky-Type Staining of Thin Layers

In some embodiments, the cytology preparation 202 is stained with a Romanowsky-type stain to obtain the Romanowsky-type stained sample 204. As used herein, the term "Romanowsky-type stain" refers to a metachromatic stain useful for staining cytology samples, wherein the stain comprises a cationic thiazine dye (such as polychrome methylene blue, azure A, azure B, azure C, azure IV, sym-dimethylthionine, thionine, methylene violet Bernsthen, methylthionoline, toluidine blue, and combinations thereof) and an anionic halogenated fluorescein dye (such as eosin A, eosin Y, eosin G, and combinations thereof). Exemplary Romanowsky-type stains include original Romanowsky stain (i.e polychrome methylene blue+eosin Y), Malachowski stain, Giemsa stain, May-Gruenwald stain, May-Gruenwald-Giemsa (MGG) stain, Jenner stain, Wright stain, Leishman stain, and DIFF-QUICK (proprietary modified Wright stain), just to name a few. An overview of the history of Romanowsky-type stains and various specific methodologies for making and using Romanowsky-type stains can be found at, for example, Bain, Horobin, Krafts I, and Krafts II. In an embodiment, the Romanowsky-type stained sample 203 is obtained by staining the cytology preparation 202 with a Romanowsky-type stain comprising azure B and eosin A or eosin Y in an alcohol solvent. The Romanowsky-type stain can be applied manually, or as part of an automated workflow. The Romanowsky-type staining can be performed before or after fixation. In some embodiments, the Romanowsky-type stain may be performed during deposition of the sample 210 on the solid support 220. In some embodiments, Romanowsky-type staining is incorporated into an automated cytology slide deposition platform 230.

As an example, in some embodiments, the COBAS m 511 automated hematology analyzer can be used to stain and fix samples that are deposited on sample carriers. As discussed previously, this system can also be used to deposit the samples, and can exercise control over a wide variety of deposition parameters to ensure that homogenous, high quality samples are applied to the sample carriers. In general, in the COBAS analyzer, a sample carrier on which a sample is deposited is positioned above a platform with multiple integrated ports. The platform can optionally include multiple offsets to maintain a spacing between the sample carrier and the platform. Various fluids, including stains, fixatives, and rinsing solutions can be applied to the sample on the sample carrier by circulating the fluids within the space between the sample carrier and the platform. As part of a preparative workflow for samples of interest, after the sample has been applied to the sample carrier as discussed previously, the sample is fixed to preserve its biological and chemical structure prior to examination. Fixatives that can be used for this purpose include chemicals used for protecting biological samples from decay, and such fixatives can impede biochemical reactions occurring in the specimen and increase the mechanical strength and stability of the specimen. To apply a fixative solution to the sample, a pump directs the fixative solution through one or more of the ports on the platform surface and into the space between the platform and the sample carrier. The fixative solution is circulated within the space, and then pumped out of the space by a pump connected to one or more additional ports on the platform surface. The process of introducing and removing fixative solutions can be repeated using the same or different fixative solutions, depending on the type of sample. Further, the frequency and flow rates for each fixing phase can be varied depending upon the nature of the sample. Following fixation, as part of the sample processing workflow, one or more stains can be applied to the sample. A variety of different stains and dyes can be applied singly or in combination. In general, a pump directs a stain solution through one or more ports in the platform and into the space between the platform and the sample carrier. The stain solution circulates within the space to ensure homogeneous contact with the sample on the sample carrier, and is then removed by a pump connected to one or more ports on the platform. Staining and evacuation phases can be repeated after a delay (e.g., a delay of between 3 seconds and 10 seconds, such as a five second delay), following a first staining phase. Moreover, additional stains can be applied in a similar manner to the sample. The frequencies, delay times, and flow rates for each staining solution can be adjusted to control the manner in which each stain is applied to the sample. The flow rate may range, e.g., from 70 to 140 microliters per second, or may be smaller or greater than the outer limits of this range (e.g., 10 to 500 microliters per second) provided the flow rate is sufficient to overcome surface tension present in the staining solution within the space between the platform and the sample carrier. Following fixation and/or staining phases, in some embodiments, one or more rinsing solutions can be used to remove residual staining solutions and/or fixative solutions from the sample. Rinse solutions can be applied during sample processing (e.g., interleaved with staining and/or fixing phases), or afterward in one or more rinse phases. For example, it may be desirable to remove residual and/or excess fluids from the sample and the space between the platform and sample carrier between fixing phases, between staining phases, and/or between fixing and staining phases. Rinse solutions that can be used include, but are not limited to, distilled water; buffered, aqueous solutions; organic solvents; and mixtures of aqueous and organic solvents, with or without buffering. To rinse the sample, a pump connected to one or more ports on the surface of the platform delivers a rinsing solution through the one or more ports and into the space between the platform and the sample carrier surface. The rinsing solution circulates within the space for a period of time, and then is pumped out the of the space by a pump connected to one or more additional ports on the platform surface. The rinsing solution can be introduced at a flow rate of, e.g., 70 microliters per second for a period of, e.g., five seconds. As with fixing and staining phases, the duration and flow rate of each rinsing phase and the number of rinsing phases can be adjusted. For example, a rinsing phase may occur once, after completion of all fixing phases, and a second rinse phase may occur once, after completion of all staining phases. Alternatively, rinse phases may be interspersed between two or more fixing phases or between two or more staining phases. During any of the fixation, staining, and rinsing phases, solutions introduced into the space between the platform and the sample carrier can be circulated in a variety of ways. In some embodiments, for example, the solutions/fluids can be introduced in a pulsatile manner through one or more platform ports, and removed through one or more additional platform ports. The non-constant, pulsatile flow can effectively function to circulate the solutions/fluids within the space so that regions of the sample are exposed relatively uniformly. In certain embodiments, mechanical agitation can be used to circulate the solutions/fluids within the space between the platform and sample carrier. Agitation can be performed by adjusting the position of the substrate carrier to vary the separation between the substrate carrier and the platform surface. Agitation can occur as part of one or more agitation phases, which can be interleaved with the other sample processing phases discussed above. To perform an agitation phase, the sample carrier can be displaced from its sample processing position vertically relative to the platform surface, and then subsequently returned to the sample processing position. Agitation phases can occur three times, once after each fixing, staining, and rinsing phase. The agitation frequency and distance for each agitation cycle and/or phase can be varied according to the extent of agitation desired to ensure proper circulation of fluid with in the platform-sample carrier space. For example, the agitation frequency for each cycle within an agitation phase may be between 10 Hz and 20 Hz. Various combinations of agitation distances (i.e., displacements of the sample carrier from the sample processing position) and frequencies can be used. For example, in some embodiments, the agitation distance is 5 microns or more (e.g., 15 microns or more, 25 microns or more, 50 microns or more, 100 microns or more, 150 microns or more, 200 microns or more, 250 microns or more, 300 microns or more, 500 microns or more, 700 microns or more, 1 mm or more). In certain embodiments, the agitation distance is between 35 microns and 350 microns. In some embodiments, the agitation cycle frequency is one cycle per second or more (e.g., two cycles per second or more, three cycles per second or more, four cycles per second or more, five cycles per second or more, seven cycles per second or more, ten cycles per second or more).

III.F Microscopic Evaluation, Digital Imaging and Image Analysis

After Romanowsky-type staining, the Romanowsky-type stained sample 203 is evaluated microscopically 212. Likewise, after biomarker staining, the biomarker-stained sample 205 is evaluated microscopically 216. In some embodiments, the microscopic evaluation may comprise scanning the sample(s), for example, on a scanning platform 240b to produce a high resolution digital images of the Romanowsky-type stained and/or biomarker-stained cells. At a basic level, the typical scanning platform 240b includes at least: (1) a microscope with lens objectives, (2) a light source (such as halogen, light emitting diode, white light, and/or multispectral light sources, depending on the dye), (3) robotics to move glass slides around (or to move the optics around the slide), (4) one or more digital cameras for image capture, (5) a computer and associated software to control the robotics and to manipulate, manage, and view digital slides. Digital data at a number of different X-Y locations (and in some cases, at multiple Z planes) on the slide are captured by the camera's charge-coupled device (CCD), and the images are joined together to form a composite image of the entire scanned surface. Common methods to accomplish this include:

(1) Tile based scanning, in which the slide stage or the optics are moved in very small increments to capture square image frames, which overlap adjacent squares to a slight degree. The captured squares are then automatically matched to one another to build the composite image; and (2) Line-based scanning, in which the slide stage moves in a single axis during acquisition to capture a number of composite image "strips." The image strips can then be matched with one another to form the larger composite image.

A detailed overview of various scanners (both fluorescent and brightfield) can be found at Farahani et al., Whole slide imaging in pathology: advantages, limitations, and emerging perspectives, Pathology and Laboratory Medicine Int'l, Vol. 7, p. 23-33 (June 2015), the content of which is incorporated by reference in its entirety. In some embodiments, the scanning platform is a stand-alone platform. Examples of commercially available slide scanners include: 3DHistech PANNORAMIC SCAN II; DigiPath PATHSCOPE; Hamamatsu NANOZOOMER RS, HT, and XR; Huron TISSUESCOPE 4000, 4000XT, and HS; Leica SCANSCOPE AT, AT2, CS, FL, and SCN400; Mikroscan D2; Olympus VS120-SL; Omnyx VL4, and VL120; PerkinElmer LAMINA; Philips ULTRA-FAST SCANNER; Sakura Finetek VISIONTEK; Unic PRECICE 500, and PRECICE 600x; VENTANA ISCAN COREO, VENTANA ISCAN HT, and VENTANA DP200; and Zeiss AXIO SCAN.Z1. Other exemplary systems and features can be found in, for example, WO2011-049608) or in U.S. Patent Application No. 61/533,114, filed on Sep. 9, 2011, entitled IMAGING SYSTEMS, CASSETTES, AND METHODS OF USING THE SAME the content of which is incorporated by reference in its entirety. In other embodiments, the scanning platform is integrated with an automated cytology preparation system, such as, for example, the COBAS m 511 platform ((integrates slide printing, fixation, staining, and image acquisition into a single automated workflow (Roche)). In some embodiments, the Romanowsky-type stained sample 202 and the biomarker-stained sample 205 are imaged on the same scanning platform 240b. In other embodiments, the Romanowsky-type stained sample 202 and the biomarker-stained sample 205 are imaged on different scanning platforms 240b.

Images generated by scanning platform 240b may be analyzed to identify one or more types of cells of interest on the image analysis system 250. Image analysis system 250 may include one or more computing devices such as desktop computers, laptop computers, tablets, smartphones, servers, application-specific computing devices, or any other type(s) of electronic device(s) capable of performing the techniques and operations described herein. In some embodiments, image analysis system 250 may be implemented as a single device. In other embodiments, image analysis system 250 may be implemented as a combination of two or more devices together achieving the various functionalities discussed herein. For example, Image analysis system 250 may include one or more server computers and a one or more client computers communicatively coupled to each other via one or more local-area networks and/or wide-area networks such as the Internet. Image analysis system 250 may include a memory, a processor, and a display. Memory may include any combination of any type of volatile or non-volatile memories, such as random-access memories (RAMs), read-only memories such as an Electrically-Erasable Programmable Read-Only Memory (EEPROM), flash memories, hard drives, solid state drives, optical discs, and the like. Processor may include one or more processors of any type, such as central processing units (CPUs), graphics processing units (GPUs), special-purpose signal or image processors, field-programmable gate arrays (FPGAs), tensor processing units (TPUs), and so forth. Display may be implemented using any suitable technology, such as LCD, LED, OLED, TFT, Plasma, etc.

The memory contains a set of instructions implemented by the processor on the digital image of the stained samples to perform the image analysis 213. For the Romanowsky-type stained samples, the set of image analysis instructions typically comprises morphological assessment of cells or cell constituents (i.e. nucleus, cytoplasm and/or membrane) to classify cell types found in the sample. For example, when the sample is a blood sample, the morphological analysis may comprise a complete blood count (CBC) analysis. CBC includes quantitation of the number of each constituent cell type-erythrocytes, leukocytes (total leukocytes, as well as relative numbers of neutrophils, lymphocytes, monocytes, eosinophils, and basophils), and platelets (total number, as well as range of sizes and mean platelet volume). For the biomarker-stained samples 205, the image analysis 213 typically comprises identification of biomarker-stained cells and/or localization of biomarker stain within the cell (i.e.

nuclear, cytoplasmic, or membrane) and/or stain pattern (i.e. homogenous or punctate) and/or stain intensity (e.g. strong, moderate, or weak) and/or number of ISH signals per cell. For example, when the sample is a blood sample, the image analysis 213 may comprise evaluating the stains for cells that express one or more protein biomarkers according to Table 6:

TABLE 6

| Biomarker | Information | Predicted localization |
|---|---|---|
| CD2 | All peripheral blood T-cells | Membrane |
| CD3 | T-cells | Membrane |
| CD4 | Effector T cell | Membrane |
| CD5 | T cells and most T cell lymphomas, a marker for CLL | Cell membrane |
| CD7 | Marker for T-ALL | Membrane |
| CD8 | Cytotoxic T cell | Membrane |
| CD10 | Acute lymphoblastic leukemia (ALL). Found on ALL cells which derive from pre-B lymphocytes | Membrane, intracellular |
| CD20 | B-cells | Membrane |
| CD23 | B-cell chronic lymphocytic leukemia (CLL) | Intracellular, Membrane |
| CD34 | AML marker. Poor prognostic factor in newly diagnosed AML | Intracellular |
| CD38 | Diagnosis of myeloma. Prognosis for CLL patients | Intracellular |
| CD45, LCA | Pan- leukocyte | Membrane |
| CD68 | Macrophages | Cytoplasm |
| CyclinD1 | Very specific for mantle cell lymphoma, Positive stain for B-CLL, Myeloma | Intracellular, nuclear stain |
| MPO | AML-M1, M2 | Intracellular |
| PAX-5 | Pan- B cells | Intracellular |
| TdT | Marker of B or T cell acute lymphoblastic leukemia/lymphoma | Intracellular |
| ZAP-70 | ZAP-70 in B cells is used as a prognostic marker in CLL identifying different forms of chronic lymphocytic leukemia (CLL) | Intracellular |

In another embodiment, the image analysis 213 is of blood sample stained for one of the panels of protein biomarkers of Table 7:

TABLE 7

| Panels | Biomarkers | Information | Localization |
|---|---|---|---|
| 1 | CD2 | All peripheral blood T-cells | Cell membrane |
| | CD4 | Effector T cells | Cell membrane |
| | CD5 | T cells and most T cell lymphomas, a marker for CLL | Cell membrane |
| | CD8 | Cytotoxic T cells | Cell membrane |
| | CD45 | Pan leukocytes | Cell membrane |
| 2 | CD3 | Pan T-cells | Cell membrane |
| | CD5 | T cells and most T cell lymphomas, Marker for CLL | Cell membrane |
| | CD10 | Diagnosis of pre B-ALL | Cell membrane |
| | CD23 | Marker for CLL | Intracellular and membrane |

TABLE 7-continued

| Panels | Biomarkers | Information | Localization |
|---|---|---|---|
| | Cyclin D1 | Positive stain for B-CLL | Nuclear, intracellular |
| 3 | Pax5 | Positive for B cell lymphomas | Intracellular |
| | CD5 | T cells and most T cell lymphomas, marker for CLL | Cell membrane |
| | CD23 | Marker for CLL | Intracellular and membrane |
| | CyclinD1 | Positive stain for B-CLL | Nuclear , intracellular |
| | CD3 | Pan T cell | Cell membrane |
| 4 | CD3 | All peripheral blood T-cells | Cell membrane |
| | CD5 | T cells and most T cell lymphomas, Marker for CLL | Cell membrane |
| | CD38 | Prognosis for CLL patients | Intracellular |
| | CD23 | Marker for CLL | Intracellular and membrane |
| | ZAP-70 | ZAP-70 B-CLL , normal T cell and NK cell | Intracellular |
| 5 | CD3 | Pan T cell marker | Membrane |
| | Pax5 | Most B cell malignancies | Intracellular |

In another example, the sample is stained by in situ hybridization for a single genomic locus, and the image analysis 213 comprises counting a number of genomic ISH signals per cell. In another example, the sample is a blood sample stained by in situ hybridization for a single genomic locus and a centromere region of the chromosome on which the genomic locus is expected to be found (termed a Dual ISH assay), and the image analysis 213 comprises counting a ratio between genomic ISH signals and centromere signals, such as, for example, HER2 and chromosome 17 centromere. In another embodiment, the sample is a blood sample stained by in situ hybridization at a genomic locus known to be involved in chromosomal translocation events, wherein a region of the genomic locus is stained with a first detectable entity on a 5' side of a breakpoint of the chromosomal translocation event and with a second detectable entity on a 3' side of the breakpoint (termed a break-apart ISH assay), and wherein the image analysis 213 comprises detection of a translocation event based upon co-localization of the $1^{st}$ and $2^{nd}$ detectable entities. Exemplary translocation events involved in cancer are discussed in detail by Parker & Zhang and Nickoloff, among many others. Additionally, online databases exist that collate different translocation events in cancers, such as the COSMIC database maintained by the Wellcome Sanger Institute.

In some embodiments, image analysis 213 further comprises annotating the location of the individually identified cells in the digital image. In some embodiments, the location of each biomarker stained cell is annotated, and the status of each cell for each biomarker is annotated. In some embodiments, this information is compared with the information obtained for the same cell in the Romanowsky-type stained image. For example, the Romanowsky-type stained sample 203 and the biomarker-stained sample 205 are imaged on the same automated imaging platform 240b, wherein the X-Y coordinates of each cell in the Romanowsky-type stained sample is annotated and the biomarker status at the same X-Y coordinate is annotated in the image of the biomarker-stained sample 205. As another example, the Romanowsky-type stained sample 203 and the biomarker-stained sample 205 are imaged on the same automated imaging platform 240b, wherein the image analysis system 250 identifies one or more cells having abnormal morphology and the X-Y coordinates of each cell having abnormal morphology in the Romanowsky-type stained sample is annotated, and the biomarker status at the same X-Y coordinate in the biomarker-stained sample 205 is also annotated. Methods and systems for automated analysis of stained samples can be found at, for example, Blom, Kumar, Nickoloff, Pajor, and van der Logt. Software packages for automated CBC analysis include, for example, the BLOODHOUND system (integrated with the COBAS m 511 system (Roche)) and CEL-LAVISION (Cella Vision AB, Sweden), which use digital morphological analysis to identify and count the constituent cells of the CBC analysis. Other exemplary commercially-available image analysis software packages that may be used in the present methods and systems include VENTANA VIRTUOSO (Roche); Definiens TISSUE STUDIO, DEVELOPER XD, and IMAGE MINER; and Visopharm BIOTOPIX, ONCOTOPIX, and STEREOTOPIX software packages.

IV. Diagnostic Workflows on Thin Layer Body Fluid Samples and Systems for Performing the Same In a specific embodiment, a workflow for cytological and biomarker analysis of thin layer body fluid samples for specific disease states is provided.

In an embodiment, the body fluid sample is deposited in a thin layer onto one or more solid supports. At least one of the samples is stained with a Romanowsky-type stain and evaluated for morphology, and at least one of the samples is stained for one or more biomarkers useful for categorizing one or more cells of the sample. In an embodiment, the sample stained with the Romanowsky-type stain is also the sample stained for the one or more biomarkers, which may be a simplex stain or a multiplex stain. In some embodiments, the biomarker stain is performed on the Romanowsky-type stained sample without performing a separate destain step. In another embodiment, an unstained sample is stained for the one or more biomarkers. Where more than one biomarker is evaluated separately, a separate sample may be provided for each biomarker, or a single printed sample may be stained for all biomarkers in a multiplex format, or a combination of simplex and multiplex stained printed samples may be used.

In a specific embodiment, the method is used for identifying cell populations in a blood sample. Exemplary methods are illustrated at FIGS. 3a and 3b.

Figure 3A:
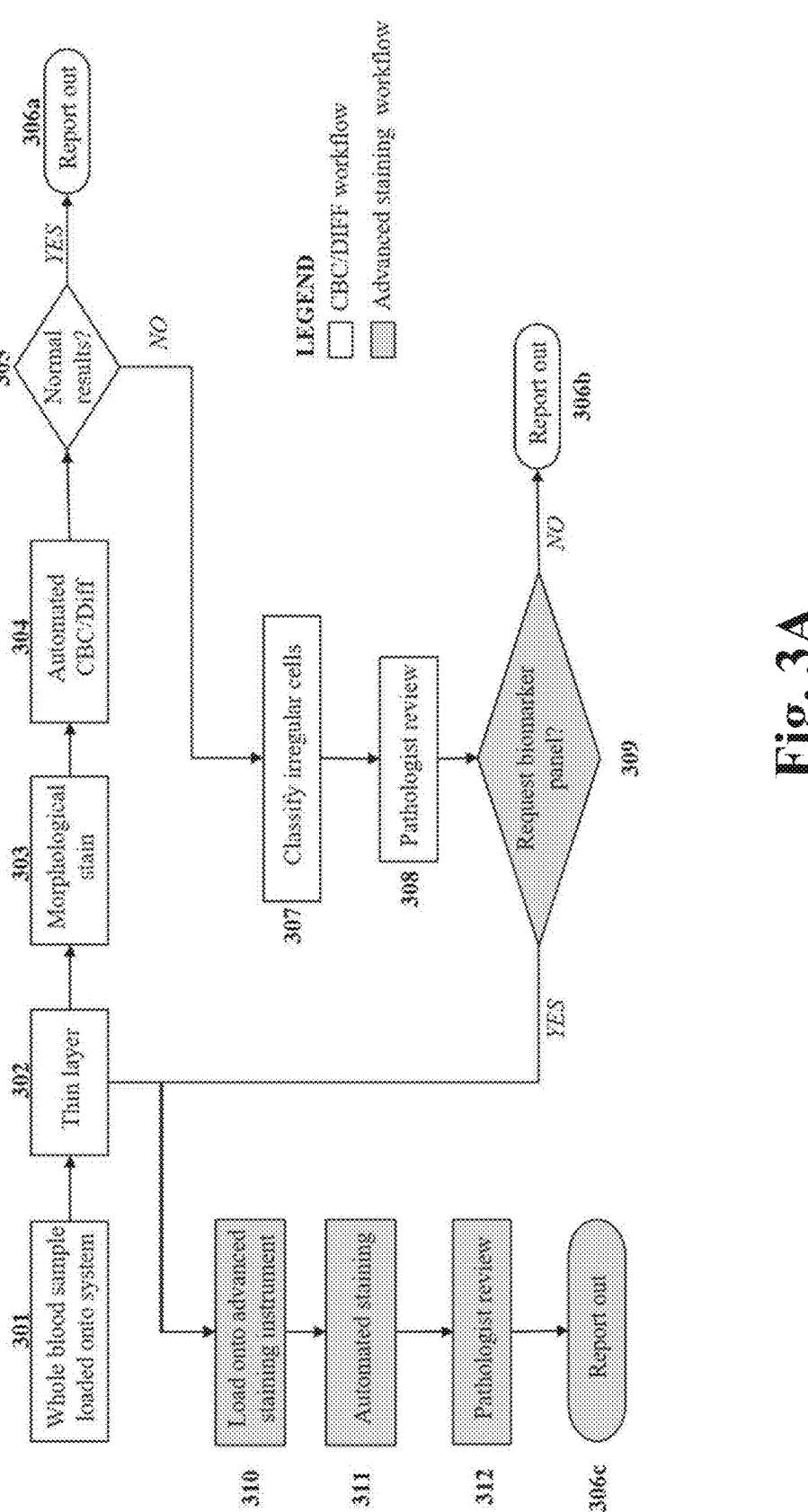
FIG. 3A illustrates an exemplary diagnostic workflow for staining and evaluating whole blood samples using thin layer-based automated CBC/DIFF and automated advanced staining.

FIG. 3A illustrates a method in which biomarker staining is triggered by pathologist evaluation CBC/DIFF results. In FIG. 3a, a whole blood sample is loaded onto an automated system for generating thin layers 301 and the blood sample is deposited in a thin layer onto one or more solid supports 302, at least one of which is stained with a morphological stain 303 (such as, for example, a Romanowsky-type stain, hematoxylin, eosin, etc.). A digital image of the morphologically-stained stained sample is generated and analyzed on an image analysis system to generate an automated complete blood count and differential analysis (CBC/DIFF) 304 to morphologically identify and quantify at least total erythrocytes, leukocytes, and platelets in the sample. The results are analyzed 305, and, if normal, a report comprising the CBC/DIFF results 306a is generated. If the CBC/DIFF is abnormal, any irregular cells identified by the image analysis system are classified 307 and flagged for review by a pathologist 308. If pathologist review 308 indicates that no biomarker panel is necessary, then a report containing the CBC/DIFF and pathologist notes 306B is generated. If a biomarker panel is ordered after pathologist review 308, then one or more thin layer slide(s) 302 are loaded onto an automated advanced staining instrument 310. The monolayer printed slide(s) are stained for one or more biomarkers 311, optionally digitized and analyzed on an image analysis system, the biomarker-stained slides (or digitized images thereof and/or image analysis results) are reviewed by a pathologist 312, and report containing the results of the CBC/DIFF, and pathologist reviews is generated 306c.

Figure 3B:
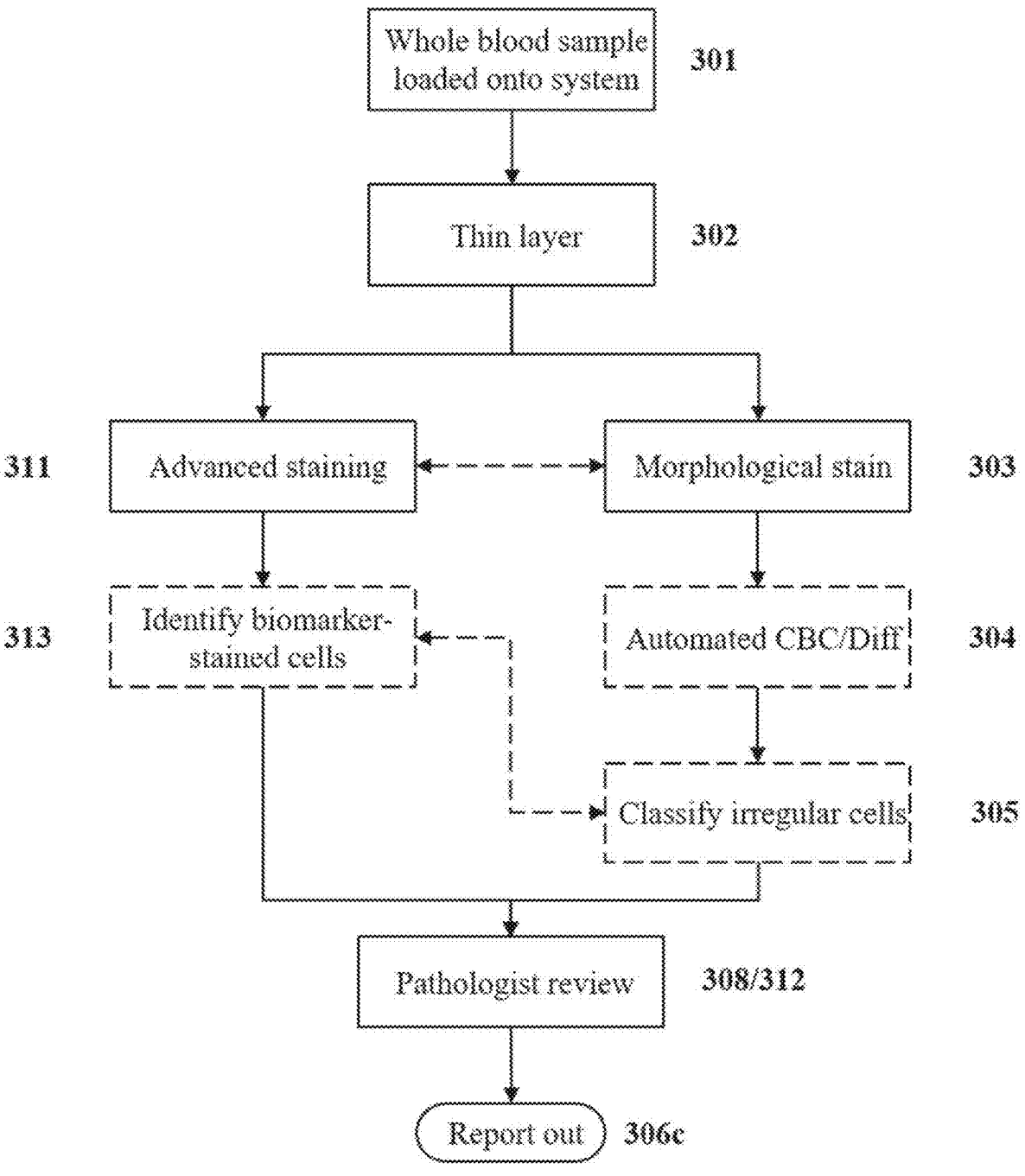
FIG. 3B illustrates another exemplary diagnostic workflow for staining and evaluating whole blood samples using thin layer-based automated CBC/DIFF and automated advanced staining. Hatched boxes indicate steps involving image analysis. Hatched arrows indicate alternative steps.

FIG. 3B illustrates a method in which biomarker staining is performed regardless of results of the morphological stain. Such a method may be useful for, for example, where it is desired to further characterize the blood components (for example, by using stains to differentiate between classes of leukocytes, monocytes, etc.). In FIG. 3*b*, a whole blood sample is loaded onto an automated system for generating thin layers 301 and the blood sample is deposited in a thin layer onto one or more solid supports 302. At least one thin layer is stained with a morphological stain 303 (such as, for example, a Romanowsky-type stain, hematoxylin, eosin, etc.) and at least one thin layer is stained for one or more biomarkers 311 on an automated advanced staining system, and digital images of the stained samples are obtained. In some embodiments, separate solid supports with thin layers are obtained for the morphological stain 303 and the biomarker stain 311 (illustrated by the separate solid arrows between 302 and 311 and between 302 and 303). In other embodiments, the solid support is first stained with the morphological stain 303, an image of the morphologically-stained sample is acquired (not illustrated), and then the same sample is stained with the biomarker stain 311 (illustrated by the dashed arrow pointing left between 303 and 311). In such an embodiment, the biomarker staining may include a de-stain step (such as the Romanowsky de-stain processes described in this disclosure) or the biomarker-specific reagent may be applied without destaining the sample. In yet other embodiments, the solid support is first stained with the biomarker stain 311, which is then stained with the morphological stain to obtain the morphologically-stained 303 (illustrated by the dashed arrow pointing right between 311 and 303). In some embodiments, the morphological stain is a counterstain applied during biomarker staining, in which case a digital image of the biomarker-stained slide may be obtained before or after morphological staining is performed. In other cases, the biomarker stained sample 311 may be destained before morphological staining, in which case a digital image of the biomarker stained sample 311 is obtained before morphological staining. In either case, a digital image of the morphologically-stained sample 303 is obtained. The digital image of the morphologically-stained sample is analyzed on an image analysis system to generate an automated complete blood count and differential analysis (CBC/DIFF) 304 to morphologically identify and quantify at least total erythrocytes, leukocytes, and platelets in the sample. If the CBC/DIFF is abnormal, any irregular cells identified by the image analysis system are classified 307. The digital image of the biomarker-stained sample is analyzed on an image analysis system to identify biomarker-stained cells 313. Where the biomarker staining and the morphological staining are performed on the same sample, the digital images may be compared to one another, such that biomarker signature(s) for irregular cells or other subsets of cells in the morphologically-stained sample can be determined. Comparison may comprise, for example, registration of the images to one another, or where X-Y positions within the images otherwise correlate with one another, identifying cells at specific X-Y positions within the two images. In cases where the biomarker stain and the morphological stain are applied without destaining, the morphology and the presence of the marker may be detected simultaneously or sequentially using specific forms of illumination of the stainings. The CBC/DIFF results, any irregular cells identified by the system, and results of the biomarker staining may then be reviewed by a pathologist 308/312. The review may comprise, for example, confirmation of CBC/DIFF results, review and/or annotation of irregular cells, evaluation of biomarker staining, etc. A report 306c may then be generated including the results of the CBC/DIFF, irregular cell identification, and biomarker staining analysis, and/or any annotations or other notations made by the pathologist.

Exemplary automated systems useful for generating thin layers from whole blood (referred to hereafter as "sample preparation systems") include cell printing systems, such as the COBAS m 511 integrated hematology analyzer from Roche, wedge smear systems, such as the SYSMEX SP-50 slidemaker-stainer, cytocentrifugation systems, such as CYTOSPIN systems from Thermo Scientific. In an embodiment, the sample preparation system is a cell printing system.

Morphological staining can be performed on the same system used to generate the thin layer, or a separate system. For example, the COBAS m 511 integrated hematology analyzer both deposits and stains cells in a single workflow. Likewise, the SYSMEX SP-50 slidemaker-stainer performs both functions. In other embodiments, samples are stained on a separate staining platform. Exemplary stand-alone staining platforms include HEMATEK-series slide stainers (Siemens Healthineers), QUICKSLIDE HemaPro Automated Hematology Stain Instrument (Hardy Diagnostics), AEROSPRAY stainers (ELITechGroup), among others. In an embodiment, the morphological stain is a Romanowsky-type stain performed on a cell printing system.

In an embodiment, the digital image(s) are generated by a scanning platform, such as those described above at section III.F. In some embodiments, the scanning platform is a stand-alone platform. Examples of commercially available slide scanners include: 3DHistech PANNORAMIC SCAN II; DigiPath PATHSCOPE; Hamamatsu NANOZOOMER RS, HT, and XR; Huron TISSUESCOPE 4000, 4000XT, and HS; Leica SCANSCOPE AT, AT2, CS, FL, and SCN400; Mikroscan D2; Olympus VS120-SL; Omnyx VL4, and VL120; PerkinElmer LAMINA; Philips ULTRA-FAST SCANNER; Sakura Finetek VISIONTEK; Unic PRECICE 500, and PRECICE 600x; VENTANA ISCAN COREO, VENTANA ISCAN HT, and VENTANA DP200; and Zeiss AXIO SCAN.Z1. Other exemplary systems and features can be found in, for example, WO/2011/049608 or in WO/2013/034430 the content of which is incorporated by reference in its entirety. In other embodiments, the scanning platform is integrated with an automated cytology preparation system, such as, for example, the COBAS m 511 platform ((integrates slide printing, fixation, staining, and image acquisition into a single automated workflow (Roche)).

Images of morphologically-stained samples generated by scanning platform are analyzed by an image analysis system programmed to perform an automated CBC/DIFF analysis. Exemplary components and analytical methods for performing slide-based automated CBC/DIFF analysis are discussed by Winkelman et al. Commercially-available image analysis systems for performing slide-based automated CBC/DIFF analysis include, for example, the BLOODHOUND system (integrated with the COBAS m 511 system (Roche)) and CELLAVISION (Beckman Coulter), which use digital morphological analysis to identify and count the constituent cells of the CBC analysis.

In an embodiment, the biomarker or biomarker panel staining is performed on an automated advanced staining system, such as those described at above at section II.C. The sample may be the morphologically-stained sample, or may be an unstained sample. In embodiments in which a morphologically-stained sample is used (such as a Romanowsky-type stained sample), the sample may be destained as described above in section II.D. Exemplary biomarker-specific reagents useful in the present methods include biomarker specific reagent capable of specifically binding to the consensus wild-type sequence one or more of the markers of Table 8:

TABLE 8

| Biomarker | Cell type | Consensus wild type protein sequence |
|---|---|---|
| CD3 | Pan T cell | SEQ ID NO: 2, 21, 22, or 23 |
| CD8 | Cytotoxic T cell | SEQ ID NO: 6 |
| CD45, LCA | Pan- leukocyte | SEQ ID NO: 12 |
| CD68 | Macrophages | SEQ ID NO: 13 |
| PAX-5 | Pan- B cells | SEQ ID NO: 16 |

The biomarker-stained sample(s) is/are analyzed to quantitate the cell types according Table 8 or to identify the cell type of the abnormal cell according to Table 8. In an embodiment, a single sample is stained in a multiplex format for each of the markers of Table 8, which single sample may optionally be the Romanowsky-type stained sample.

In another specific embodiment, where the CBC shows mild thrombocytopenia with raised mean platelet volume (MPV), the biomarker panel is selected to screen for DeGeorge syndrome, for example, by performing a T-cell subtype analysis, for example, by using biomarker-specific reagents to the consensus wild-type sequence of CD4, (SEQ ID NO: 3), CD8 (SEQ ID NO: 6), CD19 (SEQ ID NO: 19), and CD27 (SEQ ID NO: 20).

In another specific embodiment, where the CBC/DIFF indicates possible presence of a blood cancer, the biomarker staining comprises staining for one or more biomarkers useful in differential diagnosis of the blood cancer. For example, a biomarker panel may be selected to differentiate T- and B-cell lymphomas for example, by using a biomarker-specific reagent to the consensus wild-type sequence of Pax5 (SEQ ID NO: 16). In an embodiment, the slide stained for Pax5 may be the Romanowsky-type stained slide, or it may be a different printed slide. In another specific embodiment, at least one of the samples is stained with a multiplex stain with one of the panels of biomarker specific reagents according to Table 10:

TABLE 10

| Panel | Biomarkers |
|---|---|
| 1 | CD5, CD2, CD8, CD4, CD45 |
| 2 | CD5, CD3, CD23, CD10, CyclinD1 |
| 3 | Pax5, CD5, CD23, CyclinD1, CD3 |
| 4 | CD3, CD5, CD38, CD23, ZAP-70 |
| 5 | CD7, CD34, Pax5, TdT, MPO |

In an embodiment, the multiplex-stained slide may be the Romanowsky-type stained slide, or it may be a different, unstained printed slide. For panel 1, CD45 identifies all leukocytes, CD2 is used to identify peripheral T-cells, CD8 and CD4 are used to characterize the T-cell distribution (cytotoxic and helper, respectively) among the atypical cell population, CD5 is used to confirm the sample to be a lymphoma/leukemia case. Panel 5 is used to stratify ALL from AML, wherein the presence of CD7+/Tdt+/Pax5+ cells indicates the presence of ALL, whereas the presence of CD34+/MPO+ cells indicates the presence of AML. As another example, the biomarker panel may include an in situ hybridization to detect chromosome changes in blood cancer cells, such as in chronic lymphocytic leukemia (CLL) cells. In CLL, TP53 gene defects, due to deletion of the 17p13 locus and/or mutation(s) within the TP53 gene, are associated with resistance to chemoimmunotherapy and a particularly dismal clinical outcome. On these grounds, analysis of TP53 aberrations has been incorporated into routine clinical diagnostics to improve patient stratification and optimize therapeutic decisions. The predictive implications of TP53 aberrations have increasing significance in the era of novel targeted therapies, i.e., inhibitors of B-cell receptor (BcR) signaling and anti-apoptotic BCL2 family members, owing to their efficacy in patients with TP53 defects.

In another specific embodiment, where the CBC/DIFF indicates possible presence of a cardiac condition, the biomarker staining comprises staining for one or more biomarkers useful in differential diagnosis of the cardiac condition. For example, a biomarker panel may be selected to identify activated platelets, for example, by using a biomarker-specific reagent to the consensus wild-type sequence of CD38 (SEQ ID NO: 16).

In another specific embodiment, where the CBC/DIFF indicates possible presence of a microbial disease, and wherein the biomarker staining comprises staining for one or more biomarkers useful in differential diagnosis of the potential microbial disease, such as, bacterial, mycobacterial, viral, and parasitic diseases.

In another specific embodiment, where the CBC/DIFF indicates possible sepsis, and wherein the biomarker staining comprises staining for one or more biomarkers useful in differential diagnosis of the sepsis.

In another specific embodiment, where the CBC/DIFF indicates possible circulating tumor cells, and wherein the biomarker staining comprises staining for one or more biomarkers useful in identifying circulating tumor cells.

If the biomarker-stained samples are digitized, digital images may be generated using a scanning system, such as those described above at section III.F. In an embodiment, the digital images are generated on the same scanning platform as the morphologically-stained sample. In a further embodiment, the digital images of the biomarker-stained slides and the morphologically-stained slides are analyzed on the same image analysis system. In embodiments in which the morphologically-stained sample is used to generate the biomarker stained sample, the respective digital images may be matched to one another. Exemplary methods of matching digital images to one another (also referred to as "registration") are described at, for example WO/2014/140070, WO/2015/049233, and WO2018/189039, among many others. By matching the biomarker-stained and the morphologically-stained images, the image analysis system can display biomarker information for each irregular cell observed.

In an embodiment, the sample preparation system, and/or imaging system, and/or image analysis system, and/or advanced staining system are integrated into a single device or a modular system, allowing for fully automated or semi-automated workflows.

VII. EXAMPLES

Figure 4:
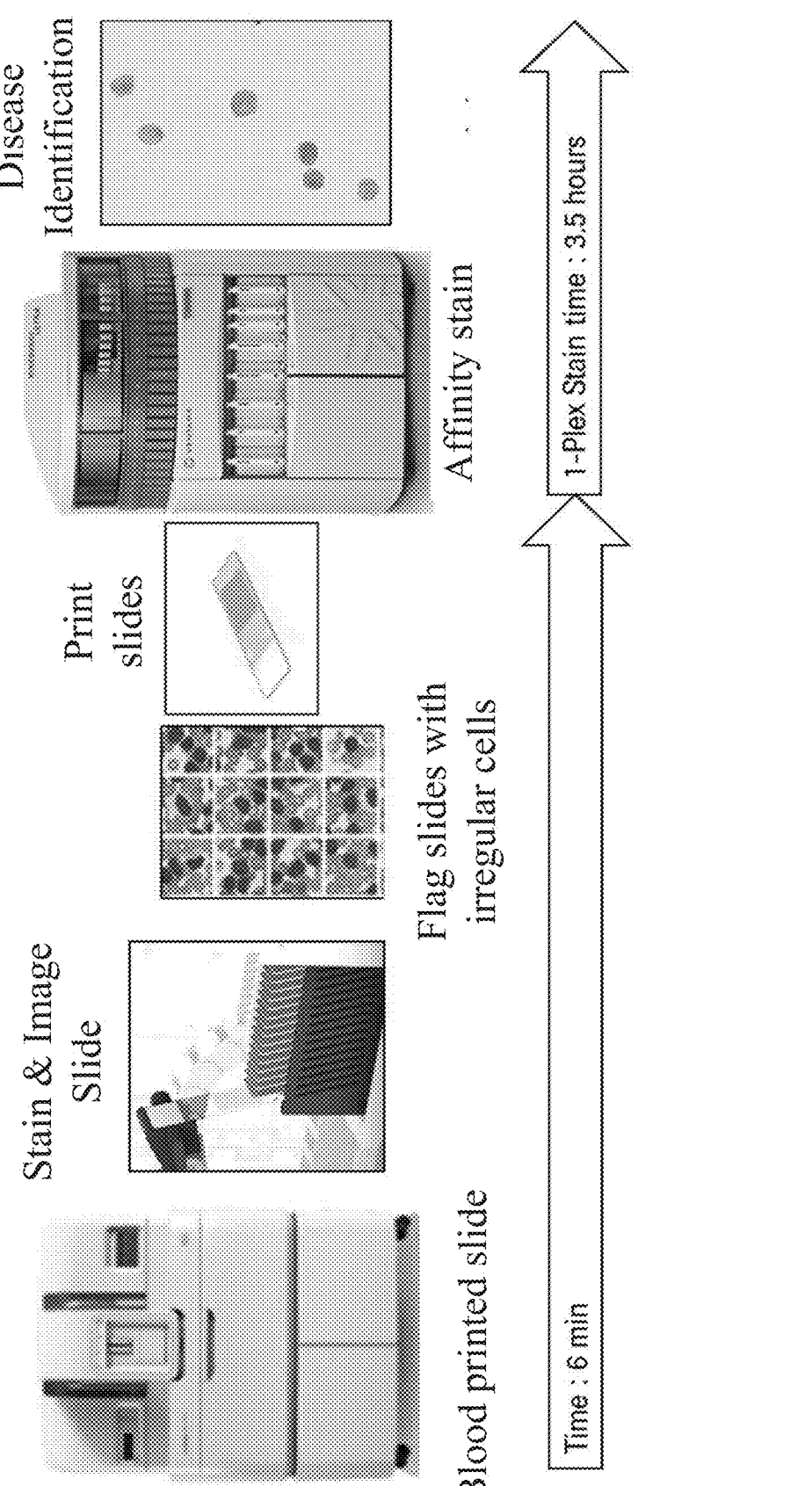
FIG. 4 is an illustration of a workflow for assessing immune cells in a printed blood sample using an automated IHC/ISH slide staining platform.

Example 1: Automated Staining of Single Biomarker on Leukocyte Population from Normal Blood Printed Slide Using DAB Detection Kit The following example illustrates feasibility of a workflow for evaluating biomarkers in a printed blood sample having a CBC report highlighting presence of atypical cells. In the typical existing diagnostic workflow, flow cytometry is used to identify the cell population based on blood samples. Here we propose a quick turnaround workflow solution by printing additional slides from the flagged patient blood and performing a simplex immunoenzymatic affinity assay on an automated immunoenzymatic/ISH platform with relevant biomarkers. The single plex assay is a short run, which takes approximately 3.5 hours. An example of the proposed workflow is illustrated at FIG. 4

Human whole blood sample (1 µL) was printed on glass slide with a COBAS m 511 integrated hematology system (Roche). Unstained slides were fixed with NBF and stained with Romanowsky-type stain. A typical slide contained red blood cells, white blood cells, and platelets printed on it.

TABLE 11

| Biomarker | Information | 1° Ab Clone (Roche Cat. No.) | Species | Predicted localization |
|---|---|---|---|---|
| CD3 | Pan T cell | 2GV6 (790-4341) | Rabbit mAb | Membrane |
| CD8 | Cytotoxic T cell | SP57 (790-4460) | Rabbit mAb | Membrane |
| CD45, LCA | Pan-leukocyte | RP2/18 (760-2505) | Mouse mAb | Membrane |
| CD68 | Macrophages | KP-1 (790-2931) | Mouse mAb | Cytoplasm |
| PAX-5 | Pan-B cells | SP34 (790-4420) | Rabbit mAb | Intracellular |

Separate slides were used for each marker. The three step assay included primary antibody of interest, anti-species secondary antibody labelled with HQ hapten, and anti-HQ HRP as a tertiary antibody. The ChromoMap DAB kit (Roche) was used to deposit diaminobenzidine (DAB) dye. The ChromoMap DAB kit includes an endogenous peroxidase inhibitor, DAB in a stabilizer solution, a $H_2O_2$ solution, and a copper sulfate solution. The study design and protocol detail is in Table 12 below.

TABLE 12

| Parameters | CD3 | CD8 | CD45 | CD68 |
|---|---|---|---|---|
| Clone | 2GV6 | SP57 | RP2/18 | KP-1 |
| Sample Type | Normal Blood | Normal Blood | Normal Blood | Normal Blood |
| Romanowsky Stain/Scan | Yes | Yes | Yes | Yes |
| Primary Antibody time | 32 min | 32 min | 32 min | 32 min |
| $2^{nd}$ Ab/Time (min) | Goat anti-Rabbit-HQ (12) | Goat anti-Rabbit-HQ (12) | Goat anti-Mouse-HQ (12) | Goat anti-Mouse-HQ (12) |
| $3^{rd}$ Ab/Time (min) | Anti HQ-HRP (12) | Anti HQ-HRP (12) | Anti HQ-HRP (12) | Anti HQ-HRP (12) |
| ChromoMap DAB Kit | Yes | Yes | Yes | Yes |

TABLE 12-continued

| Parameters | CD3 | CD8 | CD45 | CD68 |
|---|---|---|---|---|
| Hematoxylin Time (min) | 12 | 12 | 12 | 12 |
| Bluing Time (min) | 4 | 4 | 4 | 4 |

Figures 5, 6:
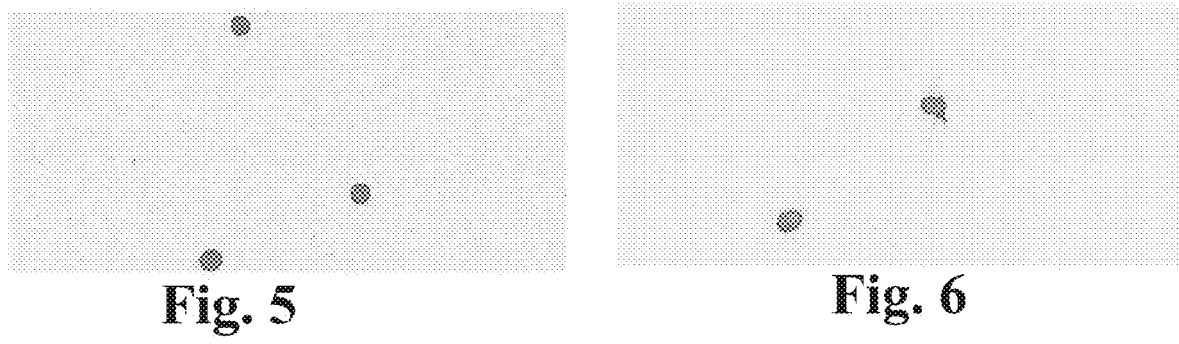
FIG. 5 is an illustration of an immunoenzymatic stain of CD3 biomarker using DAB detection on normal blood printed slide.
FIG. 6 is an illustration of an immunoenzymatic stain of CD8 biomarker using DAB detection on normal blood printed slide
Figures 7, 8:
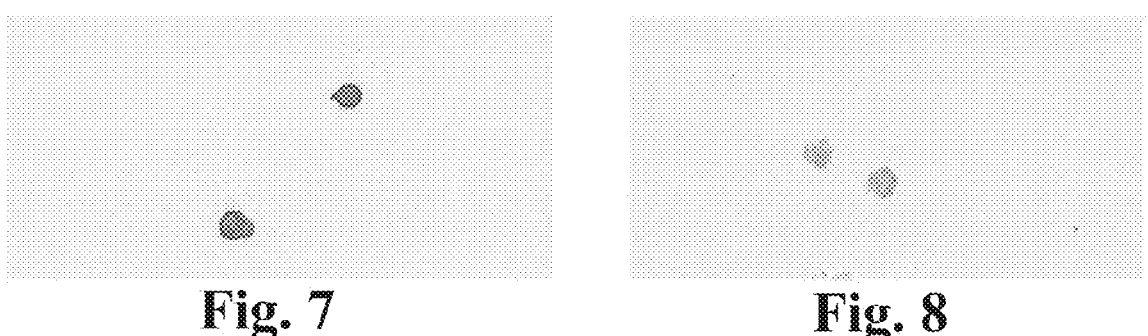
FIG. 7 is an illustration of an immunoenzymatic stain of CD45 biomarker using DAB detection on normal blood printed slide
FIG. 8 is an illustration of an immunoenzymatic stain of CD68 biomarker using DAB detection on normal blood printed slide

Results are shown at FIG. 5-7. The CD3, CD8 and CD45 antibodies stained leukocyte populations in the blood. The typical immunoenzymatic staining pattern showed a thin membrane stain on large round cells as shown in FIG. 5-7. For CD68 the punctuated stains were observed in the cytoplasmic compartment (FIG. 8). For a quick assessment of leukocyte cell population following CBC report, multiple slides can be printed and stained with different immune biomarkers using simplex DAB detection kit on an automated advanced staining platform. The turnaround time of the staining protocol is 3.5 hr.

Example 2: Simplex IHC Stain on COBAS m 511 Blood Printed Slides to Identify Disease Subtype CBC results indicating presence of atypical cells require biomarker testing to differentiating between the T and B cell malignancies are the first line of stratification. Here we show an example of disease blood stratification by using key biomarkers.

Blood slides were printed as described at Example 1. The blood had a large amount of atypical cells as evaluated by the COBAS m 511 assay. A new slide was printed from the same blood sample and fixed in 10% NBF for 30 minutes. Staining was conducted on a DISCOVERY ULTRA platform, using a cell conditioning for 24 minutes. To identify if the abnormal cells were either T or B lymphoma, a simplex DAB immunoenzymatic assay for Pax5 (a biomarker of B cell malignancy) was performed on DISCOVERY ULTRA platform. The three step assay included a rabbit anti-human Pax5 primary antibody, anti-rabbit HQ as secondary antibody, anti-HQ HRP as tertiary antibody, and ChromoMap DAB kit. The study design and protocol detail is in Table 13 below.

TABLE 13

| Parameters | PAX5 |
|---|---|
| Clone | SP34 |
| Sample Type | Disease blood |
| Romanowsky Stain/Scan | Yes |
| Primary Antibody time | 32 min |
| $2^{nd}$ Ab/Time (min) | GaR-HQ/12 |
| $3^{rd}$ Ab/Time (min) | Anti HQ-HRP/12 |
| ChromoMap DAB Kit | Yes |
| Hematoxylin Time (min) | 12 |
| Bluing Time (min) | 4 |

Figure 9:
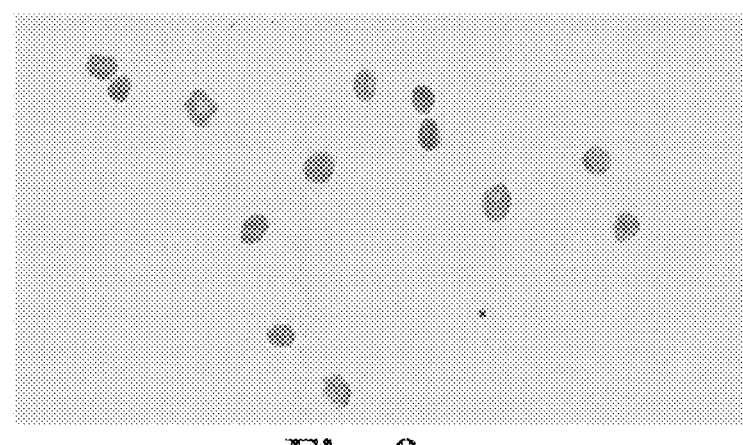
FIG. 9 is an illustration of a positive immunoenzymatic stain of Pax5 biomarker identified as a B cell malignant patient blood.

Results are shown at FIG. 9. Based on the positive DAB stain, the blood could be identified as a B cell lymphoma based on the result. Thus, we have shown that, for a quick stratification of malignant subtype following CBC report indicating presence of atypical cells, multiple slides can be printed and stained with different lymphoma biomarkers using simplex DAB detection kit and an autostainer. The turnaround time of the staining protocol is 3.5 hr.

Example 3: Reuse of Romanowsky-Type Stained Slides for IHC Evaluation with Brightfield Detection System on an Automated Tissue Staining Platform The blood slides stained with Romanowsky-type stain are a routine end-product of blood diagnostics. We propose evaluating re-use of these slides in immunoenzymatic evaluation with a chromogenic detection system. The Romanowsky-type stain was completely removed and had no interference with the immunoenzymatic stain. An exemplary workflow is illustrated at FIG. 10.

Human blood samples (1 µL) was printed on glass slide. Normal blood printed slides were fixed with 1) methanol or 2) NBF and stained with Romanowsky-type stain using DigiMac 3 staining kit (Roche). The DigiMAC3 stain pack is comprised of the following four (4) separate solutions, which are individually applied to each processed slide: DigiMAC3 fix, DigiMAC3 eosin, DigiMAC3 methylene blue, and DigiMAC3 rinse. The application of these stain solutions results in a Romanowsky-type stain such as typically used in hematologic evaluations of whole blood. Slides were scanned using a VENTANA DP 200 slide scanner to identify leukocyte population morphology and locations. Following the scan, the Romanowsky-type stained slides were re-used for CD45 immunoenzymatic staining on a DISCOVERY ULTRA autostainer using DISCOVERY Purple, DISCOVERY Teal and DISCOVERY Yellow detection kit. Cell conditioning was done for 16 minutes. The three step assay included primary antibody CD45, anti-mouse HQ as secondary antibody and anti-HQ HRP as third antibody. DISCOVERY purple and DISCOVERY Teal chromogenic detection kits were used here. For DISCOVERY yellow detection, the three step assay involved primary antibody CD45, anti-mouse NP as secondary antibody and anti-NP-AP as third antibody. The study design and protocol detail is in Table 14 below.

TABLE 14

| Parameters | CD45 | CD45 | CD45 |
|---|---|---|---|
| Clone | RP2/18 | RP2/18 | RP2/18 |
| Fixative used | Methanol or NBF | Methanol or NBF | Methanol or NBF |
| Sample Type | Normal Blood | Normal Blood | Normal Blood |
| Romanowsky Stain/Scan | Yes | Yes | Yes |
| Primary Antibody time | 32 min | 32 min | 32 min |
| $2^{nd}$ Ab/Time | GaM-HQ/12 min | GaM-NP/12 min | GaM-HQ/12 min |
| $3^{rd}$ Ab/Time | Anti HQ HRP/12 min | Anti NP AP/12 min | Anti HQ HRP/12 min |
| Detection Kit | DISCOVERY Purple | DISCOVERY Yellow | DISCOVERY Teal |
| Hematoxylin | 12 min | 12 min | 12 min |
| Bluing | 4 min | 4 min | 4 min |

Figure 11:
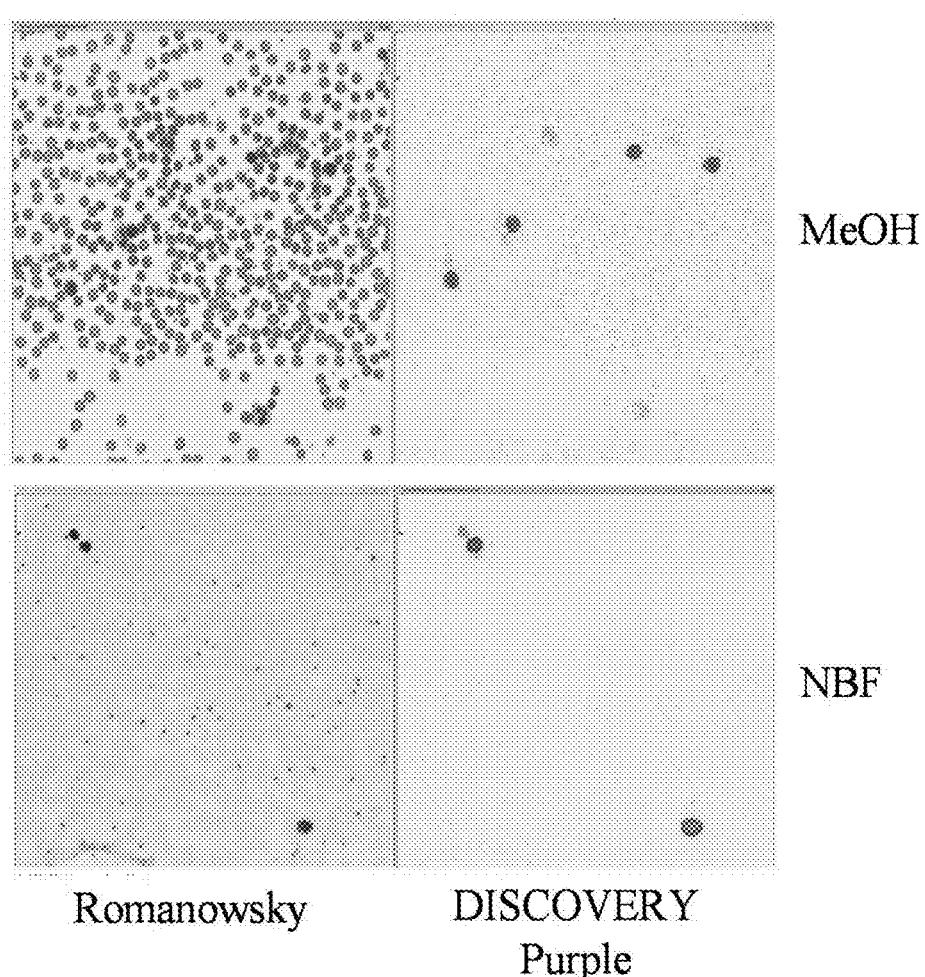
FIG. 11 is a Romanowsky-type stained blood printed slide (left column) and the same slide re-stained with CD45 and the chromogen DISCOVERY Purple on an automated platform (right column). Top row is a methanol-fixed sample. Bottom row is a neutral buffered formalin-fixed sample.
Figure 12:
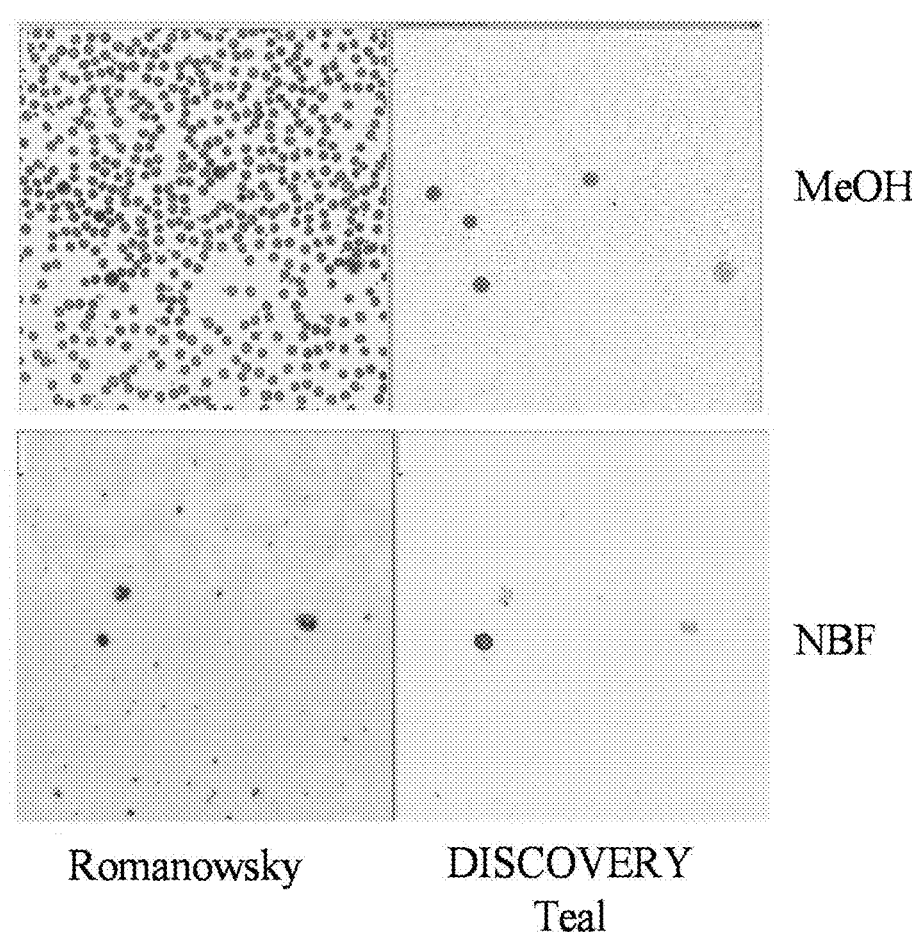
FIG. 12 is a Romanowsky-type stained blood printed slide (left column) and the same slide re-stained with CD45 and the chromogen DISCOVERY Teal on an automated platform (right column). Top row is a methanol-fixed sample. Bottom row is a neutral buffered formalin-fixed sample.
Figure 13:
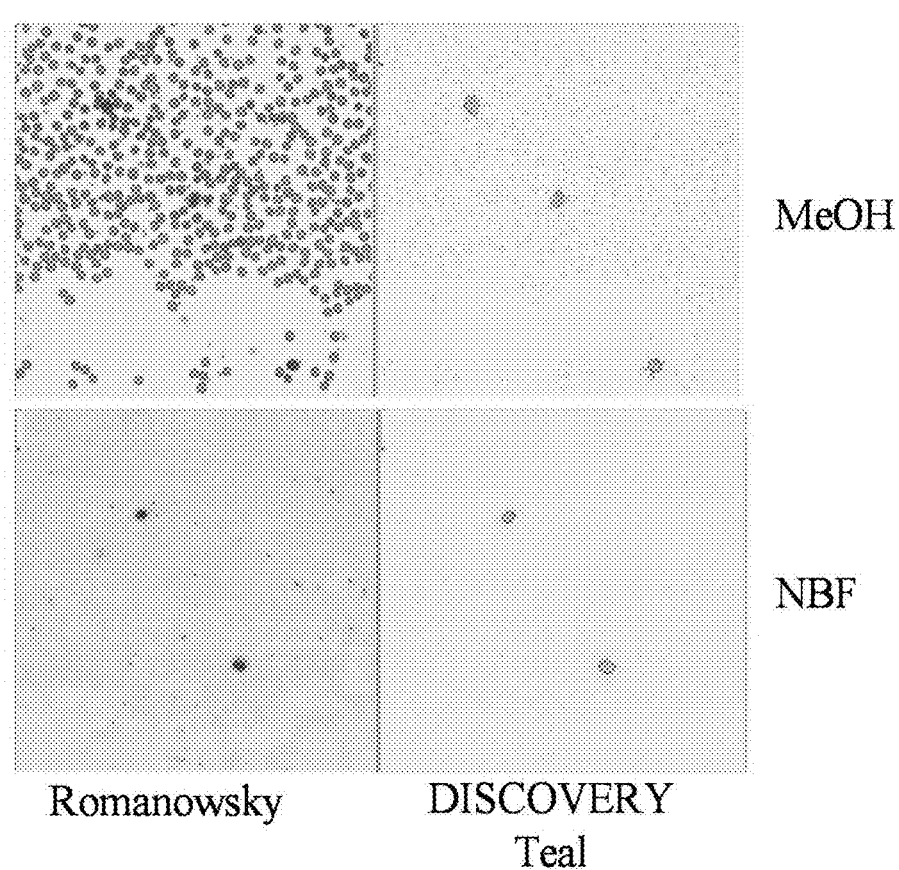
FIG. 13 is a Romanowsky-type stained blood printed slide (left column) and the same slide re-stained with CD45 and the chromogen DISCOVERY Yellow on an automated platform (right column). Top row is a methanol-fixed sample. Bottom row is a neutral buffered formalin-fixed sample.

Results are shown at FIGS. 11 (DISCOVERY Purple), 12 (DISCOVERY Teal), and 13 (DISCOVERY Yellow). The Romanowsky-type stain is completely washed away and there is no residual stain interference with immunoenzymatic staining.

Figure 14:
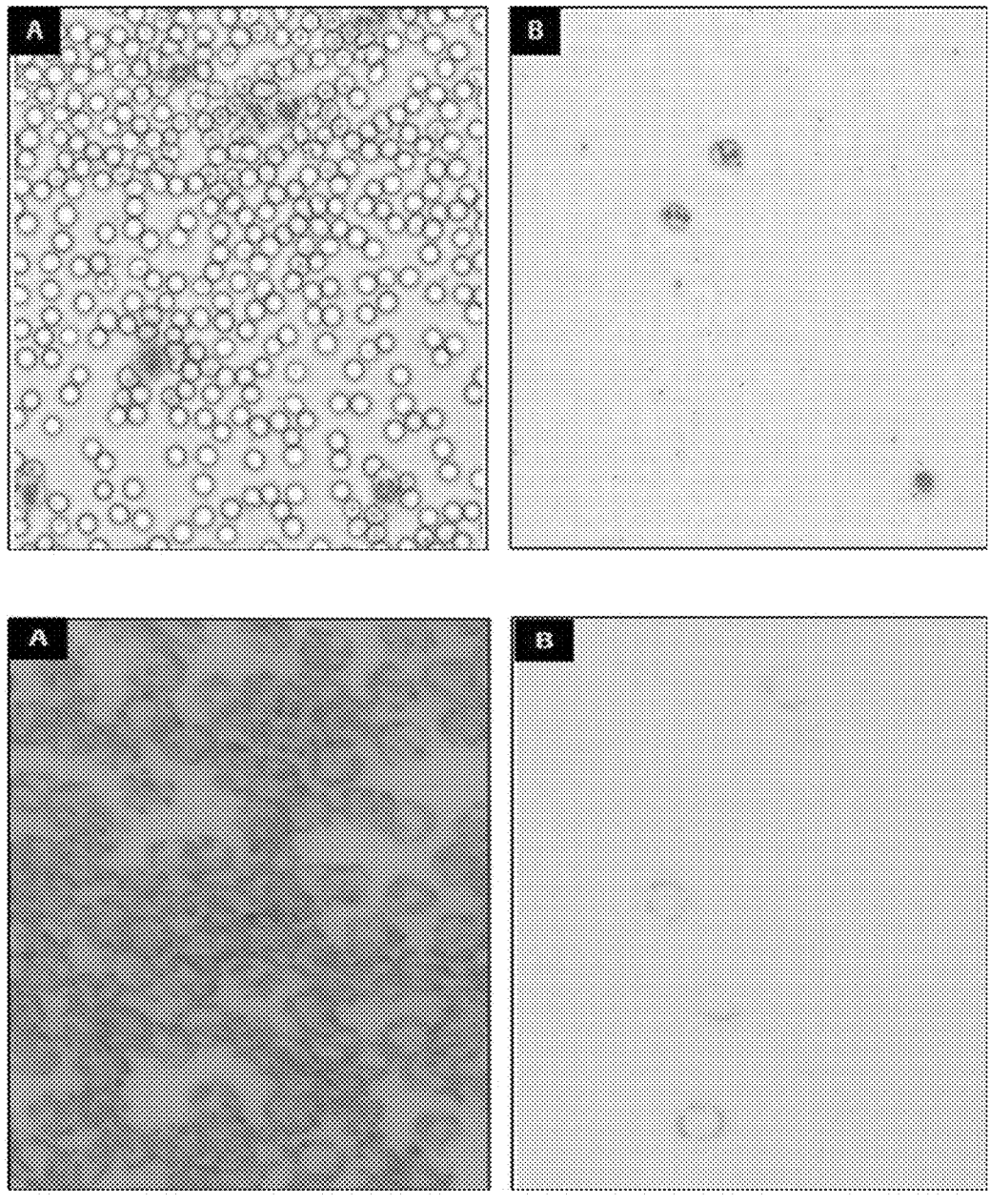
FIG. 14 is a Romanowsky-type stained blood printed slide progressively destained by CC1 and RB. Top row shows the change from Romanowsky-type stained (A) to partially destained with CC1 (B). Bottom row shows partially destained with CC1 (A) to completely destained with Reaction Buffer (B).

To identify which part of the automated staining process results in sample destaining, the reagents used in the protocol were evaluated for their ability to destain Romanowsky-type stained slides. Early stages of the protocol involved a cell conditioning step with CC1 and multiple rounds of reaction solution (RB). CC1 comprises: DI water, Tris (Base), Boric acid, EDTA (disodium dehydrate), Tween-20, ProClin 950, 6N HCl, 6N NaOH, Silicon Dioxide Nanoparticle and has a pH of 8.5. Reaction solution comprises DI water, Tris, Glacial acetic acid, Brij 35, sol, ProClin 300, and 6N NaOH and has a pH of 7.5. To test whether these reagents were responsible for destaining, a Romanowsky-type stained slide was placed in CC1 for 15 minutes and then scanned. The CC1 dipped slide was then placed in RB for 5 minutes and scanned. As can be seen at FIG. 14, CC1 treatment resulted in partial destaining of the slide, and the RB treatment resulted in complete destaining of the slides.

Thus, a cell conditioning step and at least one wash step on an automated advanced staining system is sufficient to destain Romanowsky-type stain. Further, by reusing the same slide and keeping the scan record after Romanowsky-type stain gives the opportunity to look at the same cells after biomarker stain. An X-Y coordinate recorded in scanner makes it easier to identify any atypical cell flagged during cytological analysis.

Figure 15:
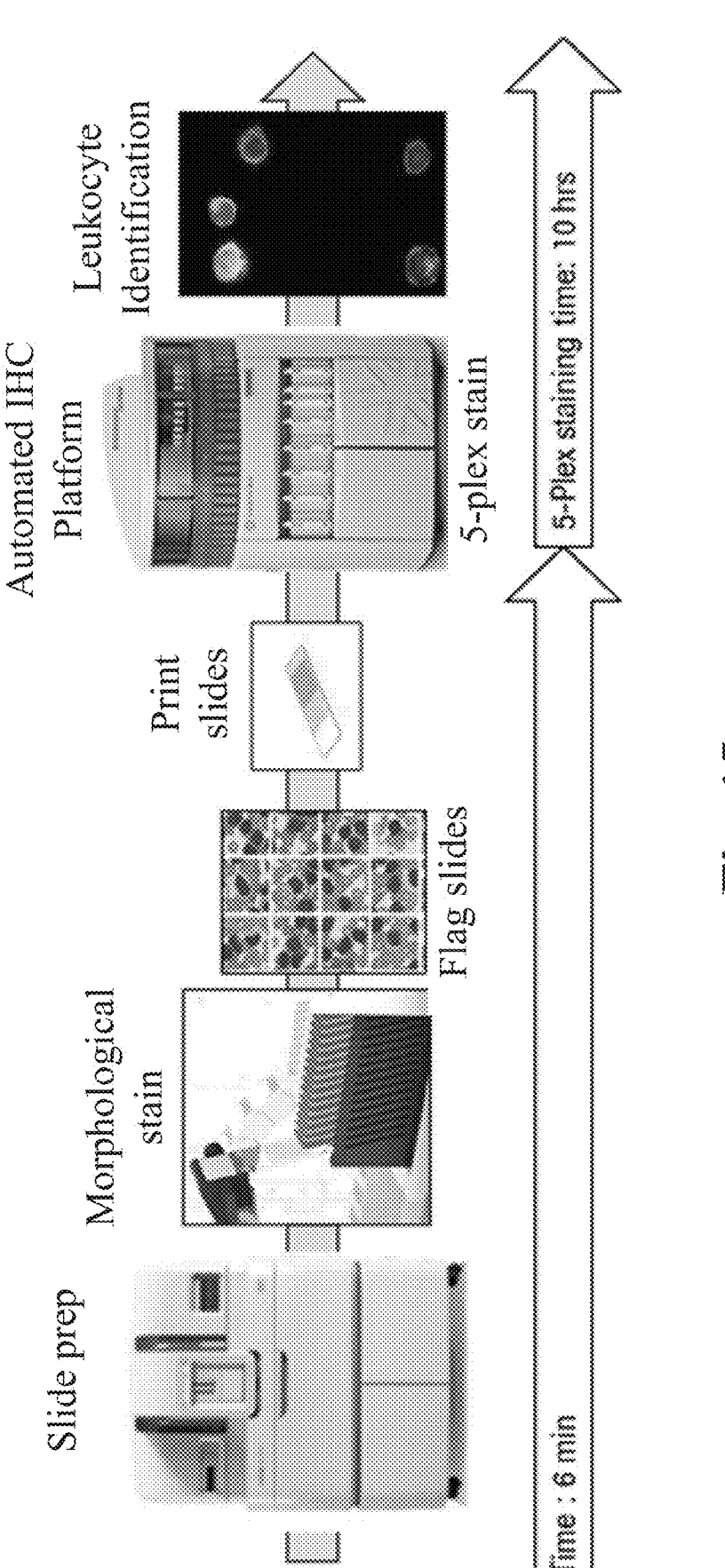
FIG. 15 is a workflow to use blood-printed slides for a 5-plex immunoenzymatic evaluation of 5 immune biomarkers.

Example 4: Stain and Image Multiple Immune Biomarkers on Normal and Diseased Blood Printed Slide Slides printed with normal or diseased blood were stained for CD3, CD4, CD20, CD45 and CD68 in a 5-plex multiplex protocol to evaluate the feasibility of performing multiplexing on a printed blood slide. An exemplary workflow is illustrated at FIG. 15. Table 15 discusses the markers detected, the cell population identified by the marker, and the staining location for each biomarker in the cellular compartment.

TABLE 15

| Biomarker | Staining cells | Predicted location |
|---|---|---|
| CD3 | Pan T-cells | Cell membrane |
| CD4 | Effector T cells | Cell membrane |
| CD20 | Pan B cell | Cell membrane |
| CD45 | Pan leukocyte | Cell membrane |
| CD68 | Macrophages | Cell membrane |

Human blood samples (3 µL) was printed on glass slide with COBAS m 511 integrated hematology system (Roche). Unstained slides were fixed with NBF before Romanowsky-type stain. A typical slide contained RBC, WBC and platelets printed on it. A 5-plex multiplex immunoenzymatic stain was then performed on a DISCOVERY ULTRA platform using a single unstained blood printed slide. The biomarker clone information is recorded in Table 16 (all reagents from Roche):

TABLE 16

| Biomarker/ Roche Cat. No. | Information | Clone | Species | Predicted localization |
|---|---|---|---|---|
| 1 Anti-CD3 790-4341 | Pan T cell | 2GV6 | Rabbit mAb | Membrane |
| 2 Anti-CD4 790-4423 | Effector T cell | SP35 | Rabbit mAb | Membrane |
| 3 Anti CD20 760-2531 | B-cell | L26 | Mouse mAb | Membrane |
| 4 Anti CD45, LCA 760-2505 | Pan-leukocyte | RP2/18 | Mouse mAb | Membrane |
| 5 Anti CD68 790-2931 | Macrophages | KP-1 | Mouse mAb | Cytoplasm |

The fluorophores that were used for staining are listed below at Table 17:

TABLE 17

| TSA-Fluor | R6G: Carboxyrhod-6G-Tyr, MW: 1001.2 | Texas Red: Rhodamine10 1-p8-Tyr MW: 1149.37 | DCC: DCC-PEG8-Tyr, MW: 803.94 | Cy5: SulphoCy5-PEG8-Tyr: MW: 1199.5 | FITC: FITC-PEG8-Tyr, MW: 950.06 |
|---|---|---|---|---|---|

DAPI was used as a counterstain. Bulk reagents that were used for the 5-plex staining are listed at Table 18:

TABLE 18

| BULK | Roche product numbers |
|---|---|
| Wash (RUO) DISCOVERY | 950-510/07311079001 |
| Liquid Coverslip (High Temperature) | 650-010/05264839001 |
| DISCOVERY CC1 | 950-500/06414575001 |
| ULTRA Cell Conditioning (ULTRA CC2) | 950-223/05424542001 |
| Reaction Solution (10x) | 950-300/05353955001 |

Detection reagents used for the 5-plex are illustrated at Table 19:

TABLE 19

| Dispensers | |
|---|---|
| DISCOVERY Goat Ig Block | 760-6008/07988214001 |
| Inhibitor, DISCOVERY | 760-4840/0717944001 |
| QD DAPI, DISCOVERY | 760-4196/05268826001 |
| DISC. OmniMap anti-Rb HRP RUO | 760-4311/5269679001 |
| DISC. OmniMap anti-Ms HRP RUO | 760-4310/5269652001 |

The stained cells were imaged using Zeiss M2 microscope and scanned on a Zeiss AXIO scanner.

The assay involves 5 sequential rounds of primary antibody stain with a heat deactivation step between each rounds. Following a short cell conditioning step of 20 minutes each primary antibody was incubated for 32 minutes and secondary antibodies for 8 minutes. The antibody fluorophore pair tested in the panel are: (1) CD20: R6G (2) CD3: DCC (3) CD4: Red610 (4) CD68: Cy5 (5) CD45: FAM. The study design is described in Table 20.

TABLE 20

| Stain Procedure | CD20 | CD3 | CD4 | CD68 | CD45 |
|---|---|---|---|---|---|
| Clone | L26 | 2GV6 | SP35 | KP-1 | 2B11PD7/26 |
| Primary antibody time | 32 min | 32 min | 32 min | 32 min | 32 min |
| 2nd Antibody/ time | GaM-HRP/ 8 min | GaR-HRP/ 8 min | GaR-HRP/ 8 min | GaM-HRP/ 8 min | GaM-HRP/ 8 min |
| H2O2 | 4 min | 4 min | 4 min | 4 min | 4 min |
| TSA-flurophore | 8 min | 8 min | 8 min | 8 min | 8 min |
| FL Dye | R6G | DCC | Red610 | Cy5 | FAM |
| DAPI | 12 min | 12 min | 12 min | 12 min | 12 min |

Figure 16:
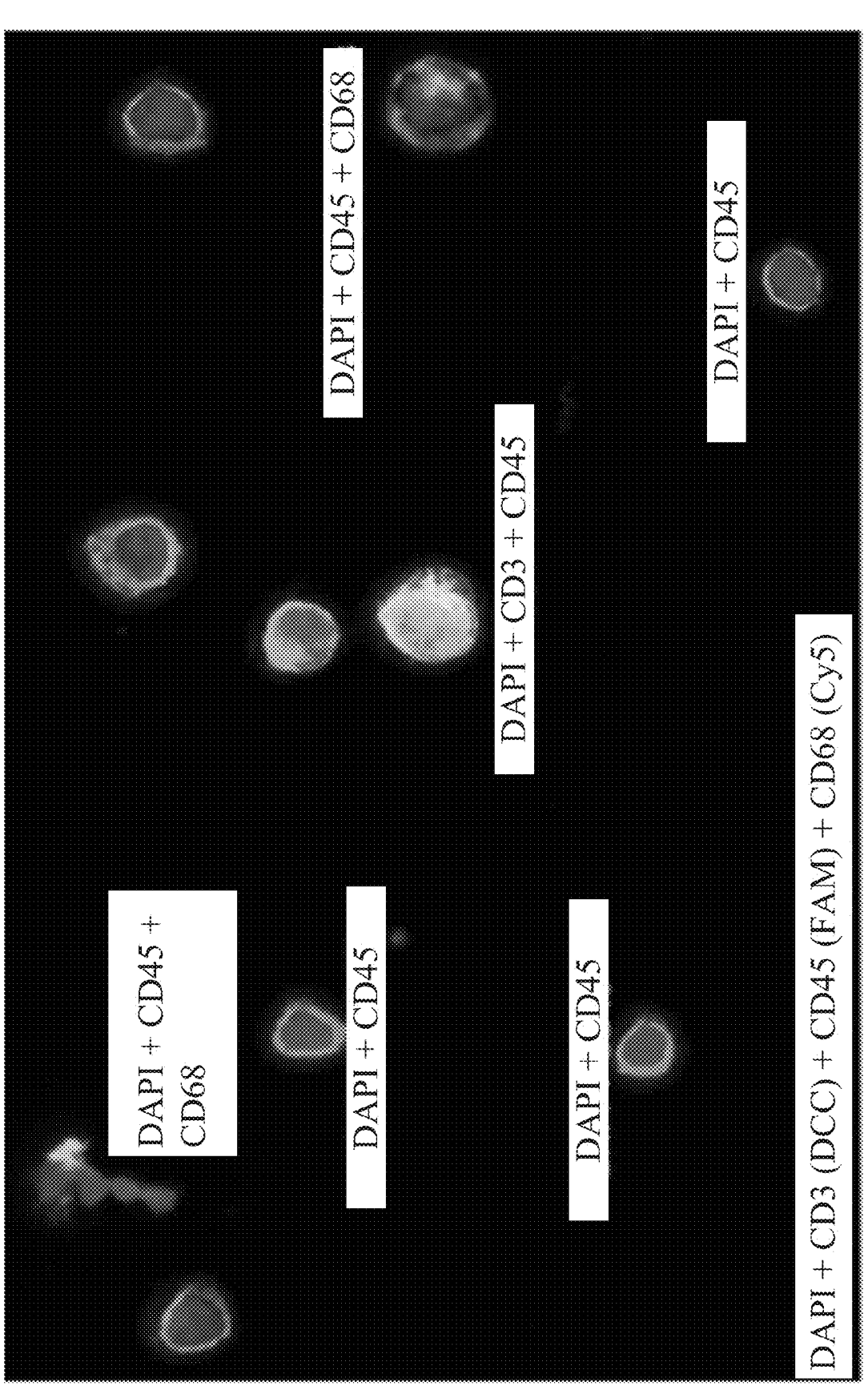
FIG. 16: Five Immune biomarkers tested on CLL blood printed sample.

Results are shown at FIG. 16. The 5-plex assay protocol successfully stained all 5 biomarkers simultaneously on a single slide. Leukocytes population was stained with CD45, a pan leukocyte marker (green). Co-registration of CD45 with different subsets of CD3 (Blue) and CD4 (Magenta) was observed. CD20 stained B cell was few in the blood. A subset of CD45 positive pan leukocyte cells also stained with both CD68 a pan macrophage biomarker and CD3 and pan T cell marker. With 4 out of 5 biomarker staining on blood printed slide, this opens up an enormous potential to marry Romanowsky-type staining technology with autostaining platforms.

Figure 17:
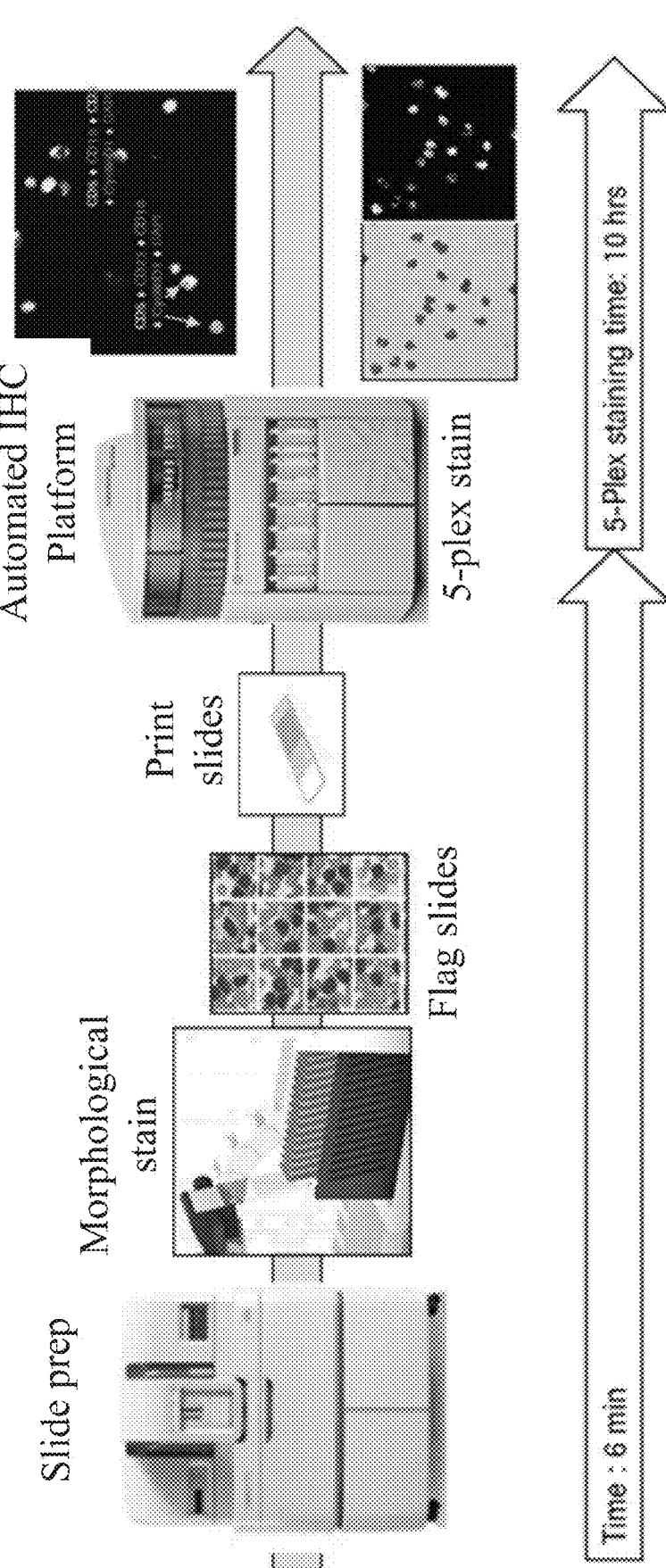
FIG. 17: A proposed workflow for evaluating CBC slides and follow-up biomarker expression using printed blood slides.

Example 5: Design and Stain of Leukocytes Population in CLL Blood with Four Different 5-Plex Panels on Automated Staining Platform A proposed workflow for evaluating CBC slides and follow-up biomarker expression using printed blood slides is illustrated at FIG. 17. A CBC slide and a few additional slides are printed using an automated blood slide printing platform. When abnormal cells are identified in the CBC slide, one or more of the additional blood slides is immunoenzymatically stained for a panel of biomarkers. By multiplexing immunoenzymatic staining, 5 biomarkers can be stained simultaneously on single blood printed slides. Co-registration of multiple biomarkers by immunofluorescence multiplexing on the same cells and same slide may help in accurate disease stratification by allowing for phenotypic evaluation on a cell-by-cell basis. Further, unique cases where co-staining of unlikely biomarkers are reported by flow, validating co-expression patterns using multiplexing immunofluorescence on same cells is a unique application of this technology.

To test this workflow, multiple 5-plex panels were tested on human blood samples (1 µL) printed on glass slide with the COBAS m 511 integrated hematology system (Roche). Unstained slides were fixed with NBF before Romanowsky-type stain. A typical slide contained RBC, WBC and platelets printed on it.

5A. Materials and Equipment

Primary antibodies used in this example are recorded in Table 21 (all from Roche):

TABLE 21

| Biomarker/ product # | Information | Clone | Species | Predicted localization (Human protein atlas) |
|---|---|---|---|---|
| CD2 760-4377 | All peripheral blood T-cells | MRQ-11 | Mouse mAb | Membrane, Secreted |
| Anti-CD3 790-4341 | Pan T cell | 2GV6 | Rabbit mAb | Membrane |
| Anti-CD4 790-4423 | Effector T cell | SP35 | Rabbit mAb | Membrane |
| Anti-CD5 790-4451 | T cell lymphoma | SP19 | Rabbit mAb | Membrane |
| Anti-CD7 790-4558 | Marker for T-ALL | SP94 | Rabbit mAb | Membrane |
| Anti-CD8 790-4460 | Cytotoxic T cell | SP57 | Rabbit mAb | Membrane |

TABLE 21-continued

| Biomarker/ product # | Information | Clone | Species | Predicted localization (Human protein atlas) |
|---|---|---|---|---|
| Anti-CD10 790-4506 | Acute lymphoblastic leukemia (ALL). Found on ALL cells which derive from pre-B lymphocytes | SP67 | Rabbit mAb | Membrane, intracellular |
| Anti CD20 760-2531 | B-cell | L26 | Mouse mAb | Membrane |
| Anti-CD23 790-4408 | B-cell chronic lymphocytic leukemia (CLL) | SP23 | Rabbit mAb | Intracellular, Membrane |
| CD34 760-2620 | AML marker. Poor prognostic factor in newly diagnosed AML | QBEnd/10 | Mouse mAb | Intracellular |
| Anti-CD38 760-4785 | Diagnosis of myeloma. Prognosis for CLL patients | SP149 [Cell Marque] | Rabbit mAb | Intracellular |
| Anti CD45, LCA 760-2505 | Pan-leukocyte | RP2/18 | Mouse mAb | |
| Anti CD68 790-2931 | Macrophages | KP-1 | Mouse mAb | Cytoplasm |
| ZAP-70 760-4278 | ZAP-70 in B cells is used as a prognostic marker in CLL | 2F3.2[Cell Marque] | Mouse mAb | Intracellular |

TABLE 21-continued

| Biomarker/ product # | Information | Clone | Species | Predicted localization (Human protein atlas) |
|---|---|---|---|---|
| | identifying different forms of chronic lymphocytic leukemia (CLL) | | | |
| Anti-CyclinD1 790-4508 | Very specific for mantle cell lymphoma, Positive stain for B-CLL, Myeloma | SP4-R | Rabbit mAb | Intracellular, nuclear stain |
| Anti-PAX-5 790-4420 | Most B cell malignancies (pre-B and mature B cell lymphomas/ leukemia) B cell lymphomas | SP34 | Rabbit mAb | Intracellular |
| TdT 760-2670 | Marker of B or T cell acute lymphoblastic leukemia/ lymphoma | [Cell Marque] | Rabbit Poly Ab | Intracellular |
| MPO 760-2659 | AML-M1, M2 | [Cell Marque] | Rabbit Poly Ab | Intracellular |

Fluorophores used in this example are recorded in Table 22 (all from Roche):

TABLE 22

| TSA-Fluor | R6G: Carboxyrhod-6G-Tyr, MW: 1001.2 | Texas Red: Rhodamine101-p8-Tyr MW: 1149.37 | DCC: DCC-PEG8-Tyr, MW: 803.94 | Cy5: SulphoCy5-PEG8-Tyr: MW: 1199.5 | FITC: FITC-PEG8-Tyr, MW: 950.06 |
|---|---|---|---|---|---|

Other reagents used on the slide stainer in this example are recorded in Table 23 (all from Roche):

TABLE 23

| Reagent | Roche catalog number |
| --- | --- |
| Wash (RUO) DISCOVERY | 950-510/07311079001 |
| Liquid Coverslip (High Temperature) | 650-010/05264839001 |
| DISCOVERY CC1 | 950-500/06414575001 |
| ULTRA Cell Conditioning (ULTRA CC2) | 950-223/05424542001 |
| Reaction Solution (10x) | 950-300/05353955001 |
| DISCOVERY Goat Ig Block | 760-6008/07988214001 |
| Inhibitor, DISCOVERY | 760-4840/0717944001 |
| QD DAPI, DISCOVERY | 760-4196/05268826001 |
| DISC. OmniMap anti-Rb HRP RUO | 760-4311/5269679001 |
| DISC. OmniMap anti-Ms HRP RUO | 760-4310/5269652001 |

The stained cells were imaged using Zeiss M2 microscope.

5B. Panel Design

Multiple cell populations were stained simultaneously on a blood printed slide to identify atypical cells and disease stage. Patient blood was printed and analyzed on COBAS m 511 hematology analyzer for CBC report. The blood samples were further tested by IHC when CBC result flagged the presence of atypical cells. Four different panels, each consisting of 5 biomarkers+DAPI counterstain were stained using a BenchMark ULTRA autostainer. Different leukocyte and lymphoma biomarkers helped identify the status of disease blood samples.

Four different 5-plex panel combinations were evaluated as recorded in Table 24:

TABLE 24

| Panels | Biomarker panel |
| --- | --- |
| 1 | CD5, CD2, CD8, CD4, CD45 |
| 2 | CD5, CD3, CD23, CD10, CyclinD1 |
| 3 | Pax5, CD5, CD23, CyclinD1, CD3 |
| 4 | CD3, CD5, CD38, CD23, ZAP-70 |

5C. Panel 1: CD5, CD2, CD8, CD4 and CD45

The 5-Plex Panel #1 involve fluorescent multiplex stain of 5 biomarkers: CD5, CD2, CD8, CD4 and CD45. Table 25 below discusses the cell population identified by IHC and the staining location in the cellular compartment. Presence of CD5 positive cells {orange} indicates a chronic lymphocytic leukemia (CLL) blood sample.

TABLE 25

| Biomarker | Staining cells | Predicted location |
| --- | --- | --- |
| CD2 | All peripheral blood T-cells | Cell membrane |
| CD4 | Effector T cells | Cell membrane |
| CD5 | T cells and most T cell lymphomas, a marker for CLL | Cell membrane |
| CD8 | Cytotoxic T cells | Cell membrane |
| CD45 | Pan leukocytes | Cell membrane |

The blood printed slides were fixed in 10% NBF for 30 minutes. Deparaffinization step was not needed on these slides in the autostainer. The assay involved 5 sequential rounds of primary antibody stain with a heat deactivation step between each rounds. Following a short cell conditioning step of 20 minutes each primary antibody was incubated for 32 minutes and secondary antibodies for 8 minutes. The antibody fluorophore pair tested in the panel 1 are: (1) CD5: R6G (2) CD8: DCC (3) CD2: Red610 (4) CD4: Cy5 (5) CD45: FAM. The study design is described in Table 26.

TABLE 26

| | Study design for panel 1 | | | | |
| --- | --- | --- | --- | --- | --- |
| Stain Procedure | CD5 | CD8 | CD2 | CD4 | CD45 |
| Clone | SP19 | SP57 | MRQ-11 | SP35 | 2B11PD7/26 |
| Primary antibody time | 32 min | 32 min | 32 min | 32 min | 32 min |
| 2nd Antibody/time | GaR-HRP/ | GaR-HRP/ | GaR-HRP/ | GaR-HRP/ | GaM-HRP/ |
| | 8 min | 8 min | 8 min | 8 min | 8 min |
| H2O2 | 4 min | 4 min | 4 min | 4 min | 4 min |
| TSA-flurophore | 8 min | 8 min | 8 min | 8 min | 8 min |
| FL Dye | R6G | DCC | Red610 | Cy5 | FAM |
| DAPI | 12 min | 12 min | 12 min | 12 min | 12 min |

Figure 18:
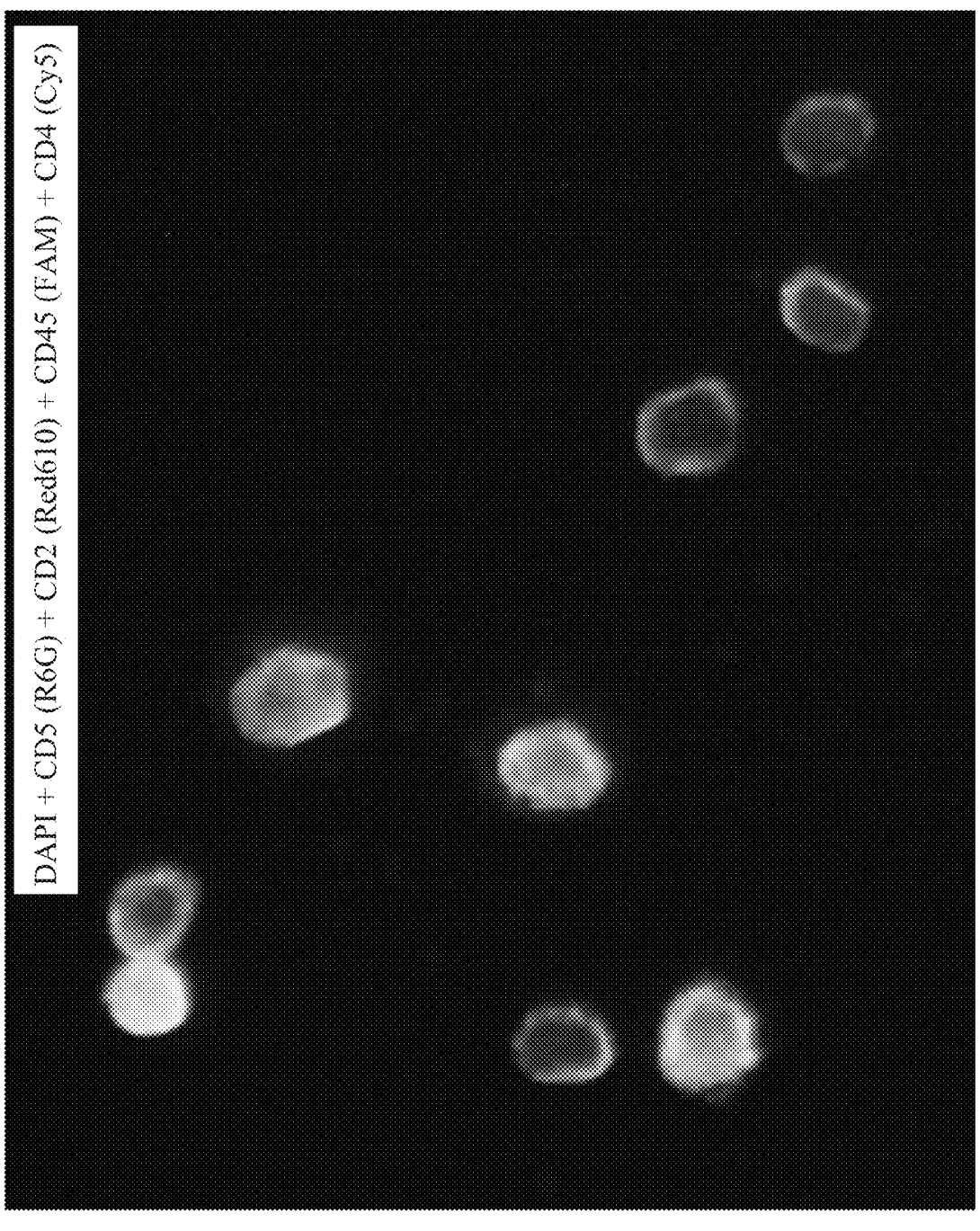
FIG. 18: Multiplex staining of CD5, CD2, CD8, CD4 and CD45 biomarker on a single slide flagged with atypical cells.

An exemplary stain can be seen at FIG. 18. The 5-plex assay protocol successfully stained all 5 biomarkers simultaneously on a single slide. Leukocytes population was stained with CD45, a pan leukocyte marker (green). Co-registration of CD45 with different subsets of CD8 (Aqua) and CD4 (Magenta) was observed. The staining of high percentage of CD5 positive cells (Orange) on the slide indicated a positive chronic lymphocytic leukemia (CLL) blood sample. All CD5 positive cells co-registered with CD45 cells. Some CD45 and CD5 cells also co-stained with CD2 (Red) that stains all peripheral blood T-cells. Panel 1 involves multiplex staining of CD5, CD2, CD8, CD4 and CD45 biomarkers. The panel identifies immune cell distribution (CD8 and CD4) among the atypical cell population in the blood printed slide. CD5 was included in the panel. CD5 is expressed in chronic lymphocytic leukemia/small lymphocytic lymphoma (CLL/SLL) and mantle cell lymphoma (MCL). Large number of CD5 positive cells (orange) indicates the blood sample to be a lymphoma/leukemia case. 5D: Panel 2: CD5, CD3, CD23, CD10, CyclinD1

The 5-Plex Panel-2 involve fluorescent multiplex stain of 5 biomarkers consisting of CD5, CD3, CD23, CD10 and Cyclin D1. Table 27 discusses the cell population identified by IHC and the staining location in the cellular compartment.

TABLE 27

| Biomarker | Staining cells | Predicted location |
|---|---|---|
| CD3 | Pan T-cells | Cell membrane |
| CD5 | T cells and most T cell lymphomas, Marker for CLL | Cell membrane |
| CD10 | Diagnosis of pre B-ALL | Cell membrane |
| CD23 | Marker for CLL | Intracellular and membrane |
| Cyclin D1 | Positive stain for B-CLL | Nuclear, intracellular |

The NBF fixed blood printed slides were sequentially stained with 5 biomarker following the staining criteria from Panel 1. The antibody fluorophore pair tested in the panel 2 are (1) CD5: R6G (2) CD3: DCC (3) CD23: Red610 (4) CD10: Cy5 (5) CyclinD1: FAM. The study design is described in Table 28 below.

TABLE 28

| | Study design for panel 2 | | | | |
|---|---|---|---|---|---|
| Stain Procedure | CD5 | CD3 | CD23 | CD10 | CyclinD1 |
| Clone | SP19 | 2GV6 | SP23 | SP67 | SP4-R |
| Primary antibody time | 12 min | 12 min | 12 min | 12 min | 12 min |
| 2nd Antibody/time | GaR-HRP/ | GaR-HRP/ | GaR-HRP/ | GaR-HRP/ | GaR-HRP/ |
| | 8 min | 8 min | 8 min | 8 min | 8 min |
| H2O2 | 4 min | 4 min | 4 min | 4 min | 4 min |
| TSA-fluorophore | 12 min | 12 min | 12 min | 12 min | 12 min |
| FL Dye | R6G | DCC | Red610 | Cy5 | FAM |
| DAPI | 12 min | 12 min | 12 min | 12 min | 12 min |

Figure 19:
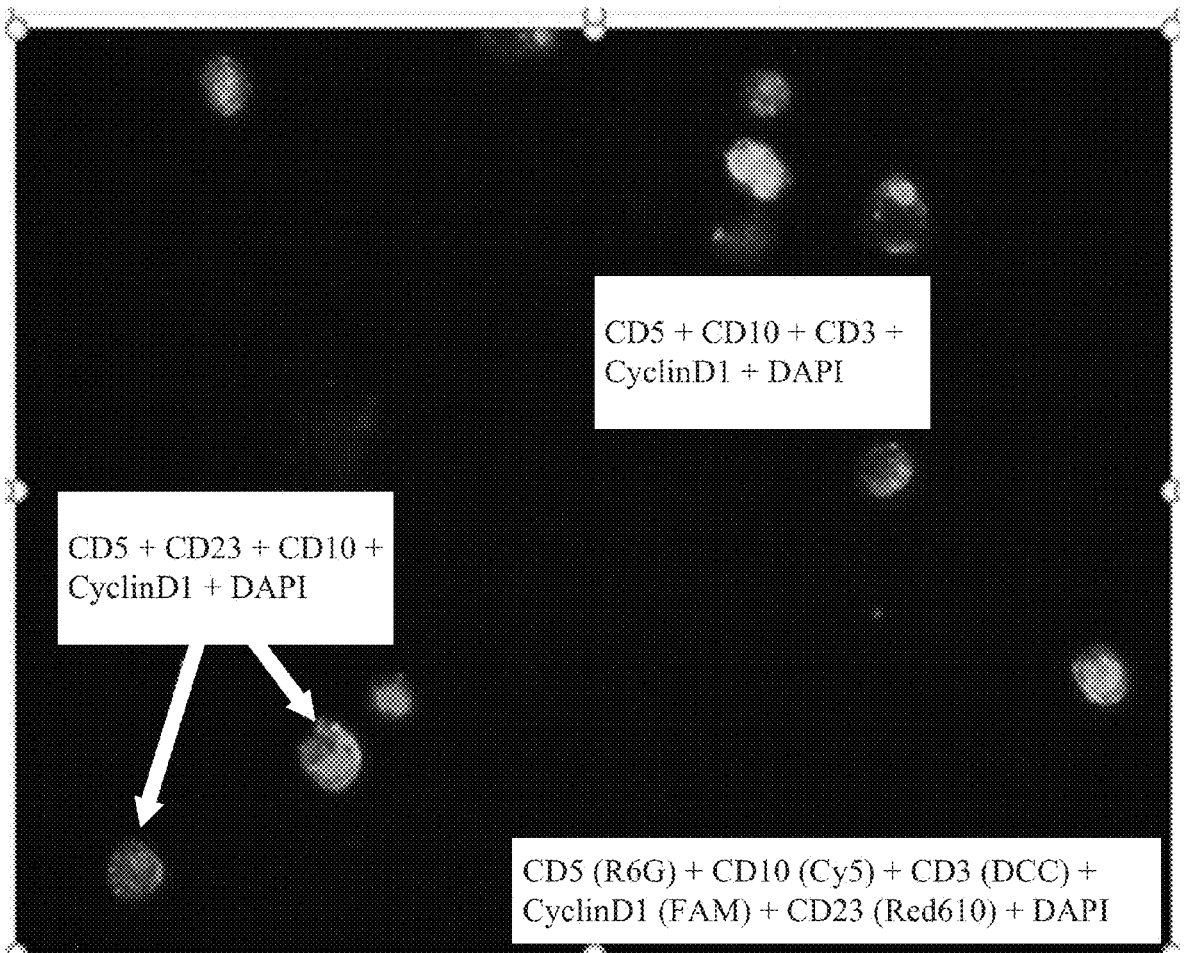
FIG. 19: Multiplex staining of CD5, CD3, CD23, CD10 and CyclinD1 biomarker on a single slide flagged with atypical cells. Cyclin D1 (green) nuclear stain is observed in multiple cells. Co registration of CD5 (orange), CD23 (red) and CD10 (magenta) are observed in some cells in this FOV.

An exemplary stain can be seen at FIG. 19. The 5-plex assay protocol successfully stained all 5 biomarkers simultaneously on a single slide. A number of cell populations stained with Cyclin D1, a key marker for identifying B-CLL. Co-registration of CD5 (orange), CD10 (magenta), CD23 Red) was observed. Closer inspection in individual channel indicated different staining pattern on same or different cells. CD3 positive cells stained with aqua.

Panel 2 involves multiplex staining of CD5, CD3, CD23, CD10 and CyclinD1 biomarkers. Panel 2 opens up a new capabilities of multiplexing diseased blood cells printed on slides. Unique observation like co-staining of CD5 and CD10 could be seen through such technology. CD5 is characteristically expressed in chronic lymphocytic leukemia/small lymphocytic lymphoma (CLL/SLL) and mantle cell lymphoma (MCL) whereas CD10 is expressed in acute precursor B- or T-cell lymphoblastic leukemia/lymphoma (ALL). The co-expression of CD5 and CD10 is unusual in B cell lymphomas and had diagnostic challenges. Cases of CD5 and CD10 co-expression has been reported in diverse subtypes of B-cell lymphoma by Dong et al. The staining of high percentage of CD5 positive cells (Orange) on the slide indicated a positive lymphomas (CLL) blood sample, whereas Cyclin D1 nuclear stain indicated mantle cell lymphoma {MCL}. Strong staining of cyclin D1 in CD5 positive MCL has been reported {Meyerson, 2006}. Such co expression pattern and identification of rare cases (Al Mussaed) is possible when multiplexing in done on same cells on same slide which is a unique application of this technology. 5E Panel 3: Pax5, CD5, CD23, CyclinD1 and CD3

The 5-Plex Panel-3 involve fluorescent multiplex stain of 5 biomarkers consisting of Pax5, CD5, CD23, CyclinD1 and CD3. Table 29 discusses the cell population identified by IHC and the staining location in the cellular compartment.

TABLE 29

| Biomarker | Staining cells | Predicted location |
|---|---|---|
| Pax5 | Positive for B cell lymphomas | Intracellular |
| CD5 | T cells and most T cell lymphomas, marker for CLL | Cell membrane |
| CD23 | Marker for CLL | Intracellular and membrane |
| CyclinD1 | Positive stain for B-CLL | Nuclear, intracellular |
| CD3 | Pan T cell | Cell membrane |

The NBF fixed blood printed slides were stained with Romanowsky-type stain and whole slide scan captured in Zeiss AXIO. The same slide is then restained with 5 biomarker following the staining criteria from Panel 1. The antibody: flurophore pair tested in the panel are: (1) Pax5: R6G (2) CD5: DCC (3) CD23: Red610 (4) Cyclin D1: Cy5 (5) CD3: FAM. The staining protocol is set forth in Table 30:

TABLE 30

| Procedure Stain | Pax5 | CD5 | CD23 | CyclinD1 | CD3 |
|---|---|---|---|---|---|
| Romanowsky stain/scan | Yes | Yes | Yes | Yes | Yes |
| Clone | SP34 | SP19 | SP23 | SP4-R | 2GV6 |
| Primary antibody time | 32 min | 32 min | 32 min | 32 min | 32 min |
| 2nd Antibody/time | GaR-HRP/ | GaR-HRP/ | GaR-HRP/ | GaR-HRP/ | GaR-HRP/ |
|  | 8 min | 8 min | 8 min | 8 min | 8 min |
| TSA-fluorophore | 12 min | 12 min | 12 min | 12 min | 12 min |
| FL Dye | R6G | DCC | Red610 | Cy5 | FAM |
| DAPI | 12 min | 12 min | 12 min | 12 min | 12 min |

The slide is rescanned in Zeiss AXIO scanner. Using Zeiss AXIO split viewer, the images from same location are placed side-by slide for pathological evaluation.

Figure 20:
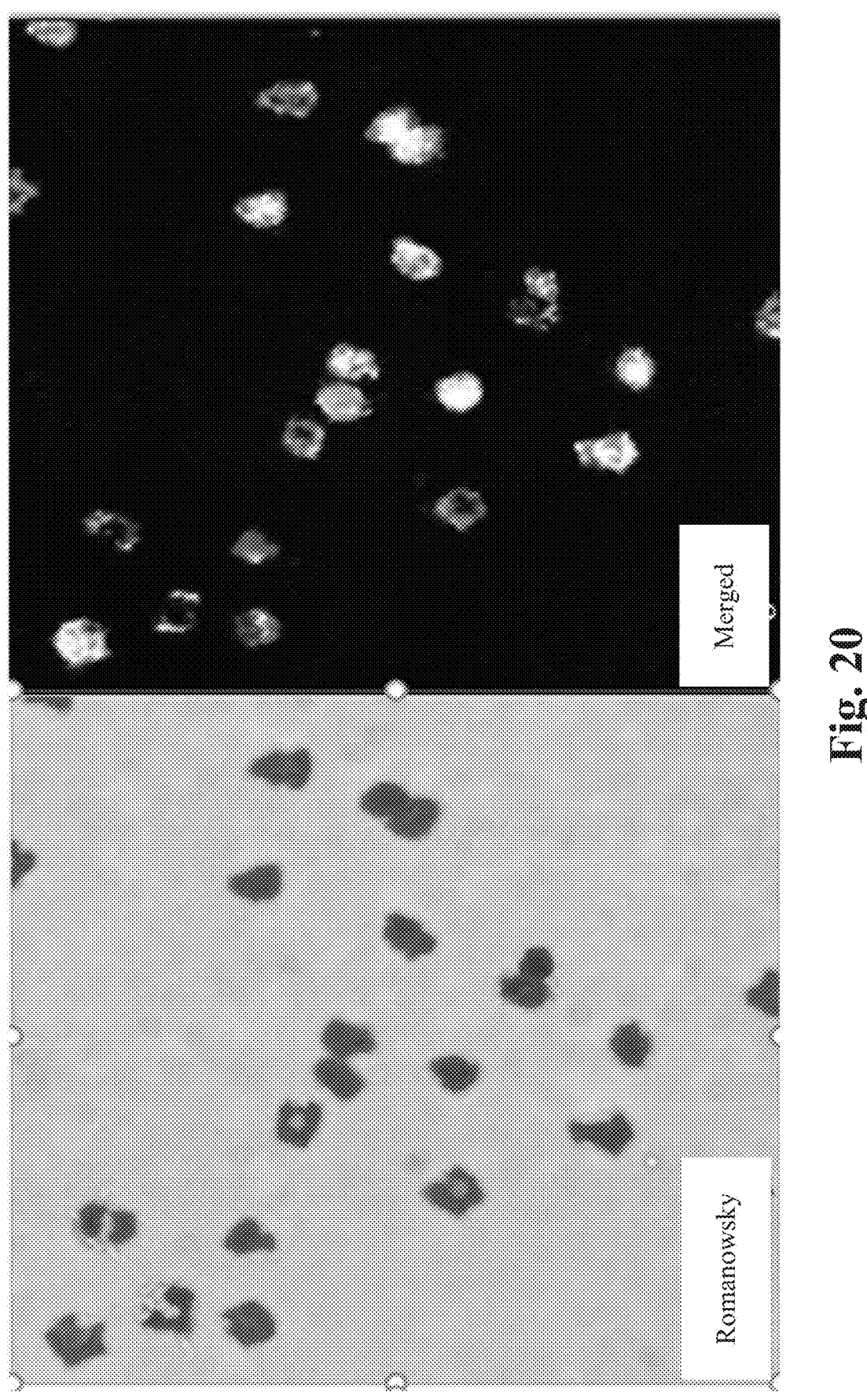
FIG. 20: Multiplex staining of Pax5, CD5, CD23, CyclinD1 and CD3 biomarker on a single slide flagged with atypical cells. Co stain of CD5 positive cells {aqua} with Pax5 (orange) cells and Cyclin D1 (magenta) nuclear stain has generated a merged white stain.

An exemplary stained slide is at FIG. 20. The 5-plex assay protocol successfully stained all 5 biomarkers simultaneously on a single slide. Most of cell population were stained with Cyclin D1 nuclear marker (magenta), a key marker for identifying B-CLL. Whereas presence of CD5 positive cells {aqua} indicates a chronic lymphocytic leukemia (CLL) blood sample. Co-registration of CD5 (aqua), Pax5 (orange) and CD23 (red) was observed. CD3 (pan T cell, green) positive cells co-registered with CD5 (T lymphoma, orange) positive cells in the FOV indicating presence of T cell lymphoma. On the other hand, positive Pax5 (orange) cells co-staining with Cyclin D1 (magenta) nuclear stain indicated presence of B-CLL in the same blood.

Panel 3 involves multiplex staining of Pax5, CD5, CD23, CyclinD1 and CD3 biomarkers. Pax5 is a valuable biomarker in the diagnosis and sub classification of lymphomas mainly for Hodgkin and B-cell non-Hodgkin lymphomas. However, co staining of Pax5, a B-Cell marker, with CD5, a T-Cell marker, is rare and suggests MPAL (Mixed Phenotype Acute Leukemia) and opens up additional application of this technology. With the availability of current tools, hematopathologists can stratify acute leukemia's to myeloid, B-lymphoid, or T-lymphoid lineages. However, classifying 5% of the cases identified as acute leukemias of ambiguous origin can be more challenging. It requires extensive multiparametric flow cytometry and immune-phenotyping for correct diagnosis. Some cases are now identified as mixed-phenotype acute leukemia (MPAL) by WHO. Porwit et al shows a case (#76, Male, 26 yrs) with dual (Pax5/CD5) positive cells and identified as MPAL, B/myeloid {Porwit, 2015}. It has been acknowledged that clinical management of MPAL cases are problematic and emphasis is laid on accurate diagnosis to identify MPAL cases and not misdiagnose as either ALL or AML. Such MPAL instances can be diagnosed by using multiplex stain on the same slide as seen in this panel with co-registration of Pax5 and CD5 in multiple cells. Multiple such cases have been cited by Steensma 2011.

5F. Panel 4: CLL Prognostic panel; CD3, CD5, CD38, CD23 and ZAP-70

The 5-Plex Panel-4 involved fluorescent multiplex stain of 5 biomarkers consisting of CD3, CD5, CD38, CD23 and ZAP-70. Table 31 discusses the cell population identified by IHC and the staining location in the cellular compartment.

TABLE 31

| Biomarker | Staining cells | Predicted location |
|---|---|---|
| CD3 | All peripheral blood T-cells | Cell membrane |
| CD5 | T cells and most T cell lymphomas, Marker for CLL | Cell membrane |
| CD38 | Prognosis for CLL patients | Intracellular |
| CD23 | Marker for CLL | Intracellular and membrane |
| ZAP-70 | ZAP-70 B-CLL, normal T cell and NK cell | Intracellular |

The NBF fixed blood printed slides were sequentially stained with 5 biomarker following the staining criteria from Panel 1. The antibody fluorophore pair tested in the panel 4 are (1) CD3: R6G (2) CD5: DCC (3) CD38: Red610 (4) CD23: Cy5 (5) and Zap-70: FAM. The study design is described in Table 32 below.

Figure 21:
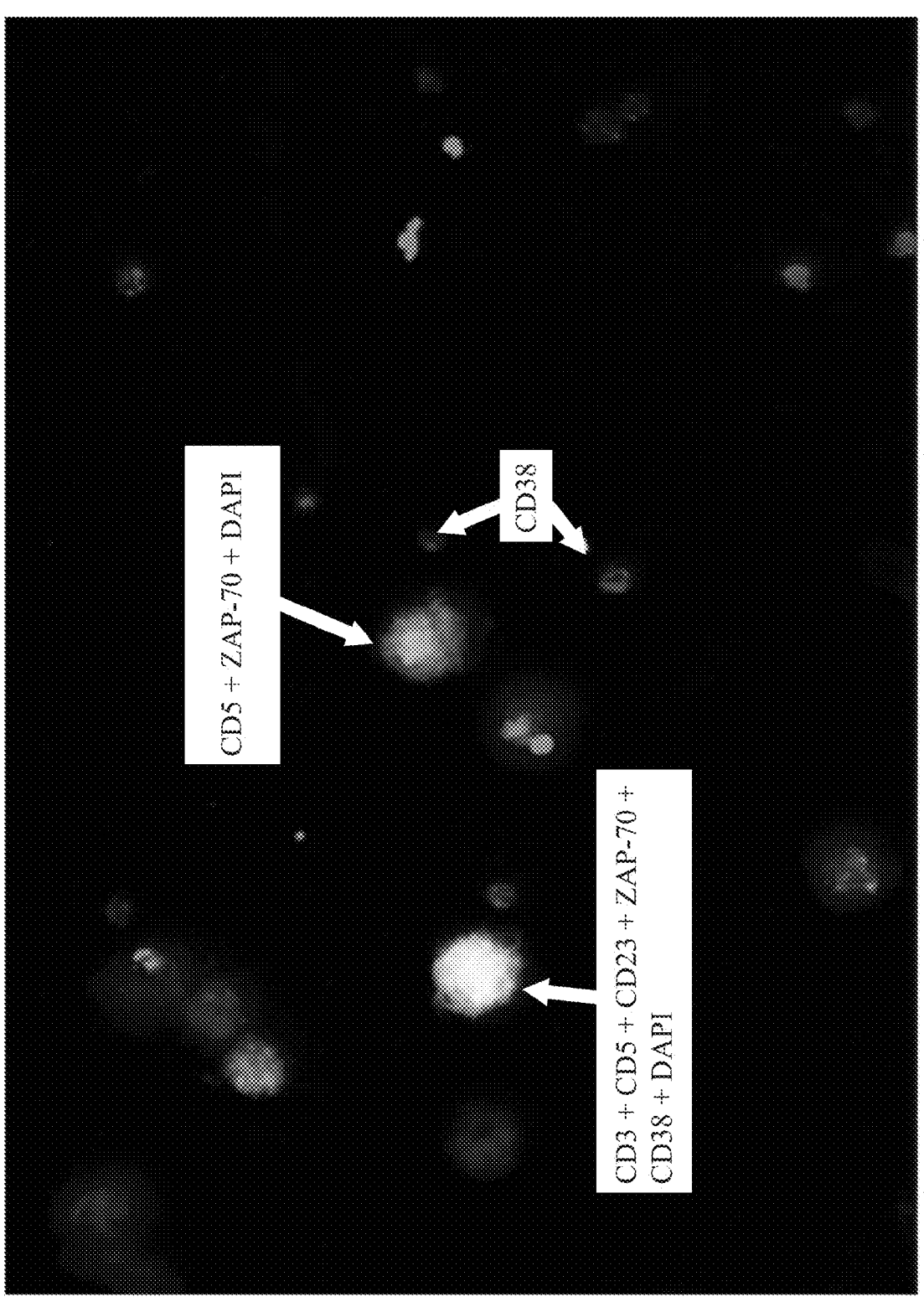
FIG. 21: Multiplex staining of CD3, CD5, CD38, CD23 and ZAP-70 biomarker on a single slide flagged with atypical cells. A cell co-registering all 5 biomarkers (CD3, CD5, CD38, CD23 and ZAP-70) is seen in the FOV. CD38 also stained the platelets seen as red dots.

An exemplary stained slide is at FIG. 21. The 5-plex assay protocol successfully stained all 5 biomarkers simultaneously on a single slide. Presence of CD23 positive marker (magenta) and CD5 (aqua) indicates a chronic lymphocytic leukemia (CLL) blood sample. In this FOV multiple cells were stained with Zap-70 (green) that co-stained with CD38 (red) positive cells. A cell co stained with CD3 (orange) and CD5 (aqua) is also observed. CD38 (red) also stained activated platelet in the blood, seen as red dots in the FOV.

TABLE 32

| Study design for panel 4 | | | | | |
|---|---|---|---|---|---|
| Stain Procedure | CD3 | CD5 | CD38 | CD23 | ZAP-70 |
| Clone | 2GV6 | SP19 | SP149 | SP23 | 2F3.2 |
| Primary antibody time | 32 min | 32 min | 32 min | 32 min | 32 min |
| 2nd Antibody/time | GaR-HRP/ | GaR-HRP/ | GaR-HRP/ | GaR-HRP/ | GaM-HRP/ |
| | 8 min | 8 min | 8 min | 8 min | 8 min |
| H2O2 | 4 min | 4 min | 4 min | 4 min | 4 min |
| TSA-flurophore | 8 min | 8 min | 8 min | 8 min | 8 min |
| FL Dye | R6G | DCC | Red610 | Cy5 | FAM |
| DAPI | 12 min | 12 min | 12 min | 12 min | 12 min |

Panel 4 involves multiplex staining of CD3, CD5, CD38, CD23 and ZAP-70 biomarkers. Panel 4 involved choice of biomarker with prognostic potential. B-cell chronic lymphocytic leukemia (B-CLL) has highly variable clinical outcome from indolent to aggressive where aggressive outcome requires immediate intensive treatments. The role of ZAP-70 expression with more aggressive clinical course is well documented (Roullet, Admirand). Evaluation of both ZAP-70 and CD38 expression has been reported to stratify patient groups to favorable or worst prognosis {Hus, 2006 #13}. By multi-marker multiplexing we observe CD5 positive cells expressing high level of cyclin D1 in nucleus and ZAP-70. Similar results have been reported by Meyerson by flow.

As can be seen at Panels 1-4, multi-marker multiplexing can stratify patients with a quick turnaround time and help in disease stratification.

Figure 22:
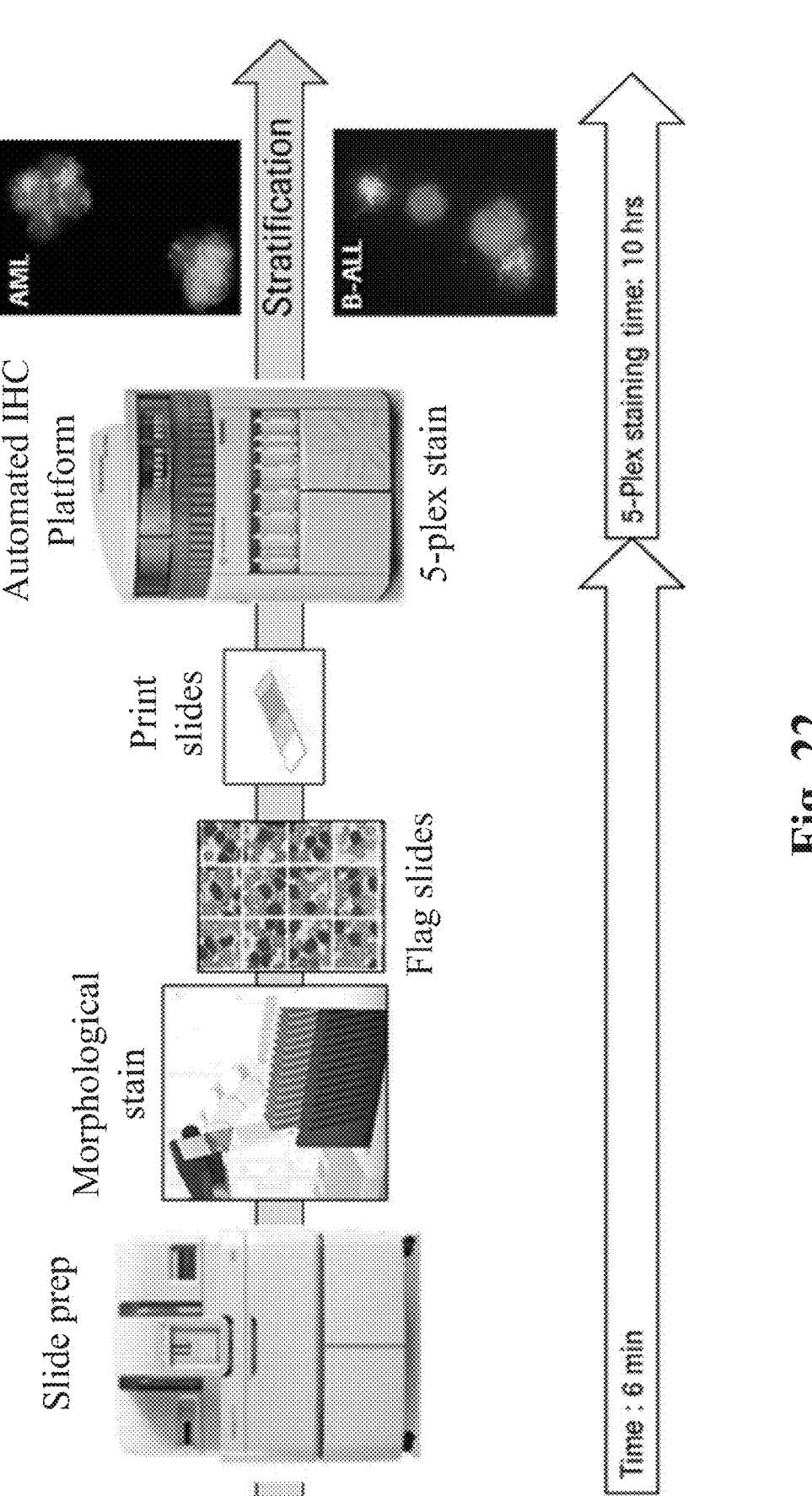
FIG. 22: Workflow for 5-plex assay design to stratify ALL and AML cases.

Example 6: Design and Stain of Leukocytes with a 5-Plex Panels on Automated Staining Platform to Stratify ALL from AML This example relates to whether atypical cells reported in CBC-printed slides can be tested with a carefully designed 5 biomarker panel to stratify ALL from AML. Staining of different biomarkers on the same slide by immunofluorescence multiplexing may help in accurate stratification of disease subtype with a fast turnaround time. An exemplary workflow is illustrated at FIG. 22. A 5-Plex stratification panel involving fluorescent multiplex stain of 5 biomarkers consisting of CD7, CD34, Pax5, TdT and MPO. Table 33 below discusses the cell population identified by IHC and the staining location in the cellular compartment.

TABLE 33

| Biomarker | Staining cells | Predicted location |
|---|---|---|
| CD7 | Marker for T-ALL | Intracellular |
| CD34 | AML marker | Intracellular |
| Pax5 | Most B cell malignancies | Intracellular |
| TdT | Marker for T-ALL | Intracellular |
| MPO | Diagnosis of acute myeloid leukemia | Intracellular |

The blood printed slides were fixed in 10% NBF for 30 minutes. Deparaffinization step was not needed on these slides in the autostainer. The assay involves 5 sequential rounds of primary antibody stain with a heat deactivation step between each rounds. Following a cell conditioning step of 20 minutes each primary antibody was incubated for 32 minutes and secondary antibodies for 8 minutes. The antibody flurophore pairs tested in the panel are: (1) CD7: R6G (2) CD34: DCC (3) Pax5: Red610 (4) TdT: Cy5 (5) MPO: FAM. The study design is described in Table 34.

TABLE 34

| Stain Procedure | CD7 | CD34 | Pax5 | TdT | MPO |
|---|---|---|---|---|---|
| Clone | SP94 | QBEnd/10 | SP34 | Rabbit Polyclonal | Rabbit Polyclonal |
| Primary antibody time | 32 min | 32 min | 32 min | 32 min | 32 min |
| 2nd Antibody/time | GaR-HRP/ 8 min | GaM-HRP/ 8 min | GaR-HRP/ 8 min | GaR-HRP/ 8 min | GaR-HRP/ 8 min |
| H2O2 | 4 min | 4 min | 4 min | 4 min | 4 min |
| TSA-flurophore | 8 min | 8 min | 8 min | 8 min | 8 min |
| FL Dye | R6G | DCC | Red610 | Cy5 | FAM |
| DAPI | 12 min | 12 min | 12 min | 12 min | 12 min |

Figure 23:
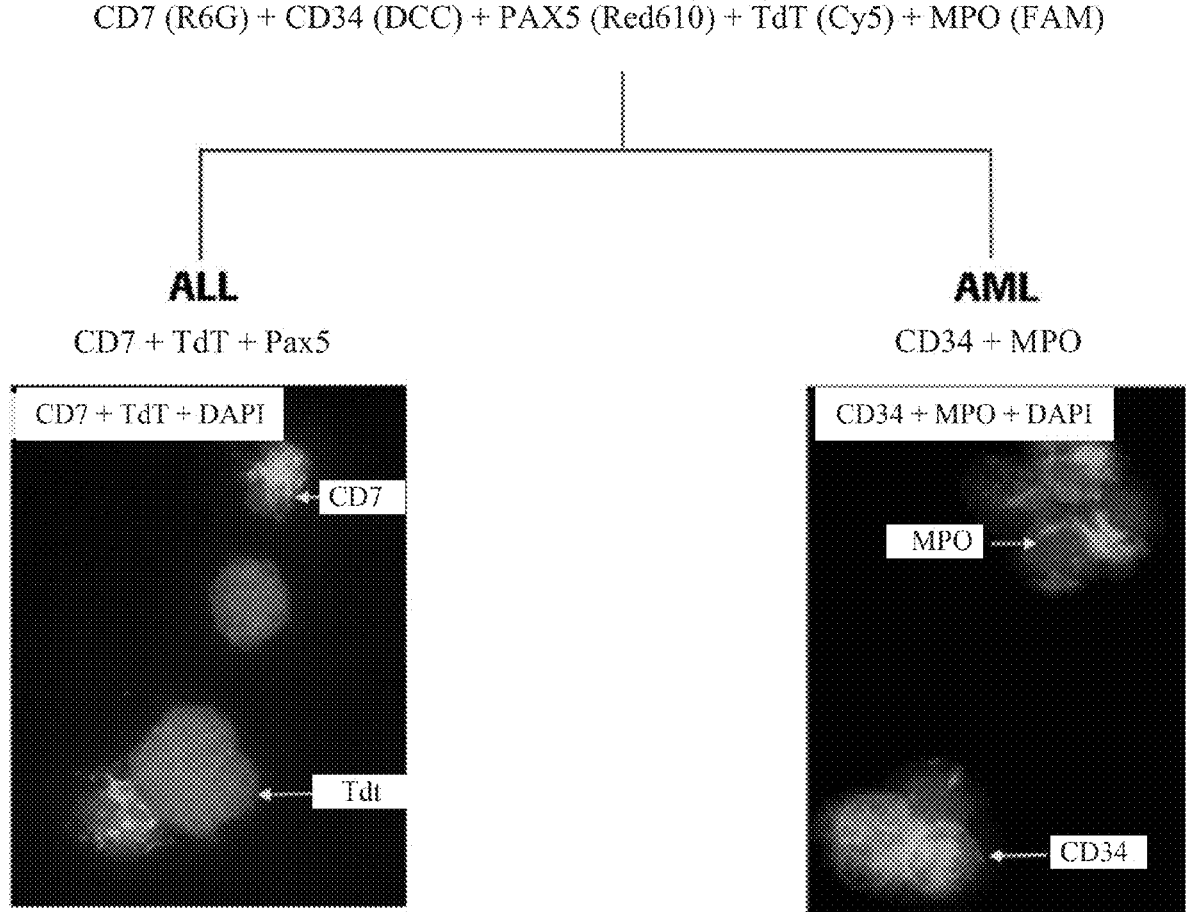
FIG. 23: A flow chart to show how to stratify AML from ALL using this workflow, and illustrative stains for both ALL and AML, including exemplary AML and ALL stains.

The 5-plex assay protocol was designed to separate out ALL from AML on slides with atypical cells. FIG. 23 is a flow chart to show how to stratify AML from ALL using this workflow, and illustrative stains for both ALL and AML. Myeloperoxidase (MPO) is a well-known marker to differentiate AML from ALL and demonstrate that the leukemic cells were derived from the myeloid lineage. In some slides we see strong expression of MPO. On the other hand, it is reported that most ALL cases express the nuclear enzyme Terminal deoxynucleotidyl Transferase (Tdt) (Chiaretti, Zini et al. 2014). ALL can be either T-ALL (CD34, Tdt, CD7) or B-ALL (CD34, Tdt, PAX-5) and AML can be identified by CD34 and MPO. CD34 is an indicator of a blasts (immature cell), so it can be seen in either case.

Exemplary stains are illustrated at FIG. 23. Multiplex staining of CD7, CD34, Pax5, Tdt and MPO biomarkers separated ALL from AML. Strong MPO (green) stain was observed in some slides and were identified as AML blood. Co registration of CD7 (orange), with Tdt (magenta) are observed in some slides that did not show any MPO stain. These slides were stratifying as ALL. In some slides there was strong expression of MPO (green) along with few CD34 positive (red stain) cells indicating AML blood. On other slides, there was no MPO stain, but CD7 (orange) positive cells with strong Tdt stained (magenta) cells. Such combination stain could be ALL blood. Pax5 (red) stain was observed along with CD7 and Tdt further identifying the blood as B-ALL.

Figure 24:
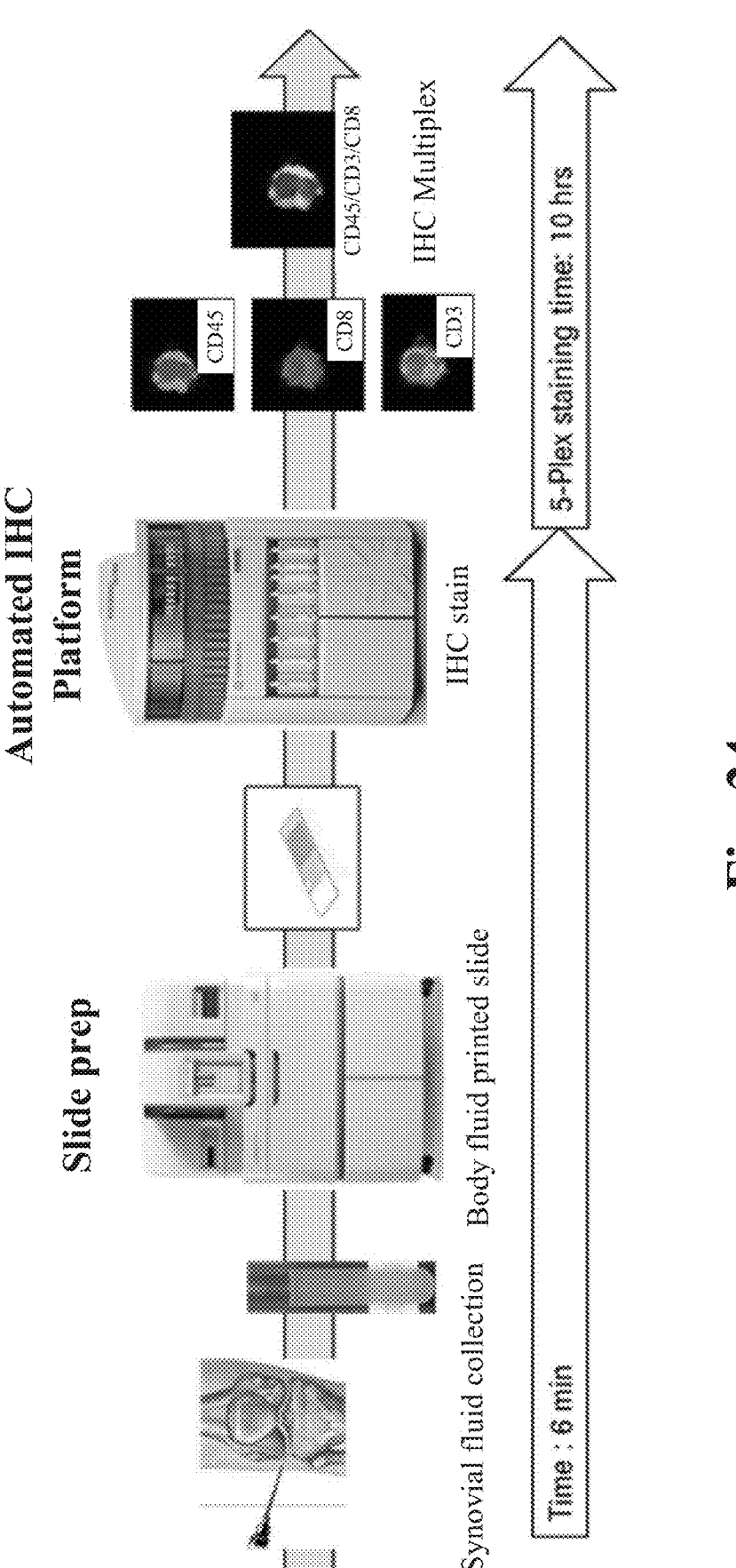
FIG. 24: Body fluid staining workflow.

Example 7: Design and Stain of Body Fluid Printed Slides with a 5-Plex Biomarker Panel on Automated Staining Platform Various body fluid like peritoneal fluids, synovial fluids, cerebrospinal fluids, or bronchial alveolar lavage are routinely tested to identify the underlying cause of inflammation. Synovial fluid analysis is helpful for determining the underlying cause of arthritis like septic arthritis. This example tests whether body fluid can be printed on slides and generate white cell count and differential count. Further, immune cell populations (T cell, B cell, macrophages, neutrophil) can be identified by affinity cytochemical staining. An exemplary workflow is illustrated at FIG. 24.

Residual samples of peritoneal fluids, synovial fluids, cerebrospinal fluids, and bronchial alveolar lavage were collected in red top tubes. Sample aliquots ranged from 2.0 ml-2.5 ml in volume. All samples were processed on glass slides with the COBAS m 511 integrated hematology system using the default profile (CBC, DIFF). Slides were reviewed for cellularity. All samples were then processed on the COBAS m 511 system using the Special Sample Option, unstained profile. The unstained slides were fixed in 10% NBF for 30 minutes.

7A: Synovial Fluid

A 5-Plex panel was tested on a synovial sample involved fluorescent multiplex stain of 5 biomarkers consisting of CD3, CD8, CD45, CD68, Oscar. No de-paraffinization step was needed on these slides in the autostainer. Following a short cell conditioning step of 20 minutes each primary antibody was incubated for 32 minutes and secondary antibodies for 8 minutes. The assay involves 5 sequential rounds of primary/secondary antibody stain with a heat deactivation step between each rounds. The antibody flurophore pairing tested are: (1) Oscar: R6G (2) CD3: DCC (3) CD8: Red610 (4) CD68: Cy5 (5) CD45: FAM. The study design is described in Table 35.

TABLE 35

| Stain Procedure | Oscar | CD3 | CD8 | CD68 | CD45 |
|---|---|---|---|---|---|
| Clone | | 2GV6 | SP57 | KP-1 | 2B11PD7/26 |
| Primary antibody time | 32 min | 32 min | 32 min | 32 min | 32 min |
| 2nd Antibody/time | GaM-HRP/ | GaR-HRP/ | GaR-HRP/ | GaM-HRP/ | GaM-HRP/ |
| | 8 min | 8 min | 8 min | 8 min | 8 min |
| H2O2 | 4 min | 4 min | 4 min | 4 min | 4 min |
| TSA-flurophore | 8 min | 8 min | 8 min | 8 min | 8 min |
| FL Dye | R6G | DCC | Red610 | Cy5 | FAM |
| DAPI | 12 min | 12 min | 12 min | 12 min | 12 min |

Table 36 below discusses the cell population tested by immunostaining and the staining location in the cellular compartment. A Zeiss AXIO was used to scan the slides.

Figure 25A:
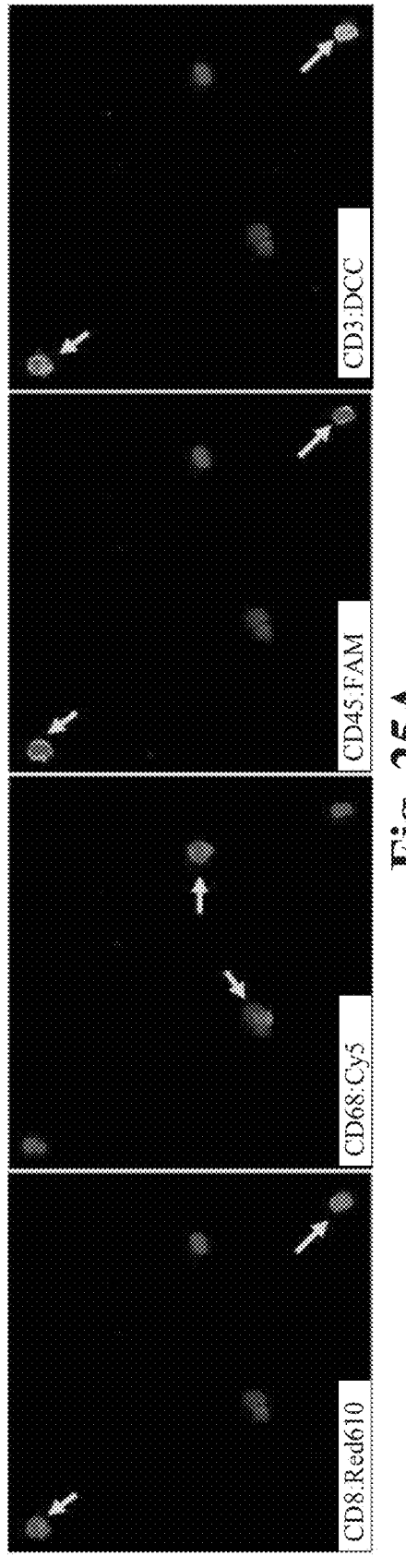
FIG. 25A: An example of multiple biomarkers on a single synovial fluid slide stained on an automated tissue staining platform.
Figure 25B:
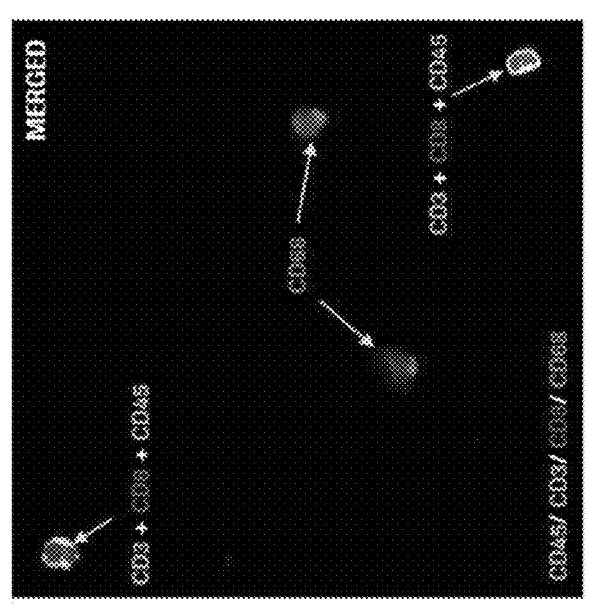
FIG. 25B: Four-plex merged images of the synovial fluid slide.

Exemplary stains are at FIGS. 25A and 25B. FIG. 25A is individual stains and FIG. 25B is a merged image. Immune cells like macrophage, CD3 positive pan T cells and a subset of CD8 positive cytotoxic T cells were identified. A number of cellular population was stained with CD45 pan leukocyte marker (FIG. 25A). Oscar, a cytokeratin antibody, did not stain any cell indicating absence of epithelial cells in the fluid.

TABLE 36

| Biomarker | Staining cells | Predicted location |
|---|---|---|
| CD3 | Pan immune T cells | Cell membrane |
| CD8 | Cytotoxic T cells | Cell membrane |
| CD68 | Macrophage | Cytoplasmic stain |
| CD45 | Pan leukocytes | Cell membrane |
| Oscar | Epithelial cells | Cell membrane |

7B: Broncho alveolar Lavage (BAL) sample

Figure 26:
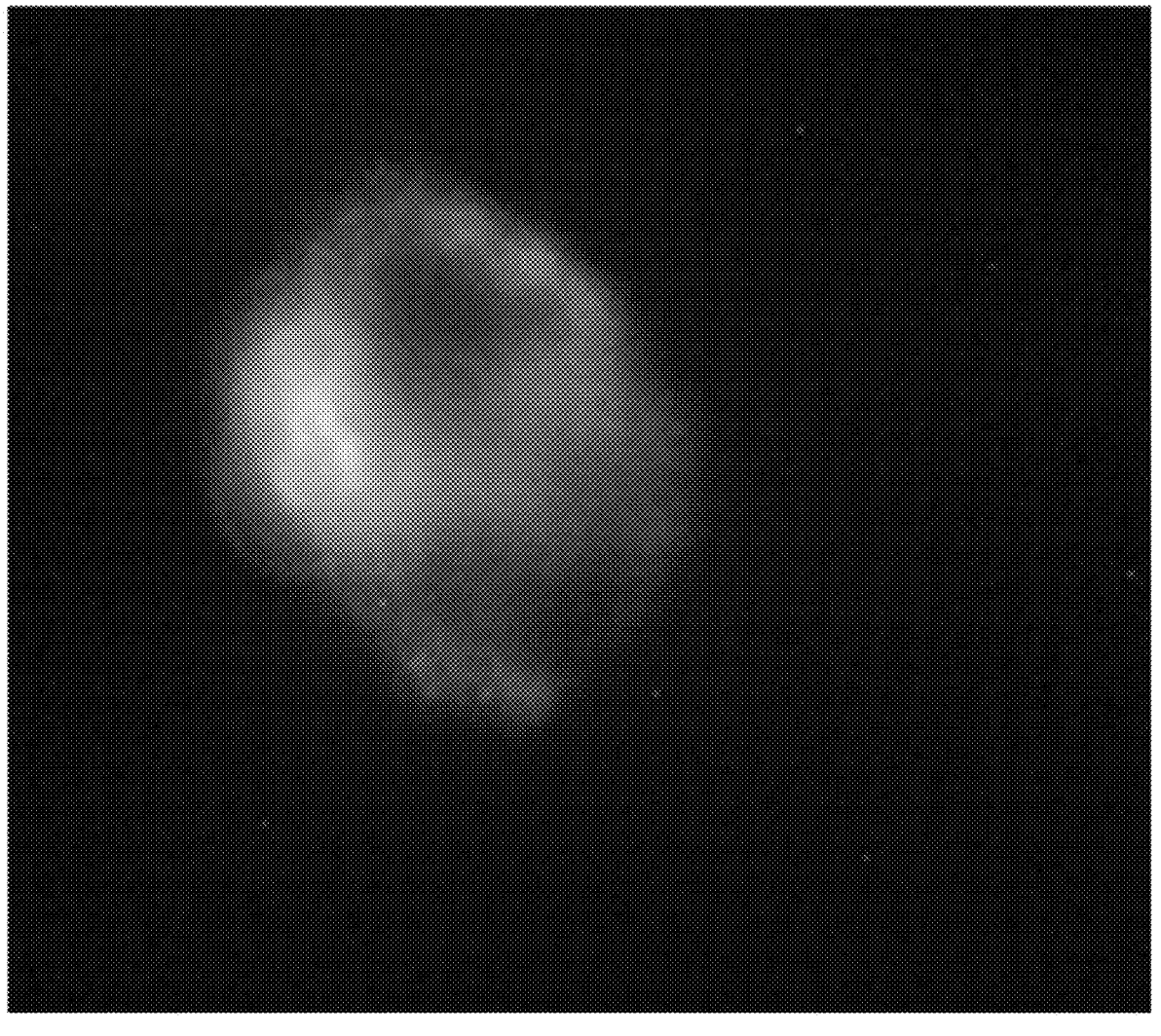
FIG. 26: 3 plex merged image consisting of CD45 (green), CD8 (red) and CD3 (aqua) is seen in a cell from BAL printed slide.

Bronchoalveolar Lavage (BAL) sample was printed on slides and the slides stained as outlined above, using an antibody flurophore pairing tested are: (1) Oscar: R6G (2) CD3: DCC (3) CD8: Red610 (4) CD68: Cy5 (5) CD45: FAM. FIG. 26 illustrates a 3 plex merged image consisting of CD45 (green), CD8 (red) and CD3 (aqua) is seen in a cell from BAL printed slide. This demonstrates that a workflow including printed slides stained with an automated advanced staining system can be used to differentiate cell populations in BAL samples.

Example 8: Platelet Stain of Blood Printed Slide with CD38 Biomarker on an Automated Tissue Staining Platform CD38 is a transmembrane protein that shows enzymatic activity involved in cellular adhesion and signaling in leukocytes. It is expressed in a variety of cell types including hematopoietic precursors, plasma cells, germinal center B cells (weakly), a subset of T and natural killer cells, erythrocytes, platelets, prostatic epithelium, and smooth and striated muscle cells. In some cases, it may be a marker of activation. CD38 expression may be useful in the diagnosis of lympho-proliferative and plasma cell proliferative disorders. Determination of CD38 expression by flow cytometry has been used as a prognostic marker on chronic lymphocytic leukemia. CD38 can also be used to identify activated platelets, which is useful in patients with abnormally functioning platelets (inherited or acquired disorders) or in certain patients at high risk of thrombosis (e.g. cardiac or cancer patients).

Figure 27:
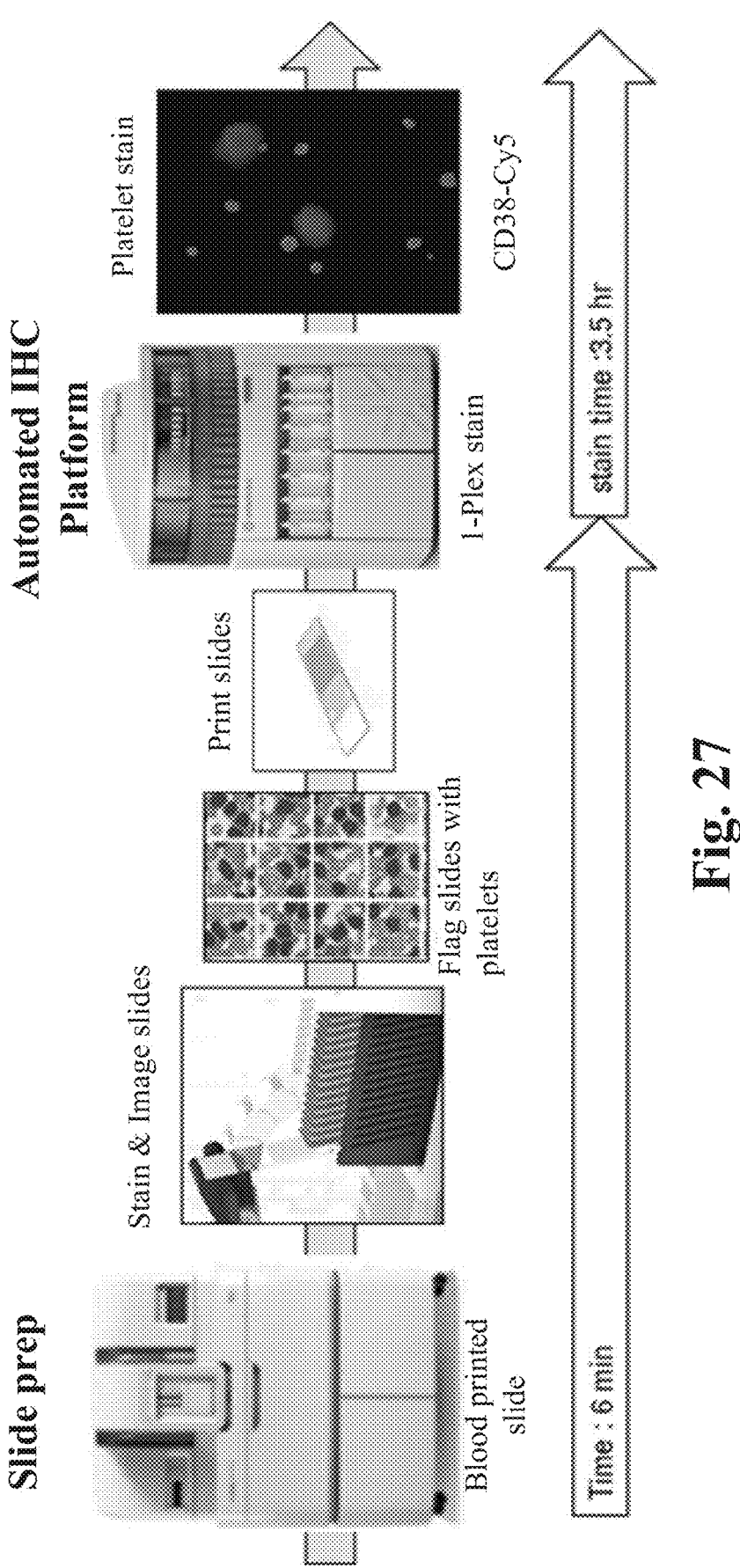
FIG. 27: Workflow of platelet staining on blood printed slide.

In the current example, we evaluated whether whole blood printed on glass slides and stained with an automated advanced staining platform could be used to evaluate platelet populations for CD38 expression. FIG. 27 illustrates the exemplary workflow.

Human blood samples (1 μL) were printed on glass slide with COBAS m 511 integrated hematology system. The blood printed slides were fixed in 10% NBF for 30 minutes and stained with Romanowsky stain. Romanowsky-stained slides were scanned with a Zeiss AXIO slide scanner. A simplex fluorescent stain with CD38 was used to identify platelet status in the patient blood printed slides generated from COBAS m 511 hematology analyzer. Cell conditioning was performed for 20 minutes. Printed slides were stained in a simplex fluorescent affinity staining format, using an anti-CD38 rabbit monoclonal primary antibody, an HRP-labeled anti-rabbit secondary antibody, a cyanine 5 fluorophore kit (DISCOVERY Cy5 kit), and a DAPI counterstain. The study design and protocol detail is in Table 37 below.

TABLE 37

| Parameters | CD38 |
|---|---|
| Primary antibody clone | SP149 |
| Sample Type | blood |
| Romanowsky Stain/Scan | Yes |
| Primary Antibody time | 32 min |
| $2^{nd}$ Ab/Time (min) | GaR-HRP/12 min |
| DISCOVERY Cy5 | Yes |
| QD-DAPI | 12 |

Figure 28:
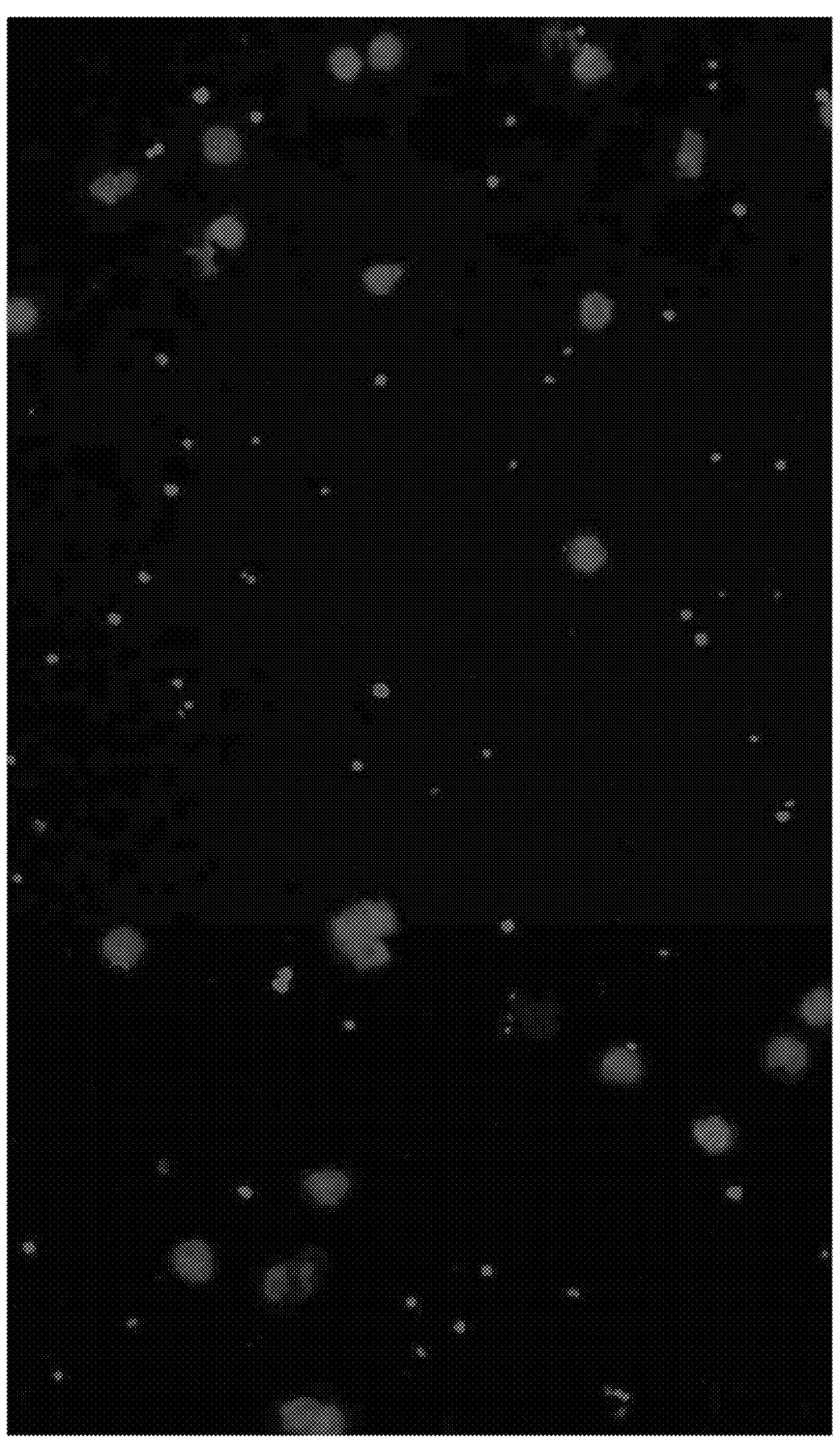
FIG. 28: An example of platelet stain on blood film stained on an automated tissue staining platform.

An exemplary image is found at FIG. 28. Clear bright red dots staining platelets were seen on the slide. The Cy5 stained dots were confirmed to be platelet by comparing the Romanowsky-type stain/scanned images of the same slide.

This example demonstrates that platelets in a Romanowsky-stained whole blood sample printed on a glass slide can be affinity stained on an automated advanced staining platform. By staining for CD38 in such an assay, platelet profiles can be tested on slides for multiple diseases. For example, expression of CD38 has been associated with a number of diseases, including HIV infection, autoimmune diseases [e.g. systemic lupus erythematosus], type II diabetes mellitus 3, osteoporosis, and cancer. For example, CD38 is expressed in a large number of hematological malignancies, including multiple myeloma (MM), CL, Waldenström's macroglobulinemia, primary systemic amyloidosis, mantle cell lymphoma, acute lymphoblastic leukemia, acute myeloid leukemia NK cell leukemia NK/T-cell lymphoma and plasma cell leukemia.

Figure 29:
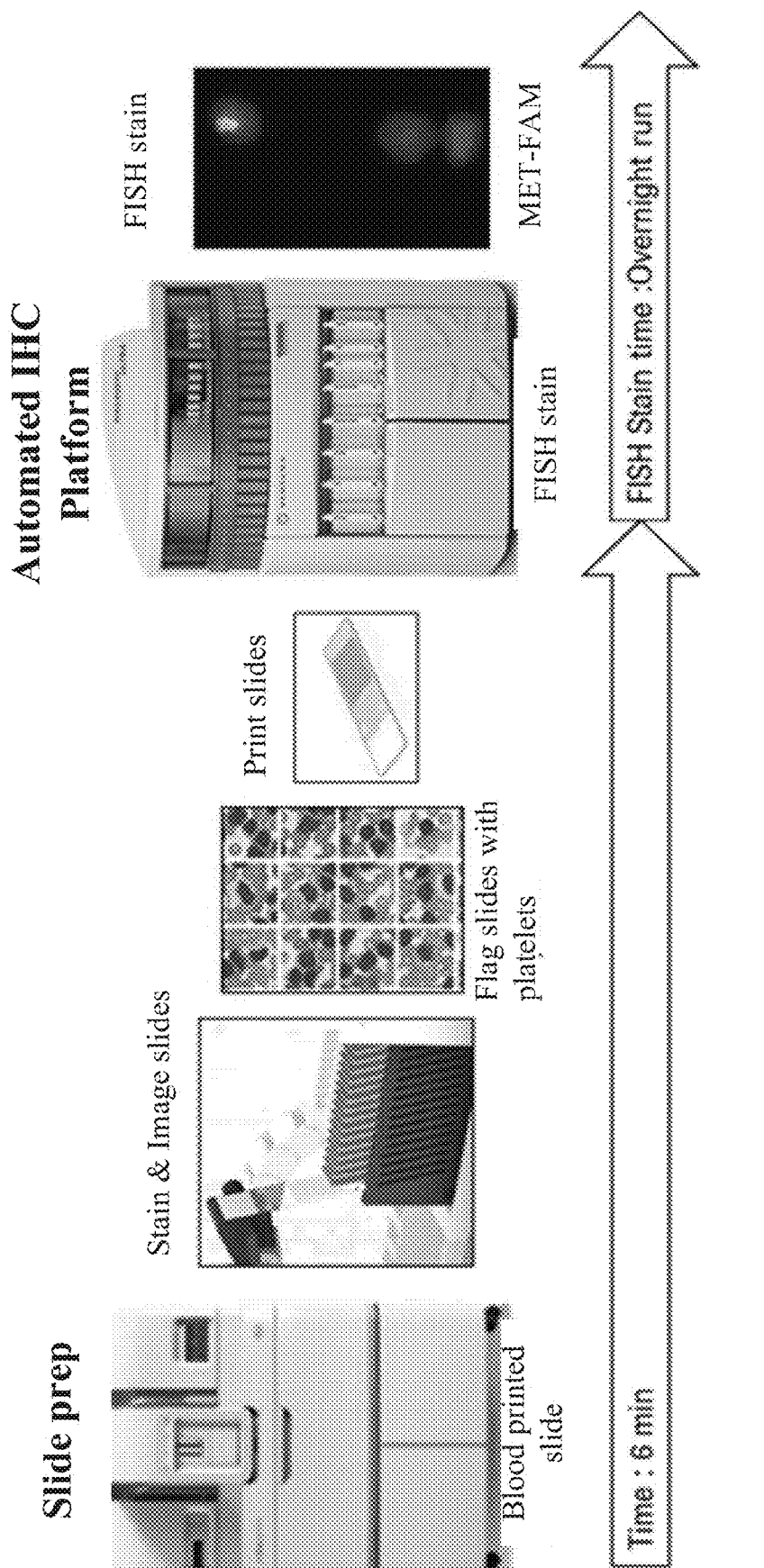
FIG. 29: Exemplary workflow for FISH staining printed slides.

Example 9: FISH Stain on Blood Printed Slide Using an Automated Tissue Staining Platform Fluorescence in situ hybridization (FISH) is commonly used to detect chromosome changes (cytogenetic analysis) in blood or bone marrow cells. FISH helps identify genetic abnormalities that may not be evident with an examination of cells under a microscope. In this example, FISH assays were tested on whole blood printed slides generated using the COBAS m 511 integrated hematology system. An exemplary workflow is illustrated at FIG. 29.

Human blood samples (1 μL) were printed on glass slides with COBAS m 511 integrated hematology system. The blood printed slides were fixed in 10% NBF for 30 minutes. The printed slides were stained in a simplex FISH format using hapten-labeled Chromosome 12 and Met probes on a BenchMark ULTRA platform. The slide was treated with ISH protease for 8 minutes to help permeabilize cellular and nuclear membranes. A digoxigenin (DIG)-labeled Chromosome 12 probe was hybridized for 6 hours on a normal blood slide followed by 3 stringent washes with saline-sodium citrate buffer (SSC). The slide was then treated with a DIG-specific monoclonal antibody conjugated to horseradish peroxidase (HRP). Rhodamine 6G was deposited by reacting the sample with a tyramide-rhodamine 6G (TSA-R6G) conjugate for 20 minutes. Slides were scanned at 40× magnification with a Zeiss M2 system. This was repeated on a diseased CLL blood printed slide by hybridizing a dinitrophenyl (DNP)-labeled MET probe for 6 hours followed by 3 stringent SSC washes. The slide was treated with HRP-conjugated DNP monoclonal antibody and amplified with a tyramide-FAM conjugate (TSA-FAM) for 60 minutes. Both slides were nuclear counterstained with DAPI.

The protocol parameters are in Table 38:

TABLE 38

| Parameters | MET | CR12 |
|---|---|---|
| Sample Type | Blood printed slide | Blood printed slide |
| CC2 | 4 min | 4 min |
| ISH-PROTEASE 3 | 8 min | 8 min |
| DISCOVERY inhibitor | 12 min | 12 min |
| HYB RDY SOL | 4 min | 4 min |
| Probe | MET-DIG | CR12-DNP |
| Hybridization | 6 hr | 6 hr |
| Enzyme conjugate | Anti DIG-HRP | Anti DNP-HRP |
| DISCOVERY FAM/R6G | 60 min | 20 min |
| QD-DAPI | 12 min | 12 min |

Figure 31:
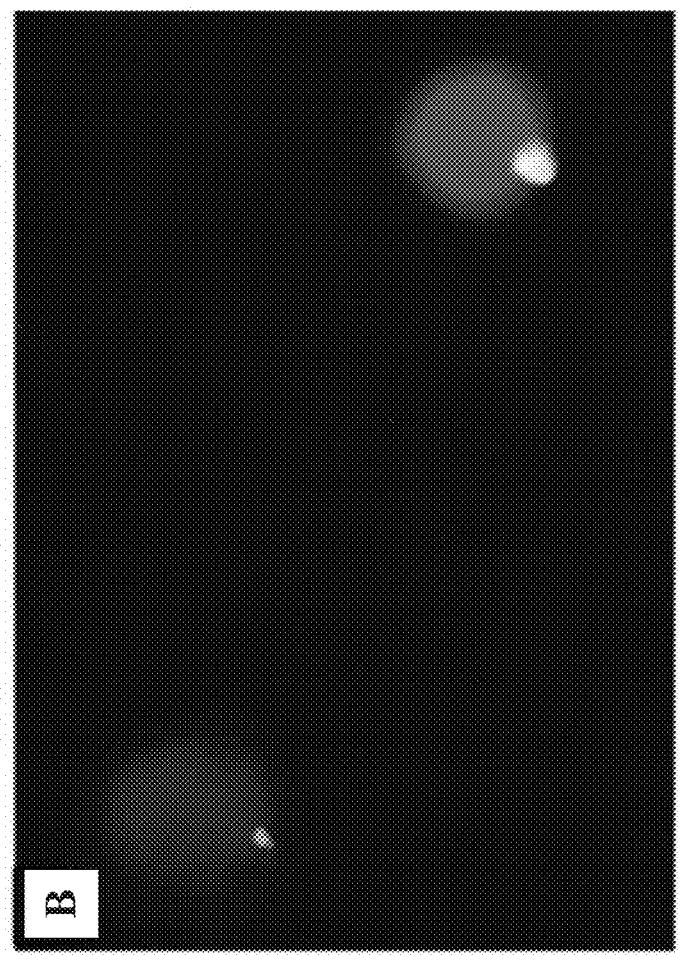
FIG. 31: An example of Met FISH stain on blood film stained on an automated tissue staining platform.
Figure 30:
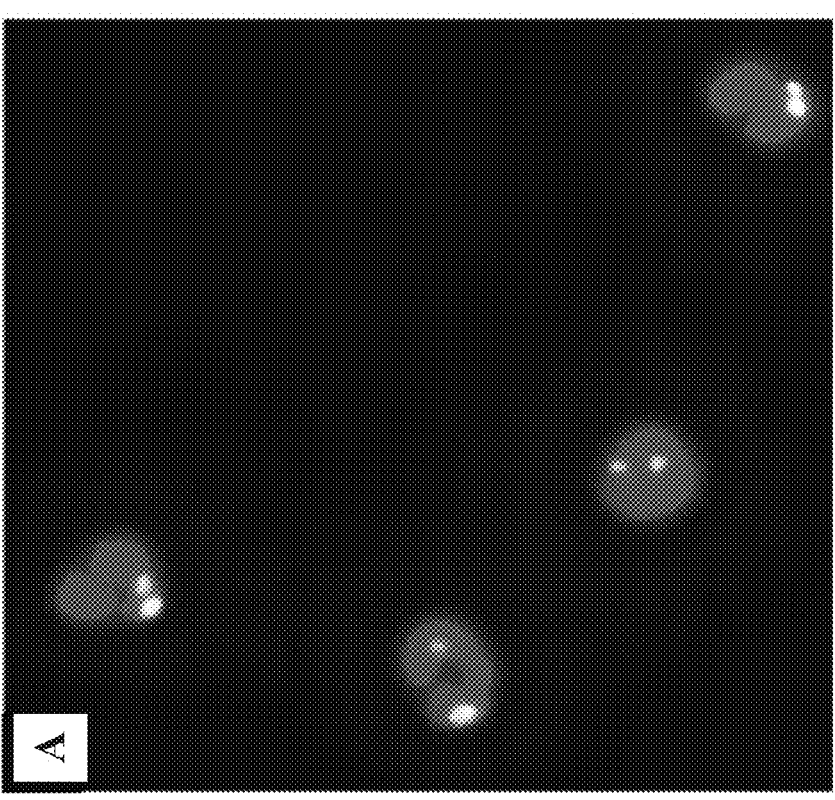
FIG. 30: An example of Chromosome 12 FISH stain on blood film stained on an automated tissue staining platform.

Exemplary stained slides are illustrated at FIGS. 30 and 31. An intense orange signal for Chromosome 12 was observed on normal blood printed slide and the blue counterstained nuclei (FIG. 30). Amplified MET expression (seen as green dots on blue counterstained nuclei) is observed in CLL blood printed slide (FIG. 31).

The success of performing FISH on whole blood printed slide opens up a number of applications, including: (1) diagnosing, prognosing, and/or selecting therapies for proliferative disease in blood samples; (2) identifying blood borne pathogens; and (3) using bone marrow or blood to monitor disease or therapy progression.

Example 10: Use Dual Markers Stain on Blood Printed Slides

The infiltration of Pax5 positive cells in the blood indicates the disease progression of B-CLL. To evaluate the ratio of T and B cells in CLL patients, 2 biomarkers were tested with both fluorescent and chromogenic detection system. Table 39 discloses biomarker information of panel 2 and staining location in cells:

TABLE 39

| Biomarker | Staining cells | Predicted location |
|---|---|---|
| CD3 | Pan T cell marker | Membrane |
| Pax5 | Most B cell malignancies | Intracellular |

Figure 32:
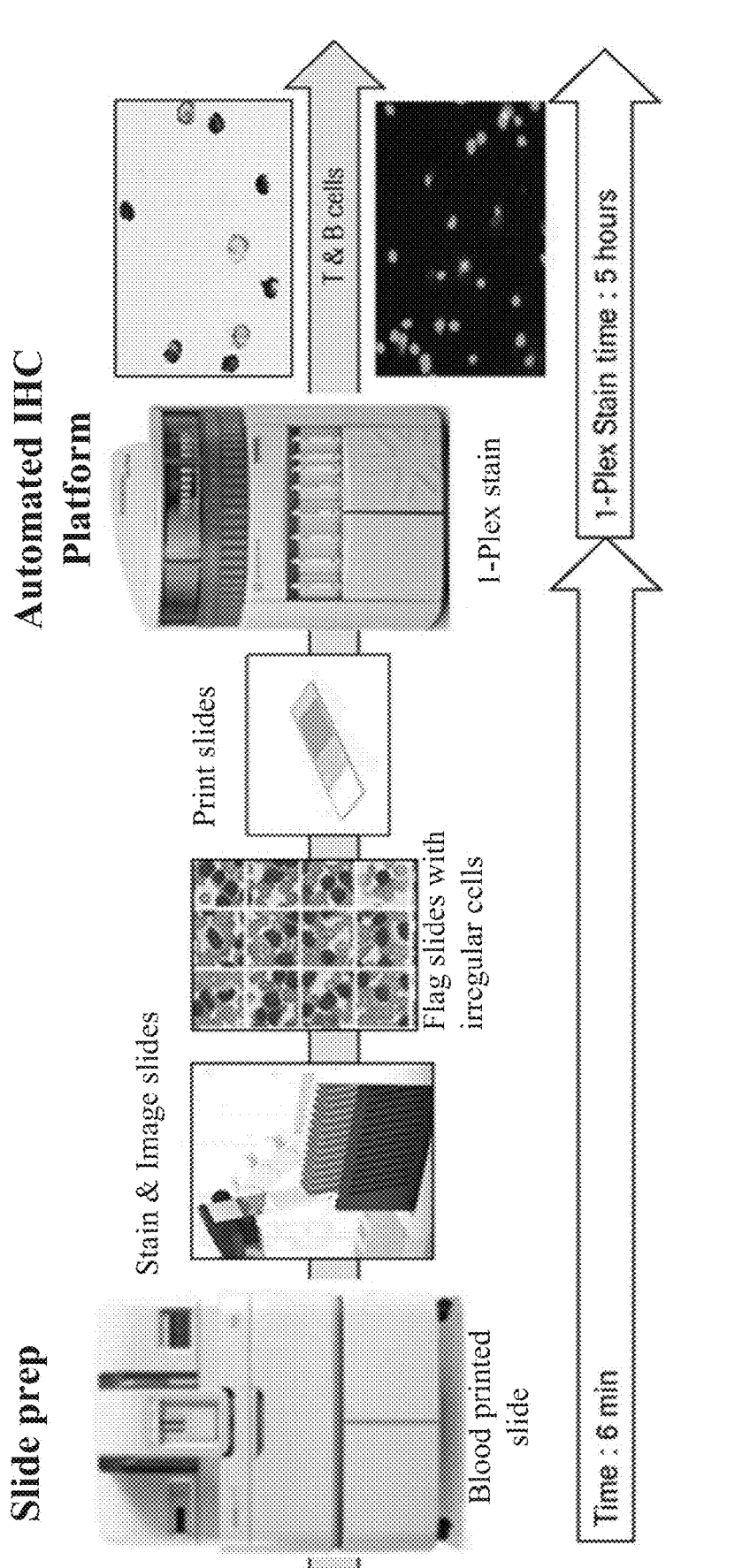
FIG. 32: A quick turnaround assay design to identify disease prognosis.

An exemplary workflow is illustrated at FIG. 32.

Human blood samples (1 µL) were printed on glass slide with COBAS m 511 integrated hematology system. Unstained slides were fixed with methanol or NBF. Cell conditioning was done for 20 minutes with primary antibody incubation for 32 minutes. The assay involves 2 sequential rounds of primary antibody stain with a heat deactivation step between each rounds. The antibody/detectable label pairings were: (a) for fluorescent detection: Pax5/R6G, and CD3/DCC duplex; and (b) for brightfield detection, Pax5/DAB and CD3/DISCOVERY Purple. A Zeiss AXIO scanner was used to scan the whole slide. The study parameters of both fluorescent and chromogenic duplex is captured in Table 40.

TABLE 40

| Parameters | Pax5 | CD3 | Pax5 | CD3 |
|---|---|---|---|---|
| Assay | Chromogenic | | Fluorescent | |
| Clone | SP34 | 2GV6 | SP34 | 2GV6 |
| Sample Type | CLL Blood | CLL Blood | CLL Blood | CLL Blood |
| 1° Antibody time | 32 min | 32 min | 32 min | 32 min |
| 2° Ab/Time | GaM-HQ/12 min | GaM-HQ/12 min | GaR-HRP/8 min | GaR-HRP/8 min |
| 3° Ab/Time | HQ-HRP/12min | HQ-HRP/12min | — | — |
| TSA-fluorophore | — | — | 8 min | 8 min |
| Detection Kit | DAB | DISCOVERY Purple | R6G | DCC |
| Hematoxylin/ Bluing | 12 min/4 min | 12 min/4 min | — | — |
| DAPI | — | — | 12 min | 12 min |

Figure 33:
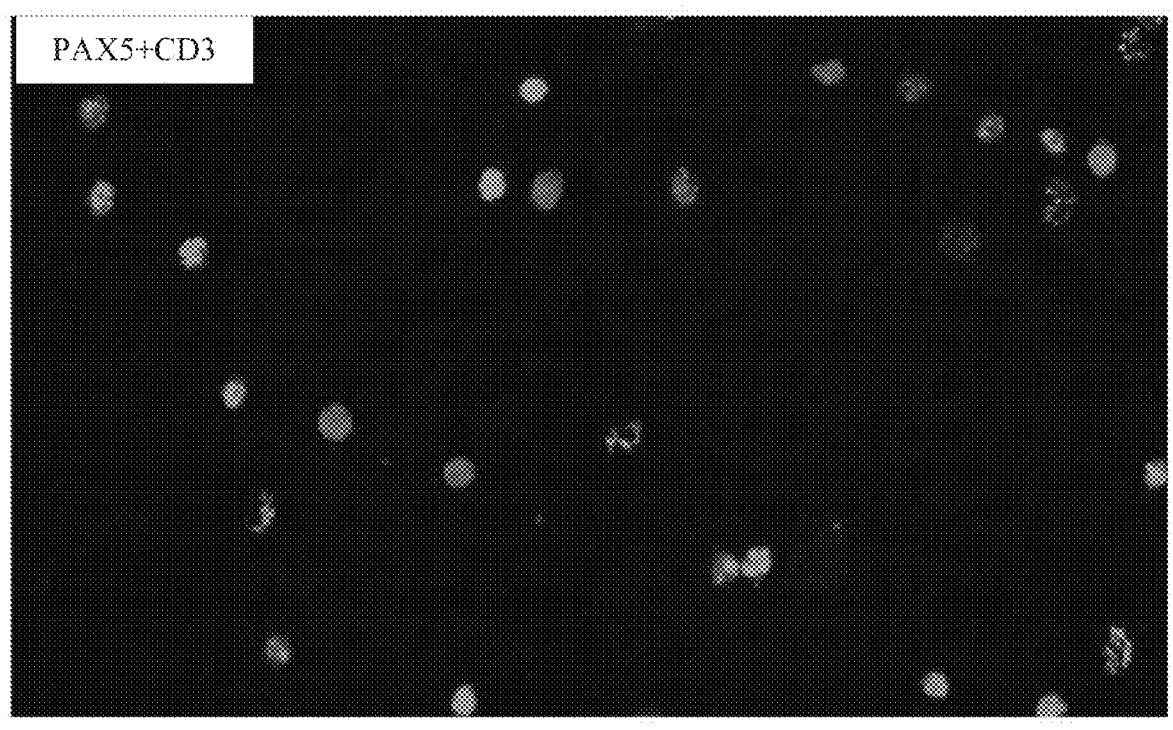
FIG. 33: Fluorescent duplex stain of Pax5 and CD3 markers stained on an automated tissue staining platform
Figure 34:
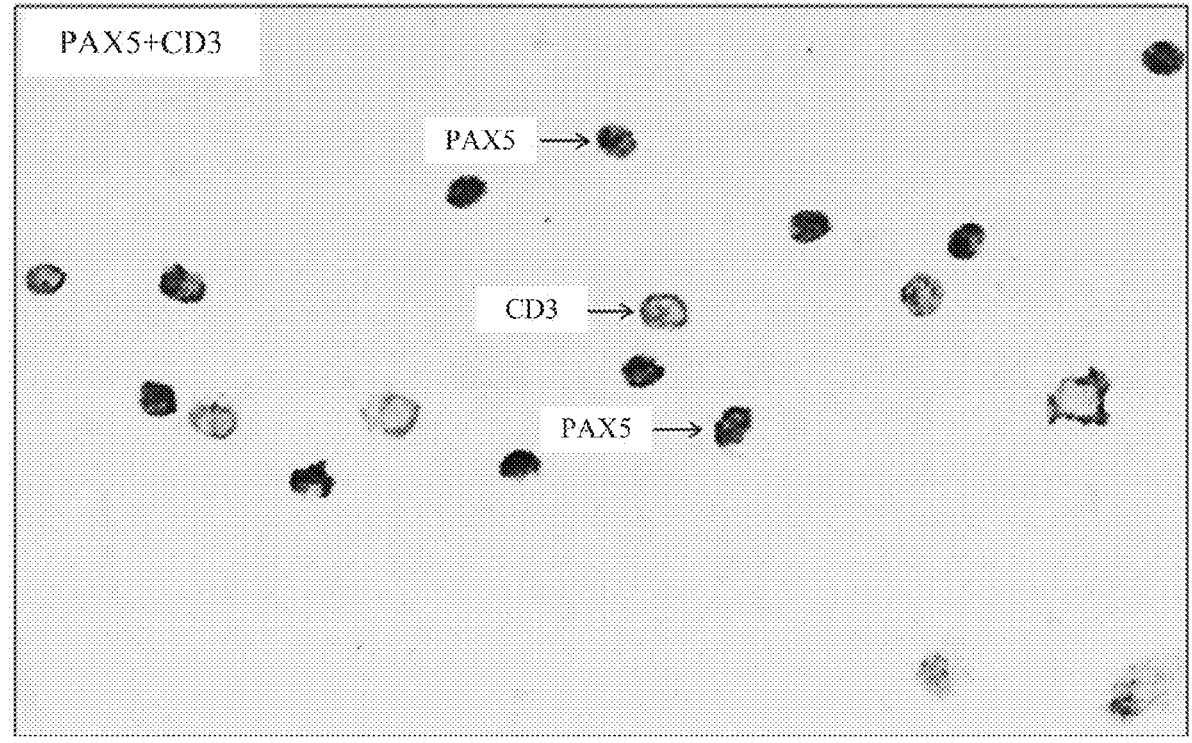
FIG. 34: Chromogenic duplex stain of Pax5 and CD3 markers stained on an automated tissue staining platform

As used in Table 40, CLL=Chronic lymphocytic leukemia; GaM-HQ=goat anti-mouse antibody conjugated to an HQ hapten; GaR-HRP=goat anti-rabbit antibody conjugated to horseradish peroxidase; and DAB=3,3'-Diaminobenzidine Exemplary stained slides are found at FIG. 33 (fluorescent) and FIG. 34 (Chromogenic). The infiltration of Pax5 positive cells were seen by both assays. The large Pax5 (green/DAB) positive cells on the slide clearly indicated the disease progression of the patient. Few CD3 (red/purple) positive cells are observed in slides indicating the immune population is outnumbered for these patients.

Pax5 positive cell infilteration in the blood indicates the disease progression. The ratio of immune cell (CD3) and cancer cell circulation is crucial for therapy decision. Normal blood should have mostly T cells, and some B cells. However, when there is an absolute lymphocytosis, and we want to figure out if this is reactive, or possible a peripheralized lymphoma, or a leukemia, such assays can be used for stratification decision. Such cases with massive B cells presence in blood, we could consider it to be lymphoma/ leukemia. On the other hand, if it is mostly T cells, it could either be reactive (generally viral), or a T cell leukemia (which is rarer).

VIII. Specifically Included Embodiments

The following embodiments are specifically contemplated as part of the disclosure. This is not intended to be an exhaustive listing of potentially claimed embodiments included within the scope of the disclosure.

Embodiment 1. An automated method of staining one or more biomarkers in a Romanowsky-type stained cytology sample without performing a separate de-stain step, said method comprising:

performing a cell conditioning step on the Romanowsky-type stained sample comprising incubating the sample for at least 5 minutes with a cell conditioning solution to obtain a conditioned and de-stained sample, and reacting the de-stained sample with one or more biomarker-specific reagents and a set of detection reagents under conditions sufficient to deposit a brightfield label or a fluorescence label in proximity to a biomarker expressed by the sample.

Embodiment 2. The method of Embodiment 1, wherein said cytology sample is deposited on a solid support in a monolayer.

Embodiment 3. The method of Embodiment 2, wherein said solid support is a microscope slide.

Embodiment 4. The method of any of Embodiments 1-3, wherein said cell conditioning step comprises a heat-induced epitope retrieval (HIER) process with a basic or acidic cell conditioning solution.

Embodiment 5. The method of any of Embodiments 1-3, wherein said cell conditioning step comprises a protease-based epitope retrieval (PBER) process.

Embodiment 6. The method of any of Embodiments 1-5, wherein the brightfield label or fluorescence label is a dye.

Embodiment 7. The method of Embodiment 6, wherein the dye is deposited by an affinity enzymatic reaction.

Embodiment 8. The method of Embodiment 7, wherein said sample is a whole blood sample, and said affinity enzymatic reaction is a simplex affinity enzymatic reaction.

Embodiment 9. The method of Embodiment 7, wherein said sample is a whole blood sample, and said affinity enzymatic reaction is a multiplex affinity enzymatic reaction that results in differential staining of a group of biomarkers with fluorescent dyes.

Embodiment 10. The method of Embodiment 7, wherein said sample is a whole blood sample, and said affinity enzymatic reaction is a multiplex affinity enzymatic reaction that results in differential staining of a group of biomarkers with brightfield dyes.

Embodiment 11. The method of any of Embodiments 7-10, wherein said affinity enzymatic reaction is selected from the group consisting of an immunoenzymatic stain, a genomic in situ hybridization stain, a mRNA in situ hybridization stain, and combinations thereof.

Embodiment 12. The method of any of Embodiments 1-11, wherein said Romanowsky-type stained sample is fixed in an alcohol-based fixative.

Embodiment 13. The method of Embodiment 12, wherein the alcohol is methanol.

Embodiment 14. The method of any of Embodiments 1-11, wherein said Romanowsky-type stained sample is fixed in an aldehyde-based fixative.

Embodiment 15. The method of Embodiment 14, wherein the aldehyde is formaldehyde.

Embodiment 16. The method of Embodiment 15, wherein the formaldehyde-based fixative is neutral-buffered formalin.

Embodiment 17. The method of any of Embodiments 1-16, wherein the one or more biomarker-specific reagents comprise at least one biomarker specifically reactive with a polypeptide comprising one of SEQ ID NO 1-18 or a nucleic acid encoding a polypeptide comprising one of SEQ ID NO: 1-18.

Embodiment 18. An automated method of performing a cytological evaluation, said method comprising:

(a) depositing cells of a cytology sample onto the solid support in a monolayer;

(b) staining the deposited cells with a Romanowsky-type stain to obtain a Romanowsky-type stained sample;

(c) capturing a digital image of the Romanowsky-type stained sample;

(d) automatically classifying cells in the digital image based on morphology and counting each classified cell type;

(e) performing an automated method of staining one or more biomarkers in a Romanowsky-type stained cytology sample without performing a separate de-stain step according to a method of any of Embodiments 1-17;

(f) capturing a digital image of the biomarker-stained stained sample;

(g) automatically classifying at least one cell in the digital image of the affinity enzymatically stained sample for biomarker-specific staining.

Embodiment 19. The method of Embodiment 18, wherein the cells of the cytology samples are deposited onto the solid support in a monolayer by printing cells of the sample onto the solid support.

Embodiment 20. The method of Embodiment 18, wherein the cytology sample is a suspension of intact cells.

Embodiment 21. The method of Embodiment 20, wherein the suspension of intact cells is selected from the group consisting of a fine needle aspirate of a tissue sample, a lavage fluid, a cervical brush sample, a buccal sample, a nasal irrigation sample, a nasal brush sample, a nasal swab sample, and a tissue sample homogenate.

Embodiment 22. The method of Embodiment 18, wherein the cytology sample is a body fluid.

Embodiment 23. The method of Embodiment 22, where the body fluid is selected from the group consisting of whole blood, a blood fraction, urine, synovial fluid, and cerebrospinal fluid.

Embodiment 24. The method of Embodiment 23, wherein the sample is a whole blood sample and the biomarker-stained sample is a simplex-stained sample.

Embodiment 25. The method of Embodiment 23, wherein the sample is a whole blood sample and the biomarker-stained sample is a multiplex-stained sample.

Embodiment 26. The method of Embodiment 24, wherein the multiplex-stained sample is differentially stained with at least two different brightfield labels.

Embodiment 27. The method of Embodiment 24, wherein the multiplex-stained sample is differentially stained with at least two different fluorescence labels.

Embodiment 28. The method of any of Embodiments 18-27, wherein the biomarker specific reagents comprise one or more biomarker-specific reagents specifically reactive with Embodiment 29. An automated method of performing a diagnostic analysis of a cytology sample, said method comprising:

(a) classifying cells in a digital image of a Romanowsky-type stained cytology sample based on morphology;

(b) classifying cells in a digital image of a biomarker-stained cytology sample based on biomarker expression, wherein the Romanowsky-type stained cytology sample and the biomarker-stained cytology sample are the same cytology sample;

(c) obtaining a diagnosis of a condition by comparing the cells classified based on morphology to the cells classified based on biomarker staining.

Embodiment 30. The method of Embodiment 29, wherein the digital image of the Romanowsky-type stained cytology sample is obtained by:

(a1) depositing cells of the cytology sample onto the solid support in a monolayer;

(a2) staining the deposited cells with a Romanowsky-type stain to obtain a Romanowsky-type stained sample; and (a3) capturing a digital image of the Romanowsky-type stained sample.

Embodiment 31. The method of Embodiment 30, wherein the cytology sample is deposited onto the solid support in a monolayer by printing cells of the sample onto the solid support.

Embodiment 32. The method of Embodiment 30 or Embodiment 31, wherein the digital image of the biomarker-stained cytology sample is obtained by:

(b1) simultaneously destaining and cell conditioning the Romanowsky-type stained sample to obtain a de-stained sample;

(b2) reacting the de-stained sample with one or more biomarker-specific reagents and a set of detection reagents under conditions sufficient to deposit a brightfield dye or a fluorescence label in proximity to a biomarker expressed by the sample to obtain the biomarker-stained sample; and (b3) capturing a digital image of the biomarker-stained stained sample.

Embodiment 33. The method of Embodiment 32, wherein the simultaneous destaining and cell conditioning comprises:

(b1a) incubating the Romanowsky-type stained sample in a cell conditioning solution for a sufficient time and at a sufficient temperature to at least partially destain the sample and to perform an epitope retrieval process, and (b1b) optionally, washing the destained sample for a sufficient time to completely de-stain the sample.

Embodiment 34. The method of Embodiment 33, wherein the epitope retrieval process comprises a heat-induced epitope retrieval (HIER) process using a basic or acidic cell conditioning solution.

Embodiment 35. The method of Embodiment 33, wherein the epitope retrieval process comprises a protease-based epitope retrieval (PBER).

Embodiment 36. The method of any of Embodiments 29-35, wherein the biomarker-stained slide is a simplex-stained sample.

Embodiment 37. The method of Embodiment 36, wherein the simplex stained sample is stained with a brightfield label.

Embodiment 38. The method of Embodiment 37, wherein the simplex-stained sample is stained with a fluorescent label.

Embodiment 39. The method of any of Embodiments 29-35, wherein the biomarker-stained slide is a multiplex-stained sample.

Embodiment 40. The method of Embodiment 39, wherein the multiplex stained sample is differentially stained with at least two different brightfield labels.

Embodiment 41. The method of Embodiment 39, wherein the multiplex-stained sample is differentially stained with at least two different fluorescent labels.

Embodiment 42. The method of any of Embodiments 29-41, wherein (b2) is an affinity enzymatic reaction.

Embodiment 43. The method of Embodiment 42, wherein the affinity enzymatic reaction is an immunoenzymatic reaction, a genomic in situ hybridization reaction, or a mRNA in situ hybridization reaction.

Embodiment 44. The method of any of Embodiments 29-43, wherein the cytology sample is a suspension of intact cells.

Embodiment 45. The method of Embodiment 44, wherein the suspension of intact cells is selected from the group consisting of a fine needle aspirate of a tissue sample, a lavage fluid, a cervical brush sample, a buccal sample, a nasal irrigation sample, a nasal brush sample, a nasal swab sample, and a tissue sample homogenate.

Embodiment 46. The method of any of Embodiments 29-43, wherein the cytology sample is a body fluid.

Embodiment 47. The method of Embodiment 46, where the body fluid is selected from the group consisting of whole blood, a blood fraction, urine, synovial fluid, and cerebrospinal fluid.

Embodiment 48. The method of Embodiment 47, wherein the body fluid is a whole blood sample.

Embodiment 49. The method of Embodiment 48, wherein the biomarkers are selected to identify a proliferative or cardiac disorder or parasitic disease.

Embodiment 50. The method of any of Embodiments 17-49, wherein the sample is fixed with an alcohol-based fixative prior to (b).

Embodiment 51. The method of Embodiment 50, wherein the alcohol is methanol.

Embodiment 52. The method of any of Embodiments 17-49, wherein the sample is fixed with an aldehyde-based fixative.

Embodiment 53. The method of Embodiment 52, wherein the aldehyde is formaldehyde.

Embodiment 54. The method of Embodiment 53, wherein the formaldehyde-based fixative is neutral-buffered formalin.

Embodiment 55. A method of diagnosing a disease state in a whole blood sample, the method comprising:

printing cells from the whole blood sample onto one or more solid supports;

performing an automated complete blood count (CBC) and automated morphological analysis on cells of at least one of the printed solid supports and identifying one or more unclassified or morphologically abnormal cells, wherein the presence of the unclassified or morphologically abnormal cells is indicative of one or more potential disease states;

staining at least one of the printed solid supports for at least one biomarker indicative of the potential disease state, wherein said staining is performed on an automated advanced staining platform; and diagnosing the disease state based upon the results of the CBC, morphological analysis, and the biomarker staining.

Embodiment 56. The method of Embodiment 55, wherein the presence or absence of biomarker-stained cells is automatically identified by image analysis.

Embodiment 57. The method of Embodiment 56, wherein the biomarker-stained cells are counted.

Embodiment 58. The method of Embodiment 57, wherein the cell counts are translated to cell concentrations.

Embodiment 59. The method of Embodiment 55-58, wherein the CBC and morphological analysis is performed on a printed sample stained with a Romanowsky-type stain.

Embodiment 60. The method of Embodiment 59, wherein the biomarker staining is performed on the Romanowsky-stained sample.

Embodiment 61. The method of Embodiment 60, wherein the Romanowsky stained sample is automatically transferred to the automated advanced staining platform.

Embodiment 62. The method of Embodiment 61, wherein the Romanowsky stained sample is automatically transferred to the automated advanced staining platform and stained with a panel of biomarker-specific reagents for molecularly characterizing the constituent cells of the slide.

Embodiment 63. The method of Embodiment 62, wherein the panel includes a plurality of markers for differentiating cell types of the constituent cells of the sample.

Embodiment 64. The method of Embodiment 63, wherein the panel includes markers for differentiating cells of hematopoetic and/or epithelial origin.

Embodiment 65. The method of Embodiment 63, wherein the differentiated cell types are selected from the group consisting of immature lymphocyte subtypes, monocyte subtypes, blasts, natural killer cells, platelet subtypes, and or circulating tumor cells.

Embodiment 66. The method of Embodiment 63, wherein the panel includes one or more markers for a microbial disease.

Embodiment 67. The method of Embodiment 61, wherein the Romanowsky-type stained sample is automatically transferred to the automated advanced staining platform upon identification of an abnormal CBC result and/or an atypical cell identified morphologically.

Embodiment 68. The method of any of Embodiments 57-67, wherein a digital image of the Romanowsky stained slide and a digital image of the biomarker-stained slide is obtained.

Embodiment 69. The method of Embodiment 68, wherein an image analysis system matches an image of at least one Romanowsky-stained cell with its corresponding biomarker-stained cells.

Embodiment 70. The method of Embodiment 69, wherein the image of the Romanowsky-stained cell with the image of the corresponding biomarker-stained cells are displayed with one another on a display.

Embodiment 71. The method of Embodiment 59, wherein the biomarker staining is performed on an unstained sample.

Embodiment 72. The method of Embodiment 71, wherein the system for performing the automated CBC and automated morphological analysis automatically generates the unstained printed sample upon identification of an abnormal CBC result and/or an atypical cell identified morphologically.

Embodiment 73. The method of Embodiment 71 or 72, wherein the biomarker-stained slide is counterstained with a morphological stain after biomarker staining.

Embodiment 74. The method of Embodiment 73, wherein the counterstained sample is subjected to automated morphological analysis.

Embodiment 75. The method of any of Embodiments 55-74, wherein the CBC indicates possible presence of a blood cancer, and wherein the biomarker staining comprises staining for one or more biomarkers useful in differential diagnosis of the blood cancer.

Embodiment 76. The method of any of Embodiments 55-74, wherein the CBC indicates possible presence of a cardiac condition, and wherein the biomarker staining comprises staining for one or more biomarkers useful in differential diagnosis of the cardiac condition.

Embodiment 77. The method of Embodiment 76, wherein the biomarker panel is selected to identify activated platelets.

Embodiment 78. The method of any of Embodiments 55-74, wherein the CBC indicates possible presence of a microbial disease, and wherein the biomarker staining comprises staining for one or more biomarkers useful in differential diagnosis of the potential microbial disease.

Embodiment 79. The method of any of Embodiments 55-74, wherein the CBC indicates possible sepsis, and wherein the biomarker staining comprises staining for one or more biomarkers useful in differential diagnosis of the sepsis.

Embodiment 80. The method of any of Embodiments 55-74, wherein the CBC indicates possible circulating tumor cells, and wherein the biomarker staining comprises staining for one or more biomarkers useful in identifying circulating tumor cells.

REFERENCES

Al Mussaed et al. Simultaneous existence of acute myeloid leukemia and chronic lymphocytic leukemia: a case report, BMC Cancer, 2016, Vol. 16, Issue 1, pp. 739

Andree et al., Challenges in circulating tumor cell detection by the CellSearch system, Molecular Oncology, 2016, Vol. 10, Issue 3, pp. 395-407.

Bain, 4-Preparation and staining methods for blood and bone marrow films, in Dacie and Lewis Practical Haematology (Twelfth Edition), 2017, pp. 50-60.

Barcia, The Giemsa Stain: Its History and Applications, History of Surgical Pathology, 2007, Vol. 15, Issue 3, pp. 292-96.

Blom et al., Systems pathology by multiplexed immunohistochemistry and whole-slide digital image analysis, Scientific Reports, 2017, Volume 7, Article number: 15580.

Bruegel et al., Multicenter evaluation of the COBAS m 511 integrated hematology analyzer, Int. J. Laboratory Hematology, Jul. 20, 2018, https://doi.org/10.1111/ijlh.12903 (e-publication ahead of print).

Buck et al., Measurement of pH. Definition, Standards, And Procedures, 2002, Pure Appl. Chem., Vol. 74, Issue 11, pp. 2169-2200.

Chiaretti, S., et al., Diagnosis and subclassification of acute lymphoblastic leukemia, 2014, Mediterr J Hematol Infect Dis, 2014, Vol. 6, Issue 1, e2014073.

Dong et al. B-Cell Lymphomas with Coexpression of CD5 and CD10, Am J Clin Pathol, 2003, Vol. 119, Issue 2, pp. 218-230.

Horobin, How Romanowsky stains work and why they remain valuable-including a proposed universal Romanowsky staining mechanism and a rational trouble-shooting scheme, Biotechnic & Histochemistry, 2011, Vol. 86, Issue 1, pp. 36-51.

Koh, Chapter Sixteen—Preparation of Cells for Microscopy using Cytospin, Methods in Enzymology, 2013, Vol. 533, pp. 235-240.

Krafts et al., The color purple: from royalty to laboratory, with apologies to Malachowski, Biotechnic & Histochemistry, 2011, Vol. 86, Issue 1, pp. 7-35 ("Krafts I").

Krafts et al., Romanowsky staining in cytopathology: history, advantages and limitations, Biotechnic & Histochemistry, 2011, Vol. 86, Issue 2, pp. 82-93 ("Krafts II").

Krebs et al., Circulating tumour cells: their utility in cancer management and predicting outcomes, Ther Adv Med Oncol., 2010, Vol. 2, Issue 6, pp. 351-365.

Kumar et al., Automated analysis of immunohistochemistry images identifies candidate location biomarkers for cancers, Proceedings of the National Academy of Sciences, Dec. 23, 2014, Vol. 111, Issue 51, pp. 18249-18254.

Ligthart et al., Unbiased and Automated Identification of a Circulating Tumour Cell Definition That Associates with Overall Survival, 2011, Vol. 6, Issue 11, e27419.

Meyerson et al., D Cyclins in CD5+ B-Cell Lymphoproliferative Disorders: Cyclin D1 and Cyclin D2 Identify Diagnostic Groups and Cyclin D1 Correlates With ZAP-70 Expression in Chronic Lymphocytic Leukemia, Am J Clin Pathol, 2006, Vol. 125, Issue 5, pp. 241-250.

Malcikova, J., et al. ERIC recommendations for TP53 mutation analysis in chronic lymphocytic leukemia-update on methodological approaches and results interpretation, Feb. 2, 2018, Leukemia, Vol. 32, Issue 5, pp. 1070-1080.

Neklason, D. W. et al., Activating mutation in MET oncogene in familial colorectal cancer, BMC Cancer, 2011, Vol. 11, No. 424.

Nickoloff et al., Mechanisms of leukemia translocations, Curr Opin Hematol, 2008, Vol. 15, Issue 4, pp. 338-345.

Pajor et al., State-of-the-art FISHing: Automated analysis of cytogenetic aberrations in interphase nuclei, Cytometry A, 2012, Volume 81 A, Issue 8, pp. 649-663

Park et al., Morphological Differences between Circulating Tumor Cells from Prostate Cancer Patients and Cultured Prostate Cancer Cells, PLOS ONE, 2014, Vol. 9, Issue 1: e85264, https://doi.org/10.1371/journal.pone.0085264.

Parker & Zhang, Fusion genes in solid tumors: an emerging target for cancer diagnosis and treatment, China J. Cancer, 2013, Vol. 32, Issue 11, pp. 594-603.

Prichard, Overview of Automated Immunohistochemistry, Arch Pathol Lab Med., 2014, Vol. 138, pp. 1578-1582.

Schlotens et al., Automated identification of circulating tumor cells by image cytometry, Cytometry A, 2012, Vol. 81, Issue 2: pp. 138-48.

Shah, J., et al. A dual colour fluorescence in situ hybridization (FISH) assay for identifying the zoonotic malaria parasite *Plasmodium knowlesi* with a potential application for the specific diagnosis of *knowlesi* malaria in peripheral-level laboratories of Southeast Asia, Parasit Vectors, 2017, Vol. 10, Issue 1, pp. 342.

Stack et al., Multiplexed immunohistochemistry, imaging, and quantitation: A review, with an assessment of Tyramide signal amplification, multispectral imaging and multiplex analysis, Methods, 2014, Vol. 70, Issue 1, pp 46-58.

Stokes, Principles of Cytocentrifugation, Laboratory Medicine, 2004, Vol. 35, Issue 7, pp. 434-437.

van de Donk, N. W., et al., Monoclonal antibodies targeting CD38 in hematological malignancies and beyond, 2016, Immunol Rev, Vol. 270, Issue 1, pp. 95-112.

van der Logt et al., Fully Automated Fluorescent in situ Hybridization (FISH) Staining and Digital Analysis of HER2 in Breast Cancer: A Validation Study, PLOS ONE, 2015; Vol. 10, Issue 4, e0123201.

Winkelman et al., A Novel Automated Slide-Based Technology for Visualization, Counting, and Characterization of the Formed Elements of Blood, Arch Pathol Lab Med, 2017, Vol. 141, pp. 1107-1112.

Zahniser & Hurley, Automated Slide Preparation System for the Clinical Laboratory, Comm. In Clinical Cytometry, 1996, Vol. 26, pp. 60-64.

The invention claimed is:

1. An automated method of performing a cytological evaluation, the method comprising:

(a) printing a monolayer of cells of a cytology sample onto a surface of a stationary solid support, wherein the monolayer of cells are arranged in parallel rows on the surface of the stationary solid support, wherein the printing comprises flowing a volume of about 0.1 to about 10 µL of the cytology sample through a movable applicator tip to the surface of the stationary solid support, wherein the movable applicator tip is movable in the x-, y-, and z-coordinate directions relative to the surface of the stationary solid support;

(b) staining the deposited cells with a Romanowsky-type stain to obtain a Romanowsky-type stained cytology sample;

(c) acquiring one or more digital images of the Romanowsky-type stained cytology sample;

(d) automatically classifying cells in the acquired one or more digital images of the Romanowsky-type stained cytology sample based on morphology to identify one or more different cell types;

(e) counting each of the identified one or more different cell types;

(f) incubating the Romanowsky-type stained cytology sample with a cell conditioning solution for at least 5 minutes to obtain a conditioned Romanowsky-type stained cytology sample; and (g) reacting the conditioned Romanowsky-type stained cytology sample with one or more biomarker-specific reagents and a set of detection reagents under conditions sufficient to deposit a brightfield label or a fluorescence label in proximity to a biomarker expressed by the conditioned Romanowsky-type stained cytology sample to provide a biomarker-stained cytology sample.

2. The method of claim 1, wherein said solid support is a microscope slide.

3. The method of claim 1, wherein the cell conditioning solution comprises a basic or acidic cell conditioning solution.

4. The method of claim 1, wherein the brightfield label or fluorescence label is a dye.

5. The method of claim 4, wherein the dye is deposited by an affinity enzymatic reaction.

6. The method of claim 5, wherein the Romanowsky-type stained cytology sample is a whole blood sample, and said affinity enzymatic reaction is a simplex affinity enzymatic reaction.

7. The method of claim 5, wherein the Romanowsky-type stained cytology sample is a whole blood sample, and the affinity enzymatic reaction is a multiplex affinity enzymatic reaction that results in differential staining of a group of biomarkers with fluorescent dyes.

8. The method of claim 5, wherein the Romanowsky-type stained cytology sample is a whole blood sample, and the affinity enzymatic reaction is a multiplex affinity enzymatic reaction that results in differential staining of a group of biomarkers with brightfield dyes.

9. The method of claim 5, wherein said affinity enzymatic reaction is selected from the group consisting of an immunoenzymatic stain, a genomic in situ hybridization stain, a mRNA in situ hybridization stain, and combinations thereof.

10. The method of claim 1, wherein the Romanowsky-type stained cytology sample is fixed in an alcohol-based fixative.

11. The method of claim 10, wherein the alcohol is methanol.

12. The method of claim 1, wherein said Romanowsky-type cytology stained sample is fixed in an aldehyde-based fixative.

13. The method of claim 12, wherein the aldehyde is formaldehyde.

14. The method of claim 13, wherein the formaldehyde-based fixative is neutral-buffered formalin.

15. The method of claim 1, wherein the one or more biomarker-specific reagents bind at least one biomarker selected from the group consisting of CD2, CD3, CD4, CD5, CD7, CD8, CD10, CD 19, CD20, CD23, CD27, CD34, CD38, CD45, CD68, CyclPBERin D1, Myeloperoxidase (MPO), Paired box protein Pax-5 (PAX5), DNA nucleotidylexotransferase (TdT), and Tyrosine-protein kinase ZAP-70 (ZAP-70).

16. The method of claim 1, wherein the cell conditioning solution is a citrate-based solution.

17. The method of claim 1, wherein the cell conditioning solution has a pH ranging from about 5 to about 6.5.

18. The method of claim 1, further comprising capturing one or more digital images of the biomarker-stained cytology sample.

19. The method of claim 18, further comprising automatically classifying at least one cell in the captured one or more digital images of the biomarker-stained cytology sample for biomarker-specific staining.

20. An automated method of performing a cytological evaluation, the method comprising:

(a) printing in concentric circles a monolayer of cells of a cytology sample onto a surface of a stationary solid support, wherein the printing comprises flowing the cytology sample through a movable applicator tip to the surface of the stationary solid support, wherein the movable applicator tip is movable in the x-, y-, and z-coordinate directions relative to the surface of the stationary solid support;

(b) staining the deposited cells with a Romanowsky-type stain to obtain a Romanowsky-type stained cytology sample;

(c) acquiring one or more digital images of the Romanowsky-type stained cytology sample;

(d) automatically classifying cells in the acquired one or more digital images of the Romanowsky-type stained cytology sample based on morphology to identify one or more different cell types;

(e) counting each of the identified one or more different cell types;

(f) incubating the Romanowsky-type stained cytology sample with a cell conditioning solution for at least 5 minutes to obtain a conditioned Romanowsky-type stained cytology sample; and (g) reacting the conditioned Romanowsky-type stained cytology sample with one or more biomarker-specific reagents and a set of detection reagents under conditions sufficient to deposit a brightfield label or a fluorescence label in proximity to a biomarker expressed by the conditioned Romanowsky-type stained cytology sample to provide a biomarker-stained cytology sample.

21. An automated method of performing a cytological evaluation, the method comprising:

(a) printing in parallel rows or in concentric circles a monolayer of cells of a cytology sample onto a surface of a stationary solid support, wherein the printing comprises flowing the cytology sample through a movable applicator tip to the surface of the stationary solid support;

(b) staining the deposited cells with a Romanowsky-type stain to obtain a Romanowsky-type stained cytology sample;

(c) acquiring one or more digital images of the Romanowsky-type stained cytology sample;

(d) automatically classifying cells in the acquired one or more digital images of the Romanowsky-type stained cytology sample based on morphology to identify one or more different cell types;

(e) counting each of the identified one or more different cell types;

(f) incubating the Romanowsky-type stained cytology sample with a cell conditioning solution comprising a proteolytic enzyme for at least 5 minutes to obtain a conditioned Romanowsky-type stained cytology sample; and (g) reacting the conditioned Romanowsky-type stained cytology sample with one or more biomarker-specific reagents and a set of detection reagents under conditions sufficient to deposit a brightfield label or a fluorescence label in proximity to a biomarker expressed by the conditioned Romanowsky-type stained cytology sample to provide a biomarker-stained cytology sample.

* * * * *